(12) United States Patent
Choudhary et al.

(10) Patent No.: US 12,227,742 B2
(45) Date of Patent: Feb. 18, 2025

(54) NUCLEIC ACID MODIFIERS

(71) Applicants: THE BROAD INSTITUTE, INC., Cambridge, MA (US); THE BRIGHAM AND WOMEN'S HOSPITAL, INC., Boston, MA (US)

(72) Inventors: Amit Choudhary, Boston, MA (US); Donghyun Lim, Cambridge, MA (US); Kurt Cox, Cambridge, MA (US); Soumyashree Ashok Gangopadhyay, Boston, MA (US)

(73) Assignees: The Broad Institute, Inc., Cambridge, MA (US); The Brigham and Women's Hospital, Inc., Boston, MA (US)

( * ) Notice: Subject to any disclaimer, the term of this patent is extended or adjusted under 35 U.S.C. 154(b) by 491 days.

(21) Appl. No.: 16/758,840

(22) PCT Filed: Oct. 23, 2018

(86) PCT No.: PCT/US2018/057182
§ 371 (c)(1),
(2) Date: Apr. 23, 2020

(87) PCT Pub. No.: WO2019/135816
PCT Pub. Date: Jul. 11, 2019

(65) Prior Publication Data
US 2021/0214724 A1    Jul. 15, 2021

Related U.S. Application Data

(60) Provisional application No. 62/575,948, filed on Oct. 23, 2017, provisional application No. 62/765,347, filed on Aug. 20, 2018.

(51) Int. Cl.
| | | |
|---|---|---|
| *C12N 15/11* | (2006.01) | |
| *A61K 9/51* | (2006.01) | |
| *A61K 31/18* | (2006.01) | |
| *A61K 31/336* | (2006.01) | |
| *A61K 31/655* | (2006.01) | |
| *A61K 31/7088* | (2006.01) | |
| *A61K 38/46* | (2006.01) | |
| *A61K 47/60* | (2017.01) | |
| *C12N 9/22* | (2006.01) | |
| *C12N 15/90* | (2006.01) | |

(52) U.S. Cl.
CPC ............ *C12N 15/11* (2013.01); *A61K 9/5153* (2013.01); *A61K 31/18* (2013.01); *A61K 31/336* (2013.01); *A61K 31/655* (2013.01); *A61K 31/7088* (2013.01); *A61K 38/465* (2013.01); *A61K 47/60* (2017.08); *C12N 9/22* (2013.01); *C12N 15/902* (2013.01); *C12N 15/907* (2013.01); *C12N 2310/20* (2017.05); *C12N 2800/80* (2013.01)

(58) Field of Classification Search
CPC ........ C12N 15/11; C12N 9/22; C12N 15/902; C12N 15/907; C12N 2310/20; C12N 2800/20; C12N 2800/80; C12N 15/111; C12N 15/102; A61K 9/5153; A61K 31/18; A61K 31/336; A61K 31/655; A61K 31/7088; A61K 38/465; A61K 47/60
See application file for complete search history.

(56) References Cited

U.S. PATENT DOCUMENTS

| | | |
|---|---|---|
| 5,580,859 A | 12/1996 | Felgner et al. |
| 5,589,466 A | 12/1996 | Felgner et al. |
| 5,593,972 A | 1/1997 | Weiner et al. |
| 5,846,946 A | 12/1998 | Huebner et al. |
| 5,869,326 A | 2/1999 | Hofmann |
| 6,740,525 B2 | 5/2004 | Roelvink et al. |
| 6,828,439 B1 | 12/2004 | Zaleski |
| 6,911,199 B2 | 6/2005 | Vigne et al. |
| 7,256,036 B2 | 8/2007 | Legrand et al. |
| 7,259,015 B2 | 8/2007 | Kingsman et al. |
| 7,303,910 B2 | 12/2007 | Bebbington et al. |
| 7,344,872 B2 | 3/2008 | Gao et al. |
| 7,351,585 B2 | 4/2008 | Mitrophanous et al. |
| 7,745,651 B2 | 6/2010 | Heyes et al. |
| 7,799,565 B2 | 9/2010 | Maclachlan et al. |
| 7,803,397 B2 | 9/2010 | Heyes et al. |

(Continued)

FOREIGN PATENT DOCUMENTS

| | | |
|---|---|---|
| EP | 1519714 A1 | 4/2005 |
| EP | 1664316 A1 | 6/2006 |

(Continued)

OTHER PUBLICATIONS

Abudayyeh et al., C2c2 is a single-component programmable RNA-guided RNA-targeting CRISPR effector. Science, 2016, vol. 353, Issue 6299: pp. 1-11. (Year: 2016).*

(Continued)

*Primary Examiner* — Ganapathirama Raghu
(74) *Attorney, Agent, or Firm* — F. Brent Nix, Esq.; Johnson, Marcou, Isaacs & Nix, LLC

(57) ABSTRACT

The present inventions generally relate to site-specific delivery of nucleic acid modifiers and includes novel DNA-binding proteins and effectors that can be rapidly programmed to make site-specific DNA modifications. The present inventions also provide a synthetic all-in-one genome editor (SAGE) systems comprising designer DNA sequence readers and a set of small molecules that induce double-strand breaks, enhance cellular permeability, inhibit NHEJ and activate HDR, as well as methods of using and delivering such systems.

26 Claims, 30 Drawing Sheets
Specification includes a Sequence Listing.

(56) References Cited

U.S. PATENT DOCUMENTS

| | | | |
|---|---|---|---|
| 7,838,658 B2 | 11/2010 | Maclachlan et al. |
| 7,901,708 B2 | 3/2011 | Maclachlan et al. |
| 7,915,399 B2 | 3/2011 | Maclachlan et al. |
| 7,982,027 B2 | 7/2011 | Maclachlan et al. |
| 8,044,019 B2 | 10/2011 | Uno et al. |
| 8,058,069 B2 | 11/2011 | Yaworski et al. |
| 8,071,082 B2 | 12/2011 | Zugates et al. |
| 8,101,741 B2 | 1/2012 | Maclachlan et al. |
| 8,188,263 B2 | 5/2012 | Maclachlan et al. |
| 8,236,943 B2 | 8/2012 | Lee et al. |
| 8,283,333 B2 | 10/2012 | Yaworski et al. |
| 8,372,951 B2 | 2/2013 | Chang et al. |
| 8,404,658 B2 | 3/2013 | Hajjar et al. |
| 8,454,972 B2 | 6/2013 | Nabel et al. |
| 8,575,305 B2 | 11/2013 | Gait et al. |
| 8,614,194 B1 | 12/2013 | Chen et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,410,129 B2 | 8/2016 | Ranki et al. |
| 11,001,829 B2 | 5/2021 | Zhang et al. |
| 11,124,796 B2 | 9/2021 | Sharp et al. |
| 11,236,313 B2 * | 2/2022 | Cotta-Ramusino .... C12N 15/10 |
| 11,352,647 B2 * | 6/2022 | Zhang ............... C12N 15/1089 |
| 2002/0150626 A1 | 10/2002 | Kohane et al. |
| 2004/0013648 A1 | 1/2004 | Kingsman et al. |
| 2005/0019923 A1 | 1/2005 | Uchegbu et al. |
| 2005/0123596 A1 | 6/2005 | Kohane et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0111106 A1 | 4/2009 | Mitrophanous et al. |
| 2009/0215879 A1 | 8/2009 | Diprimio et al. |
| 2009/0285780 A1 | 11/2009 | Lee |
| 2010/0129793 A1 | 5/2010 | Mirkin |
| 2010/0317109 A1 | 12/2010 | Maden et al. |
| 2011/0117189 A1 | 5/2011 | Mazzone et al. |
| 2011/0212179 A1 | 9/2011 | Liu |
| 2011/0293571 A1 | 12/2011 | Widdowson et al. |
| 2011/0293703 A1 | 12/2011 | Mahon et al. |
| 2012/0251618 A1 | 10/2012 | Schrum et al. |
| 2012/0295960 A1 | 11/2012 | Palfi et al. |
| 2013/0244279 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0302401 A1 | 11/2013 | Ma et al. |
| 2014/0113857 A1 | 4/2014 | Walensky |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0301951 A1 | 10/2014 | Liu et al. |
| 2014/0308304 A1 | 10/2014 | Manoharan et al. |
| 2014/0310830 A1 | 10/2014 | Zhang et al. |
| 2014/0328759 A1 | 11/2014 | Cullis et al. |
| 2014/0348900 A1 | 11/2014 | Zhu |
| 2015/0010526 A1 | 1/2015 | Liu |
| 2015/0071903 A1 | 3/2015 | Liu et al. |
| 2015/0105538 A1 | 4/2015 | Chromy et al. |
| 2015/0118216 A1 | 4/2015 | Liu et al. |
| 2015/0140070 A1 | 5/2015 | Heartlein et al. |
| 2015/0232883 A1 | 8/2015 | Dahlman et al. |
| 2015/0250725 A1 | 9/2015 | Bader et al. |
| 2015/0291966 A1 | 10/2015 | Zhang |
| 2016/0082126 A1 | 3/2016 | Wang et al. |
| 2016/0122707 A1 | 5/2016 | Swee |
| 2016/0129120 A1 | 5/2016 | Xu et al. |
| 2016/0174546 A1 | 6/2016 | Berg et al. |
| 2016/0200779 A1 | 7/2016 | Liu et al. |
| 2016/0257951 A1 | 9/2016 | Koizumi et al. |
| 2016/0304854 A1 | 10/2016 | Izpisua Belmonte |
| 2016/0340660 A1 | 11/2016 | Zhang |
| 2016/0367686 A1 | 12/2016 | Anderson et al. |
| 2017/0002355 A1 | 1/2017 | Appella |
| 2017/0003245 A1 | 1/2017 | Lindsay |
| 2017/0079916 A1 | 3/2017 | Khan et al. |
| 2017/0152553 A1 | 6/2017 | Ismagilov |
| 2017/0166893 A1 | 6/2017 | Doudna |
| 2018/0112255 A1 | 4/2018 | Chen et al. |

FOREIGN PATENT DOCUMENTS

| | | |
|---|---|---|
| EP | 1766035 A1 | 3/2007 |
| EP | 1781593 A2 | 5/2007 |
| EP | 2771468 B1 | 2/2015 |
| EP | 2784162 B1 | 4/2015 |
| EP | 2764103 B1 | 8/2015 |
| WO | 97/49450 A1 | 12/1997 |
| WO | 98/52609 A1 | 11/1998 |
| WO | 2004/015075 A2 | 2/2004 |
| WO | 2008/042973 A2 | 4/2008 |
| WO | 2011/008730 A2 | 1/2011 |
| WO | 2013/093648 A2 | 6/2013 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/186348 A2 | 11/2014 |
| WO | 2014/186366 A1 | 11/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/065964 A1 | 5/2015 |
| WO | 2015/089364 A1 | 6/2015 |
| WO | 2015/089419 A2 | 6/2015 |
| WO | 2015/089486 A2 | 6/2015 |
| WO | 2016/027264 A1 | 2/2016 |
| WO | 2016054326 A1 | 4/2016 |
| WO | 2016106244 A1 | 6/2016 |
| WO | 2016/186745 A1 | 11/2016 |
| WO | 2016186946 A1 | 11/2016 |
| WO | 2016205554 A1 | 12/2016 |
| WO | 2016205759 A1 | 12/2016 |
| WO | 2017048969 A1 | 3/2017 |

(56) References Cited

FOREIGN PATENT DOCUMENTS

| WO | 2017070632 A2 | 4/2017 |
|---|---|---|
| WO | 2017127807 A1 | 7/2017 |
| WO | 2017147446 A1 | 8/2017 |

OTHER PUBLICATIONS

Liu et al., C2c1-sgRNA Complex Structure Reveals RNA Guided DNA Cleavage Mechanism. Cell, 2017, vol. 65: 310-322. (Year: 2017).*

Nishimasu et al., Crystal Structure of *Staphylococcus aureus* Cas9. Cell, 2015, vol. 162: 1113-1126. (Year: 2015).*

Yamada T., Crystal Structure of the Minimal Cas9 from Campylobacter jejuni Reveals the Molecular Diversity in the CRISPR-Cas9. Systems Mol. Cell., 2017, vol. 65: 1109-121. (Year: 2017).*

Yanik et al., In vivo genome editing as a potential treatment strategy for inherited retinal dystrophies. Prog. Ret. Eye Res., 2017, vol. 56: 1-18. (Year: 2017).*

Oakes BL., Engineering CRISPR-Cas9 Systems to Expand Functionality. Ph. D. Thesis Dissertation, Univ. Calif., Berkeley, Spring 2017, pp. 1-96. (Year: 2017).*

Sternberg et al., Conformational control of DNA target cleavage by CRISPR-Cas9. Nature, 2015, vol. 527: 110-113. (Year: 2015).*

Canver et al., Functional interrogation of non-coding DNA through CRISPR genome editing. Methods, 2017, vol. 121-12: 118-129. (Year: 2017).*

Casini A., PhD., "Better safe than sorry: new CRISPR/Cas9 tools for improved genome engineering". Ph.D., Thesis, 2015-2016, Univ. of Trento., Italy, pp. 1-141. (Year: 2016).*

Koonin et al., Origins and evolution of CRISPR-Cas systems. Phil. Trans. R. Soc. B 374: 20180087, 2018, pp. 1-16. (Year: 2018).*

Komor et al., CRISPR-Based Technologies for the Manipulation of Eukaryotic Genomes. Cell, 2017, vol. 168: 20-35. (Year: 2017).*

International Search Report and Written Opinion issued by the United States Patent and Trademark Office, as International Searching Authority on Aug. 2, 2019 for PCT/US2018/057182.

Chen, et al., "Enhanced proofreading governs CRISPR-Cas9 targeting accuracy", Nature, vol. 550, No. 7676, pp. 407-410, , Sep. 20, 2017.

Chu, et al., "Increasing the efficiency of homology-directed repair for CRISPR-Cas9-induced precise gene editing in mammalian cells", Nature Biotechnology, vol. 33, No. 5, pp. 543-548, Mar. 24, 2015.

Greco, et al., "SCR7 is neither a selective nor a potent inhibitor of human DNA ligase IV", DNA Repair, vol. 43, pp. 18-23, May 7, 2016.

Aird, et al., "Increasing Cas9-Mediated Homology-Directed Repair Efficiency Through Covalent Tethering of DNA Repair Template", Communications Biology, vol. 1, No. 54, 2018, 6 pages.

Anders, et al., "Structural Basis of PAM-Dependent Target DNA Recognition by the Cas9 Endonuclease", Nature, vol. 513, No. 7519, Sep. 25, 2014, 22 pages.

Bahal, et al., "Sequence-Unrestricted, Watson-Crick Recognition of Double Helical B-DNA by (R)-MiniPEG-γPNAs", ChemBioChem, vol. 13, Issue 1, Jan. 2, 2012, 56-60.

Briner, et al., "Guide RNA Functional Modules Direct Cas9 Activity and Orthogonality", Molecular Cell, vol. 56, Issue 2, Oct. 23, 2014, 7 pages.

Cai-Xia, et al., "DNA-Binding and Cleavage Studies of Zinc(II) Mixed-polypyridyl Complex", Chinese Journal of Chemistry, vol. 24, No. 8, 2006, 1006-1012.

Chen, et al., "Rational Design of Human DNA Ligase Inhibitors That Target Cellular DNA Replication and Repair", Cancer Research, vol. 68, No. 9, May 1, 2008, 3169-3177.

Colis, et al., "The Cytotoxicity of (−)-Lomaiviticin a Arises from Induction of Double-Strand Breaks in DNA", Nature Chemistry, vol. 6, 2014, 504-510.

Cong, et al., "Multiplex Genome Engineering Using CRISPR/Cas Systems", Science, vol. 339, No. 6121, Feb. 15, 2013, 819-823.

Deltcheva, et al., "CRISPR RNA Maturation by Trans-Encoded Small RNA and Host Factor Rnase III", Nature, vol. 471, No. 7340, Mar. 31, 2011, 602-607.

Desbouis, et al., "Copper(II), zinc(II) and nickel(II) Complexes as Nuclease Mimetics", Coordination Chemistry Reviews, vol. 256, No. 11-12, 2012, 897-937.

Egholm, et al., "PNA Hybridizes to Complementary Oligonucleotides Obeying the Watson-Crick Hydrogen-Bonding Rules", Nature, vol. 365, No. 6446, 1993, 566-568.

Fonfara, et al., "Phylogeny of Cas9 Determines Functional Exchangeability of Dual-RNA and Cas9 among Orthologous type II CRISPR-Cas Systems", Nucleic acids research, vol. 42, No. 4, Nov. 22, 2013, 2577-2590.

Fu, et al., "High Frequency Off-Target Mutagenesis Induced by CRISPR-Cas Nucleases in Human Cells", Nature Biotechnology, vol. 31, No. 9, Sep. 2013, 822-826.

Guimaraes, et al., "Site-Specific C-Terminal and Internal Loop Labeling of Proteins Using Sortase-Mediated Reactions", Nature Protocols. vol. 8, No. 9, Sep. 2013, 1787-1799.

Hemphill, et al., "Optical Control of CRISPR/Cas9 Gene Editing", Journal of the American Chemical Society, vol. 137, No. 17, 2015, 5642-5645.

Herzon, S.B., "The Mechanism of Action of (−)-Lomaiviticin A", Accounts of Chemical Research, vol. 50, No. 10, Sep. 28, 2017, 2577-2588.

Hsu, et al., "DNA Targeting Specificity of Rna-Guided Cas9 Nucleases", Nature Biotechnology, vol. 31, No. 9, Sep. 2013, 827-832.

Jayathilaka, et al., "A Chemical Compound That Stimulates the Human Homologous Recombination Protein RAD51", Proceedings of the National Academy of Sciences of the United States, vol. 105, No. 41, Oct. 14, 2008, 15848-15853.

Jiang, et al., "A Cas9-guide RNA Complex Preorganized for Target DNA Recognition", Science, vol. 348, No. 6242, 2015, 1477-1481.

Jinek, et al., "A Programmable Dual-RNA-Guided DNA Endonuclease in Adaptive Bacterial Immunity", Science, vol. 337, No. 6096, Aug. 17, 2012, 816-821.

Jinek, et al., "Structures of Cas9 Endonucleases Reveal RNA-Mediated Conformational Activation", Science, vol. 343, Mar. 2014, 13 pages.

Kim, et al., "A Guide to Genome Engineering with Programmable Nucleases", Nature Reviews Genetics, vol. 15, May 2014, 321-334.

Komor, et al., "Editing the Genome Without Double-Stranded DNA Breaks", ACS Chemical Biology, vol. 13, No. 2, Feb. 16, 2018, 383-388.

Konermann, et al., "Genome-Scale Transcriptional Activation by an Engineered CRISPR-Cas9 Complex", Nature, vol. 517, No. 7536, Jan. 29, 2015, 583-588.

Maji, et al., "Multidimensional Chemical Control of CRISPR-Cas9", Nature Chemical Biology, vol. 13, No. 1, Jan. 2017, 11 pages.

Makarova, et al., "An Updated Evolutionary Classification of Crispr-Cas Systems", Nature Reviews Microbiology, vol. 13, No. 11, Nov. 2015, 31 pages.

Mali, et al., "CAS9 Transcriptional Activators for Target Specificity Screening and Paired Nickases for Cooperative Genome Engineering", Nature Biotechnology, vol. 31, No. 9, Sep. 2013, 17 pages.

Maruyama, et al., "Increasing the Efficiency of Precise Genome Editing with CRISPR-Cas9 by Inhibition of Nonhomologous End Joining", Nature Biotechnology, vol. 33, No. 5, 2015, 538-542.

Nielsen, et al., "Sequence-Selective Recognition of DNA by Strand Displacement with a Thymine-Substituted Polyamide", Science, vol. 254, No. 5037, 1991, 1497-1500.

Nishimasu, et al., "Crystal Structure of Cas9 in Complex with Guide RNA and Target DNA", Cell, vol. 156, Feb. 27, 2014, 935-949.

Pattanayak, et al., "High-Throughput Profiling of Off-Target DNA Cleavage Reveals RNA-Programmed Cas9 Nuclease Specificity", Nature Biotechnology, vol. 31, No. 9, Sep. 2013, 839-843.

Pawelczak, et al., "Modulating DNA Repair Pathways to Improve Precision Genome Engineering", ACS Chemical Biology, vol. 13, No. 2, 2017, 389-396.

Pinder, et al., "Nuclear Domain 'Knock-In' Screen for the Evaluation and Identification of Small Molecule Enhancers of CRISPR-

(56) References Cited

OTHER PUBLICATIONS

Based Genome Editing", Nucleic Acids Research, vol. 43, No. 19, XP055342317, Oct. 1, 2015, 9379-9392.
Ran, et al., "In Vivo Genome Editing using *Staphylococcus aureus* Cas9", Nature, vol. 520, No. 7546, Apr. 1, 2015, 30 pages.
Ricciardi, et al., "Peptide Nucleic Acids as a Tool for Site-Specific Gene Editing", Molecules, vol. 23, No. 632, 2018, 15 pages.
Richardson, et al., "Enhancing Homology-Directed Genome Editing by Catalytically Active and Inactive Crispr-Cas9 using Asymmetric Donor DNA", Nature Biotechnology, vol. 34, No. 3, Mar. 2016, 339-344.
Savic, et al., "Covalent Linkage of the DNA Repair Template to the CRISPR/Cas9 Complex Enhances Homology-Directed Repair", Elife, vol. 7, No. e33761, May 29, 2018, 18 pages.
Schmohl, et al., "Sortase-Mediated Ligations for the Site-Specific Modification of Proteins", Current Opinion in Chemical Biology, vol. 22, 2014, 122-128.
Shell, et al., "Hydrolytic DNA Cleavage by Non-Lanthanide Metal Complexes", Current Organic Chemistry, vol. 11, No. 17, 2007, 1525-1542.
Slaymaker, et al., "Rationally Engineered Cas9 Nucleases with Improved Specificity", Science, vol. 351, No. 6268, Jan. 1, 2016, 84-88.
Srivastava, et al., "An Inhibitor of Nonhomologous End-Joining Abrogates Double-Strand Break Repair and Impedes Cancer Progression", Cell, vol. 151, Dec. 21, 2012, 1474-1487.
Theile, et al., "Site-Specific N-Terminal Labeling of Proteins Using Sortase-Mediated Reactions", Nature Protocols, vol. 8, No. 9, Sep. 2013, 13 pages.
Thierry, et al., "Dual and Opposite Effects of hRAD51 Chemical Modulation on HIV-1 Integration", Chemistry & Biology, vol. 22, No. 6, Jun. 2015, 712-723.
Woo, et al., "Structural Basis for DNA Cleavage by the Potent Antiproliferative Agent (−)-Lomaiviticin A", Proceedings of the National Academy of Sciences, vol. 113, Mar. 15, 2016, 2851-2856.
Wright, et al., "Rational Design of a Split-Cas9 Enzyme Complex", Proceedings of the National Academy of Sciences of the United States of America, vol. 112, No. 10, Mar. 10, 2015, 2984-2989.
Zetsche, et al., "A Split-Cas9 Architecture for Inducible Genome Editing and Transcription Modulation", Nature Biotechnology, vol. 33, No. 2, Feb. 2015, 139-142.
Zhang, et al., "Design of Artificial Metallonucleases with Oxidative Mechanism", Science in China Series B: Chemistry, vol. 52, No. 4, 2009, 402-414.

\* cited by examiner

Lanes
1: Ladder
2: Skip
3: Restriction Enzyme Digested DNA
4: DNA only (100 ng/μL)
5: C 1.15 (10 μM)
6: C 1.15 (12 μM)
7: C 1.15 (14 μM)
9: C 1.15 (10 μM + UV)
10: C 1.15 (12 μM + UV)
11: C 1.15 (14 μM + UV)
12: C 1.15 (10 μM + UV + TCEP (500 μM))
13: C 1.15 (12 μM + UV + TCEP)
14: C 1.15 (14 μM + UV + TCEP)
14: Skip
15: Ladder Lanes
1: Ladder
2: Skip
3: Restriction Enzyme Digested DNA
4: DNA only (100 ng/ μL)
5: C 1.15 (16 μM)
6: C 1.15 (18 μM)
7: C 1.15 (20 μM)
9: C 1.15 (16 μM + UV)
10: C 1.15 (18 μM + UV)
11: C 1.15 (20 μM + UV)
12: C 1.15 (16 μM + UV + TCEP (500 μM))
13: C 1.15 (18 μM + UV + TCEP)
14: C 1.15 (20 μM + UV + TCEP)
14: Skip
15: Ladder Lanes
1: Ladder
2: Skip
3: Restriction Enzyme Digested DNA
4: DNA only (100 ng/μL)
5: C 1.15 (10 μM)
6: C 1.15 (12 μM)
7: C 1.15 (14 μM)
9: C 1.15 (10 μM + UV)
10: C 1.15 (12 μM + UV)
11: C 1.15 (14 μM + UV)
12: C 1.15 (10 μM + UV + DTT (500 μM))
13: C 1.15 (12 μM + UV + DTT)
14: C 1.15 (14 μM + UV + DTT)
14: Skip
15: Ladder Lanes
1: Ladder
2: Skip
3: Restriction Enzyme Digested DNA
4: DNA only (100 ng/ μL)
5: C 1.15 (16 μM)
6: C 1.15 (18 μM)
7: C 1.15 (20 μM)
9: C 1.15 (16 μM + UV)
10: C 1.15 (18 μM + UV)
11: C 1.15 (20 μM + UV)
12: C 1.15 (16 μM + UV + DTT (500 μM))
13: C 1.15 (18 μM + UV + DTT)
14: C 1.15 (20 μM + UV + DTT)
14: Skip
15: Ladder Lanes
1: Ladder
2: Restriction Enzyme Digested DNA
3: DNA only (100 ng/ μL)
4: C 1.15 (16 μM + UV (30 min))
5: C 1.15 (16 μM + UV (32 min))
6: C 1.15 (16 μM + UV (33 min))
7: C 1.15 (16 μM + UV (34 min))
9: C 1.15 (16 μM + UV (35 min))
10: C 1.15 (16 μM + UV (40 min))
11: C 1.15 (16 μM + UV (45 min))
12: C 1.15 (16 μM + UV (50 min))
13: C 1.15 (16 μM + UV (55 min))
14: C 1.15 (16 μM + UV (60 min))
15: Ladder

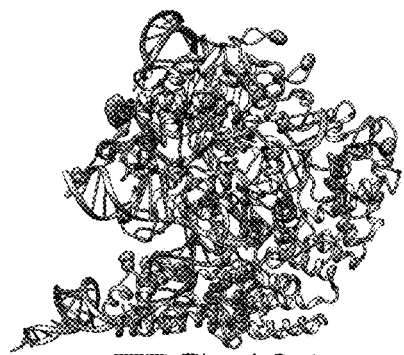
FIG. 13A
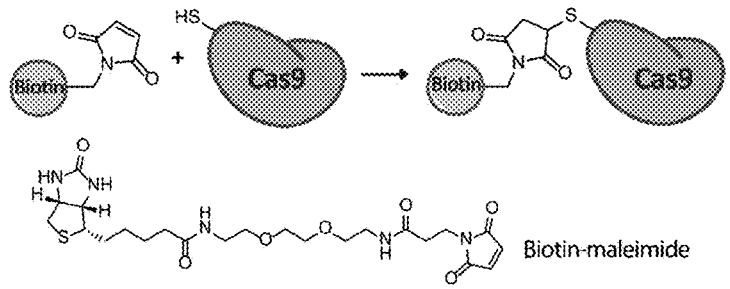
FIG. 13B
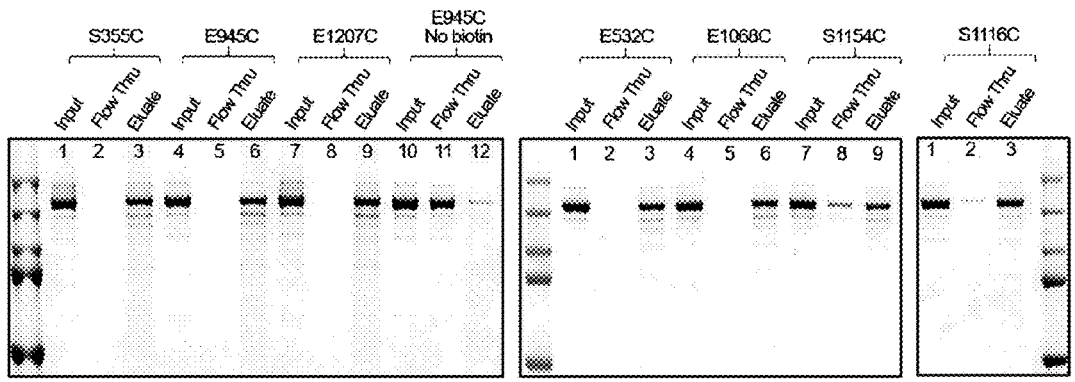
FIG. 13C
| Mutants | Labeling efficiency |
|---|---|
| S355C | 100% |
| E532C | 100% |
| E945C | 100% |
| E1068C | 100% |
| S1116C | 94% |
| S1154C | 70% |
| E1207C | 100% |
FIG. 13D
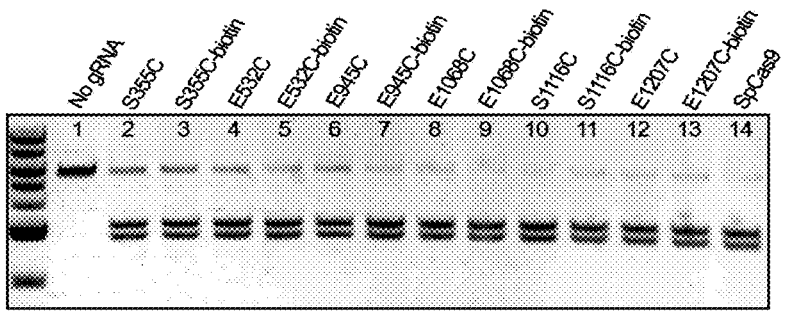
FIG. 13E
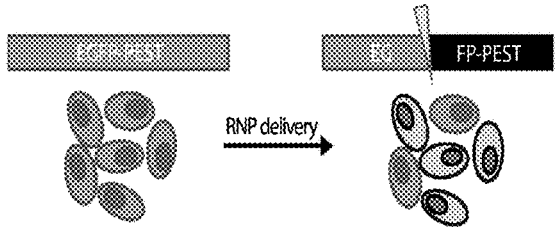
FIG. 13F
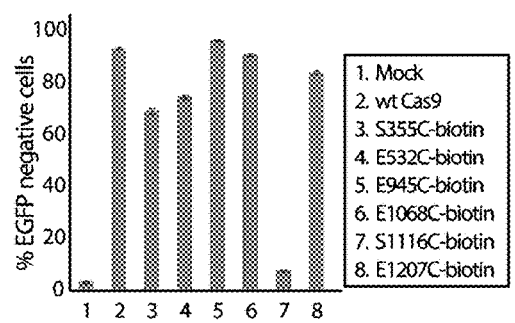
FIG. 13G

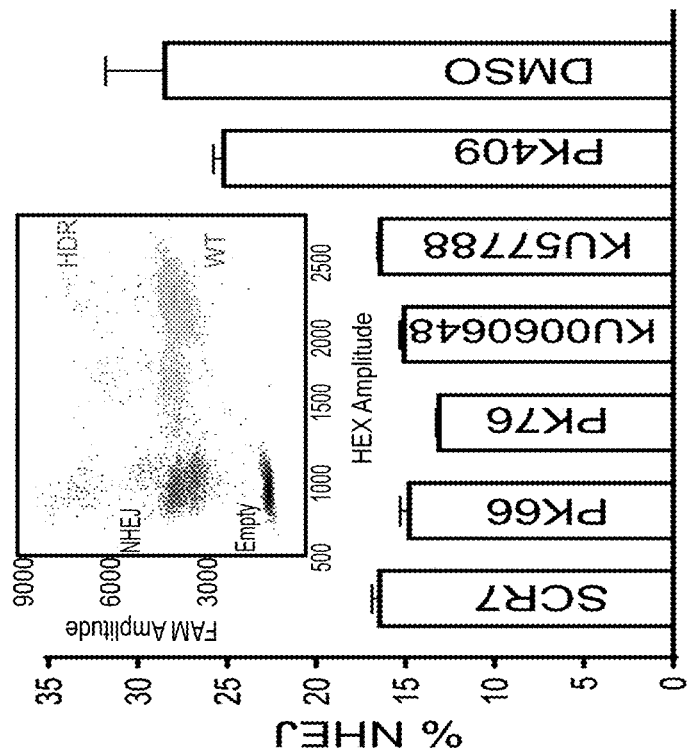
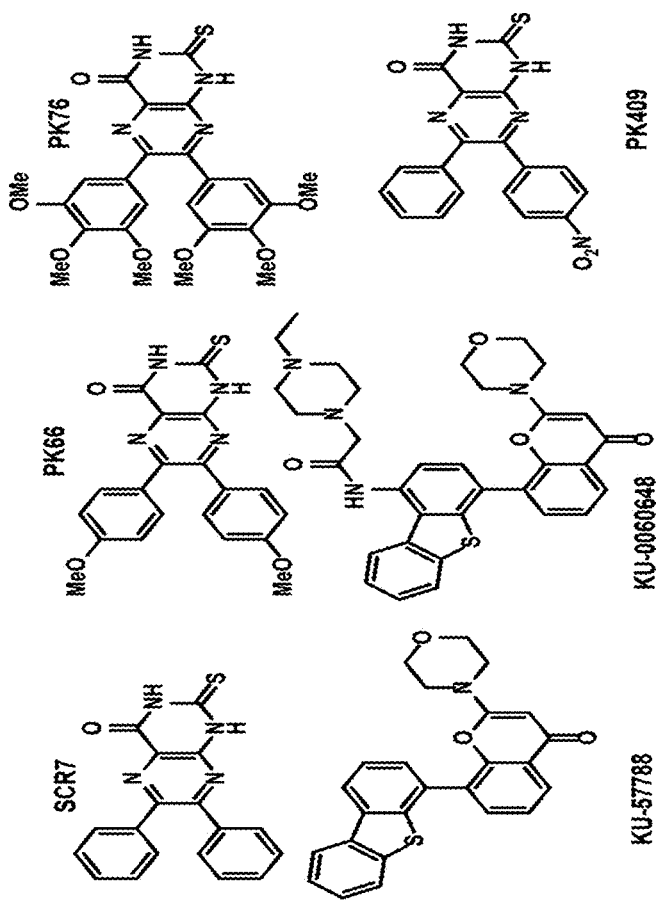
FIG. 14A
FIG. 14B

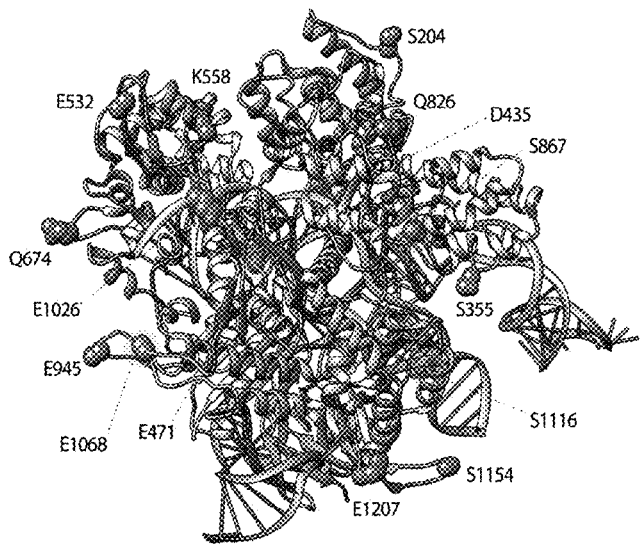
FIG. 15A
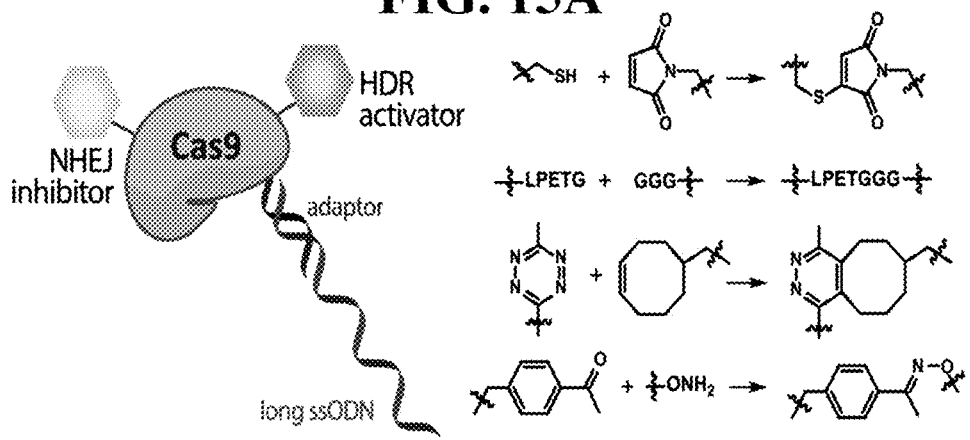
FIG. 15B
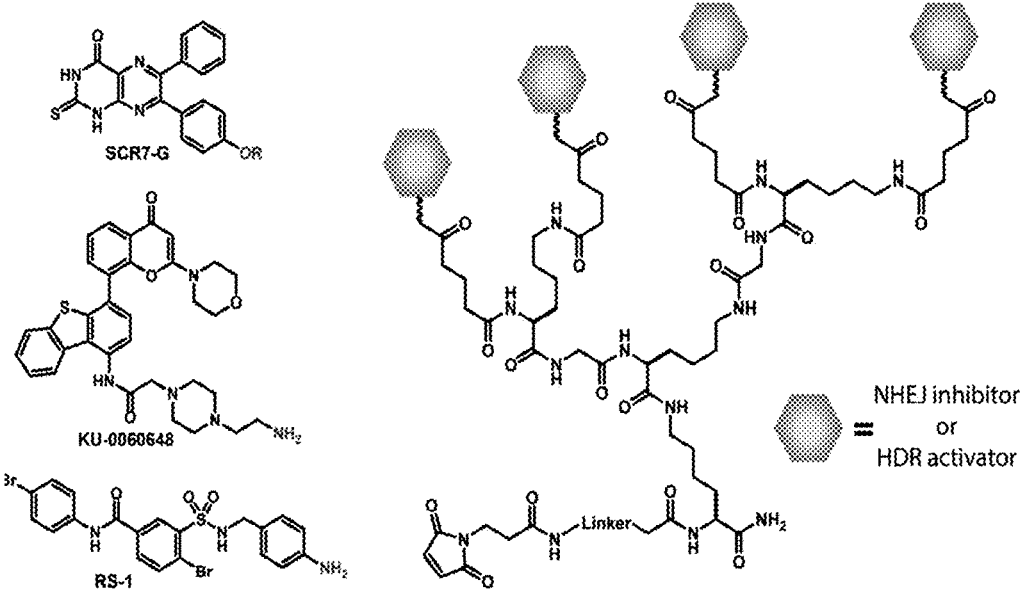
FIG. 15C  FIG. 15D

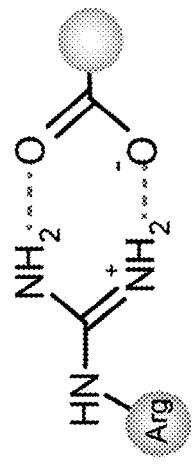
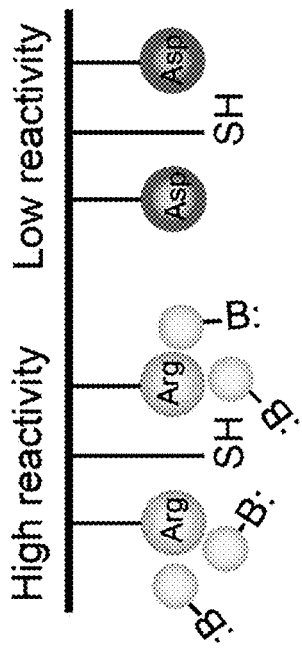
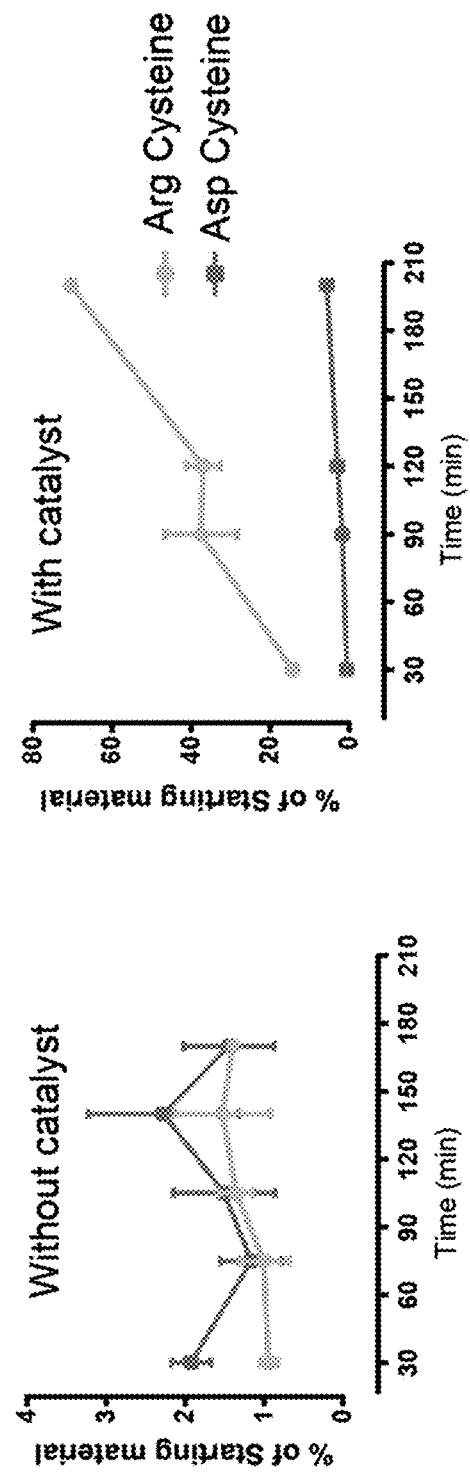
FIG. 16A
FIG. 16B
FIG. 16C

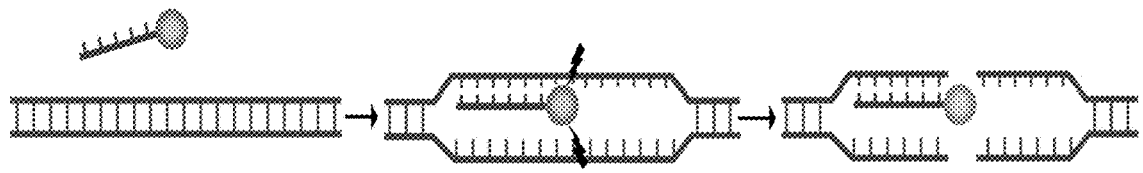
FIG. 17A
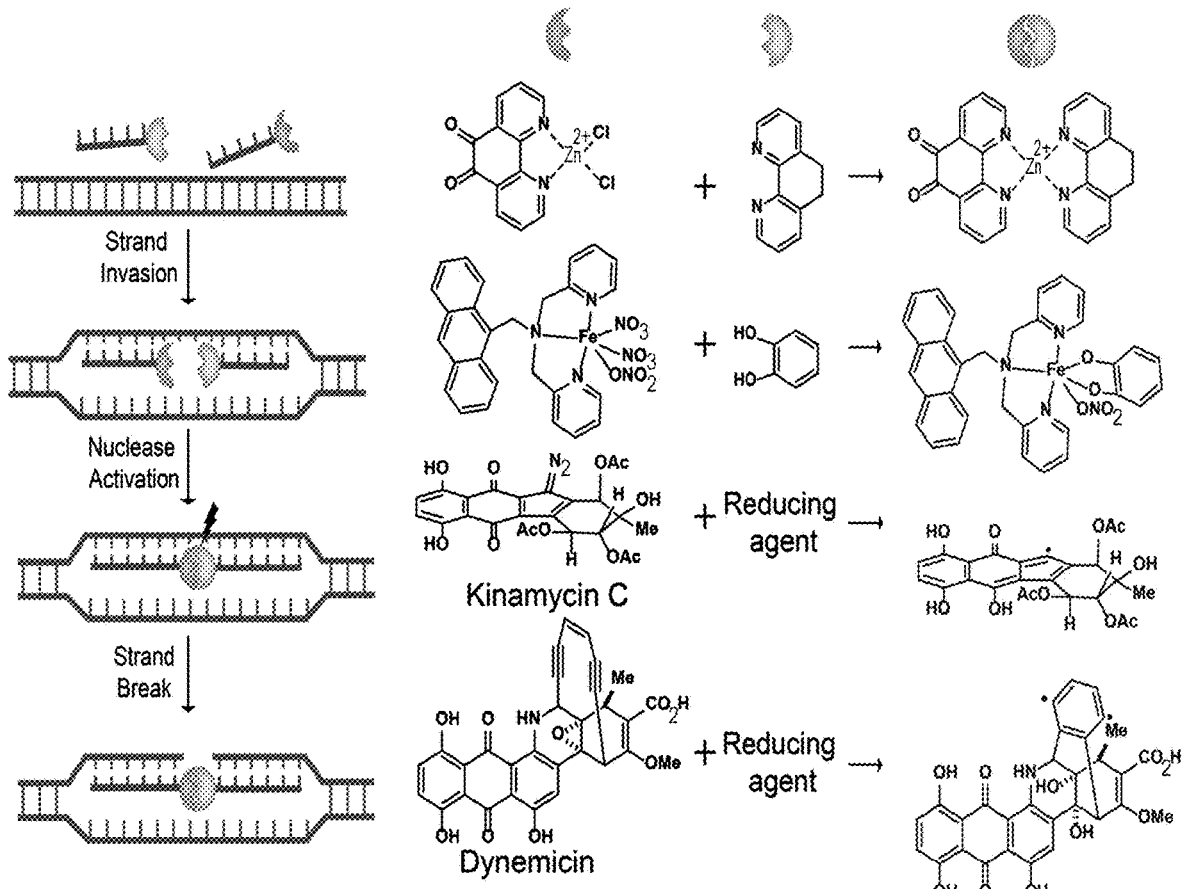
FIG. 17B  FIG. 17C
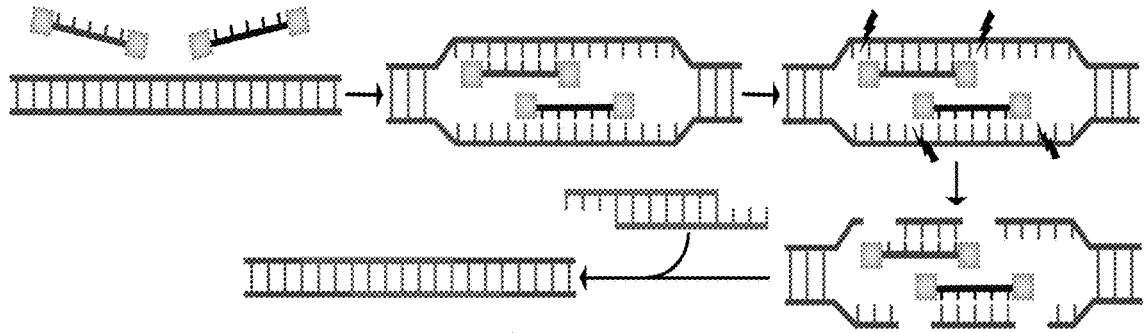
FIG. 17D

Class 1. Diazofluorenes

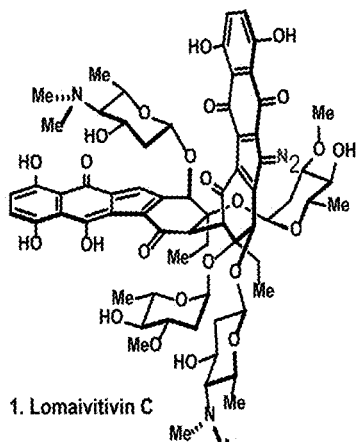

1. Lomaivitivin C

2. Epoxy-kinamycin (FL-120B)

FIG. 18A

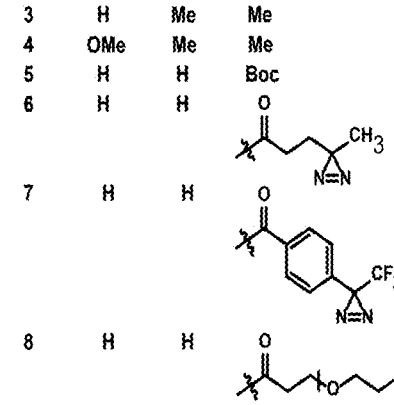

| | $R_2$ | $R_2$ | $R_3$ |
|---|---|---|---|
| 3 | H | Me | Me |
| 4 | OMe | Me | Me |
| 5 | H | H | Boc |
| 6 | H | H | (acyl-diazirine-Me) |
| 7 | H | H | (aryl-CF3-diazirine) |
| 8 | H | H | (PEG-maleimide) |

FIG. 18B

Class 2. Nitracrines

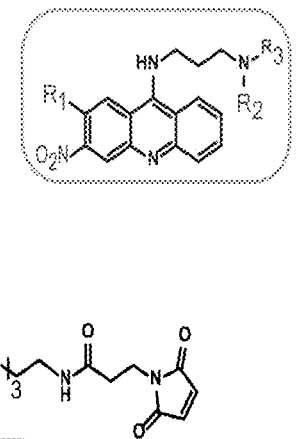

Class 3. Metal complex

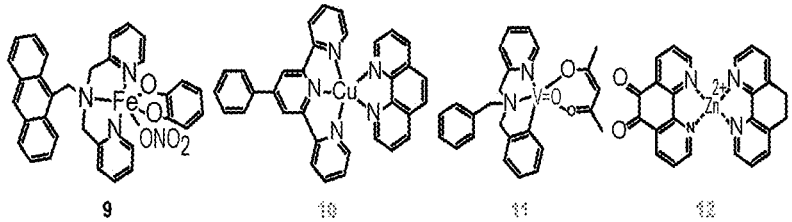

Class 4. Enediyene

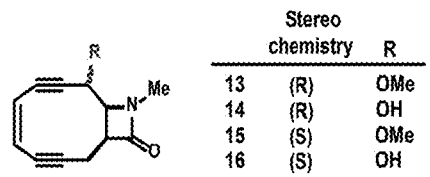

| | Stereochemistry | R |
|---|---|---|
| 13 | (R) | OMe |
| 14 | (R) | OH |
| 15 | (S) | OMe |
| 16 | (S) | OH |

FIG. 18D

Class 5. Methoxsalen derivative

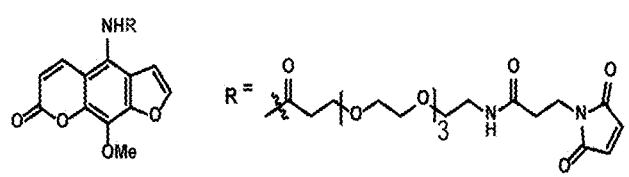

FIG. 18E

Class 6. Daunorubicin derivative

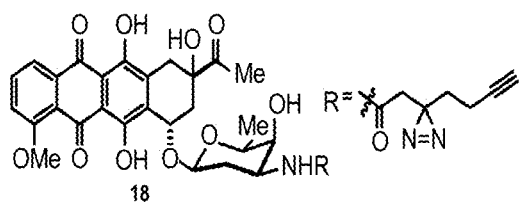

Class 7. Juglones

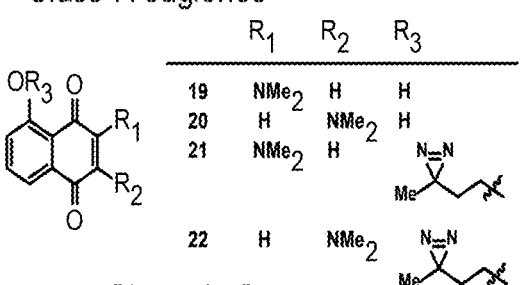

| | $R_1$ | $R_2$ | $R_3$ |
|---|---|---|---|
| 19 | NMe$_2$ | H | H |
| 20 | H | NMe$_2$ | H |
| 21 | NMe$_2$ | H | (diazirine-Me) |
| 22 | H | NMe$_2$ | (diazirine-Me) |

FIG. 18G

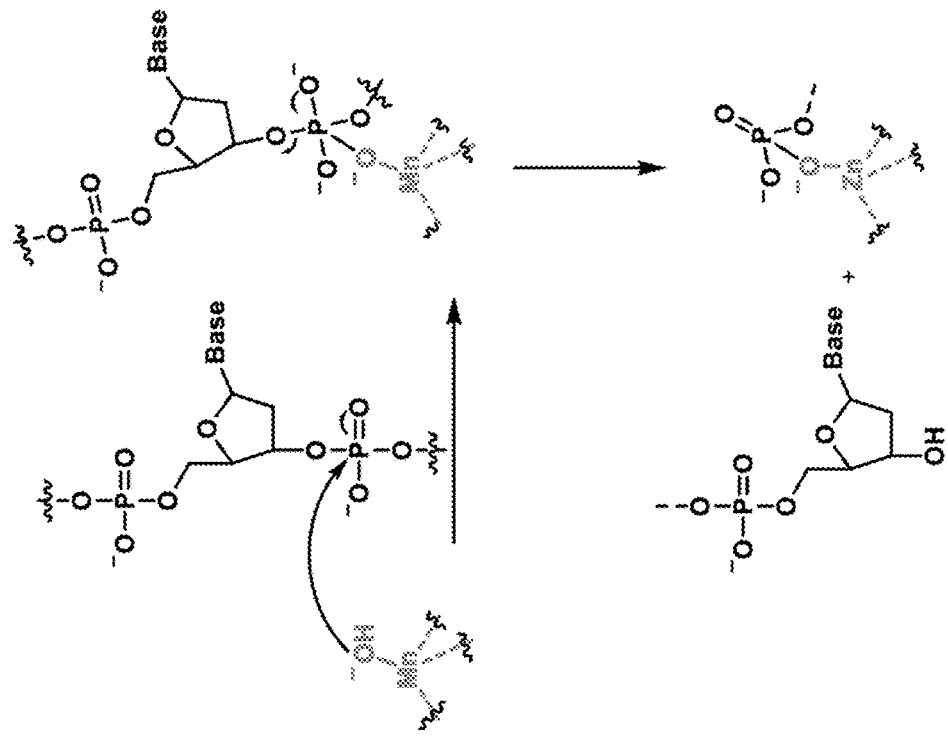
- Ce(IV)$_2$-HXTA
  Triaminocylohexane Zn(II) complex 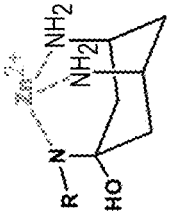
- Cu(II) neamine 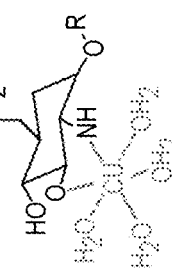
- Cu(II)$_2$-bipy-thymine 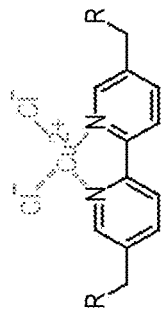
- Fe(III)$_2$-bis-acridine 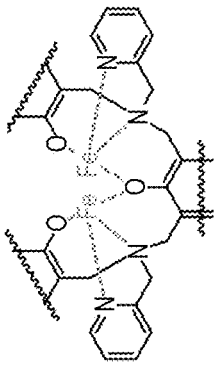
FIG. 20

Gray: Cas9
Blue: gRNA
Green: dsDNA

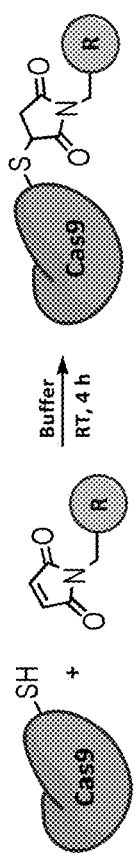
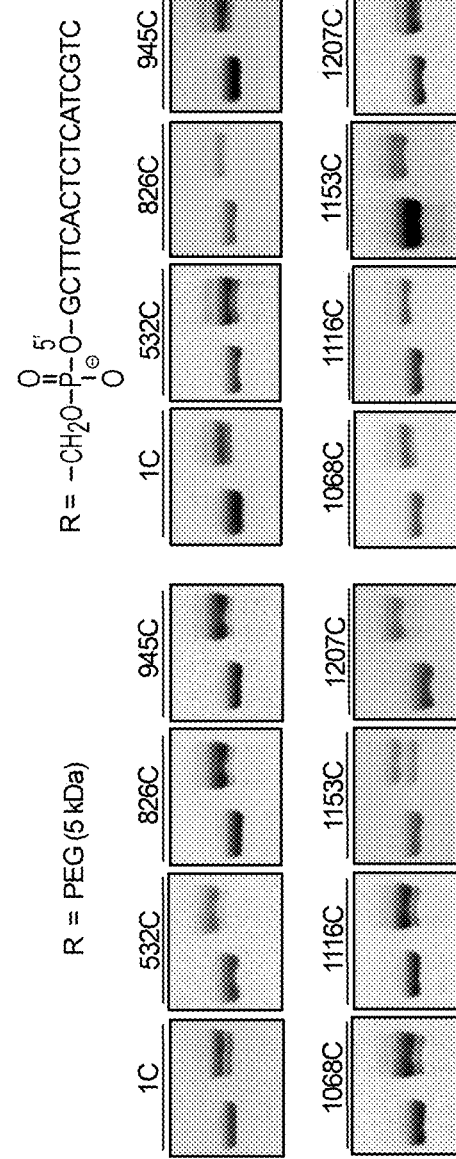
FIG. 26
FIG. 27

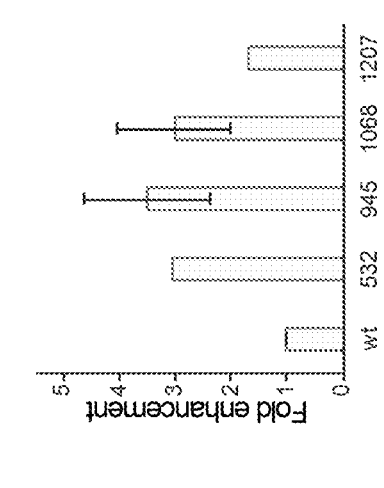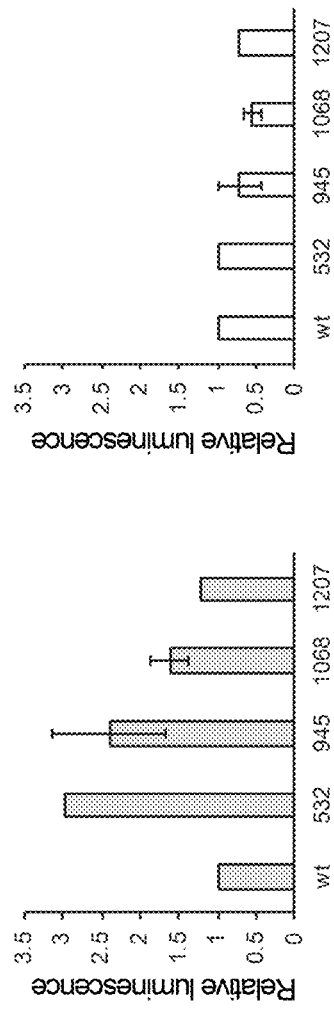
FIG. 29
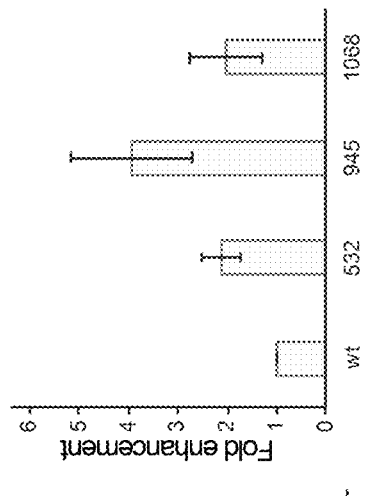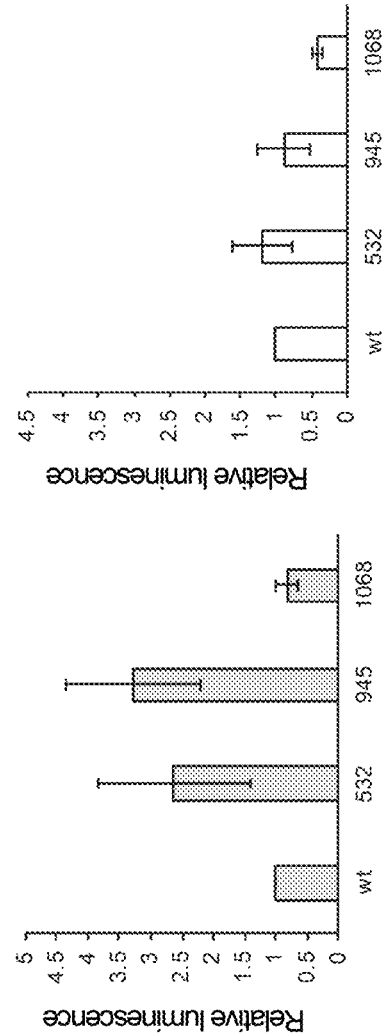
FIG. 30

NUCLEIC ACID MODIFIERS

CROSS REFERENCE TO RELATED APPLICATIONS

This application is a National Stage Application of International Application No. PCT/US2018/057182, filed Oct. 23, 2018, which claims the benefit of U.S. Provisional Application No. 62/575,948, filed Oct. 23, 2017, and U.S. Provisional Application No. 62/765,347 filed Aug. 20, 2018. The entire contents of the above-identified applications are hereby fully incorporated herein by reference.

STATEMENT AS TO FEDERALLY FUNDED RESEARCH

This invention was made with government support under contract number N66001-17-2-4055 awarded by the Defense Advanced Research Projects Agency, Grant No. W911NF1610586 awarded by the Army Research Office, and Grant No. AI126239 awarded by the National Institutes of Health. The government has certain rights in the invention.

REFERENCE TO AN ELECTRONIC SEQUENCE LISTING

The contents of the electronic sequence listing (BROD-2770US.ST25.txt"; Size is 8 Kilobytes and it was created on Jan. 16, 2023) is herein incorporated by reference in its entirety.

TECHNICAL FIELD

The present inventions generally relate to nucleic acid modifiers with novel DNA readers and effectors that can be rapidly programmed to make site-specific DNA modifications. Among other aspects, the DNA readers provide features of Clustered Regularly Interspaced Short Palindromic Repeats (CRISPR), CRISPR proteins (e.g., Cas, Cas9, Cpf1, C2c1, Cas13 and the like), CRISPR-Cas or CRISPR systems or CRISPR-Cas complexes, components thereof, peptide nucleic acid (PNA), nucleic acid molecules, vectors, involving the same and uses of all of the foregoing.

BACKGROUND

Of the three elements of central dogma (Proteins, RNA, and DNA), nearly all therapeutic agents target proteins. Genome and RNA editing have ushered in an era where DNA and RNA can be potential targets, expanding the scope of therapeutic targets to both the coding and non-coding regions of the genome. However, the agents used to accomplish genome editing do not display attributes of a typical therapeutic agent, and in many cases, the activity of these agents are described as genome vandalism rather than genome editing. As such, there is much room to expand the repertoire of genome editors.

There is an urgent need to develop countermeasures that will rectify any accidental or malevolent genomic alterations in an organism or population. Currently, such genomic alterations can be corrected using CRISPR-nucleases. Following induction of double-strand breaks by the nuclease, most cells adopt Non-Homologous End Joining (NHEJ) repair pathway over Homology Directed Repair (HDR), resulting in random insertions and deletions (indels). The in vivo applications face additional challenges. This state-of-art of genomic remediation method is unsuitable for countermeasures for multiples reasons. First, HDR pathways are poorly activated in most cells and nearly always out-competed by non-homologous end joining (NHEJ) resulting in imprecise, error-prone, and uncontrolled genetic alterations. Second, efficient cellular delivery of CRISPR-nucleases requires the development of paradigm shifting delivery technologies that are currently unavailable. Third, owing to delivery issues, multiplex genomic remediation on a scale to match the genomic diversity present in a population is not feasible. Fourth, CRISPR-based systems are sensitive to proteases/nucleases, limiting their use in multiple countermeasure scenarios (e.g., ecosystem setting). Fifth, the slow kinetics of CRISPR-system will be problematic from a countermeasure perspective, where often fast genomic remediation is desired. Sixth, the components of the CRISPR-system (i.e., a large protein and RNA) potentially will be difficult and expensive to mass-produce.

CRISPR-Cas9 from *S. pyogenes* was evolved for rapid and efficient destruction of phage DNA but lacks the functionalities needed for precision genome edits. Following a double-strand break in a knock-in experiment, an exogenously supplied single-stranded oligo donor (ssODN) is integrated at the break site. This integration can be facilitated if the ssODN is readily available at the break site. Further, local inhibition of the NHEJ pathway and/or local activation of HDR at the strand-break site can also tip the balance in favor of DNA recombination. Several small-molecule inhibitors of NHEJ pathway and HDR activators have been reported. However, the mutagenicity and toxicity of genome-wide NHEJ inhibition or HDR activation severely limit the utility of such molecules. There is also a need to improve homology-directed repair (HDR) efficiency. Increased efficiency of repair is highly desirable in disease models and therapies.

Precise genome targeting technologies are needed to enable systematic reverse engineering of causal genetic variations by allowing selective perturbation of individual genetic elements, as well as to advance synthetic biology, biotechnological, and medical applications. There remains a need for new genome engineering technologies.

Citation or identification of any document in this application is not an admission that such document is available as prior art to the present invention.

SUMMARY

The present disclosure provides a synthetic all-in-one genome editor (SAGE) comprising designer DNA sequence readers and a set of small molecules that induce double-strand breaks and enhance DNA repair by homology directed repair (HDR).

In one aspect, the disclosure relates to an engineered, non-naturally occurring nucleic acid modifying system, comprising: (a) an engineered, non-naturally occurring CRISPR/Cas protein; (b) a guide nucleic acid, wherein the guide nucleic acid directs sequence specific binding of the CRISPR/Cas protein to a target nucleic acid; and (c) one or more effector components, wherein the one or more effector components facilitate DNA repair by homology directed repair (HDR).

In certain embodiments, the one or more effector components comprise one or more single-stranded oligo donors (ssODNs). In certain embodiments, the one or more effector components comprise one or more NHEJ inhibitors. In certain embodiments, the one or more effector components comprise one or more HDR activators. In certain embodiments, the one or more effector components comprise a single-stranded oligo donor (ssODN), one or more NHEJ inhibitors, and one or more HDR activators.

The CRISPR/Cas protein can be selected from the group consisting of an engineered Cas9, Cpf1, Cas12b, Cas12c, Cas13a, Cas13b, Cas13c, and Cas13d protein. In certain embodiments, the CRISPR/Cas protein is an engineered Cas9 protein. The CRISPR/Cas protein can comprise one or more engineered cysteine amino acids. In a preferred embodiment, the CRISPR/Cas protein is an SpCas9 protein comprising C80S and C574S mutations and one or more mutations selected from the group consisting of M1C, S204C, D435C, E532C, Q674C, Q826C, S867C, E945C, 51025C, E1026C, N1054C, E1068C, 51116C, K1153C, E1207C. In certain embodiments, the CRISPR/Cas protein comprises a sortase recognition sequence Leu-Pro-Xxx-Thr-Gly (SEQ ID NO: 1). In certain embodiments, the CRISPR/Cas protein comprises one or more unnatural amino acid p-Acetyl Phenylalanine (pAcF), or one or more unnatural amino acid comprising tetrazine.

In some embodiments, the one or more effector components further comprise one or more adaptor oligonucleotides, wherein one adaptor oligonucleotide hybridizes with one ssODN. The one or more adaptor oligonucleotides can be at least 10 nucleotides, at least 13 nucleotides, at least 15 nucleotides, or at least 17 nucleotides. In some embodiments, each adaptor oligonucleotide and the hybridizing ssODN have at least 13 overlapping nucleotides. The guide nucleic acid can be a guide RNA molecule.

In some embodiments, the NHEJ inhibitor is an inhibitor of DNA ligase IV, KU70, or KU80. The NHEJ inhibitor can be a small molecule. For example, the NHEJ inhibitor can be selected from the group consisting of SCR7-G, KU inhibitor, and analogs thereof. In some embodiments, the NHEJ inhibitor is adenovirus 4 E1B55K or E4orf6. In some embodiments, the HDR activator is a small molecule. For example, the HDR activator is RS1 or analogs thereof. The HDR activator can also stimulate RAD51 activity.

In some embodiments, the one or more effector components are linked to the CRISPR/Cas protein. For example, the one or more effector components can be covalently linked to the CRISPR/Cas protein. In some embodiments, the one or more effector components are linked to the CRISPR/Cas protein via cysteines, sortase chemistry, or unnatural amino acids. In some embodiments, the one or more effector components are linker modified. The linker can comprise a maleimide group, PEG, or a poly-Gly peptide. In some embodiments, the one or more adaptor oligonucleotides can be linked to the CRISPR/Cas protein via thiol-maleimide chemistry.

In certain embodiments, the guide nucleic acid is in a duplex with the target nucleic acid. The target nucleic acid can comprise chromosomal DNA, mitochondrial DNA, viral, bacterial, or fungal DNA, or viral, bacterial, or fungal RNA.

In another aspect, the present disclosure relates to a method for enhancing HDR at one or more target loci in a target cell, comprising delivering the above described system to the target cell. The system can be delivered to the target cell via electroporation or lipid-mediated delivery.

In yet another aspect, the present disclosure relates to an engineered, non-naturally occurring nucleic acid modifying system, comprising: a) a first engineered, non-naturally occurring DNA reader, wherein the first DNA reader binds a target nucleic acid; and b) a first effector component, wherein the first effector is a small molecule and modifies the target nucleic acid. In certain embodiments, the first DNA reader is a peptide nucleic acid (PNA) polymer, or transcript activator-like effector (TALE). In certain embodiments, the first DNA reader is a PNA polymer.

In some embodiments, the first effector component is a small molecule synthetic nuclease. The first effector component can be selected from the group consisting of diazofluorenes, nitracrines, metal complexes, enediynes, methoxsalen derivatives, daunorubicin derivatives, and juglones. In some embodiments, the synthetic nuclease can be a single strand breaking small molecule, or a double strand breaking small molecule.

In certain embodiments, the first effector component can be linked to the first DNA reader. For example, the first effector component can be covalently linked to the first DNA reader. The first effector component can comprise one or more maleimide, azide, or alkyne functional groups and the first DNA reader comprises a PEG linker comprising one or more thiol, alkyne, or azide functional groups.

In further embodiments, the system can comprise a second DNA reader and a second effector component. The first effector component can be covalently linked to the first DNA reader and the second effector component can also be covalently linked to the second DNA reader.

In some embodiments, both the first and second DNA readers are PNA polymers.

In some embodiments, the first effector component can be an inactive small molecule synthetic nuclease and the second effector component can a trigger reagent, wherein the trigger reagent activates the small molecule synthetic nuclease. For example, the first effector component is Kinamycin C and the second effector component is a reducing agent. Or the first effector component is dynemicin and the second effector component is a reducing agent.

In some embodiments, the first effector component comprises a first fragment of a reactive group of a small molecule synthetic nuclease and the second effector component comprises a second fragment of the reactive group of the small molecule synthetic nuclease, wherein the small molecule synthetic nuclease is only active when the first fragment and the second fragment are together.

In further embodiments, the system can comprise a third and a fourth effector component. In some embodiments, both the first and second DNA readers are PNA polymers, and the first, second, third, and fourth effector component are small molecule single strand breaking synthetic nucleases. In other embodiments, the first and second synthetic nucleases are linked to the first PNA polymer, and the third and fourth synthetic nucleases are linked to the second PNA polymer.

In some embodiments, they system can further comprise one or more single-stranded oligo donors (ssODNs). In other embodiments, the system can further comprise one or more NHEJ inhibitors and/or one or more HDR activators. The NHEJ inhibitor can be an inhibitor of DNA ligase IV, KU70, or KU80. The NHEJ inhibitor can also be a small molecule, for example, the NHEJ inhibitor can be selected from the group consisting of SCR7-G, KU inhibitor, and analogs thereof. The HDR activator can be a small molecule, for example, the HDR activator is RS1 or analogs thereof. The HDR activator can also stimulate RAD51 activity.

In some embodiments, the target nucleic acid can comprise chromosomal DNA, mitochondrial DNA, viral, bacterial, or fungal DNA, or viral, bacterial, or fungal RNA.

In further embodiments, the system can comprise a delivery enhancer. The delivery enhancer can be a cellular permeability enhancer.

In another aspect, the present disclosure relates to a method of precise genome editing in a cell or tissue, comprising delivering the above described system to the cell or tissue. The system can be delivered into the cell or tissue using Poly(lactic co-glycolic acids) (PLGA) nanoparticles.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

FIG. 13A is a crystal structure showing cysteines on engineered Cas9 that were used for conjugation (PDB ID: 5F9R). FIG. 13B is diagram showing biotin-maleimide conjugation to cysteine thiol. FIG. 13C is a set of gel electrophoresis images showing streptavidin pull-down following biotin-maleimide conjugation to Cas9. Flow thru represents unbiotinylated Cas9 and eluate represents biotinylated Cas9. FIG. 13D is a table showing labeling efficiencies of optimized conjugation conditions (8 µM Cas9 Cys mutant, 500 µM biotin-maleimide at room-temperature for 3 hrs). FIG. 13E is a gel electrophoresis image demonstrating in vitro DNA cleavage assay for cysteine and biotin-labeled variants of Cas9. FIG. 13F is a cartoon depicting an eGFP disruption assay. FIG. 13G is a graph showing quantification of activity of biotin-labelled Cas9 variants using the eGFP disruption assay.

FIG. 14A is an image showing small-molecule inhibitors of NHEJ pathway. FIG. 14B is a graph demonstrating NHEJ inhibition by the small-molecule inhibitors in a ddPCR pathway. The dose for the reported activity are: SCR7 (2 µM), PK66 (2 µM), PK76 (1 µM), PK409 (0.5 µM), KU5788 (0.5 µM), and KU0060648 (0.5 µM). The analog PK 76 was the most potent inhibitor of NHEJ. Inset shows a typical distribution of droplets for four conditions.

FIG. 15A is a crystal structure showing potential sites for engineered cysteines on Cas9. FIG. 15B is a schematic showing an example of SynGEM (left) with possible conjugation chemistries (right). The conjugation can be effected via cysteines, sortase, or using unnatural amino acids bearing tetrazine or acetylphenyl alanine. FIG. 15C is a diagram showing structures and potential linker attachment sites for known NHEJ inhibitors and HDR activators. FIG. 15D is a diagram showing a reported scaffold for multivalent display of NHEJ inhibitors or HDR activators on Cas9.

FIG. 16A a schematic showing that "Arg cysteines" have dramatically higher reactivity than "Asp cysteines" which can be exploited for dual conjugation. FIG. 16B is a diagram depicting that base catalysts cluster around "Arg cysteines" by salt-bridge interactions. FIG. 16C is a graph showing that reactivity enhancements of "Arg cysteines" over "Asp cysteines" is not seen in the absence of the catalyst (left), but is observed in the presence of the catalyst (right). Note that the overall % conjugation is also dramatically and selectively improved upon addition of the catalyst.

FIG. 17A is a schematic showing a miniGEM bearing a dimer of synthetic nuclease. FIG. 17B is a schematic showing split miniGEMs wherein the activity of the synthetic nuclease is triggered by an agent located on another PNA. FIG. 17C is a diagram depicting proposed examples of split synthetic nucleases. FIG. 17D is a schematic showing an example of a cut-and-paste editor where synthetic nuclease introduces single strand breaks.

FIG. 18A-18G depict natural and synthetic small-molecules that cleave or modify DNA. Compounds numbered 1-9, 13-16, 18-22 have been synthesized. FIG. 18A is a diagram showing diazofluorenes. FIG. 18B is a diagram showing nitracrines. FIG. 18C is a diagram showing metal complexes. FIG. 18D is a diagram showing enediynes. FIG. 18E is a diagram showing methoxsalen derivatives. FIG. 18F is a diagram showing daunorubicin derivatives. FIG. 18G is a diagram showing juglones.

FIG. 20 is a diagram showing that some metal complexes induce strand breaks hydrolytically.

FIG. 26 is a diagram showing labeling scheme and results. Cas9 single cysteine mutants were produced and labeled by thiol-maleimide chemistry. Because maleimide selectively reacts with thiol, site-selective Cas9 conjugation could be achieved. At first, the labeling efficiency was checked of each mutants by using maleimide-PEG as a model system. The results show SDS-PAGE data to see the mobility shift after labeling. Left lane is before labeling, and right lane is after labeling. As can be seen from these results, many of the mutants were labeled with maleimide-PEG in high labeling efficiencies. Then, the mutants were labeled with the adaptor DNA. The labeling efficiency with the DNA was also high, and similar pattern to the PEG labeling is observed. For example, 1153C labeling efficiency was low both in PEG labeling and DNA labeling.

FIG. 27 is a set of gel pictures showing electrophoretic mobility shift assay to see the binding between Cas9-adaptor and ssODN. The adaptor-containing Cas9 was checked to see if binding to the ssODN which has the complementary sequence. As shown in the gel shift assay, 'Cas9 1068C-adaptor' protein was bound to DNA while wild type protein was not bound to the ssODN.

In FIG. 28B, the first panel shows the data from the HiBiT assay using ssODN which has adaptor binding site. The second panel shows data from control experiments using ssODN which does not have adaptor binding site. The third panel data shows the fold enhancement by ssODN conjugation when compared to no-conjugation. Among these Cas9-adaptors, 532-adapter and 945-adapter retained enzymatic activity while enhancing the HDR. Therefore, a double cysteine mutant (532C/945C) is currently being made and going to be labeled with two ssODNs in order to see further enhancement of HDR efficiency.

FIG. 29 are a set of graphs showing HiBiT assay results in MDA-MB-231 cells. HDR was also boosted in this cell line.

FIG. 30 are a set of graphs showing Lipofectamine transfection data demonstrating that Cas9-adaptor enhances HDR regardless of the transfection method in U2OS cells. It was found that the Cas9-ssODN conjugation also enhances HDR efficiency when RNP is delivered by Lipofectamine CRISPR Max.

Figure 1:
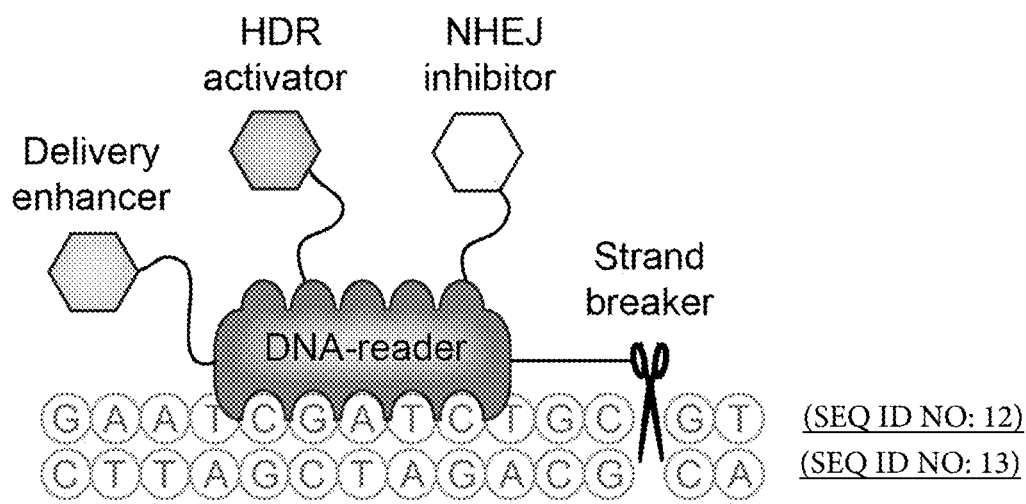
FIG. 1 is a diagram depicting a typical synthetic all-in-one genome editor (SAGE) comprising a designer DNA sequence reader and displaying small molecules for double-strand breaks, NHEJ inhibition, HDR activation, and enhancement of cellular and nuclear delivery.

The following detailed description, given by way of example, but not intended to limit the invention solely to the specific embodiments described, may best be understood in conjunction with the accompanying drawings.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The present disclosure provides a synthetic all-in-one genome editor (SAGE) comprising designer DNA sequence readers and a set of small molecules that induce double-strand breaks, enhance cellular permeability, inhibit NHEJ and activate HDR (FIG. 1). The central problem of the CRISPR-system is the large size of the nuclease domains (>100 kDa). In SAGE, small molecules (<500 Da) preferably conduct the functions of these nuclease domains resulting in dramatic size reduction, which enhances cellular delivery and allows multiplexed genome editing on an unprecedented scale. The cellular delivery is further enhanced using small molecules that improve membrane permeability. Precise genome editing may comprise NHEJ inhibition and HDR activation locally at the site of the double-strand break, a feature missing from the current CRISPR-systems. In preferred embodiments, SAGE bears small molecules that activate HDR and suppress NHEJ locally at the genomic site of the double-strand breaks. SAGE's backbone, which may be made from synthetic polymer, and in certain embodiments is engineered to be resistant to degradation by proteases/nucleases, or harsh conditions of temperature, pH, and humidity. SAGE is fast acting since host does not synthesize/assemble its components (unlike CRISPR-system). Since SAGE components are synthetic polymers and small molecules, the infrastructure for their mass production is already in place. Further, SAGE provides a countermeasure for correcting unwanted genomic alteration in an organism or population.

In an aspect, the invention provides a composition comprising a nucleic acid modifier. In an aspect, the invention provides a composition for site specific delivery of a nucleic acid modifier.

In an aspect, the SAGEs provide at a most basic level a molecule or molecules that bind target nucleic acid; and an effector component that modifies, directs breaks, or induces breaks in target nucleic acid. Advantageously the target nucleic acids can include DNA or RNA, for example chromosomal or mitochondrial DNA, viral, bacterial or fungal DNA or viral bacterial, or fungal RNA.

The one or more molecules that bind target nucleic acid comprise, in some embodiments, a nucleic acid binding domain, which in preferred embodiments is an engineered, non-naturally occurring CRISPR/Cas protein. In some embodiments, the CRISPR protein is truncated, in some embodiments, the CRISPR/Cas protein comprises one or more engineered amino acids or unnatural amino acids. The CRISPR/Cas proteins are in some embodiments an engineered Cas9, Cpf1, Cas12b, Cas12c, Cas13a, Cas13b, Cas13c, or Cas13d protein. The molecule that binds target nucleic acid may be provided with a guide nucleic acid that directs sequence specific binding of the CRISPR/Cas protein to a target nucleic acid.

In other embodiments, the one or molecules that bind target nucleic acid comprise at least five or more transcript activator-like effector (TALE) monomers and at least one or more half-monomers specifically ordered to a target locus of interest.

In embodiments, the one or more molecules that bind target nucleic acid are one or more engineered-non-naturally occurring DNA readers. In some embodiments, the DNA reader is a peptide nucleic acid (PNA) polymer or a TALE.

The effector component in embodiments may comprise one or more effector domains, which in some instances are a single strand nuclease, double strand nuclease, a helicase, a methylase, a demethylase, an acetylase, a deacetylase, a deaminase, an integrase, a recombinase or a cellular uptake activity associated domains.

The effector domain can comprise a small molecule that induces single or double strand breaks in the target nucleic acid. In some embodiments, the one or more effector components facilitate DNA repair by homology directed repair (HDR), and can be one or more single-stranded oligo donors (ssODNs), NHEJ inhibitors, or HDR activators.

In embodiments when a DNA reader is the molecule that binds a target nucleic acid, the effector component is a small molecule that can be a small molecule synthetic nuclease. The system with DNA readers may contain more than one DNA reader, preferably a PNA polymer. One or more effector components can be provided as more than one fragment that is only active when the fragments are together.

In certain embodiments, the invention comprises the following modular components: (i) single- or double-strand breaker, (ii) NHEJ inhibitor, (iii) HDR activator, (iv) designer DNA-sequence reader, (v) nuclear localization sequence, and (vi) enhancers of cellular permeability. The nuclease function may be effected by small-molecules (e.g., Lomaiviticin, Kinamycin C) that can induce DNA double-strand breaks. NHEJ inhibition and HDR activation can be accomplished by appending small molecule inhibitors of NHEJ (e.g., SCR7-G, KU inhibitors) and small molecule activators of HDR (e.g., RS1, RAD51 activators).

In an aspect, the invention provides a vector system for delivery of a nucleic acid modifier or delivery of a composition comprising a nucleic acid modifier to a mammalian cell or tissue.

In an aspect, the invention provides a nucleic acid modifying system comprising a nucleic acid modifier or a composition comprising a nucleic acid modifier.

In an aspect, the invention provides a particle delivery system for delivery of a nucleic acid modifier or delivery of a composition comprising a nucleic acid modifier to a mammalian cell or tissue. In certain embodiments, the particle delivery system is a nanoparticle delivery system comprised of polymers, which can comprise poly(lactic co-glycolic acids) (PLGA) polymers. In embodiments, the particle delivery system comprises a hybrid virus capsid protein or hybrid viral outer protein, wherein the hybrid virus capsid or outer protein comprises a virus capsid or outer protein attached to at least a portion of a non-capsid protein or peptide. The genetic material of a virus is stored within a viral structure called the capsid. The capsid of certain viruses is enclosed in a membrane called the viral envelope. The viral envelope is made up of a lipid bilayer embedded with viral proteins including viral glycoproteins. As used herein, an "envelope protein" or "outer protein" means a protein exposed at the surface of a viral particle that is not a capsid protein. For example, envelope or outer proteins typically comprise proteins embedded in the envelope of the virus. Non-limiting examples of outer or envelope proteins include, without limit, gp41 and gp120 of HIV, hemagglutinin, neuraminidase and M2 proteins of influenza virus.

In an aspect, the invention provides a method of repairing DNA damage in a cell or tissue, the method comprising contacting the damaged DNA of the cell or tissue with a nucleic acid modifier or a composition comprising a nucleic acid modifier.

In one aspect, the invention provides a DNA repair kit comprising a nucleic acid modifier or a composition comprising a nucleic acid modifier.

Semi-Synthetic Genome Editor with Multifunctionality (SynGEM)

In embodiments, an engineered, non-naturally occurring complex is provided and includes i) an engineered, non-naturally occurring nucleic acid-guided molecule comprising a nucleic acid binding domain, one or more effector domains and a guide. In embodiments, the nucleic acid-guided molecule complexes with a guide that comprises a polynucleotide. The guide can direct sequence specific binding of the nucleic acid-guided molecule to a target nucleic acid. Compared to an analogous naturally-occurring nucleic acid-guided molecule, such as site-specific guided nuclease, the engineered, non-naturally-occurring nucleic acid-guided complex may truncated. In some embodiments, the nucleic acid-guided molecule is an engineered, non-naturally occurring CRISPR/Cas protein. In some embodiments, the one or more effector domains is heterologous. The nucleic acid binding domain and the one or more effector domains can be covalently linked or non-covalently associated. When the compositions are provided as a complex, the complexes can be inducible or switchable, which preferably occurs when the one or more effector domains are non-covalently associated.

In an aspect, the invention provides a nucleic acid modifier which comprises a nucleic acid binding domain linked to an effector domain. The nucleic acid binding domain comprises one or more domains of a CRISPR protein which bind to a programmable system guide which directs complex formation of the nucleic acid modifier with the guide nucleic acid and the target nucleic acid. The nucleic acid binding domain in one embodiment does not contain a NUC lobe of a CRISPR protein, or the nucleic acid binding domain contains fewer than 50% of the amino acids of the naturally occurring CRISPR protein.

In one aspect, the invention provides SynGEMs that enhance HDR at the double-strand break site. Multiple conjugation sites on engineered CRISPR/Cas proteins are identified that allow accommodation of molecular conjugation using novel, multivalent, or orthogonal conjugation chemistries without loss of activity. The capacities of Cas proteins can be augmented by bioactive small molecules. In certain embodiments, engineered Cas proteins can be monoconjugated with ssODN, NHEJ inhibitors, or HDR activators. Complexes can be identified with a maximum enhancement of HDR. In certain embodiments, engineered CRISPR/Cas proteins can be multivalently conjugated with NHEJ inhibitors or HDR activators. In certain embodiments, engineered CRISPR/Cas proteins can be conjugated with ssODN, NHEJ inhibitors, and HDR activators using orthogonal conjugation chemistries. SynGEMs can be optimized for disease-specific ex vivo applications of interest to the members of somatic Cell Genome Editing (SCGE) Consortia. SynGEMs allow precise genome edits while mitigating toxicity and mutagenesis arising from global NHEJ inhibition or HDR activation.

Nucleic Acid Binding Domain

CRISPR systems, such as the CRISPR/Cas or the CRISPR-Cas system (both terms may be used interchangeably throughout this application) do not require the generation of customized proteins to target specific sequences but rather a single CRISPR enzyme can be programmed by a short RNA molecule to recognize a specific nucleic acid target, such as DNA or RNA target, in other words the CRISPR enzyme can be recruited to a specific nucleic acid target using said short RNA molecule. Adding the CRISPR system to the repertoire of genome sequencing techniques and analysis methods may significantly simplify the methodology and accelerate the ability to catalog and map genetic factors associated with a diverse range of biological functions and diseases. To utilize the CRISPR system effectively for genome editing without deleterious effects, it is critical to understand aspects of engineering and optimization of these genome engineering tools, which are aspects of the claimed invention.

In an embodiment the nucleic acid modifier comprises Repeat Variable Diresidues (RVDs) of a TALE protein or a portion thereof linked to one or more effector domains. In an embodiment the nucleic acid modifier comprises the recognition (REC) lobe of a CRISPR protein linked to one or more effector domains. In an embodiment the nucleic acid modifier comprises domains/subdomains of Cas9 linked to one or more effector domains. In an embodiment the nucleic acid modifier comprises domains/subdomains of Cpf1 linked to one or more effector domains. In an embodiment the nucleic acid modifier comprises domains of a Cas13 protein linked to one or more effector domains.

In an embodiment of a nucleic acid modifier, the nucleic acid binding domain and the effector domain are linked by a linker comprising an inducible linker, a switchable linker, a chemical linker, PEG or (GGGGS) (SEQ ID NO: 10) repeated 1-3 times.

In some general embodiments, the nucleic acid modifying protein is used for multiplex targeting comprises and/or is associated with one or more effector domains. In some more specific embodiments, the nucleic acid modifying protein used for multiplex targeting comprises one or more domains of a deadCas9 as defined herein elsewhere.

CRISPR System

In certain embodiments, the nucleic acid modifying system is derived advantageously from a type II CRISPR system. In some embodiments, one or more elements of a nucleic acid modifying system is derived from a particular organism comprising an endogenous CRISPR system, such as *Streptococcus pyogenes*. In preferred embodiments of the invention, the nucleic acid modifying system derives from a type II CRISPR system and the nucleic acid modifying protein comprises one or more domains of a Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the nucleic acid modifying protein has DNA cleavage activity, similar to Cas9. In some embodiments, the nucleic acid modifying protein directs cleavage of one or both strands at the location of a target sequence, such as within the target sequence and/or within the complement of the target sequence. In some embodiments, the nucleic acid modifying protein directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a nucleic acid modifying protein comprising one or more Cas9 domains that is mutated to with respect to a corresponding wild-type domains such that the nucleic acid modifying protein lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a nucleic acid modifying protein substantially lacking all DNA cleavage activity. In some embodiments, a D10A mutation is combined with one or more of H840A, N854A, or N863A mutations to produce a nucleic acid modifying protein substantially lacking all DNA cleavage activity. In some embodiments, a nucleic acid modifying protein is considered to substantially lack all DNA cleavage activity when the DNA cleavage activity of the protein is about no more than 25%, 10%, 5%, 1%, 0.1%, 0.01%, or less of the DNA cleavage activity of the protein comprising non-mutated form of the enzyme domains; an example can be when the DNA cleavage activity of the protein comprising the mutated enzyme domain is nil or negligible as compared with the protein comprising the non-mutated enzyme domain. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred.

One or more domains belonging to orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, StCas9 and so forth. Enzymatic action by one or more domains of Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through one or more domains of Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target comprising, consisting essentially of, or consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array comprising, consisting essentially of, or consisting of a single spacer flanked by two direct repeats (DRs) is also encompassed by the term "tracr-mate sequences"). In certain embodiments, a nucleic acid modifying protein may be constitutively present or inducibly present or conditionally present or administered or delivered. nucleic acid modifying protein optimization may be used to enhance function or to develop new functions, one can generate chimeric nucleic acid modifying proteins. And one or more domains of Cas9 may be used as a generic DNA binding protein.

In an advantageous embodiment, the present invention encompasses effector proteins identified in a Type V CRISPR-Cas loci, e.g. a Cpf1-encoding loci denoted as subtype V-A. Presently, the subtype V-A loci encompasses cas1, cas2, a distinct gene denoted cpf1 and a CRISPR array. Cpf1 (CRISPR-associated protein Cpf1, subtype PRE-FRAN) is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in all Cas9 proteins, and the RuvC-like domain is contiguous in the Cpf1 sequence, in contrast to Cas9 where it contains long inserts including the HNH domain. Accordingly, in particular embodiments, the nucleic acid modifying protein comprises a RuvC-like nuclease domain.

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this novel CRISPR-Cas system appears to be similar to that of type II-B. Furthermore, similar to Cas9, the Cpf1 protein contains a readily identifiable C-terminal region that is homologous to the transposon ORF-B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF-B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin E V. Methods Mol Biol. 2015; 1311:47-75). However, as described herein, Cpf1 is denoted to be in subtype V-A to distinguish it from C2c1p which does not have an identical domain structure and is hence denoted to be in subtype V-B.

The nucleic acid-targeting system may be derived advantageously from a Type VI CRISPR system. In some embodiments, one or more elements of a nucleic acid-targeting system is derived from a particular organism comprising an endogenous RNA-targeting system. In particular embodiments, the Type VI RNA-targeting, the nucleic acid modifying protein comprises one or more domains of C2c2Cas enzyme. In an embodiment of the invention, there is provided a nucleic acid modifying protein which comprises one or more domains of C2c2, wherein the amino acid sequence of the one or more domains have at least 80% sequence homology to the wild-type sequence of one of more domains of any of *Leptotrichia shahii* C2c2, Lachnospiraceae bacterium MA2020 C2c2, Lachnospiraceae bacterium NK4A179 C2c2, *Clostridium aminophilum* (DSM 10710) C2c2, Carnobacterium *gallinarum* (DSM 4847) C2c2, *Paludibacter propionicigenes* (WB4) C2c2, *Listeria weihenstephanensis* (FSL R9-0317) C2c2, Listeriaceae bacterium (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria* seeligeri C2c2.

In an embodiment of the invention, the nucleic acid modifying protein comprises at least one HEPN domain, including but not limited to HEPN domains described herein, HEPN domains known in the art, and domains recognized to be HEPN domains by comparison to consensus sequences and motifs.

SpCas9 is an RNA-guided nuclease from the microbial CRISPR-Cas system that can be targeted to specific genomic loci by single guide RNAs (sgRNAs). See, e.g., WO2015/089364. SpCas9 comprises abilobed architecture composed of target recognition and nuclease lobes, accommodating a sgRNA:DNA duplex in a positively-charged groove at their interface. Whereas the recognition lobe is essential for sgRNA and DNA binding, the nuclease lobe contains the HNH and RuvC nuclease domains, which are properly positioned for the cleavage of complementary and non-complementary strands of the target DNA, respectively.

SpCas9 consists of two lobes, a recognition (REC) lobe and a nuclease (NUC) lobe. The REC lobe can be divided into three regions, a long α-helix referred to as Bridge helix (BH) (residues 60-93), the REC1 (residues 94-179 and 308-713), and REC2 (residues 180-307) domains. The NUC lobe consists of the RuvC (residues 1-59, 718-769, and 909-1098), HNH (residues 775-908), and PAM-interacting (PI) (residues 1099-1368) domains. The negatively-charged sgRNA:DNA hybrid duplex is accommodated in a positively-charged groove at the interface between the REC and NUC lobes. In the NUC lobe, the RuvC domain is assembled from the three split RuvC motifs (RuvC I-III), which interfaces with the PI domain to form a positively-charged surface that interacts with the 3' tail of the sgRNA. The HNH domain lies in between the RuvC II-III motifs and forms only a few contacts with the rest of the protein.

The REC lobe of SpCas9 interacted with the repeat:anti-repeat duplex: The REC lobe comprises the REC1 and REC2 domains. REC1 adopted an elongated, α-helical structure comprising 26 α-helices (α2-α5 and α12-α33) and two β-sheets (β6/β10 and β7-β9), whereas REC2 adopted a six-helix bundle structure (α6-α11). A Dali search (Holm and Rosenstrom, 2010) revealed that the REC lobe did not share structural similarity with other known proteins, indicating that it is a Cas9-specific effector domain.

The REC lobe is one of the least conserved regions across the three families of Cas9 within the Type II CRISPR system (IIA, IIB and IIC) and many Cas9s contain significantly shorter REC lobes. The REC lobe may be truncated. Consistent with the observation that the REC2 domain does not contact the bound sgRNA:DNA hybrid duplex, a Cas9 mutant lacking the REC2 domain (Δ175-307) showed ~50% of the wild-type Cas9 activity, indicating that the REC2 domain is not critical for DNA cleavage. The lower cleavage efficiency may be attributed in part to the reduced levels of Cas9 (Δ175-307) expression relative to that of the wild-type protein. In striking contrast, deletion of the crRNA repeat-interacting region (Δ97-150) or tracrRNA anti-repeat-interacting region (Δ312-409) of the REC1 domain abolished DNA cleavage activity, indicating that the recognition of the repeat:anti-repeat duplex by the REC1 domain is critical for Cas9 function.

The PAM-interacting (PI) domain confers PAM specificity: The NUC lobe contains the PI domain, which adopts an elongated structure comprising seven α-helices (α47-α53), a three-stranded antiparallel β-sheet (β18-β20), a five-stranded antiparallel β-sheet (β21-β23, β26 and β27), and two-stranded antiparallel β-sheet (β24 and β25). Similar to the REC lobe, the PI domain also represents a novel protein fold unique to the Cas9 family.

The locations of the bound complementary strand DNA and the active site of the RuvC domain in the present structure suggest that the PI domain is positioned to recognize the PAM sequence on the non-complementary strand of the target DNA. Applicants tested whether replacement of the S. pyogenes Cas9 (SpCas9; Cas9 in this study) PI domain with that of an orthologous Cas9 protein recognizing a different PAM would be sufficient to alter SpCas9 PAM specificity. The Streptococcus thermophilus CRISPR-3 Cas9 (St3Cas9) shares ~60% sequence identity with SpCas9; furthermore, their crRNA repeats and tracrRNAs are interchangeable (Fonfara et al., 2013). However, SpCas9 and St3Cas9 require different PAM sequences (5'-NGG for Cas9 and 5'-NGGNG for St3Cas9) for target DNA cleavage (Fonfara et al., 2013).

Two PI domains were swapped to generate two chimeras, Sp-St3Cas9 (SpCas9 with the PI domain of St3Cas9) and St3-SpCas9 (St3Cas9 with the PI domain of SpCas9) and examined their cleavage activities for target DNA sequences bearing 5'-NGG PAM (5'-GGGCT) or 5'-NGGNG PAM (5'-GGGCG). SpCas9 and St3-SpCas9, but not St3Cas9, cleaved the target DNA with 5'-NGG PAM, indicating that the PI domain of SpCas9 is required for the recognition of 5'-NGG PAM and is sufficient to alter the PAM recognition of St3Cas9. Sp-St3Cas9 retained cleavage activity for the target DNA with 5'-NGG PAM, albeit at a lower level than that of SpCas9. Additionally, deletion of the PI domain (Δ1099-1368) abolished the cleavage activity, indicating that the PI domain is critical for Cas9 function. These results reveal that the PI domain is a major determinant of PAM specificity.

The RuvC domain targets the non-complementary strand DNA: The RuvC domain consists of a six-stranded mixed β-sheet (β1, β2, β5, β11, β14 and β17) flanked by α-helices (α34, α35 and α40-α46) and two additional two-stranded antiparallel β-sheets (β3/β4 and 015/016). It shares structural similarity with retroviral integrase superfamily members characterized by an RNase H fold, such as Escherichia coli RuvC (PDB code 1HJR, 13% identity, root-mean-square deviation (rmsd) of 3.4 Å for 123 equivalent Ca atoms) (Ariyoshi et al., 1994) and Thermus thermophilus RuvC (PDB code 4LD0, 17% identity, rmsd of 3.4 Å for 129 equivalent Ca atoms) (Ariyoshi et al., 1994) and Thermus thermophilus RuvC (PDB code 4LD0, 17% identity, rmsd of 3.4 Å for 129 equivalent Ca atoms) (Gorecka et al., 2013). RuvC nucleases have four catalytic residues (e.g., Asp7, Glu70, His143 and Asp146 in T. thermophilus RuvC), and cleave Holliday junctions through a two-metal mechanism (Ariyoshi et al., 1994; Chen et al., 2013; Gorecka et al., 2013). Asp10 (Ala), Glu762, His983 and Asp986 of the Cas9 RuvC domain are located at positions similar to those of the catalytic residues of T. thermophilus RuvC, consistent with the previous results that the D10A mutation abolished cleavage of the non-complementary DNA strand and that Cas9 requires Mg2+ ions for cleavage activity (Gasiunas et al., 2012; Jinek et al., 2012). Moreover, alanine substitution of Glu762, His983 or Asp986 also converted Cas9 into nickases. Each nickase mutant was able to facilitate targeted double strand breaks using pairs of juxtaposed sgRNAs, as demonstrated with the D10A nickase previously (Ran et al., 2013). This combination of structural observations and mutational analysis suggest that the Cas9 RuvC domain cleaves the non-complementary strand of the target DNA through the two-metal mechanism previously observed for other retroviral integrase superfamily nucleases.

It is important to note that there are key structural dissimilarities between the Cas9 RuvC domain and RuvC nucleases, explaining their functional differences. Unlike the Cas9 RuvC domain, RuvC nucleases forms a dimer and recognize a Holliday junction (Gorecka et al., 2013). In addition to the conserved RNase H fold, the RuvC domain of Cas9 has additional structural elements involved in the interactions with the guide:DNA duplex (an end-capping loop between α43 and α44), and the PI domain/stem loop 3 (β-hairpin formed by β3 and β4).

The HNH domain targets the complementary strand DNA: The HNH domain comprises a two-stranded antiparallel β-sheet (β12 and β13) flanked by four α-helices (α36-α42). Likewise, it shares structural similarity with HNH endonucleases characterized by a ββα-metal fold, such as the phage T4 endonuclease VII (Endo VII) (Biertumpfel et al., 2007) (PDB code 2QNC, 8% identity, rmsd of 2.6 Å for 60 equivalent Cα atoms) and *Vibrio vulnificus* nuclease (Li et al., 2003) (PDB code 1OUP, 8% identity, rmsd of 2.9 Å for 78 equivalent Cα atoms). HNH nucleases have three catalytic residues (e.g., Asp40, His41, and Asn62 in Endo VII), and cleave nucleic acid substrates through a single-metal mechanism (Biertumpfel et al., 2007; Li et al., 2003). In the structure of the Endo VII N62D mutant in complex with a Holliday junction, a Mg2+ ion is coordinated by Asp40, Asp62, and oxygen atoms of the scissile phosphate group of the substrate, while His41 acts as a general base to activate a water molecule for catalysis. Asp839, His840, and Asn863 of the Cas9 HNH domain correspond to Asp40, His41, and Asn62 of Endo VII, respectively, consistent with the observation that His840 is critical for the cleavage of the complementary DNA strand (Gasiunas et al., 2012; Jinek et al., 2012). The N863A mutant functions as a nickase, indicating that Asn863 participates in catalysis. These observations suggest that the Cas9 HNH domain may cleave the complementary strand of the target DNA through a single-metal mechanism as observed for other HNH superfamily nucleases. However, in the present structure, Asn863 of Cas9 is located at a position different from that of Asn62 in Endo VII (Biertumpfel et al., 2007), whereas Asp839 and His840 (Ala) of Cas9 are located at positions similar to those of Asp40 and His41 of Endo VII, respectively. This might be due to the absence of divalent ions, such as Mg2+, in Applicants' crystallization solution, suggesting that Asn863 can point towards the active site and participate in catalysis. Whereas the HNH domain shares a ββα-metal fold with other HNN endonuclease, their overall structures are different, consistent with the differences in their substrate specificities.

sgRNA recognizes target DNA via Watson-Crick base pairing: The sgRNA consists of crRNA- and tracrRNA-derived sequences connected by an artificial tetraloop. The crRNA sequence can be subdivided into guide (20-nt) and repeat (12-nt) regions, and the tracrRNA sequence likewise into anti-repeat (14-nt) and three tracrRNA stem loops. The crystal structure reveals that the sgRNA binds the target DNA to form a T-shaped architecture comprising a guide:DNA duplex, repeat:anti-repeat duplex and stem loops 1-3. The repeat:anti-repeat duplex and stem loop 1 are connected by a single nucleotide (A51), and stem loops 1 and 2 are connected by a 5-nt single-stranded linker (nucleotides 63-67).

The guide (nucleotides 1-20) and target DNA (nucleotides 3'-23') form the guide:DNA hybrid duplex via 20 Watson-Crick base pairs, with the conformation of the duplex distorted from a canonical A-form RNA duplex. The crRNA repeat (nucleotides 21-32) and tracrRNA anti-repeat (nucleotides 37-50) form the repeat:anti-repeat duplex via nine Watson-Crick base pairs (U22:A49-A26:U45 and G29:C40-A32:U37). Within this region, G27, A28, A41, A42, G43, and U44 are unpaired, with A28 and U44 flipped out from the duplex. The nucleobases of G27 and A41 stack with the A26:U45 and G29:C40 pairs, respectively, and the 2-amino group of G27 interacts with the backbone phosphate group between G43 and U44, stabilizing the duplex structure. G21 and U50 form a wobble base pair at the three-way junction between the guide:DNA/repeat:anti-repeat duplexes and stem loop 1, stabilizing the T-shaped architecture.

As expected from the RNA-fold predictions of the nucleotide sequence, the tracrRNA 3' tail (nucleotides 68-81 and 82-96) form stem loops 2 and 3 via four and six Watson-Crick base pairs (A69:U80-U72:A77 and G82:C96-G87:C91), respectively. Previously unappreciated, nucleotides 52-62 also form a stem loop (stem loop 1) via three Watson-Crick base pairs (G53:C61, G54:C60 and C55:G58), with U59 flipped out from the stem. Stem loop 1 is stabilized by the G62-G53:C61 stacking interaction and the G62-A51/A52 polar interactions.

The guide:DNA and repeat:anti-repeat duplexes are accommodated and deeply buried in a positively-charged groove at the interface of the two lobes, while the rest of the sgRNA extensively interacts with the positively-charged surface on the back side of the protein. In Mol A, the 3'-terminal bases of the target DNA (3'-ACC complementary to the PAM) are not visible in the electron density map. In contrast, the two adjacent bases (3'-AC) in Mol B are not recognized by Cas9, although they are structurally ordered due to the crystal packing interactions and are visible in the electron density map. These observations suggest that the 3'-ACC sequence complementary to the PAM (5'-TGG) is not recognized by Cas9, consistent with the previous biochemical data demonstrating that Cas9-catalyzed DNA cleavage requires the 5'-NGG PAM on the non-complementary strand, but not the 3'-NCC sequence on the complementary strand (Jinek et al., 2012).

Previous studies showed that although sgRNA with a 48-nt tracrRNA tail (referred to as sgRNA(+48)) is a minimal region for the Cas9-catalyzed DNA cleavage in vitro (Jinek et al., 2012), sgRNAs with extended tracrRNA tails, sgRNA(+67) and sgRNA(+85), dramatically improved Cas9 cleavage activity in vivo (Hsu et al., 2013). The present structure revealed that sgRNA(+48), sgRNA(+67) and sgRNA(+85) contain stem loop 1, stem loops 1-2 and stem loops 1-3, respectively. These observations indicated that, whereas stem loop 1 is essential for the formation of the functional Cas9-sgRNA complex, stem loops 2 and 3 further support the stable complex formation as well as enhance sgRNA stability, thus improving the in vivo activity.

To confirm the significance of each sgRNA structural component on Cas9 function, a number of sgRNAs with mutations in the repeat:anti-repeat duplex, stem loops 1-3, and the linker between stem loops 1 and 2 were considered. Whereas stem loops 2 and 3 as well as the linker region can tolerate a large number of mutations, the repeat:anti-repeat duplex and stem loop 1 are critical for Cas9 function. Moreover, the sgRNA sequence can tolerate a large number of mutations. These results highlight the functional significance of the structure-dependent recognition of the repeat:anti-repeat duplex by Cas9.

Conserved arginines clustered on Bridge helix play a critical role in sgRNA:DNA interaction: the crRNA guide region is primarily recognized by the REC lobe. The backbone phosphate groups of the crRNA guide region (nucleotides 4-6 and 13-20) interact with the REC1 domain (Arg165, Gly166, Arg403, Asn407, Lys510, Tyr515 and Arg661) and Bridge helix (Ala59, Arg63, Arg66, Arg70, Arg71, Arg74 and Arg78) and the 2'-hydroxyl groups of C15, U16 and G19 hydrogen bond with Tyr450, Arg447/Ile448 and Thr404 in the REC1 domain, respectively. These observations suggested that the Watson-Crick faces of eight PAM-proximal nucleotides of the Cas9-bound sgRNA are exposed to the solvent, thus serving as a nucleation site for pairing with the target complementary strand. This is consistent with previous reports that the 10-12 bp PAM-proximal "seed" region is critical for Cas9-catalyzed DNA cleavage (Cong et al., 2013; Fu et al., 2013; Hsu et al., 2013; Jinek et al., 2012; Mali et al., 2013a; Pattanayak et al., 2013).

Mutational analysis demonstrated that the R66A, R70A and R74A mutations on Bridge helix markedly reduced DNA cleavage activities, highlighting the functional significance of the recognition of the sgRNA "seed" region by the Bridge helix. Although Arg78 and Arg165 also interact with the "seed" region, the R78A and R165A mutants showed only moderately decreased activities. These results may reflect that, whereas Arg66, Arg70 and Arg74 form bifurcated salt bridges with the sgRNA backbone, Arg78 and Arg165 form a single salt bridge with the sgRNA backbone. A cluster of arginine residues on the Bridge helix are highly conserved among Cas9 proteins in the Type II-A-C systems, suggesting that the Bridge helix is a universal structural feature of Cas9 proteins involved in recognition of the sgRNA and target DNA. This notion is supported by a previous observation that a strictly conserved arginine residue, equivalent to Arg70 of S. pyogenes Cas9, is essential for the function of Francisella novicida Cas9 in the Type II-B system (Sampson et al., 2013). Moreover, the alanine mutation of the repeat:anti-repeat duplex-interacting residues (Arg75 and Lys163) and stem loop 1-interacting residue (Arg69) resulted in decreased DNA cleavage activity, confirming the functional importance of the recognition of the repeat:anti-repeat duplex and stem loop 1 by Cas9.

The crRNA guide region is recognized by Cas9 in a sequence-independent manner except for the U16-Arg447 and G18-Arg71 interactions. This base-specific G18-Arg71 interaction may partly explain the observed preference of Cas9 for sgRNAs having guanines in the four PAM-proximal guide sequences (Wang et al., 2014).

The REC1 and RuvC domains facilitate RNA-guided DNA targeting: Cas9 recognizes the 20-bp DNA target site in a sequence-independent manner. The backbone phosphate groups of the target DNA (nucleotides 1', 9'-11', 13', and 20') interact with the REC1 (Asn497, Trp659, Arg661 and Gln695), RuvC (Gln926), and PI (Glu1108) domains. The C2' atoms of the target DNA (nucleotides 5', 7', 8', 11', 19', and 20') form van der Waals interactions with the REC1 domain (Leu169, Tyr450, Met495, Met694 and His698) and RuvC domain (Ala728). These interactions are likely to contribute towards discriminating between DNA vs. RNA targets by Cas9. The terminal base pair of the guide:DNA duplex (G1:C20') is recognized by the RuvC domain via end-capping interactions; the nucleobases of sgRNA G1 and target DNA C20' interact with the side chains of Tyr1013 and Val1015, respectively, whereas the 2'-hydroxyl and phosphate groups of sgRNA G1 interact with Val1009 and Gln926, respectively. These end-capping interactions are consistent with the previous observation that Cas9 recognizes a 17-20-bp guide:DNA duplex, and that extended guide sequences are degraded in cells and do not contribute to improving sequence specificity (Mali et al., 2013a; Ran et al., 2013). Taken together, these structural findings explain the RNA-guided DNA targeting mechanism of Cas9.

The repeat:anti-repeat duplex is recognized by the REC and NUC lobes in a sequence-dependent manner: The repeat:anti-repeat duplex is extensively recognized by the REC and NUC lobes. The backbone phosphate groups of the crRNA repeat (nucleotides 24, 26, and 27) and anti-repeat (nucleotides 41, 45, 46, and 48-50) interact with the REC1 domain (Arg115, His116, His160, Lys163, Arg340, and Arg403), PI domain (Lys1113), and Bridge helix (Lys76). The 2'-hydroxyl groups of the crRNA repeat (nucleotides 22-24) and anti-repeat (nucleotides 43-45 and 47) hydrogen bond with the REC1 domain (Leu101, Ser104, Phe105, Ile135, Tyr359, and Gln402) and the PI domain (Ile1110 and Tyr1131).

In contrast to the sequence-independent recognition of the guide region, there are sequence-dependent interactions between Cas9 and the repeat:anti-repeat duplex. The nucleobase of the flipped U44 is sandwiched between the side chains of Tyr325 and His328, with its N3 atom hydrogen bonded with the carbonyl group of Tyr325, while that of unpaired G43 stacks with the side chain of Tyr359 and hydrogen bonds with the side chain of Asp364. Finally, the nucleobases of U23/A49 and A42/G43 hydrogen bond with the side chain of Arg1122 and the main-chain carbonyl group of Phe351, respectively.

In the present structure, the repeat:anti-repeat duplex is recognized primarily by the REC lobe, which is divergent in sequence and length among Cas9 orthologs within the Type II-A-C systems, consistent with the previous observation that Cas9 and sgRNA are interchangeable only between closely related Type II systems (Fonfara et al., 2013). The three PAM-distal base pairs (C30:G39-A32:U37) are not recognized by Cas9 and protrude from the complex, consistent with a proposed model in which a Cas9-bound repeat:anti-repeat duplex is processed by the host RNase III enzyme (Deltcheva et al., 2011).

The nucleobases of G21 and U50 in the G21:U50 wobble pair stack with the terminal C20:G1' pair in the guide:DNA duplex and the side chain of Tyr72 on Bridge helix, respectively, with the U50 O4 atom hydrogen bonded with the side chain of Arg75 Notably, A51 adopts the syn-conformation, and is oriented in the direction opposite to U50. The nucleobase of A51 is sandwiched between the Phe1105 side chain in the PI domain and the U63 nucleobase in the linker, with its N7 and N1 atoms hydrogen bonded with the main-chain amide group of Phe1105 and the G62 2'-hydroxyl group in stem loop 1, respectively. Whereas a repeat:anti-repeat duplex is diverse in sequence and length among the Type II-A-C systems, the G21:U50 base pair is highly conserved among Cas9s (Fonfara et al., 2013), suggesting that this wobble pairing is a universal structural feature involved in the three-way junction formation.

SpCas9 sgRNA: Recognition of the repeat:anti-repeat duplex is sequence-dependent and multiple mutations significantly reduce Cas9 activity. Notably, replacement of G43, which forms a base-specific hydrogen bond with Asp364, with adenine reduced Cas9 activity by over 3-fold. In addition, replacement of the flipped U44 in the repeat:anti-repeat duplex with adenine resulted in over a 5-fold drop in cleavage activity, whereas replacement of U44 with another pyrimidine base (cytosine) did not significantly affect cleavage activity. Thus, base-specific recognition of sgRNA nucleotides, e.g., G43 and U44, plays an important role in sgRNA recognition by Cas9.

sgRNA stem loops 1-3 interact with Cas9: Stem loop 1 is primarily recognized by the REC lobe together with the PI domain. The backbone phosphate groups of stem loop 1 (nucleotides 52, 53, and 59-61) interact with the REC1 domain (Leu455, Ser460, Arg467, Thr472, and Ile473), PI domain (Lys1123 and Lys1124), and Bridge helix (Arg70 and Arg74), with the 2'-hydroxyl group of G58 hydrogen bonded with Leu455 in the REC1 domain. A52 interacts with Phe1105 through a face-to-edge n-n stacking interaction, and the flipped U59 nucleobase hydrogen bonds with the side chain of Asn77.

Stem loops 2 and 3, and the single-stranded linker are primarily recognized by the NUC lobe; this contrasts with stem loop 1 and the guide:DNA/repeat:anti-repeat duplexes, which are recognized by both of the NUC and REC lobes. The backbone phosphate groups of the linker (nucleotides 63-65 and 67) interact with the RuvC domain (Glu57, Lys742, and Lys1097), PI domain (Thr1102), and Bridge helix (Arg69), with the 2'-hydroxyl groups of U64 and A65 hydrogen bonded with Glu57 and His721, respectively. The nucleobase of C67 hydrogen bonds with the main-chain amide group of Val1100.

Stem loop 2 is recognized by Cas9 via the interactions between the NUC lobe and the non-Watson-Crick A68:G81 pair, which is formed by direct (between the A68 N6 and G81 06 atoms) and water-mediated (between the A68 N1 and G81 N1 atoms) hydrogen-bonding interactions. The nucleobases of A68 and G81 contact the side chains of Ser1351 and Tyr1356, respectively, with the A68:G81 pair recognized by Thr1358 via a water-mediated hydrogen bond. The 2'-hydroxyl group of A68 hydrogen bonds with the side chain of His1349, and the 2-amino group of G81 hydrogen bonds with the main-chain carbonyl group of Lys33.

Stem loop 3 interacts with the NUC lobe more extensively relative to stem loop 2. The backbone phosphate groups of C91 and G92 interact with the RuvC domain (Arg40 and Lys44), while the nucleobases of G89 and U90 hydrogen bond with Gln1272 and Glu1225/Ala1227, respectively. The nucleobases of A88 and C91 are recognized by the side chain of Asn46 via multiple hydrogen-bonding interactions.

Structural flexibility of Cas9 and sgRNA: Although the HNH domain cleaves the complementary strand of the target DNA at a position three nucleotides upstream of the PAM sequence (Gasiunas et al., 2012; Jinek et al., 2012), in the present structure the HNH domain is positioned away from the scissile phosphate group of the bound complementary strand. A structural comparison of Mol A and Mol B provided mechanistic insights into the complementary strand cleavage by the HNH domain. In Mol A, the HNH domain is followed by the α40 helix of the RuvC domain, which is connected with the α41 helix by an α40-α41 linker (residues 919-925). Whereas in Mol A residues 913-925 form the C-terminal portion of the α43 helix and α43-α44 linker, in Mol B these residues form an extended α-helix, which is directed toward the cleavage site of the complementary strand. These observations suggest that the HNH domain can approach and cleave the target DNA through conformational changes in the segment connecting the HNH and RuvC domains.

Moreover, the structural comparison revealed a conformational flexibility between the REC and NUC lobes. Compared to Mol A, Mol B adopts a more open conformation, in which the two lobes are rotated by 150 at a hinge loop between Bridge helix and the strand β5 in the RuvC domain. The bound sgRNA also undergoes an accompanying conformational change at the single-stranded linker, which interacts with the hinge loop. Applicants also observed an accompanying displacement of the β17-β18 loop of the PI domain, which interacts with the repeat:anti-repeat duplex and the α2-α3 loop of the REC1 domain. Notably, there is no direct contact between the two lobes in the present structure, except for the interactions between the α2-α3 and β17-β18 loops, suggesting that Cas9 is highly flexible in the absence of the sgRNA. The flexible nature of Cas9 is likely to play a role in the assembly of the Cas9-sgRNA-DNA ternary complex.

In certain embodiments, the complex of nucleic acid binding domain with the guide resembles the complex of SpCas9 with crRNA and tracrRNA and/or the complex of SpCas9 with sgRNA. In an embodiment of the invention, the nucleic acid binding domain comprises residues which correspond with respect to binding of guide and target to amino acids of SpCas9 that interact with the guide and/or target. Such amino acids of SpCas9 that interact with guide and/or target include, without limitation, amino acids that interact with the portions of the guide such as stem loop 1, stem loop 3, and/or the repeat:antirepeat duplex, as well as the guide:target heteroduplex. Each of the residues of the nucleic acid binding domain may interact with the guide and/or the guide:target heteroduplex through the amino acid backbone, side chain, or both. Where the interaction is by the amino backbone, there is greater leeway to vary the amino acid side chain at that position. Also, the residues of the nucleic acid binding domain may interact with the sugar-phosphate backbone or a base of the guide or guide:target heteroduplex. With respect to the guide:target heteroduplex, interactions with the sugar-phosphate backbone are preferred which allows for unrestricted sequence variation of the target sequence and the targeting sequence of the guide.

As described elsewhere herein, guides of the invention can comprise ribonucleotides, deoxyribonucleotides, and nucleotide analogs, for example, there can be variation in the sugar-phosphate backbone with nucleic acid binding domains adjusted accordingly.

In an embodiment of the invention, the nucleic acid binding domain comprises amino binding residues which correspond to amino acids of SpCas9. In an embodiment of the invention, the nucleic acid binding domain comprises one or more of the following domains, whole or in part: RuvC, bridge helix, REC1, and PI. In an embodiment of the invention, the nucleic acid binding domain comprises binding residues which correspond to all or a subset of the following amino acids of SpCas9: Lys30, Lys33, Arg40, Lys44, Asn46, Glu57, Thr62, Arg69, Asn77, Leu101, Ser104, Phe105, Arg115, His116, Ile135, His160, Lys163, Arg165, Gly166, Tyr325, His328, Arg340, Phe351, Asp364, Gln402, Arg403, Thr404, Asn407, Arg447, Ile448, Leu455, Ser460, Arg467, Thr472, Ile473, Lys510, Tyr515, Trp659, Arg661, Met694, Gln695, His698, His721, Ala728, Lys742, Gln926, Val1009, Lys1097, Val1100, Gly1103, Thr1102, Phe1105, Ile110, Tyr1113, Arg1122, Lys1123, Lys1124, Tyr1131, Glu1225, Ala1227, Gln1272, His1349, Ser1351, and Tyr1356.

Of the amino acids above, SpCas9 amino acids that interact with the guide primarily through the SpCas9 amino acid backbone are Lys33, Lys44, Glu57, Ala59, Leu101, Phe105, Ile135, Gly166, Phe351, Thr404, Ile448, Leu455, Ile473, Trp659, Val1009, Val1100, Gly1103, Phe1105, Ile110, Tyr1113, Lys1124, Tyr1131, Glu1225, and Ala1227.

In an embodiment of the invention, the nucleic acid binding domain comprises binding residues which correspond to all or a subset Ala59, Arg63, Arg66, Arg70, Arg74, Arg78, Lys, Tyr515, Arg661, Gln926, and Val009 of SpCas9, which interact with the sugar-phosphate backbone of the guide in the guide:target duplex. In an embodiment of the invention, the nucleic acid binding domain comprises binding residues which correspond to all or a subset of Leu169, Tyr450, Met495, Asn497, Trp659, Arg661, Met694, Gln695, His698, Aca728, Gln926, and/or Glu1108 of SpCas9, which interact with the sugar-phosphate backbone of the target in the guide:target duplex.

Truncated CRISPR proteins of the invention generally comprise all or portions of nucleic acid binding domains of whole CRISPR proteins while nuclease functions are removed. Accordingly, the invention includes binding domains that are homologous to nucleic acid binding domains of CRISPR proteins such as SpCas9, SaCas9, Cpf1 and orthologs, and can be 60%, 70%, 80%, 90%, or 95% identical over the range of amino acid locations in common. Amino acid residues likely to be conserved between binding domains of the invention and the various CRISPR proteins include those identified in the tables below for SpCas9, SaCas9, and Cpf1. Accordingly, in an embodiment, a nucleic acid binding domain comprises binding residues which correspond to one or more of the amino acids of SpCas9 in the following table.

| SpCas9 amino acid | aa part interacting with nucleic acid | | Nucleic acid interaction | | Nucleic acid location | | Domain |
|---|---|---|---|---|---|---|---|
| | side chain | backbone | sugar-phosphate | base | guide | guide-target duplex or PAM | |
| Lys30 | x | | x | | x | | RuvC |
| Lys33 | | x | | x | x | | RuvC |
| Arg40 | x | | x | | x | | RuvC |
| Lys44 | | x | x | | x | | RuvC |
| Asn46 | x | | | x | x | | RuvC |
| Glu57 | | x | x | | x | | RuvC |
| Ala59 | | x | x | | | x | RuvC |
| Thr62 | x | | | | x | | BH |
| Arg63 | | | x | | | x | BH |
| Arg66 | x | | x | | | x | BH |
| Arg69 | x | | | | x | | BH |
| Arg70 | x | | x | | | x | BH |
| Arg71 | x | | | x | | x | BH |
| Arg74 | x | | x | | | x | BH |
| Asn77 | x | | | | x | | BH |
| Arg78 | x | | x | | | x | BH |
| Leu101 | | x | | | x | | REC1 |
| Ser104 | x | | | | x | | REC1 |
| Phe105 | | x | x | | x | | REC1 |
| Arg115 | x | | | | x | | REC1 |
| His116 | x | | | | x | | REC1 |
| Ile135 | | x | | | x | | REC1 |
| His160 | x | | | | x | | REC1 |
| Lys163 | x | | | | x | | REC1 |
| Arg165 | x | | x | | | | REC1 |
| Gly166 | | x | | x | | x | REC1 |
| Tyr325 | x | x | | x | x | | REC1 |
| His328 | x | | | x | x | | REC1 |
| Arg340 | x | | x | | x | | REC1 |
| Phe351 | | x | | x | x | | REC1 |
| Asp364 | x | | | x | x | | REC1 |
| Gln402 | x | | x | | x | | REC1 |
| Arg403 | x | | x | | | x | REC1 |
| Thr404 | | | | | | x | REC1 |
| Asn407 | x | | x | | | x | REC1 |
| Arg447 | x | | | x | x | | REC1 |
| Ile448 | | x | | | | x | REC1 |
| Tyr450 | x | x | x | | | x | REC1 |
| Leu455 | | x | x | | x | | REC1 |
| Ser460 | x | | x | | x | | REC1 |
| Arg467 | x | | | x | x | | REC1 |
| Thr472 | x | | | x | x | | REC1 |
| Ile473 | | x | | x | x | | REC1 |
| Met495 | x | | x | | | x | REC1 |
| Asn497 | x | x | x | | | x | REC1 |
| Lys510 | x | | x | | | x | REC1 |
| Tyr515 | x | | x | | | x | REC1 |
| Trp659 | | x | x | | | x | REC1 |
| Arg661 | x | | x | | | x | REC1 |
| Met694 | x | | x | | | x | REC1 |
| Gln695 | x | | x | | | x | REC1 |
| His698 | x | | x | | | x | REC1 |
| His721 | x | | x | x | | | RuvC |
| Ala728 | x | | x | | | | RuvC |
| Lys742 | x | | x | | x | | RuvC |
| Gln926 | x | | x | | | x | RuvC |
| Val1009 | | x | x | | | x | RuvC |
| Tyr1013 | x | | | x | | x | RuvC |
| Val1015 | x | | | x | | x | RuvC |
| Lys1097 | x | | x | | x | | RuvC |
| Val1100 | | x | | x | | | PI |
| Thr1102 | x | | x | | x | | PI |
| Gly1103 | | x | | x | x | | PI |
| Phe1105 | | x | | x | x | | PI |
| Glu1108 | | x | x | | | x | PI |
| Ile1110 | | x | x | | x | | PI |
| Tyr1113 | | x | x | | x | | PI |
| Arg1122 | x | | | x | x | | PI |
| Lys1123 | x | | x | | x | | PI |
| Lys1124 | | x | x | | x | | PI |
| Tyr1131 | | x | x | | x | | PI |
| Glu1225 | | x | | x | x | | PI |
| Ala1227 | | x | | x | x | | PI |
| Gln1272 | x | | | x | x | | PI |
| His1349 | x | | x | | x | | PI |
| Ser1351 | x | | | x | x | | PI |
| Tyr1356 | x | | | x | x | | PI |

In an embodiment, the nucleic acid binding domain comprises a truncation as to all or part of the NUC lobe of SpCas9. In an embodiment, the nucleic acid binding domain comprises a truncation as to one or more of the RuvCI, RuvC II, RuvC III, HNH and PI domains of SpCas9. In an embodiment an SpCas9 truncation is truncated as to all or part of the HNH domain (residues 775-908) and/or the RuvCIII domain (residues 909-1098). In an embodiment, the nucleic acid binding domain comprises a truncation as to the REC3 domain of SpCas9 (residues 498-712). In certain embodiments, the SpCas9 portions remaining may be linked directly or through a linker, including but not limited to a GGG linker, a GGS linker, or a (GGGGS)$_n$ (SEQ ID NO: 10) linker.

SaCas9 has a bilobed architecture consisting of a REC lobe (residues 41-425) and a NUC lobe (residues 1-40 and 435-1053). See, e.g., WO2015/089486. The two lobes are connected by an arginine-rich bridge helix (residues 41-73) and a linker loop (residues 426-434). The NUC lobe consists of the RuvC (residues 1-40, 435-480 and 650-774), HNH (residues 520-628), WED (residues 788-909) and PI (residues 910-1053) domains. The RuvC and WED domains are connected by a phosphate lock loop (residues 775-787). The PI domain can be divided into a Topo-homology (TOPO) domain and a C-terminal domain as in SpCas9 (Jinek et al., 2014). The RuvC domain consists of three separate motifs (RuvC-I-III) and interacts with the HNH and PI domains. The HNH domain is connected to the RuvC-II and RuvC-III by L1 (residues 481-519) and L2 (residues 629-649) linker regions, respectively. In a crystal, the active site of the HNH domain is found located away from the cleavage site in the target DNA strand (the phosphodiester linkage between dC3 and dA4), indicating that the described structure represents an inactive state, as in the case of the SpCas9-sgRNA-target DNA complex structures (Anders et al., 2014; Nishimasu et al., 2014). SpCas9 undergoes conformational rearrangements upon guide RNA binding, to form the central channel between the REC and NUC lobes (Anders et al., 2014; Jiang et al., 2015; Jinek et al., 2014; Nishimasu et al., 2014). In the absence of the guide RNA, SpCas9 and AnCas9 adopt a closed conformation, where the active site of the HNH domain is covered by the RuvC domain. In contrast, the ternary and quaternary complex structures of SpCas9 adopt an open conformation and has the central channel, which accommodates the guide RNA-target DNA heteroduplex (referred to as a guide:target heteroduplex). In a quaternary complex SaCas9 adopts a similar open conformation to form the central channel, which accommodates the guide:target heteroduplex. Thus, these structural observations suggested that the guide RNA-induced conformational activation is conserved between SaCas9 and SpCas9.

SaCas9 sgRNA-target DNA complex: The sgRNA consists of the guide region (G1-C20), repeat region (G21-G34), tetraloop (G35-A38), anti-repeat region (C39-C54), stem loop 1 (A56-G68) and single-stranded linker (U69-U73), with A55 connecting the anti-repeat region and stem loop 1. See, e.g., WO2016/205759. No electron density was observed for U73 at the 3' end, suggesting that U73 is disordered in the structure. The guide region (G1-C20) and the target DNA strand (dG1-dC20) form an RNA-DNA heteroduplex (referred to as a guide:target heteroduplex), whereas the target DNA strand (dC(−8)-dA(−1)) and the non-target DNA strand (dT1*-dG8*) form a PAM-containing duplex (referred to as a PAM duplex). The repeat (G21-G34) and anti-repeat (C39-C54) regions form a distorted duplex (referred to as a repeat:anti-repeat duplex) via 13 Watson-Crick base pairs. The unpaired nucleotides (C30, A43, U44 and C45) form an internal loop, which is stabilized by a hydrogen bonding-interaction between the O2 of U44 and the N4 of C45. The repeat:anti-repeat duplex is recognized by the REC and WED domains. Indeed, a GAU insertion into the repeat region, which would disrupt the internal loop, reduced the Cas9-mediated DNA cleavage, confirming the functional importance of the distorted structure of the repeat:anti-repeat duplex.

Stem loop 1 is formed via three Watson-Crick base pairs (G57:C67-C59:G65) and two non-canonical base pairs (A56:G68 and A60:A63). U64 does not base pair with A60, and is flipped out of the stem loop. The N1 and N6 of A63 hydrogen bond with the 2' OH and N3 of A60, respectively. G68 stacks with G57:C67, with the G68 N2 interacting with the backbone phosphate group between A55 and A56. A55 adopts the syn conformation, and its adenine base stacks with U69. In addition, the N1 of A55 hydrogen bonds with the 2' OH of G68, stabilizing the basal region of stem loop 1. An adenosine nucleotide immediately after the repeat:anti-repeat duplex is highly conserved among CRISPR-Cas9 systems, and equivalent adenosine A51 in the SpCas9 crRNA:tracrRNA also adopts the syn conformation (Anders et al., 2014; Nishimasu et al., 2014), suggesting conserved key roles of an adenosine connecting the repeat:anti-repeat duplex and stem loop 1.

The SpCas9 sgRNA contains three stem loops (stem loops 1-3), which interact with Cas9 and contribute to the complex formation (Nishimasu et al., 2014). The sgRNA lacking stem loops 2 and 3 supports the Cas9-catalyzed DNA cleavage in vitro but not in vivo, indicating the importance of stem loops 2 and 3 for the cleavage activity in vivo (Hsu et al., 2013; Jinek et al., 2012; Nishimasu et al., 2014). The nucleotide sequence of the SaCas9 sgRNA indicated that it contains two stem loops (stem loops 1 and 2) based on its nucleotide sequence. Truncation of putative stem loop 2 remarkably improved the quality of the crystals. As in SpCas9, the sgRNA lacking stem loop 2 supported Cas9-catalyzed DNA cleavage in vitro but not in vivo, suggesting that secondary structures on the 3' tail of the SaCas9 sgRNA are important for in vivo function.

Tetraloop and stem loop 2 of the SpCas9 sgRNA are exposed to the solvent (Anders et al., 2014; Nishimasu et al., 2014). Thus, these two loops are available for the fusion of RNA aptamers, and the three components system consisting of (1) catalytically inactive SpCas9 (D10A/N863A) fused with a VP64 transcriptional activator domain, (2) a MS2 bacteriophage coat protein fused with β65 and HSF1 transcriptional activator domains, and (3) the engineered sgRNA fused to MS2-interacting RNA aptamers can induce the RNA-guided transcriptional activation of target endogenous loci (Konermann et al., 2015). To examine whether tetraloop and stem loop 2 of the SaCas9 sgRNA are available for the MS2-interacting aptamer fusion, Applicants co-expressed in HEK293F cells the three components, (1) dSpCas9 (D10A/N863A)-VP64 or dSaCas9 (D10A/N580A)-VP64, (2) its engineered sgRNA, and (3) MS2-β65-HSF1, and then monitored the transcriptional activation of two different endogenous genes (ASCL1 and MYOD1). The results showed that the dSaCas9-based activator induces the transcription activation of the ASCL1 and MYOD1 genes at levels comparable to those of the dSpCas9-based activator. These results indicate that the SaCas9 sgRNA has solvent-exposed stem loop 2, and demonstrate that the engineered SaCas9 sgRNA can recruit multiple MS2-fused proteins.

The guide:target heteroduplex is accommodated in the central channel between the REC and NUC lobes. The sugar-phosphate backbone of the PAM-distal region (A3-U6) of the sgRNA interacts with the REC lobe (Thr238, Tyr239, Lys248, Tyr256, Arg314, Asn394 and Gln414). In SpCas9 and SaCas9, the RNA-DNA base pairing in the 8 bp PAM-proximal "seed" region in the guide:target heteroduplex is critical for Cas9-catalyzed DNA cleavage (Hsu et al., 2013; Jinek et al., 2012; Ran et al., 2015). Consistent with this, the phosphate backbone of the sgRNA seed region (C13-C20) is extensively recognized by the bridge helix (Asn44, Arg48, Arg51, Arg55, Arg59 and Arg60) and the REC lobe (Arg116, Gly117, Arg165, Gly166, Asn169 and Arg209), as in the case of SpCas9. In addition, the 2' OH groups of C15, U16, U17 and G19 interact with the REC lobe (Gly166, Arg208, Arg209 and Tyr211). These structural findings suggest that the sgRNA binds to SaCas9, with its seed region pre-ordered in an A-form conformation for base-paring with the target DNA strand, as proposed for SpCas9 (Jiang et al., 2015). In addition, the sugar-phosphate backbone of the target DNA strand interacts with the REC lobe (Tyr211, Trp229, Tyr230, Gly235, Arg245, Gly391, Thr392, and Asn419) and the RuvC domain (Leu446, Tyr651 and Arg654). Together, there structural findings explain the RNA-guided DNA targeting mechanism of SaCas9. Notably, the REC lobe of SaCas9 shares structural similarity with those of SpCas9 (PDB code 4UN3, 26% identity, rmsd of 1.9 Å for 177 equivalent Cα atoms) and AnCas9 (PDB ID 4OGE, 16% identity, rmsd of 3.2 Å for 167 equivalent Cα atoms), indicating that the Cas9 orthologs recognize the guide:target heteroduplex in a similar manner.

Recognition Mechanism of the crRNA:tracrRNA Scaffolds

The repeat:anti-repeat duplex is recognized by the REC and WED domains, primarily through interactions between the sugar-phosphate backbone and protein. Consistent with our data showing that the sgRNA containing the fully-paired repeat:anti-repeat duplex fails to support Cas9-catalyzed DNA cleavage, the internal loop (C30, U44 and C45) is extensively recognized by the WED domain. The 2' OH and O2 of C30 hydrogen bond with Tyr868 and Lys867, respectively, and the phosphate groups of U31, C45 and U46 interact with Lys870, Arg792 and Lys881, respectively. These structural observations explain the structure-dependent recognition of the repeat:anti-repeat duplex by SaCas9.

Stem loop 1 is recognized by the bridge helix and REC lobe. The phosphate backbone of stem loop 1 interact with the bridge helix (Arg47, Arg54, Arg55, Arg58 and Arg59) and the REC lobe (Arg209, Gly216 and Ser219). The 2' OH of A63 hydrogen bonds with His64. The flipped-out U64 is recognized by Glu213 and Arg209 via hydrogen-bonding and stacking interactions, respectively. A55 is extensively recognized by the phosphate lock loop. The N6, N7 and 2' OH of A55 hydrogen bond with Asn780/Arg781, Leu783 and Lys906, respectively. Lys57 interacts with the phosphate group between C54 and A55, and the side chain of Leu783 form hydrophobic contacts with the adenine bases of A55 and A56. The phosphate backbone of the linker region electrostatically interacts with the RuvC domain (Arg452, Lys459 and Arg774) and the phosphate lock loop (Arg781), and the guanine base of G80 stacks with the side chain of Arg47 on the bridge helix.

Recognition Mechanism of the 5'-NNGRRT-3' PAM

SaCas9 recognizes the 5'-NNGRRN-3' PAM with a preference for a thymine base at the 6th position (Ran et al., 2015), which is distinct from the 5'-NGG-3' PAM of SpCas9. In the present structures containing either the 5'-TTGAAT-3' PAM or the 5'-TTGGGT-3' PAM, the PAM duplex is sandwiched between the WED and PI domains, and the PAM in the non-target DNA strand is read out from the major groove side by the PI domain. dT1* and dT2* form no direct contact with the protein. Consistent with the observed requirement for the 3rd G in the 5'-NNGRRT-3' PAM, the 06 and N7 of dG3* forms bidentate hydrogen bonds with the side chain of Arg1015, which is anchored via salt bridges with Glu993 in both complexes. In the 5'-TTGAAT-3' PAM complex, the N7 atoms of dA4* and dA5* form direct and water-mediated hydrogen bonds with Asn985 and Asn985/Asn986/Arg991, respectively. In addition, the N6 of dA5* forms a water-mediated hydrogen bond with Asn985. Similarly, in the 5'-TTGGGT-3' PAM complex, the N7 atoms of dG4* and dG5* form direct and water-mediated hydrogen bonds with Asn985 and Asn985/Asn986/Arg991, respectively. The 06 of dG5* forms a water-mediated hydrogen bond with Asn985. These structural findings explain the ability of SaCas9 to recognize the purine nucleotides at positions 4 and 5 in the 5'-NNGRRT-3' PAM. The 04 of dT6* hydrogen bonds with Arg991, explaining the preference of SaCas9 to the 6th T in the 5'-NNGRRT-3' PAM. Single alanine mutants of these PAM-interacting residues reduced cleavage activities in vivo, and double mutations abolished the activity, confirming the importance of Asn985, Asn986, Arg991, Glu993 and Arg1015 for PAM recognition. In addition, the phosphate backbone of the PAM duplex is recognized from the minor groove side by the WED domain (Tyr789, Tyr882, Lys886, Ans888, Ala889 and Leu909) in a manner distinct from SpCas9. Together, our structural and functional data reveal the mechanism of relaxed recognition of the 5'-NNGRRT-3' PAM by SaCas9.

Mechanism of Target DNA Unwinding

In the quaternary complex structure of SpCas9, Glu1108 and Ser1109 in the phosphate lock loop hydrogen bond with the phosphate group between dA(−1) and dT1 in the target DNA strand (referred to as +1 phosphate), and contribute to unwinding of the target DNA (Anders et al., 2014). The present structure revealed that SaCas9 also has the phosphate lock loop, although the phosphate lock loops of SaCas9 and SpCas9 share limited sequence similarity. In the present structure of SaCas9, the +1 phosphate between dA(−1) and dG1 in the target DNA strand hydrogen bonds with the main-chain amide groups of Asp786 and Thr787 and the side-chain Og atom of Thr787 in the phosphate lock loop. These interactions result in the rotation of the +1 phosphate, thereby facilitating base-pairing between dG1 in the target DNA strand and C20 in the sgRNA. Indeed, the SaCas9 T787A mutant showed reduced DNA cleavage activity, confirming the functional significance of Thr787 in the phosphate lock loop. Together, these data indicated that the molecular mechanism of the target DNA unwinding is conserved among SaCas9 and SpCas9.

RuvC and HNH Nuclease Domains

The RuvC domain of SaCas9 has an RNase H fold, and shares structural similarity with those of SpCas9 (PDB code 4UN3, 25% identity, rmsd of 2.5 Å for 191 equivalent Cα atoms) and *Actinomyces naeslundii* Cas9 (AnCas9) (PDB code 4OGE, 17% identity, rmsd of 3.0 Å for 170 equivalent Cα atoms). The catalytic residues of SaCas9 (Asp10, Glu477, His701 and Asp704) are located at positions similar to those of SpCas9 (Asp10, Glu762, His983 and Asp986) and AnCas9 (Asp17, Glu505, His736 and Asp739). The D10A, E477A, H701A and D704A mutants of SaCas9 showed almost no DNA cleavage activities. These observations indicated that the SaCas9 RuvC domain cleaves the non-target DNA strand through a two-metal ion mechanism as in other endonucleases of the RNase H superfamily (Gorecka et al., 2013).

The HNH domain of SaCas9 has an aab-metal fold, and shares structural similarity with those of SpCas9 (PDB code 4UN3, 27% identity, rmsd of 1.8 Å for 93 equivalent Cα atoms) and AnCas9 (PDB code 4OGE, 18% identity, rmsd of 2.6 Å for 98 equivalent Cα atoms). The catalytic residues of SaCas9 (Asp556, His557 and Asn580) are located at positions similar to those of SpCas9 (Asp839, His840 and Asn863) and AnCas9 (Asp581, His582 and Asn606), although Asn863 is oriented away from the active site in the ternary and quaternary complex structures of SpCas9. The D556A, H557A and N580A mutants of SaCas9 showed almost no DNA cleavage activities). These observations indicated that the SaCas9 HNH domain cleaves the target DNA strand through a one-metal ion mechanism as in other aab-metal endonucleases (Biertumpfel et al., 2007).

A structural comparison of SaCas9 with SpCas9 and AnCas9 revealed that the RuvC and HNH domains are connected by α-helical linker, L1 and L2, and that there are notable differences in the relative arrangements between the two nuclease domains. A biochemical study suggested that the binding of the PAM duplex to SpCas9 facilitates the cleavage of the target DNA strand by the HNH domain (Sternberg et al., 2014). However, in the quaternary complex structures of SaCas9 and SpCas9, the HNH domains are located away from the cleavage site of the target DNA strand. A structural comparison of SaCas9 with *Thermus thermophilus* RuvC in complex with a Holliday junction substrate (Gorecka et al., 2013) indicated steric clashes between the L1 linker and the modeled non-target DNA strand bound to the active site of the SaCas9 RuvC domain. These observations suggested that the binding of the non-target DNA strand to the RuvC domain may contribute to triggering a conformational change in the L1, thereby bringing the HNH domain to the scissile phosphate group in the target DNA strand.

Conserved Mechanism of RNA-Guided DNA Targeting

Previous structural studies revealed that SpCas9 undergoes conformational rearrangements upon guide RNA binding, to form the central channel between the REC and NUC lobes (Anders et al., 2014; Jinek et al., 2014; Nishimasu et al., 2014). In the absence of the guide RNA, SpCas9 adopts a closed conformation, where the active site of the HNH domain is covered by the RuvC domain. In contrast, the ternary and quaternary complex structures of SpCas9 adopt an open conformation and have the central channel, which accommodates the guide:target heteroduplex. The quaternary complex structure of SaCas9 adopts an open conformation and has the central channel, which accommodates the guide:target heteroduplex. Thus, the guide RNA-induced conformational rearrangement is conserved among SaCas9 and SpCas9.

The REC lobes of SaCas9 and SpCas9 (PDB code 4UN3) share structural similarity (25% identity, rmsd of 2.9 Å for 353 equivalent Cα atoms), and recognize the guide:target heteroduplex in a similar manner. In particular, the seed region of the sgRNA is commonly recognized by the arginine cluster on the bridge helix in SaCas9 and SpCas9. AnCas9 (PDB ID 4OGE) also has a REC lobe similar to those of SaCas9 and SpCas9. These observations suggested that the recognition mechanism of the guide:target heteroduplex is conserved among Cas9 orthologs.

Structural Basis for the Orthogonal Recognition of sgRNA Scaffolds

A comparison of the quaternary complex structures of SaCas9 and SpCas9 reveals that the structurally diverse REC and WED domains recognize the distinct structural features of the repeat:anti-repeat duplex, allowing cognate sgRNAs to be distinguished in an orthogonal manner. The SpCas9 WED domain adopts a compact loop conformation (Nishimasu et al., 2014; Anders et al., 2014). In contrast, the SaCas9 WED domain has a new fold comprising a twisted five-stranded β-sheet flanked by four α-helices. The AnCas9 WED domain has yet a different fold containing three antiparallel β-hairpins (Jinek et al., 2014). These structural differences in the WED domains are consistent with variations in sgRNA scaffolds among CRISPR-Cas9 systems (Fonfara et al., 2014; Briner et al., 2014; Ran et al., 2015).

The REC lobe also contributes to the orthogonal recognition of sgRNA scaffolds. Although the REC lobes of SaCas9 and SpCas9 share structural similarity, the SpCas9 REC lobe has four characteristic insertions (Ins 1-4), which are absent in the SaCas9 REC lobe. Ins 2 (also known as the REC2 domain) forms no contact with the nucleic acids in the SpCas9 structures and is dispensable for DNA cleavage activity (Nishimasu et al., 2014), consistent with the absence of Ins2 in SaCas9. Ins 1 and 3 recognize the SpCas9-specific internal loop in the repeat:anti-repeat duplex, while in SaCas9 the WED domain recognizes the internal loop in the repeat:anti-repeat duplex, as described above. In addition, Ins 4 interacts with stem loop 1 of the SpCas9 sgRNA, which is shorter than that of the SaCas9 sgRNA. Together, these structural observations demonstrate that the Cas9 orthologs recognize their cognate sgRNA in an orthogonal manner, using a combination of the structurally diverse REC and WED domains.

Structural Basis for the Distinct PAM Specificities

A structural comparison of SaCas9, SpCas9 and AnCas9 revealed that, despite lacking sequence homology, their PI domains share a similar protein fold. The PI domains consist of the Topo-homology domain, which comprises three-stranded anti-parallel β-sheet (β1-β3) flanked by several α helices, and the C-terminal domain, which comprises twisted six-stranded anti-parallel β-sheet (β4-β9) (the β7 in SpCas9 adopts a loop conformation). In both SaCas9 and SpCas9, the major groove of the PAM duplex is read out by the β5-β7 region in their PI domains. The 3rd G in the 5'-NNGRRT-3' PAM is recognized by Arg1015 in SaCas9, and the 3rd G in the 5'-NGG-3' PAM is recognized by Arg1335 in SpCas9 and in a similar manner. However, there are also notable differences in the PI domains of SaCas9 and SpCas9, consistent with their distinct PAM specificities. Arg1333 of SpCas9, which recognizes the 2nd G in the NGG PAM, is replaced with Pro1013 in SaCas9. In addition, SpCas9 lacks amino acid residues equivalent to Asn985/Asn986 (β5) and Arg991 (β6) of SaCas9, because the β5-β6 region of SpCas9 is shorter than that of SaCas9. Moreover, Asn985, Asn986, Arg991 and Arg1015 in SaCas9 are replaced with Asp1030, Thr1031, Lys1034 and Lys1061 in AnCas9, respectively, suggesting that the PAM for AnCas9 is different from those for SaCas9 and SpCas9. Together, these structural findings demonstrated that distinct PAM specificities of Cas9 orthologs are primarily defined by their structurally diverse PI domains.

Structure-Guided Engineering of SaCas9 Transcription Activators and Inducible Nucleases Using the crystal structure of SaCas9, we conducted structure-guided engineering to further expand the CRISPR-Cas9 toolbox. Given the similarities in the overall domain organization of SaCas9 and SpCas9, we initially explored the feasibility of engineering the SaCas9 sgRNA to develop robust transcription activators. In the SpCas9 structure, the tetraloop and stem loop 2 of the sgRNA are exposed to solvent (Anders et al., 2014; Nishimasu et al., 2014) and permitted insertion of RNA aptamers into the sgRNA to create robust RNA-guided transcription activators (Konermann et al., 2015). To generate the SaCas9-based activator system, we created a catalytically inactive version of SaCas9 (dSaCas9) by introducing D10A and N580A mutations to inactivate the RuvC and HNH domains, respectively, and attached VP64 to the C-terminus of dSaCas9. The sgRNA scaffold was modified with the insertion of MS2 aptamer stem loop (MS2-SL) to allow recruitment of MS2-β65-HSF1 transcriptional activation modules. To evaluate the dSaCas9-based activator design, we constructed a transcriptional activation reporter system consisting of tandem sgRNA target sites upstream of a minimal CMV promoter driving the expression of the fluorescent reporter gene mKate2 (Zhang et al., 2011). We included an additional transcriptional termination signal upstream of the reporter cassette to reduce the background previously observed in a similar reporter design (Cong et al., 2012). We observed robust activation of mKate2 transcription when we expressed the engineered sgRNA complementary to the target sites, whereas the non-binding sgRNA had no detectable effect. Based on a screening of different sgRNA designs with this reporter assay, we found that insertions of MS2-SL into the tetraloop and putative stem loop 2 are able to induce strong activation in our reporter system, whereas insertion of MS2-SL into stem loop 1 yielded modest activation, consistent with the structural data. The single insertion of MS2-SL into the tetraloop was the simplest design that yielded strong transcriptional activation. Using this optimal sgRNA design, we further tested activation of endogenous targets in the human genome. We selected two guides each for the human ASCL1 and MYOD1 genomic loci, and demonstrated that the dSaCas9-based activator system was able to activate both genes to levels comparable to those of the dSpCas9-based activator (Konermann et al., 2013). Given that the sgRNAs for SaCas9 and SpCas9 are not interchangeable, the SaCas9-based transcription activator platform complement the SpCas9-based activator systems by allowing for independent activation of different sets of genes.

The SpCas9 structure also facilitated the rational design of split-Cas9s (Zetsche et al., 2015; Wright et al., 2015), which can be further engineered into an inducible system (Zetsche et al., 2015). Our SaCas9 structure reveals several flexible regions in SaCas9 that could likewise serve as potential split sites. We created three versions of a split-SaCas9, two of which showed robust cleavage activity at the endogenous EMX1 target locus. Using the best split design, we then tested inducible schemes based on the abscisic acid (ABA) sensing system (Liang et al., 2011) as well as two versions of the rapamycin-inducible FKBP/FRB system (Banaszynski et al., 2005). All three systems were able to support inducible SaCas9 cleavage activity, demonstrating the possibility of an inducible, split-SaCas9 design; however, further optimization will increase its efficiency and reduce its background activity.

In certain embodiments, the complex of nucleic acid binding domain with the guide resembles the complex of SaCas9 with crRNA and tracrRNA and/or the complex of SaCas9 with sgRNA. In an embodiment of the invention, the nucleic acid binding domain comprises residues which correspond with respect to binding of guide and target to amino acids of SaCas9 that interact with the guide and/or target. Such amino acids of SaCas9 that interact with guide and/or target include, without limitation, amino acids that interact with the portions of the guide such as stem loop 1, stem loop 2, phosphate lock loop, and/or the repeat:antirepeat duplex, as well as the guide:target heteroduplex. Each of the residues of the nucleic acid binding domain may interact with the guide and/or the guide:target heteroduplex through the amino acid backbone, side chain, or both. Where the interaction is by the amino backbone, there is greater freedom to vary the amino acid side chain at that position. Also, the residues of the nucleic acid binding domain may interact with the sugar-phosphate backbone or a base of the guide or guide:target heteroduplex. With respect to the guide:target heteroduplex, interactions with the sugar-phosphate backbone are preferred which allows for unrestricted sequence variation of the target sequence and the targeting sequence of the guide.

In an embodiment of the invention, the nucleic acid binding domain comprises amino binding residues which correspond to amino acids of SaCas9. In an embodiment of the invention, the nucleic acid binding domain comprises one or more of the following domains, whole or in part: RuvC, bridge helix, REC, WED, phosphate lock loop (PLL), and PI. In an embodiment of the invention, the nucleic acid binding domain comprises binding residues which correspond to all or a subset of the following amino acids of SaCas9: Asn47, Lys50, Arg54, Lys57, Arg58, Arg61, His62, His111, Lys114, Gly162, Val164, Arg165, Arg209, Glu213, Gly216, Ser219, Asn780, Arg781, Leu783, Leu788, Ser790, Arg792, Asn804, Lys867, Tyr868, Lys870, Lys878, Lys879, Lys881, Leu891, Tyr897, Arg901, and Lys906.

Of the amino acids above, SaCas9 amino acids that interact with the guide primarily through the SaCas9 amino acid backbone are Gly162, Val164, Arg165, Arg209, Gly216, Arg781, Leu788, Tyr868, Lys870, Lys878, Lys879, Lys881, and Arg901.

In an embodiment of the invention, the nucleic acid binding domain comprises binding residues which correspond to all or a subset of Asn44, Arg48, Arg51, Arg55, Arg59, Arg60, Arg116, Gly117, Arg165, Gly166, Arg208, Arg209, Tyr211, Thr238, Tyr239, Lys248, Tyr256, Arg314, and Asn394, of SaCas9, which interact with the sugar-phosphate backbone of the guide in the guide:target duplex. In an embodiment of the invention, the nucleic acid binding domain comprises binding residues which correspond to all or a subset of Tyr211, Trp229, Tyr230, Gly235, Arg245, Gly391, Thr392, Asn419, Leu446, Tyr651, and Arg654 of SaCas9, which interact with the sugar-phosphate backbone of the target in the guide:target duplex.

In an embodiment of the invention, the nucleic acid binding domain comprises binding residues which correspond to one or more of the amino acids of SaCas9 in the following table.

| SaCas9 amino acid | aa part interacting with nucleic acid | | Nucleic acid interaction | | Nucleic acid location | | Domain |
|---|---|---|---|---|---|---|---|
| | side chain | backbone | sugar-phosphate | base | guide | duplex or PAM | |
| Asn44 | x | | x | | | x | BH |
| Arg47 | x | | x | | x | | BH |
| Arg48 | x | | x | | | x | BH |
| Lys50 | x | | | x | x | | BH |
| Arg51 | x | | x | | | x | BH |
| Arg54 | x | | x | | x | | BH |
| Arg55 | x | | x | | | x | BH |
| Lys57 | x | | x | | x | | BH |
| Arg58 | x | | x | | x | | BH |
| Arg59 | x | | x | | | x | BH |
| Arg60 | x | | x | | | x | BH |
| Arg61 | x | | x | | x | | BH |
| His62 | x | | x | | | x | BH |
| His111 | x | | | | | x | REC |
| Lys114 | x | | | | | x | REC |
| Arg116 | x | | x | | | x | REC |
| Gly117 | | x | x | | | x | REC |
| Gly 162 | | x | | | x | | REC |
| Val164 | | x | | | x | | REC |
| Arg165 | x | x | | | x | x | REC |
| Gly166 | | x | x | | | x | REC |
| Arg208 | x | | x | | | x | REC |
| Arg209 | x | x | x | x | x | x | REC |
| Tyr211 | x | | x | | | x | REC |
| Glu213 | x | | | x | x | | REC |
| Gly216 | | x | x | | x | | REC |
| Ser219 | x | | x | | x | | REC |
| Trp229 | x | | x | | | x | REC |
| Tyr230 | x | | x | | | x | REC |
| Gly235 | x | | x | | | x | REC |
| Thr238 | x | | x | | | x | REC |
| Tyr239 | x | | x | | | x | REC |
| Arg245 | x | | x | | | x | REC |
| Lys248 | x | | x | | | x | REC |
| Tyr256 | x | | x | | | x | REC |
| Arg314 | x | | x | | | x | REC |
| Gly391 | x | | x | | | x | REC |
| Thr392 | x | | x | | | x | REC |
| Asn394 | x | | x | | | x | REC |
| Gln414 | x | | | x | | x | REC |
| Asn419 | x | | x | | | x | REC |
| Arg452 | x | | x | | | | RuvC |
| Lys459 | x | | x | | | | RuvC |
| Arg774 | x | | x | | | | RuvC |
| Leu446 | x | | x | | | x | RuvC |
| Tyr651 | x | | x | | | x | RuvC |
| Arg654 | x | | x | | | x | RuvC |
| Asn780 | x | | | x | x | | PLL |
| Arg781 | x | x | x | x | x | | PLL |
| Leu783 | x | | x | x | x | | PLL |
| Asp786 | | x | x | | | x | PLL |
| Thr787 | x | x | x | | | x | PLL |
| Leu788 | | x | x | | x | | WED |
| Tyr789 | x | | x | | | x | WED |

-continued

| SaCas9 amino acid | aa part interacting with nucleic acid | | Nucleic acid interaction | | Nucleic acid location | | Domain |
|---|---|---|---|---|---|---|---|
| | side chain | backbone | sugar-phosphate | base | guide | duplex or PAM | |
| Ser790 | x | | x | | x | | WED |
| Arg792 | x | | x | | x | | WED |
| Asn804 | x | | x | | x | | WED |
| Lys867 | x | | | x | x | | WED |
| Tyr868 | | x | x | | x | | WED |
| Lys870 | | x | x | | x | | WED |
| Lys878 | | x | x | | x | | WED |
| Lys879 | | x | x | | x | | WED |
| Lys881 | | x | x | | x | | WED |
| Tyr882 | x | | x | | | x | WED |
| Lys886 | | x | x | | | x | WED |
| Leu891 | x | | x | | x | | WED |
| Tyr897 | x | | | x | x | | WED |
| Arg901 | | x | x | | x | | WED |
| Lys906 | x | | x | | x | | WED |
| Asn985 | x | | | x | | x | PI |
| Asn986 | x | | | x | | x | PI |
| Arg991 | x | | | x | | x | PI |
| Arg1015 | x | | | x | | x | PI |

In an embodiment, the nucleic acid binding domain comprises a truncation as to all or part of the NUC lobe of SaCas9. In an embodiment, the nucleic acid binding domain comprises a truncation as to one or more of the RuvCI, RuvC II, RuvC III, HNH, WED, and PI domains of SaCas9. In an embodiment the nucleic acid binding domain comprises a truncation as to all or part of residues 220-422 of the REC domain, residues 520-629 of the HNH domain, residues 630-649 of the L2 domain, and/or residues 650-775 of the RuvCIII domain. In certain embodiments, the SaCas9 portions remaining may be linked directly or through a linker, including but not limited to a GGG linker, a GGS linker, or a (GGGGS)$_n$ (SEQ ID NO: 10) linker.

Cpf1 is an RNA-guided nuclease from the microbial CRISPR-Cas system that can be targeted to specific genomic loci by crRNAs. Cpf1 consists of two lobes, a recognition (REC) lobe and a nuclease (NUC) lobe. AsCpf1 amino acids are generally assigned to portions of AsCpf1 as indicated as described in Table 1. See, e.g., International Application PCT/US2017/014568. The REC lobe can be divided into two domains, the REC1 and REC2 domains. The NUC lobe consists of the RuvC (residues 884-939, 957-1065, and 1262-1307), NUC (residues 1066-1261), PAM-interacting (PI) (residues 598-718) domains, and WED (residues 1-23, 526-597, and 719-883). The negatively-charged crRNA-DNA hybrid duplex is accommodated in a positively-charged groove at the interface between the REC and NUC lobes. In the NUC lobe, the RuvC domain is assembled from the three split RuvC motifs (RuvC I-III), which interfaces with the PI domain to form a positively-charged surface that interacts with the 3' tail of the crRNA. The $2^{nd}$ nuclease domain lies in between the RuvC II III motifs and forms only a few contacts with the rest of the protein.

The following amino acid positions of interest are identified based on the overall structure:

| AsCpf1 amino acid interactions | | | |
|---|---|---|---|
| Residue Number (in AsCpf1) | Domain | Possible Role | Effect of mutation |
| D861 | Interdoma in region | RNA Binding (not directly) | Substitution may disrupt RNA binding. Potentially required for cleaving pre-crRNA during crRNA maturation. |
| R862 | Interdoma in region | RNA Binding (not directly) | Substitution may disrupt RNA binding. |
| R863 | Interdoma in region | RNA Binding (packing) | Substitution may disrupt RNA binding. |
| W382 | Rec2 but needs confirmation | DNA/RNA binding (ring-stacking between W sidechain and DNA/RNA bases) | Substitution may disrupt DNA/RNA binding. May be involved in positioning DNA/RNA for cut(s). Reduced activity. |
| E993 | RuvC | | Inactivating |
| D1263 | RuvC | | Reduced activity |
| D980 | RuvC | | Inactivating |
| W958 | Interface of BH-like and Rec2 | Stabilize bridge domain hydrophobic interaction with REC2 | Substitution may disrupt protein stability. Reduced activity. |
| K968 | RuvC | DNA binding (H-bonding) and interhelix packing in RuvC | Substitution may disrupt DNA binding and protein stability |
| R951 | BH-like | DNA binding (packing against DNA and positive charge; stabilize bridge domain from H bonds within bridge domain | Substitution may disrupt DNA binding; maybe destabilize bridge domain. Reduced activity |
| R1226 | $2^{nd}$ Nuclease (if present) | Cleavage (structural role is electrostatic interaction between RuvC and $2^{nd}$ nuclease) | Disrupt protein stability. Reduced activity Nickase |
| S1228 | $2^{nd}$ Nuclease (if present) | Cleavage (surface exposed) | Affect solubility No direct effect on activity |

-continued

| AsCpf1 amino acid interactions ||||
| Residue Number (in AsCpf1) | Domain | Possible Role | Effect of mutation |
| --- | --- | --- | --- |
| D1235 | 2nd Nuclease (if present) | Cleavage (H-bonds with R1226 side chain) | Disrupt protein stability. Reduced activity |
| K548 | PI | PAM Interaction (H-bond with DNA) | Reduce/remove TTT specificity Reduced activity with some guides. |
| M604 | PI | PAM Interaction | Reduced activity |
| K607 | PI | PAM Interaction (positive charge between O of PAM-T and DNA sugar O) | Reduce/remove TTT specificity Reduced activity Reduced PAM recognition |
| T167 | PI | PAM Interaction (VDW and H-bond with DNA) | Conservative change, but would lose the stability from VDW between DNA-T in PAM and T167-Cγ Reduced activity with certain guides |
| N631 | PI | Surface exposed | Affect DNA specificity |
| N630 | PI | Surface exposed | Affect specificity |
| NK547 | PI | H-bonds with K689 in adjacent beta-strand | Disrupt PI domain stability |
| DK163 | PI | Solvent exposed; sidechain not modeled | Attachment site |
| Q571 | PI | Solvent exposed; in loop | Attachment site |
| K1017 | RuvC | May contribute positive charge to DNA-binding or contact target strand at certain point in reaction | disrupt DNA binding |
| R955 | BH | Contacts Target DNA strand; H-bonds bases in DNA/RNA groove; positive charge | Disrupt DNA/RNA binding |
| K1009 | RuvC | Contacts Non-Target DNA strand; solvent exposed in current structure | Lack of positive charge may disrupt DNA binding; affect specificity |
| R909 | RuvC | Contacts Non-Target DNA strand; solvent exposed in current structure | Lack of positive charge may disrupt DNA binding of non-target strand; affect specificity |
| R912 | RuvC | Contacts Non-Target DNA strand; H-bonds within RuvC and provides positive charge to solvent | Lack of positive charge may disrupt DNA binding of non-target strand |
| R1072 | 2nd nuclease (if present) | Contacts Non-Target DNA strand; solvent exposed in current structure | Lack of positive charge may disrupt DNA binding of non-target strand; affect specificity |
| R1226 | 2nd nuclease (if present) | Contacts Non-Target DNA strand; electrostatic interaction with E911 of RuvC | Disrupt protein stability Reduced activity Nickase |
| 1189-1197 | 2nd nuc (if present) | Activator fusion region | |
| 1200-1208 | 2nd nuc (if present) | | |
| E372 | Cap domain; Rec2 | RNA-binding | May disrupt RNA-binding/activity |
| 398-400 | cap domain; Rec2 | Exposed | |
| 380-383-> AAAA | cap domain; Rec2 | Ring stacking with DNA/RNA bases | Disrupt DNA/RNA binding; interesting plow domain |
| 362-420-> AAAA | cap domain; Rec2 | | |
| K15 | RNA loop; RuvC/ID region | Electrostatic interaction with RNA | knockout RNA binding/processing |
| K810 | RNA loop; Ins | Supplies positive charge near RNA loop | |

| AsCpf1 amino acid interactions | | | |
|---|---|---|---|
| Residue Number (in AsCpf1) | Domain | Possible Role | Effect of mutation |
| H755 | RNA loop; ID region | Binds RNA | |
| K557 | RNA loop; WED | Distant from RNA; part of WED core | |
| E857 | RNA loop | | |
| K943 | RNA loop | | |
| K1022 | RNA loop | | |
| K1029 | RNA loop | | |
| K942 | "BH" | Solvent exposed; | Attachment site |
| K949 | "BH" | Solvent exposed; | Attachment site |
| P1163-1173 | 2nd nuc (if present) | "helicase" Hairpin, hypothesized to direct DNA or RNA strands | Affect DNA/RNA binding |
| A1230-1233 | 2nd nuc (if present) | | Affect activity |
| T1152-D1148 | 2nd nuc (if present) | | Affect activity |
| 1076-1249-> GGG | 2nd nuc (if present) | | Affect activity |
| R84 | Inner positive charges | | Affect activity/specificity |
| K87 | | | |
| K200 | | | |
| H206 | | | |
| R210 | | | |
| R301 | | | |
| R699 | | | |
| K705 | | | |
| K887 | | | |
| R891 | | | |
| K942 | | | |
| K949 | | | |
| K1086 | | | |
| K1089 | | | |
| R1094 | | | |
| R1127 | | | |
| R1220 | | | |
| Q1224A 995-1005-> GGGGG | Inner positive charges | | |
| N178 | Conserved N | | Affect stability/activity |
| N197 | | | Affect stability/activity |
| N204 | | | Affect stability/activity |
| N259 | | | Affect stability/activity |
| N278 | | | Affect stability/activity |
| N282 | | | Affect stability/activity |
| N519 | | | Affect stability/activity |
| N747 | | | Affect stability/activity |
| N759 | | | Affect stability/activity |
| N878 | | | Affect stability/activity |
| N889 | | | Affect stability/activity |
| T167S | | PAM recognition | Relax PAM specificity to TTN; preserve cleavage efficiency |
| R176A | REC1 | heteroduplex recognition | Reduced activity |
| R192A | REC1 | heteroduplex recognition | Reduced activity |
| D749A | WED | pre-crRNA processing | |
| H761A | WED | pre-crRNA processing | |
| G783P | WED | heteroduplex recognition | Reduced activity |
| H872A | WED | pre-crRNA processing | |

As discussed, AsCpf1 adopts a bilobed architecture consisting of an α-helical recognition (REC) lobe and a nuclease (NUC) lobe, with the crRNA-target DNA heteroduplex bound to the positively charged, central channel between the two lobes. The REC lobe consists of REC1 and REC2 domains, whereas the NUC lobe consists of the RuvC domain and three additional domains, denoted A, B and C.

The REC1 domain comprises 14 α helices, while the REC2 domain comprises 9 α helices and 2 β strands that form a small antiparallel sheet. Domains A and B appear to play functional roles similar to those of the WED (Wedge) and PI (PAM-interacting) domains of Cas9, respectively, although the two domains of AsCpf1 are structurally unrelated to the WED and PI domains (described below). Domain C appears to be involved in DNA cleavage (described below). Thus, domains A, B and C are referred to as the WED, PI and Nuc domains, respectively. The WED domain is assembled from three separate regions (WED-I-III) in the Cpf1 sequence The WED domain can be divided into a core subdomain comprising a 9-stranded, distorted antiparallel β sheet (β1-β8 and β13) flanked by 7 α helices (α1-α6 and α9), and a subdomain comprising 4 β strands (β9-β12) and 2 α helices (α7 and α8).

Examination of the Cpf1 sequence alignment revealed that helices α7 and α8 are not conserved among Cpf1 homologs. The PI domain comprises 7 α helices (α1-α7) and a β hairpin (β1 and β2), and is inserted between the WED-II and WED-III regions, whereas the REC lobe is inserted between the WED-I and WED-II regions.

The RuvC domain contains the three motifs (RuvC-I-III), which form the endonuclease active center. A characteristic helix (referred to as the bridge helix) is located between the RuvC-I and RuvC-II motifs, and connects the REC and NUC lobes (described below). The Nuc domain is inserted between the RuvC-II and RuvC-III motifs.

Structure of the Cpf1 crRNA and Target DNA

The crRNA consists of the 24-nt guide segment (G1-C24) and the 19-nt scaffold (A(−19)-U(−1)) (referred to as the 5'-handle). The nucleotides G1-C20 in the crRNA and the nucleotides dC1-dG20 in the target DNA strand form the 20-bp RNA-DNA heteroduplex. The nucleotide A21 in the crRNA is flipped out and adopts a single-stranded conformation. No electron density was observed for the nucleotides A22-C24 in the crRNA and the nucleotides dT21-dG24 in the target DNA strand, suggesting that these regions are flexible and disordered in the crystal structure. The nucleotides dG(−10)-dT(−1) in the target DNA strand and the nucleotides dC(−10*)-dA(−1*) in the non-target DNA strand form a duplex structure (referred to as the PAM duplex).

The crRNA 5'-handle adopts a pseudoknot structure rather than a simple stem-loop structure predicted from its nucleotide sequence. Specifically, the G(−6)-A(−2) and U(−15)-C(−11) in the 5'-handle form a stem structure, via five Watson-Crick base pairs (G(−6):C(−11)-A(−2):U(−15)), whereas C(−9)-U(−7) in the 5'-handle adopt a loop structure. U(−1) and U(−16) form a non-canonical U•U base pair. U(−10) and A(−18) form a reverse Hoogsteen A•U base pair, and participate in pseudoknot formation. The O4 and the 2'-OH of U(−10) hydrogen bond with the 2'-OH and the N1 of A(−19), respectively. In addition, the N3 and the O4 of U(−17) hydrogen bond with the O4 of U(−13) and the N6 of A(−12), respectively, thereby stabilizing the pseudoknot structure. Importantly, U(−1), U(−10), U(−16) and A(−18) in the crRNA are conserved among the CRISPR-Cpf1 systems, indicating that Cpf1 crRNAs form similar pseudoknot structures.

Recognition of the 5'-Handle of the crRNA

The 5'-handle of the crRNA is bound at the groove between the WED and RuvC domains. The U(−1)•U(−16) base pair in the 5'-handle is recognized by the WED domain in a base-specific manner. U(−1) and U(−16) hydrogen bond with His761 and Arg18/Asn759, respectively, while U(−1) stacks on His761. These interactions explain the previous finding that the U•U base pair at this position is critical for the Cpf1-mediated DNA cleavage. The N6 of A(−19) hydrogen bonds with Leu807 and Asn808, while the base moieties of A(−18) and A(−19) form stacking interactions with Ile858 and Met806, respectively. Moreover, the phosphodiester backbone of the 5'-handle forms an extensive network of interactions with the WED and RuvC domains. The residues involved in the crRNA 5'-handle recognition are largely conserved in the Cpf1 protein family, highlighting the functional relevance of the observed interactions between AsCpf1 and the crRNA.

Recognition of the crRNA-Target DNA Heteroduplex

The crRNA-target DNA heteroduplex is accommodated within the positively charged, central channel formed by the REC1, REC2 and RuvC domains, and is recognized by the protein in a sequence-independent manner. The PAM-distal and PAM-proximal regions of the heteroduplex are recognized by the REC1-REC2 domains and the WED-REC1-RuvC domains, respectively. Arg951 and Arg955 in the bridge helix and Lys968 in the RuvC domain, which interact with the phosphate backbone of the target DNA strand, are conserved among the Cpf1 family members. Notably, the sugar-phosphate backbone of the nucleotides G1-A8 in the crRNA forms multiple contacts with the WED and REC1 domains, and the base pairing within the 5-bp PAM-proximal, "seed" region is important for Cpf1-mediated DNA cleavage. These observations suggest that, in the Cpf1-crRNA complex, the seed of the crRNA guide is preordered in a nearly A-form conformation and serves as the nucleation site for pairing with the target DNA strand, as observed in the Cas9-sgRNA complex. In addition, the backbone phosphate group between dT(−1) and dC1 of the target DNA strand (referred to as +1 phosphate) is recognized by the side chain of Lys780 and the main-chain amide group of Gly783. This interaction results in the rotation of the +1 phosphate group, thereby facilitating base paring between dC1 in the target DNA strand and G1 in the crRNA, as also observed in the Cas9-sgRNA-target DNA complexes. These residues involved in the heteroduplex recognition are conserved in most members of the Cpf1 family, and the R176A, R192A, G783P and R951A mutants exhibited reduced activities, confirming the functional relevance of these residues. Together, these observations reveal the RNA-guided DNA recognition mechanism of Cpf1.

The structure of the AsCpf1-crRNA-target DNA complex provides mechanistic insights into the RNA-guided DNA cleavage by Cpf1. Structural comparison between Cpf1 and Cas9, so far the only available structures of class 2 (single protein) effectors, illuminates a degree of similarity in their overall architectures even though the proteins lack sequence similarity outside the RuvC domain. Both effector proteins are of roughly the same size and adopt distinct bilobed structures, in which the two lobes are connected by the characteristic bridge helix and the crRNA-target DNA heteroduplex is accommodated in the central channel between the two lobes. However, despite this similarity, only the RuvC nuclease domains of Cas9 and Cpf1 are homologous, whereas the rest of the proteins share neither sequence nor structural similarity.

One of the striking features of the Cas9 structure is the nested arrangement of the two unrelated, HNH and RuvC nuclease domains, which cleave the target and non-target DNA strands, respectively. In Cas9, the HNH domains is inserted between strand β4 and helix α1 of the RNase H fold in the RuvC domain. In contrast, Cpf1 lacks the HNH domain and instead contains an unrelated, novel domain which is inserted at the different position (albeit also between RuvC-II and RuvC-III motifs), i.e. between strand 35 and helix α3 of the RNase H fold. The data indicated that, analogous to the HNH domain of Cas9, the novel domain of Cpf1 cleaves the target DNA strand—hence the designation Nuc domain. Notably, the Nuc domain of Cpf1 is located at a position suitable to cleave the single-stranded region of the target DNA strand outside the heteroduplex, whereas the HNH domain of Cas9 cleaves the target DNA strand within the heteroduplex. These structural differences can also explain why Cpf1 induces a staggered DNA double-strand break in the PAM-distal site, whereas Cas9 creates a blunt end in the PAM-proximal site. In addition, one conserved polar residue of this domain (Arg1226 in AsCpf1) was shown to be essential for DNA cleavage and an active RuvC domain is required for cleavage of both DNA strands.

Structural comparison between Cpf1 and Cas9 reveals a striking degree of apparent structural and functional convergence between Cpf1 and Cas9. Intriguingly, Cpf1 and Cas9 employ distinct structural features to recognize the seed region in the crRNA and the +1 phosphate group in the target DNA, thereby achieving RNA-guided DNA targeting. In Cas9, the seed region is anchored by an arginine cluster in the bridge helix between the RuvC and REC domains, whereas the +1 phosphate group is recognized by the "phosphate lock" loop between the RuvC and WED domains. In contrast, in Cpf1, the seed region is anchored by the WED and REC domains, whereas the +1 phosphate group is recognized by the WED domain.

The AsCpf1 structure also shows notable differences in the PAM recognition mechanism between Cpf1 and Cas9. In Cas9, the PAM nucleotides in the non-target DNA strand are primarily read out from the major groove side, via hydrogen-bonding interactions with specific residues in the PI domain. In *Streptococcus pyogenes* Cas9, the 2nd G and 3rd G in the 5'-NGG-3' PAM are recognized by Arg1333 and Arg1335 in the PI domain, via bidentate hydrogen bonds, respectively. In contrast, in AsCpf1, the PAM nucleotides in both the target and non-target DNA strands are read out by the PI domain from both the minor and major groove sides. In particular, as observed in other protein-DNA complexes, the conserved lysine residue (Lys607 in AsCpf1) in the PI domain is inserted into the narrow minor groove of the PAM duplex, and plays critical roles in the PAM recognition. These structural observations show that, whereas Cas9 recognizes the PAM primarily via a base readout mechanism, Cpf1 combines base and shape readout to recognize the PAM. These mechanistic differences in the PAM recognition can explain why, whereas Cas9 orthologs recognize G-rich, diverse PAM sequences, widely different members of the Cpf1 family recognize similar T-rich PAMs.

In certain embodiments, the complex of nucleic acid binding domain with the guide resembles the complex of AsCpf1 with guide RNA. In an embodiment of the invention, the nucleic acid binding domain comprises residues which correspond with respect to binding of guide and target to amino acids of AsCpf1 that interact with the guide and/or target. Such amino acids of AsCpf1 that interact with guide and/or target include, without limitation, amino acids that interact with the portions of the guide such as the 5' handle and/or the guide:target heteroduplex. Each of the residues of the nucleic acid binding domain may interact with the guide and/or the guide:target heteroduplex through the amino acid backbone, side chain, or both. Where the interaction is by the amino backbone, there is greater freedom to vary the amino acid side chain at that position. Also, the residues of the nucleic acid binding domain may interact with the sugar-phosphate backbone or a base of the guide or guide:target heteroduplex. With respect to the guide:target heteroduplex, interactions with the sugar-phosphate backbone are preferred which allows for unrestricted sequence variation of the target sequence and the targeting sequence of the guide.

In an embodiment of the invention, the nucleic acid binding domain comprises amino binding residues which correspond to amino acids of AsCpf1. In an embodiment of the invention, the nucleic acid binding domain comprises one or more of the following domains, whole or in part: WED, REC1, REC2, PI, bridge helix, and RuvC. In an embodiment of the invention, the nucleic acid binding domain comprises binding residues which correspond to all or a subset of the following amino acids of AsCpf1 which interact with the guide: Lys15, Arg18, Lys748, Gly753, His755, Gly756, Lys757, Asn759, His761, Arg790, Met806, Leu807, Asn808, Lys809, Lys810, Lys852, His856, Ile858, Arg863, Tyr940, Lys943, Asp966, His977, Lys1022 and Lys1029.

Of the amino acids above, SaCas9 amino acids that interact with the guide primarily through the AsCpf1 amino acid backbone are Gly753, His755, Gly756, Lys757, His761, Leu807, Lys809, Lys810, and Asp966.

In an embodiment of the invention, the nucleic acid binding domain comprises binding residues which correspond to all or a subset Tyr47, Lys51, Arg176, Arg192, Gly270, Gln286, Lys273, Lys307, Leu310, Lys369, Lys414, His 479, Asn515, Arg518, Lys530, Glu786, His872, Arg955, and Gln956, of AsCpf1, which interact with the sugar-phosphate backbone of the guide in the guide:target duplex. In an embodiment of the invention, the nucleic acid binding domain comprises binding residues which correspond to all or a subset of Asn178, Ser186, Asn278, Arg301, Thr315, Ser376, Lys524, Lys603, Lys780, Gly783, Gln784, Arg951, Ile964, Lys965, Gnl1014, Phe1052, and Ala1053 of AsCpf1, which interact with the sugar-phosphate backbone of the target in the guide:target duplex.

In an embodiment of the invention, the nucleic acid binding domain comprises binding residues which correspond to one or more of the amino acids of AsCpf1 in the following table.

AsCpf1 aa part interacting Nucleic acid Nucleic acid location Domain Amino acid with nucleic acid interaction

| AsCpf1 Amino acid | aa part interacting with nucleic acid | | Nucleic acid interaction | | Nucleic acid location guide-target duplex or PAM | Domain |
|---|---|---|---|---|---|---|
| | side chain | backbone | sugar-phosphate | base | guide | |
| Lys15 | x | | x | | x | WED |
| Thr16 | x | | | x | x | WED |
| Arg18 | x | | | x | x | WED |
| Tyr47 | x | | x | | x | REC1 |
| Lys51 | x | | x | | x | REC1 |
| Gly270 | | x | x | | x | REC1 |
| Asn175 | x | | | x | x | REC1 |
| Arg176 | x | | x | | x | REC1 |
| Asn178 | x | | x | | x | REC1 |
| Ser186 | x | x | x | | x | REC1 |
| Arg192 | x | | x | | x | REC1 |
| Lys273 | | x | x | | x | REC1 |
| Asn278 | x | | x | | x | REC1 |
| Asn282 | x | | | x | x | REC1 |
| Gln286 | x | | x | x | x | REC1 |
| Lys307 | x | x | x | | x | REC1 |
| Leu310 | x | | x | | x | REC1 |
| Thr315 | x | | x | | x | REC1 |
| Ser376 | x | | x | | x | REC1 |
| Lys369 | x | | x | | x | REC2 |
| Trp382 | x | | | x | x | REC2 |
| His479 | x | | x | | x | REC2 |
| Asn515 | x | | x | | x | REC2 |
| Arg518 | x | | x | | x | REC2 |
| Lys524 | | x | x | | x | REC2 |
| Lys530 | x | | x | | x | WED |
| Lys603 | x | | x | | x | PI |
| Lys748 | x | | x | x | | WED |
| Gly753 | | x | x | x | | WED |
| His755 | | x | x | x | | WED |
| Gly756 | | x | x | x | | WED |

-continued

| AsCpf1 Amino acid | aa part interacting with nucleic acid | | Nucleic acid interaction | | Nucleic acid location | | Domain |
|---|---|---|---|---|---|---|---|
| | side chain | backbone | sugar-phosphate | base | guide | guide-target duplex or PAM | |
| Lys757 | | x | x | | x | | WED |
| Asn759 | x | | | x | x | | WED |
| His761 | x | x | | | x | x | WED |
| Lys780 | x | | x | | | x | WED |
| Gly783 | | x | | | | x | WED |
| Gln784 | x | | x | | | x | WED |
| Glu786 | x | | x | | | x | WED |
| Arg790 | x | | x | | x | | WED |
| Met806 | x | | x | x | x | | WED |
| Leu807 | | x | | x | x | | WED |
| Asn808 | x | | x | x | x | | WED |
| Lys809 | | x | x | | x | | WED |
| Lya810 | | x | x | | x | | WED |
| Lys852 | x | | x | | x | | WED |
| His856 | x | | x | x | x | | WED |
| Ile858 | x | | | x | x | | WED |
| Arg863 | x | x | x | | x | | WED |
| His872 | x | | x | | | x | WED |
| Tyr940 | | x | x | | x | | BH |
| Lys943 | | x | x | | x | | BH |
| Arg951 | x | | x | | | x | BH |
| Arg955 | x | | x | | | x | BH |
| Gln956 | x | | x | | | x | BH |
| Ile964 | | x | x | | | x | BH |
| Lys965 | | x | x | | | x | RuvC |
| Asp966 | | x | x | | x | | BH |
| His977 | x | | x | | x | | RuvC |
| Gln1014 | x | | x | | | x | RuvC |
| Lys1022 | x | | x | | x | | RuvC |
| Lys1029 | x | | x | | x | | RuvC |

In an embodiment, the nucleic acid binding domain comprises a truncation as to all or part of the NUC lobe of AsCpf1. In an embodiment, the nucleic acid binding domain comprises a truncation as to one or more of the RuvCI, RuvC II, RuvC III, HNH and PI domains of Cpf1. In an embodiment, the nucleic acid binding domain comprises a truncation as to all or part of the REC2 domain (residues 320-526) of AsCpf1. In an embodiment, the nucleic acid binding domain comprises a truncation as to all or part of HNH domain (residues 775-908) and/or the RuvCIII domain (residues 909-1098). In an embodiment, the nucleic acid binding domain comprises a truncation as to the NUC domain (residues 1066-1261), the RuvC-II (residues 957-1065), and/or the RuvC-III domain (residues 1262-1307). In certain embodiments, the SpCas9 portions remaining may be linked directly or through a linker, including but not limited to a GGG linker, a GGS linker, or a (GGGGS)$_n$ (SEQ ID NO: 10) linker.

In certain embodiments, a nucleic acid binding domain is linked to one or more effector domains. In certain embodiments, the linkage is a covalent linkage. In certain embodiments, the linkage comprises members of a specific binding pair. In certain embodiments, the linkage comprises an inducible linkage. In certain embodiments the nucleic acid binding domain is associated with an effector domain through binding of the guide. For example, the effector domain can be covalently linked to the guide, attached to the guide through members of a specific binding pair, or by an inducible linkage. In certain embodiments, the effector domain is comprised in the DNA binding protein, for example where the DNA binding domain binds to a nucleic acid and by binding to the nucleic acid blocks transcription, or where the DNA binding domain is designed to interact with components of transcription or translation machinery.

Effector Domain

In certain embodiments, a nucleic acid binding domain is linked to one or more effector domains. Effector domains include, without limitation, a transcriptional activator, a transcriptional repressor, a recombinase, a transposase, a histone remodeler, a demethylase, a DNA methyltransferase, a cryptochrome, a light inducible/controllable domain, a chemically inducible/controllable domain, an epigenetic modifying domain, or a combination thereof. Effector domains further provide activities, such as locating proteins of the invention, non-limiting examples including cellular permeability enhancers or cell penetrating peptides, nuclear localization signals, nuclear export signals, capsid proteins, cell surface recognition such as ligands of cell surface receptors, and the like.

When there is more than one effector domain, the linkage to each binding domain can be the same or different. For example, in one non-limiting embodiment, a first linkage is covalent and a second linkage is inducible. In another non-limiting embodiment, a first linkage is covalent while a second linkage is covalent and cleavable. To illustrate, a first linkage can be, for example, to a cell penetrating peptide which is cleaved or otherwise dissociates from the nucleic acid binding domain upon or after entry into a cell wherein a second effector domain such as a NLS directs the protein to the cell nucleus.

In an embodiment the nucleic acid binding domain and the effector domain are linked by a cleavable or biodegradable linker.

In an embodiment, the one or more effector domains comprise a nuclease. In an embodiment, the one or more effector domain comprises a small molecule capable of inducing single- or double-stranded breaks.

In an embodiment, the one or more effector domains comprise one or more nuclear localization signals (NLSs). In an embodiment, the one or more effector domains comprise a cellular permeability enhancer. In an embodiment, the one or more effector domains comprises a recombination template.

In one aspect, the invention provides an engineered, non-naturally occurring nucleic acid modifying system, comprising: (a) an engineered, non-naturally occurring CRISPR/Cas protein; (b) a guide nucleic acid, wherein the guide nucleic acid directs sequence specific binding of the CRISPR/Cas protein to a target nucleic acid; and (c) one or more effector components, wherein the one or more effector components facilitate DNA repair by HDR.

In another aspect, the invention provides a method of precise genome editing in a cell or tissue, comprising delivering the nucleic acid modifying system to the cell or tissue.

Local Inhibition of NHEJ and Activation of HDR

The invention provides improving HDR to accompany targeted cleavage of nucleic acids. Improvements in HDR can be accomplished by inhibition of NHEJ, enhancement of HDR, or both.

Figure 2:
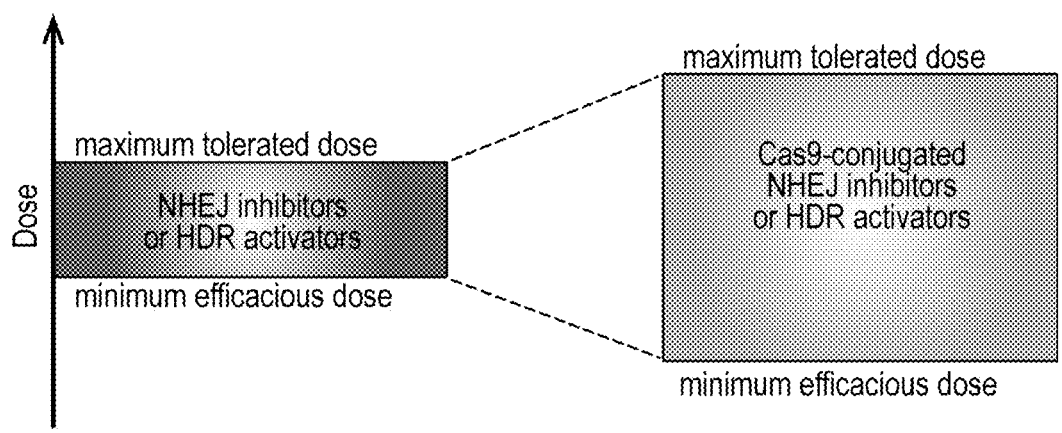
FIG. 2 is a diagram depicting that targeted delivery of NHEJ inhibitors or HDR activators to a DNA strand break site by conjugating them to a nucleic acid reader will improve the HDR efficiency by lowering the minimum efficacious dose and increasing the maximum tolerated a dose of the inhibitors and activators.
Figure 3A:
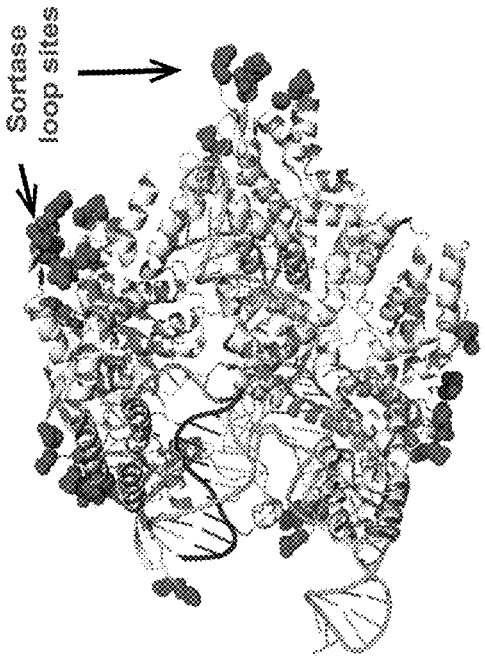
FIG. 3A is a diagram demonstrating sortase-mediated labeling of Cas9.

Several small molecule inhibitors of NHEJ pathway have been identified and their application to cells have modestly enhanced HDR. Similarly, multiple HDR activators increase HDR efficiency. However, the on-target toxicity of global NHEJ inhibition or global HDR activation in a cell severely limits the utility of such approaches. Ideally, NHEJ inhibition or HDR activation locally near the site of, e.g., a Cas9 mediated double strand break is more efficient and safe (FIG. 2). Such a targeted approach lowers the minimum efficacious dose of the inhibitors or activators and increases the maximum tolerated dose of the inhibitors or activators.
Sortase-Mediated Ligation A method to inhibit NHEJ and activate HDR locally comprises linking an inhibitor of NHEJ and/or an activator of HDR to a nucleic acid targeting moiety. For example, a Cas9 nuclease can be engineered to accommodate a single or multiple sortase recognition sequences (Leu-Pro-Xxx-Thr-Gly (SEQ ID NO: 1)), where Xxx is any amino acid) at which position effector moieties can be linked. Sortase is a transpeptidase that cleaves its recognition sequence between Thr-Gly and ligates an acceptor peptide containing an N-terminal glycine to the newly formed Thr carboxylate (FIG. 3A). Engineering sortase recognition sequences onto Cas9 or other nucleic acid-targeting moiety allows site-specific conjugation of any chemical payload. Insertion sites can be regions previously validated as cut sites for split Cas9, particularly those for which the N and C fragments have been shown to have a high affinity for each other.

One way to validate insertion sites in Cas9 or other nucleic acid-targeting moiety as to tolerance to modification is by sortase-mediated ligation of the model substrate Gly-Gly-Gly-Lys(Biotin) (SEQ ID NO: 2). The biotin handle allows efficient detection of Cas9 modification by immunoblotting and facilitates enrichment of labeled protein through affinity purification with anti-biotin or streptavidin. Cas9 activity has been validated using an EGFP based screening assay, wherein a U2OS.EGFP cell line is exposed to Cas9 containing a guide RNA sequence targeting EGFP, leading to loss of EGFP fluorescence. Active biotin-ligated Cas9 proteins can be validated for in vivo efficacy. Using the positively charged transfection agent, such as RNAiMAX, biotin-ligated Cas9-sgRNA ribonucleoproteins can be transfected into U2OS.EGFP cell lines, comparing the loss of GFP fluorescence to the introduction of wtCas9.

Sortase-mediated ligation allows attachment to the surface of Cas9 or other nucleic acid targeting moiety many non-native chemicals that can enhance the activity and modulate the effects of Cas9. A particularly powerful example of this is in the local modulation of the NHEJ/HDR pathway in cells. Methods for inhibiting NHEJ to boost HDR are typically achieved through gene knockout of key NHEJ components such as DNA ligase IV, KU70, or KU80. Small molecule inhibitors of DNA ligase IV (SCR7; herein compound 1.21, also known as SCR7-G) have been described, but their cellular toxicity prohibits use at high concentration and may interfere with global, Cas9-independent DNA repair. Instead, Cas9-SortLoop proteins are used as a scaffold for multivalent display of NHEJ-inhibited compounds to control the spatial reach of their effects, enabling local enhancement of HDR.

Figure 4A:
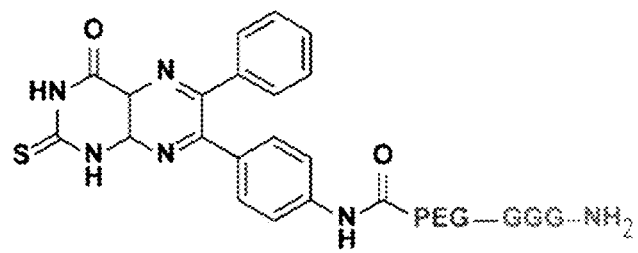
FIG. 4A is a diagram depicting conjugate of SCR7.
Figure 4B:
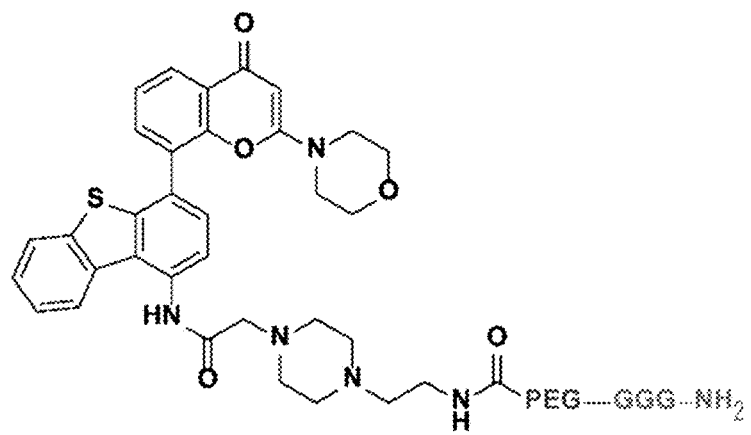
FIG. 4B is a diagram depicting conjugate of KU inhibitor.

In an embodiment of the invention, small molecule inhibitors of NHEJ are linked to a poly-glycine tripeptide through PEG for sortase-mediated ligation (FIG. 4). Based on the reported structure-activity relationship of NHEJ inhibitor L189, SCR7 (structure as reported by Srivastava), and SCR7-G, rings 1, 2, and 3 are involved in the target-engagement while the presence of ring 4 increases the hindrance and thus helps to block the ligase more efficiently. Conjugation of a poly-glycine peptide with the para-carboxylic moiety in the ring 4 will retain activity. This method provides a simple and effective strategy to ligate Cas9 with NHEJ inhibitors to precisely enhance HDR pathway near the Cas9 target site while keeping the global DNA repair unaffected. In an embodiment of the invention, nucleic acid targeting moiety conjugates based on small molecule inhibitor of DNA-dependent protein kinase (DNA-PK) or heterodimeric Ku (KU70/KU80). KU-0060648 is one of the most potent KU-inhibitors, which can also be functionalized with poly-glycine and used for Cas9-functionalization.

Increasing local NHEJ inhibitor molarity is also effective in vivo. For example, Cas9-NHEJ inhibitor can be complexed with sgRNA and delivered into appropriate patient-derived cells. The following table provides an exemplary list of mutations that can be rectified.

TABLE 1

Exemplary list of mutations to rectify

| PKD type | Harris ID/ Coriell ID | Gene | Exon | Mutation | Mutation call |
|---|---|---|---|---|---|
| Dominant | OX3502/- | PKD1 | 1 | C39Y | Highly likely pathogenic |
| Dominant | OX3504/- | PKD1 | 15 | E1929X | Definitely pathogenic |
| Recessive | OX3688 | PKHD1 | 3 | T36M | Definitely pathogenic |

The extent of HDR can be quantified using next-generation sequencing and data analysis platform that have been used previously.

Figure 4C:
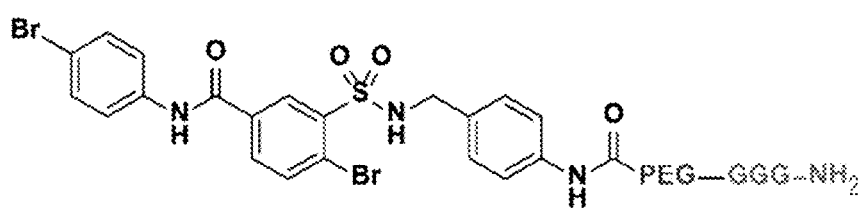
FIG. 4C is a diagram depicting conjugate of RS1.

In an embodiment, the same approach can be utilized to local enhance HDR without NHEJ inhibition. RAD51 is a protein involved in strand exchange and the search for homology regions during HDR repair. The phenylbenzamide RS1, discovered by high-throughput screening against a 10,000-compound library, was identified as a small-molecule RAD51-stimulator (FIG. 4C). RS1 has also been evaluated as a potent enhancer for Cas9-based genome editing, and has been shown to inhibit HIV-1 integration and decrease of viral replication. Thus, RS1-ligated Cas9 may be used to enhance HDR of Cas9-mediated repair. Docking analysis using a homology model of RAD51 showed that the terminal phenyl group at the benzylsulfamoyl handle on the phenylbenzamide scaffold is amenable for the attachment of a peptide linker incorporating N-terminal glycine residues, which could be ligated with the acyl intermediate formed between the threonine of cleaved Cas9-LPXT and sortase. The assays previously described can be used to assess the degree of local HDR enhancement.

In an embodiment the nucleic acid modifier comprises an effector domain, the effector domain comprising an activator of homology-directed repair (HDR) and/or an inhibitor of non-homologous end joining (NHEJ). In an embodiment the activator of HDR is a small molecule. In an embodiment the activator of HDR is an activator of RAD51. In an embodiment the activator of HDR is linked to the nucleic acid binding domain.

In an embodiment the nucleic acid modifier comprises an inhibitor of NHEJ, the inhibitor comprising a DNA ligase IV inhibitor. In an embodiment, the inhibitor of NHEJ comprises a small molecule. In an embodiment the inhibitor of NHEJ is linked to the nucleic acid binding domain.

In an embodiment, the effector domain comprises a repressor domain, an activator domain, a transposase domain, an integrase domain, a recombinase domain, a resolvase domain, an invertase domain, a protease domain, a DNA methyltransferase domain, a DNA hydroxylmethylase domain, a DNA demethylase domain, a histone acetylase domain, a histone deacetylase domain or a cellular uptake activity associated domain.

In some embodiments, one or more effector domains may be associated with or tethered to CRISPR enzyme and/or may be associated with or tethered to modified guides via adaptor proteins. These can be used irrespective of the fact that the CRISPR enzyme may also be tethered to a virus outer protein or capsid or envelope, such as a VP2 domain or a capsid, via modified guides with aptamer RAN sequences that recognize correspond adaptor proteins.

In some embodiments, one or more effector domains comprise a transcriptional activator, repressor, a recombinase, a transposase, a histone remodeler, a demethylase, a DNA methyltransferase, a cryptochrome, a light inducible/controllable domain, a chemically inducible/controllable domain, an epigenetic modifying domain, or a combination thereof. Advantageously, the effector domain comprises an activator, repressor or nuclease.

In some embodiments, an effector domain can have methylase activity, demethylase activity, transcription activation activity, transcription repression activity, transcription release factor activity, histone modification activity, RNA cleavage activity or nucleic acid binding activity, or activity that a domain identified herein has.

Examples of activators include β65, a tetramer of the herpes simplex activation domain VP16, termed VP64, optimized use of VP64 for activation through modification of both the sgRNA design and addition of additional helper molecules, MS2, β65 and HSF1 in the system called the synergistic activation mediator (SAM) (Konermann et al, "Genome-scale transcriptional activation by an engineered CRISPR-Cas9 complex," Nature 517(7536):583-8 (2015)); and examples of repressors include the KRAB (Kruppel-associated box) domain of Kox1 or SID domain (e.g. SID4X); and an example of a nuclease or nuclease domain suitable for a effector domain comprises Fok1.

Suitable effector domains for use in practice of the invention, such as activators, repressors or nucleases are also discussed in documents incorporated herein by reference, including the patents and patent publications herein-cited and incorporated herein by reference regarding general information on CRISPR-Cas Systems.

Miniature Genome Editor with Multifunctionality (Mini-GEMs)

In one aspect, the invention provides an engineered, non-naturally occurring nucleic acid modifying system, comprising: a) a first engineered, non-naturally occurring DNA reader, wherein the first DNA reader binds a target nucleic acid; and b) a first effector component, wherein the first effector is a small molecule and modifies the target nucleic acid. The DNA reader can be a peptide nucleic acid (PNA) polymer, or transcript activator-like effector (TALE).

In some embodiments, the nucleic acid modifying systems utilizing a non-naturally occurring DNA reader such as a PNA polymer is referred to as a miniGEM. The miniGEMs disclosed can be ~30% of the size of Cas9 guide RNA complex. The size reduction stems from the use of synthetic small-molecule effector components (<500 Da), in place of the large nuclease domains (>100 kDa) employed by Cas9. Further, in miniGEM, PNAs will act as high fidelity DNA readers as well as a scaffold for display of synthetic nucleases, further reducing the size compared to that of Cas9-guide RNA complex. This size reduction will allow facile delivery of multiple miniGEMs into a cell type of interest and may even allow highly multiplexed editing. The synthetic nature of miniGEM also lowers the cost of both mass production and storage that is often associated with protein/nucleic-acid based therapeutic agents. Thus, miniGEMs provide a novel platform to enhance cellular delivery and allow multiplexed precision genome editing on an unprecedented scale.

In some embodiments, the activity of synthetic nucleases can be masked using pro-drug strategies enabling tissue-specific activation of miniGEMs. Some synthetic nucleases require specific triggers and others can be split into two components, affording additional control of specificity and activity of miniGEM. Fourth, the synthetic nature of the editor allows display of additional functionalities. For example, effector components can comprise ssODNs, NHEJ inhibitors or HDR activators for precise genome edits can be utilized.

In some embodiments, the engineered nucleic acid modifying systems can be tuned for varying potencies, including low (>10 µM), medium (0.5-10 µM), and high (<1 nM) with single or double-strand cleavage activity.

DNA Reader

The designer nucleic acid sequence readers include target nucleic acid binding molecules designed like CRISPR systems to recognize nucleic acid sequences using a programmable guide. In certain embodiments, the designer nucleic acid sequence readers comprise one or more peptide nucleic acids (PNAs) polymers. The nucleic acid sequence readers further include readers designed like Transcription Activator-Like Effectors (TALEs) to recognize DNA using two variable amino acid residues for each base being recognized. The invention employs peptidomimetics (e.g., unnatural amino acids, peptoids) and commonly employed chemistries for secondary structure pre-organization (e.g., "stapling," side-chain crosslinking, hydrogen-bond surrogating) to miniaturize a TALE-like system providing nucleotide sequence readers that are proteolytically and chemically stable. In some embodiments, the nucleic acid binding domain may comprise at least five or more Transcription activator-like effector (TALE) monomers and at least one or more half-monomers specifically ordered to target the genomic locus of interest linked to at least one or more effector domains are further linked to a chemical or energy sensitive protein. This leads to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus) and result in activation or repression of target gene expression.

In certain embodiments, the sequence readers comprise or are engineered from zinc finger proteins, meganucleases, argonaute, or other nucleic acid binding domains.

Peptide Nucleic Acids (PNAs)

In some embodiments, the DNA reader is a PNA. PNAs act as high fidelity DNA readers as well as a scaffold for display of synthetic nucleases, further reducing the size compared to that of Cas9-guide RNA complex. This size reduction will allow facile delivery of multiple miniGEMs into a cell type of interest and may even allow highly multiplexed editing. Advantageously, PNAs are resistant to degradation by proteases/nucleases. Second, the synthetic nuclease can be positioned anywhere along the PNA backbone allowing a way to introduce designer cuts a feature extremely difficult to achieve with CRISPR-associated nucleases.

In some embodiments, templates for HDR can also be directly conjugated to the PNA backbone, enhancing their local concentration and improving the rate of genome integration at the desired site.

While multiple high fidelity DNA readers exist, PNAs can be chosen for multiple reasons. First, PNAs are DNA analogs with neutral synthetic backbone in place of the negatively charged phosphodiester backbone of DNA. This neutral charge allows high-affinity binding to DNA compared to those attained by DNA/DNA or DNA/RNA hybrids. Second, next-generation PNAs (e.g., TPNA) are preorganized for binding to B-DNA in a sequence-unrestricted manner via Watson-Crick recognition. Third, the synthetic backbone of PNAs makes them resistant to proteases/nucleases. Fourth, a PNA/DNA mismatch is more destabilizing than a DNA/RNA mismatch, which could potentially reduce the off-target effects. Finally, efficient in vivo delivery of PNAs has been demonstrated for several disease systems by many groups.

In some embodiments, editors will induce four precisely spaced nicks on the genomic DNA, excising ~20 base pairs fragment and leaving behind high-affinity "sticky ends." Simultaneously, this editor will facilitate delivery of a high-concentration of an exogenous DNA (~20 base pair) that will hybridize to the sticky ends and be inserted into the genome. Here the fact that the single-strand breaking small-molecules can be positioned at any site on the PNA will be leveraged, essentially allowing the introduction of any type of DNA break.

In some preferred embodiments, the nucleic acid modifying system can include two or more PNA molecules.

Small Effector Component

Small effector components, can be in some embodiments, a small molecule synthetic nuclease, that in some embodiments is selected from the group consisting of diazofluorenes, nitracrines, metal complexes, enediynes, methoxsalen derivatives, daunorubicin derivatives and juglones. Embodiments can include a second, third or fourth effector component, which can be small molecule single strand breaking nucleases.

Single stranded oligo donors as described, one or more NHEJ inhibitors and/or HDR activators may be included, as described herein.

In some embodiments, a PNA can be conjugated with a double strand breaking small-molecule. In some embodiments, the systems provide two PNA molecules, each bearing a fragment of the split-small molecule nucleases. In some embodiments, the split-small molecule nucleases are metal complexes. For example, the zinc-complex (FIG. 17C) has two ligands and an editor can be provided where a PNA strand bears the phenanthroline ligand while another PNA strand bears the remaining zinc complex. Similarly for the iron complex of FIG. 17C, the catechol moiety can be on PNA while the iron ion can be borne by the other PNA. In these two cases, it can be envisioned that the DNA acts as template for facilitating the coming together of two reactive components—a strategy that has been employed for DNA templated synthesis of molecules. Here, the high effective molarity drives a reaction that otherwise would not proceed efficiently in absence of the DNA template. Embodiments include systems comprising two PNAs, one of the PNA strands will bear an inactive small-molecule while the other PNA will bear the trigger. For example, Kinamycin C and Dynemicin require a reducing agent (e.g., TCEP, GSH) to generate the carbon-radicals necessary for the strand cleavage.

Diazofluorenes. This class includes the natural products lomaiviticin C, A and kinamycins that contain the diazofluorene functional group. Some of these synthetic nucleases induce break upon stimulation by reducing agents. Nucleophilic addition to electrophilic diazofluorene triggers homolytic decomposition pathways that produce carbon-centered radicals from the diazo group. These radicals abstract hydrogen atoms from the deoxyribose of DNA, a process known to initiate strand cleavage.

Nitracrines. These compounds induce DNA strand breaks via intercalation. The polyaromatic chromopore of nitracrine confers a planar structure, allowing them to intercalate into DNA by stacking between base pairs. This process driven by stacking and charge-transfer interactions between the aromatic systems of the nitracrine compounds and the DNA bases, resulting in unwinding of the helix.

Metal complexes. Over last two decades, chemists have designed and synthesized >1000 metal complexes that cleave DNA by various mechanisms. Broadly, these complexes cleave DNA by either hydrolytic or oxidative mechanisms. The hydrolytic mechanisms are reminiscent of those encountered in nucleases where metal chelates the phosphate backbone making them prone to hydrolysis by a nearby base (usually a hydroxide ion). Oxidative cleavage mechanisms may involve reactive oxygen species (e.g., hydroxyl radical) or other diffusible oxidant. Singlet oxygen ($^1O2$) is another radical species derived from oxygen, which is often involved in the oxidative cleavage of DNA with energy transfer. Oxidative cleavage has to be carefully controlled as the radicals can diffuse to non-target sites. Metal complexes that operate via hydrolytic mechanism are prioritized.

Enediynes. This class of natural products is characterized by either nine- and ten-membered rings containing two triple bonds separated by a double bond. Some examples include calicheamicin, esperamicin, dynemicin and neocarzinostatin. These natural products exhibit DNA cleavage activity through the generation of active biradical species via Bergman cyclization. In addition, the neocarzinostatin chromophore, which does not contain the classical conjugated enediyne system, demonstrates a very similar DNA cleavage mechanism via the generation biradical species through the Myers-Saito cyclization. Some enediynes are stable until they interact with DNA and subsequently become activated. After binding to minor groove, a nucleophile (eg: glutathione) attacks the central sulfur atom of the trisulfide group, resulting in the formation of a thiol which then performs an intramolecular Michael addition onto the proximally positioned Œ ±,Œ ≤-unsaturated ketone moiety to unlock the enediyne warhead. This reaction converts the trigonal bridgehead position to a tetragonal center leading to a significant change in structural geometry that induces strain on the 10 membered ring. Bergman cycloaromatization of the enediyne structural motif relieves the strain in the molecule while generating a highly reactive benzenoid diradical. This diradical then abstracts hydrogen from both strands of the duplex DNA leading to a double stranded break.

DNA modifiers. DNA modifier such as methoxsalen intercalates DNA and upon photoactivation forms [2+2] cycloadducts with adjacent bases. Daunorubicin is oxidized to semi-quinone, an unstable metabolite with the release of reactive oxygen species, which are also release by Juglones.

Conjugation of Strand-Breakers to PNA

In the PNA based genome editor that is envisioned, the PNA serves as the designer DNA reader that can be customized to target any desired genomic sequence while the DNA strand breaks will be induced by synthetic nucleases. In some embodiments, small molecules are covalently conjugated to the PNA. In some embodiments, the small molecule strand breaker can be covalently conjugated utilizing maleimide, azide or alkyne functional groups on the small molecules while installing a PEG linker with thiol, alkyne or azide functional handles on the PNA respectively to allow for efficient conjugation. By varying the length of the PEG linker, it is possible to effect the DNA cut close to or away from the PNA binding site, which provides additional flexibility in designing the DNA cut sites. To create staggered double stranded breaks on the DNA, two PNA molecules can be conjugated to single strand breakers at both N and C termini designed to bind the target DNA in a staggered fashion. In this manner, four staggered cuts in the DNA such that the donor DNA with complementary staggered ends can anneal to bring about precise genomic modification without involving DNA repair pathway.

HDR Enhancement Using miniGEMs.

NHEJ inhibitors and HDR activators can be displayed on the synthetic nucleic acid modifiers to enhance HDR as discussed. Simultaneous display of NHEJ inhibitors/HDR activators and DNA strand breakers requires multiple attachment sites on the PNA. The peptide backbone of the PNA provides such additional sites of attachment, including using functionalized PEG linkers (alkyne, azide, cyclooctyne etc.) that are commercially available can be employed for conjugation of NHEJ inhibitors at the Œ ≥ position. Functionalization of PNA at the Œ ≥ position by attachment of (R)-diethylene glycol miniPEG (MP) transforms a randomly folded PNA into a right handed helix providing right handed helical, R-MPŒ ≥PNA oligomers that hybridize to DNA and RNA with greater affinity and sequence selectivity than the parental PNA oligomers. Further, the miniPEG PNA has also been successfully used in ex vivo and in vivo studies for gene editing applications.

Guides that May be Used in the Present Invention

As used herein, the term "guide", "crRNA" or "guide RNA" or "single guide RNA" or "sgRNA" or "one or more nucleic acid components" of a nucleic acid modifying protein comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid modifying system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. In some embodiments, the target sequence may be DNA. In some embodiments, the target sequence may be any RNA sequence. In some embodiments, the target sequence may comprise both DNA and RNA, for example one or more DNA nucleotides with the rest being RNA, or one or more RNA nucleotides with the rest being DNA. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and G M Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In general, the nucleic acid modifying system may be as used in the foregoing documents, such as WO 2014/093622 (PCT/US2013/074667) and refers collectively to transcripts and other elements involved in the expression of or directing the activity of nucleic acid modifying-associated genes, including sequences encoding one or more domains of a Cas gene, for example, one of more domains of a Cas9 gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous nucleic acid modifying system), a guide sequence (also referred to as a "spacer" in the context of an endogenous nucleic acid modifying system), or "RNA(s)" as that term is herein used (e.g., RNA(s) to guide nucleic acid modifying protein, e.g. CRISPR RNA and transactivating (tracr) RNA or a single guide RNA (sgRNA) (chimeric RNA)) or other sequences and transcripts derived from a CRISPR locus. In general, a nucleic acid modifying system is characterized by elements that promote the formation of a nucleic acid modifying complex at the site of a target sequence (also referred to as a protospacer in the context of an endogenous nucleic acid modifying system). In the context of formation of a nucleic acid modifying complex, "target sequence" refers to a sequence to which a guide sequence is designed to have complementarity, where hybridization between a target sequence and a guide sequence promotes the formation of a nucleic acid modifying complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a nucleic acid modifying system comprises one or more nuclear exports signals (NESs). In some embodiments, a nucleic acid modifying system comprises one or more NLSs and one or more NESs. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a nucleic acid modifying protein to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a nucleic acid modifying protein to a target sequence may be assessed by any suitable assay. For example, the components of a nucleic acid modifying system sufficient to form a nucleic acid modifying complex, including the guide sequence to be tested and the nucleic acid modifying protein, may be provided to a host cell having the corresponding target sequence, such as by transfection with vectors encoding the components of the nucleic acid modifying sequence, followed by an assessment of preferential cleavage within the target sequence, such as by Surveyor assay as described herein. Similarly, cleavage of a target polynucleotide sequence may be evaluated in a test tube by providing the target sequence, components of a nucleic acid modifying complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of nucleic acid modifying systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the nucleic acid modifying system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding nucleic acid modifying protein to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the nucleic acid modifying complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it may be important to control the concentration of nucleic acid modifying protein mRNA and guide RNA delivered. Optimal concentrations of nucleic acid modifying protein mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, nucleic acid modifying nickase mRNA (for example nucleic acid modifying protein comprising one or more domains of S. pyogenes Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous nucleic acid modifying system, formation of a nucleic acid modifying complex (comprising a guide sequence hybridized to a target sequence and complexed with one or more nucleic acid modifying proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a nucleic acid modifying complex, such as by hybridization along at least a portion of the tracr sequence to all or a portion of a tracr mate sequence that is operably linked to the guide sequence.

In some embodiments, guides of the invention comprise RNA. In certain embodiments, guides of the invention comprise DNA. In certain embodiments, guides of the invention comprise both RNA and DNA. In other words, guides of the invention may comprise both Ribonucleic acid (RNA) and/or Deoxyribonucleic acid (DNA). For areas where secondary structure is preferred or required, then Ribonucleic acid (RNA) is most useful. However, in other areas, such as a sequence complementary to the target sequence, then some or potentially all of the nucleotides may be Deoxyribonucleic acid (DNA). This may be designed subject to the functional requirements of the user. Blends of RNA to DNA may be about 100:0; 90:10; 80:20; 70:30; 60:40; 50:50; 40:60; 30:70; 20:80; 10:90; or 0:1000. Due to the utility of RNA secondary structure in some embodiments, the RNA:DNA ratio in the guide molecule may be 80:20; 70:30; 60:40; or 50:50. The Ribonucleic acid (RNA) and/or Deoxyribonucleic acid (DNA) may also be modified and so forth as described below.

In certain embodiments, guides of the invention comprise non-naturally occurring nucleic acids and/or non-naturally occurring nucleotides and/or nucleotide analogs, and/or chemically modified nucleotides (i.e. nucleotides comprising chemical modifications). Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3' phosphorothioate (MS), or 2'-O-methyl 3' thio-PACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015; Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI: 10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target DNA and one or more deoxyribonucleotides and/or nucleotide analogs in a region that binds to Cas9, Cpf1, or C2c1. In an embodiment of the invention, deoxyribonucleotides and/or nucleotide analogs are incorporated in engineered guide structures, such as, without limitation, 5' and/or 3' end, stem-loop regions, and the seed region. In certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl-3'-phosphorothioate (MS), S-constrained ethyl(cEt), or 2'-O-methyl-3'-thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In one aspect of the invention, the guide comprises a modified crRNA for Cpf1, having a 5'-handle and a guide segment further comprising a seed region and a 3'-terminus. In some embodiments, the modified guide can be used with a Cpf1 of any one of *Acidaminococcus* sp. BV3L6 Cpf1 (AsCpf1); *Francisella tularensis* subsp. Novicida U112 Cpf1 (FnCpf1); L. bacterium MC2017 Cpf1 (Lb3Cpf1); *Butyrivibrio proteoclasticus* Cpf1 (BpCpf1); Parcubacteria bacterium GWC2011_GWC2_44_17 Cpf1 (PbCpf1); Peregrinibacteria bacterium GW2011_GWA_33_10 Cpf1 (PeCpf1); *Leptospira inadai* Cpf1 (LiCpf1); *Smithella* sp. SC_K08D17 Cpf1 (SsCpf1); L. bacterium MA2020 Cpf1 (Lb2Cpf1); *Porphyromonas crevioricanis* Cpf1 (PcCpf1); *Porphyromonas macacae* Cpf1 (PmCpf1); Candidatus Methanoplasma *termitum* Cpf1 (CMtCpf1); *Eubacterium eligens* Cpf1 (EeCpf1); *Moraxella bovoculi* 237 Cpf1 (MbCpf1); *Prevotella disiens* Cpf1 (PdCpf1); or L. bacterium ND2006 Cpf1 (LbCpf1).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (melΨ), 5-methoxyuridine (5moU), inosine, 7-methylguanosine, 2'-O-methyl-3'-phosphorothioate (MS), S-constrained ethyl(cEt), phosphorothioate (PS), or 2'-O-methyl-3'-thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 or 10 nucleotides in the 3'-terminus are chemically modified. Such chemical modifications at the 3'-terminus of the Cpf1 CrRNA improve gene cutting efficiency (see Li, et al., Nature Biomedical Engineering, 2017, 1:0066). In a specific embodiment, 5 nucleotides in the 3'-terminus are replaced with 2'-fluoro analogues. In a specific embodiment, 10 nucleotides in the 3'-terminus are replaced with 2'-fluoro analogues. In a specific embodiment, 5 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU.

Synthetically Linked Guides

In one aspect, the guide comprises a tracr sequence and a tracr mate sequence that are chemically linked or conjugated via a non-phosphodiester bond. In some embodiments, the tracr sequence and the tracr mate sequence are considered to be fused together or contiguous. In one aspect, the guide comprises a tracr sequence and a tracr mate sequence that are chemically linked or conjugated via a non-nucleotide loop. In some embodiments, the tracr and tracr mate sequences are joined via a non-phosphodiester covalent linker. Examples of the covalent linker include but are not limited to a chemical moiety selected from the group consisting of carbamates, ethers, esters, amides, imines, amidines, aminotriazines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, the tracr or tracr mate sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once the tracr and the tracr mate sequences are functionalized, a covalent chemical bond or linkage can be formed between the two oligonucleotides. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences can be chemically synthesized. The tracer and tracr mate alone/individually, synthesized together in the form of a fusion, or synthesized separately and chemically linked. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In some embodiments, the tracr and tracr mate sequences can be covalently linked using various bioconjugation reactions, loops, bridges, and non-nucleotide links via modifications of sugar, internucleotide phosphodiester bonds, purine and pyrimidine residues. Sletten et al., Angew. Chem. Int. Ed. (2009) 48:6974-6998; Manoharan, M. Curr. Opin. Chem. Biol. (2004) 8: 570-9; Behlke et al., Oligonucleotides (2008) 18: 305-19; Watts, et al., Drug. Discov. Today (2008) 13: 842-55; Shukla, et al., ChemMedChem (2010) 5: 328-49.

In some embodiments, the tracr and tracr mate sequences can be covalently linked using click chemistry. In some embodiments, the tracr and tracr mate sequences can be covalently linked using a triazole linker. In some embodiments, the tracr and tracr mate sequences can be covalently linked using Huisgen 1,3-dipolar cycloaddition reaction involving an alkyne and azide to yield a highly stable triazole linker (He et al., ChemBioChem (2015) 17: 1809-1812; WO 2016/186745). In some embodiments, the tracr and tracr mate sequences are covalently linked by ligating a 5'-hexyne tracrRNA and a 3'-azide crRNA. In some embodiments, either or both of the 5'-hexyne tracrRNA and a 3'-azide crRNA can be protected with 2'-acetoxyethyl orthoester (2'-ACE) group, which can be subsequently removed using Dharmacon protocol (Scaringe et al., J. Am. Chem. Soc. (1998) 120: 11820-11821; Scaringe, Methods Enzymol. (2000) 317: 3-18).

In some embodiments, the tracr and tracr mate sequences can be covalently linked via a linker (e.g., a non-nucleotide loop) that comprises a moiety such as spacers, attachments, bioconjugates, chromophores, reporter groups, dye labeled RNAs, and non-naturally occurring nucleotide analogues. More specifically, suitable spacers for purposes of this invention include, but are not limited to, polyethers (e.g., polyethylene glycols, polyalcohols, polypropylene glycol or mixtures of ethylene and propylene glycols), polyamines group (e.g., spennine, spermidine and polymeric derivatives thereof), polyesters (e.g., poly(ethyl acrylate)), polyphosphodiesters, alkylenes, and combinations thereof. Suitable attachments include any moiety that can be added to the linker to add additional properties to the linker, such as but not limited to, fluorescent labels. Suitable bioconjugates include, but are not limited to, peptides, glycosides, lipids, cholesterol, phospholipids, diacyl glycerols and dialkyl glycerols, fatty acids, hydrocarbons, enzyme substrates, steroids, biotin, digoxigenin, carbohydrates, polysaccharides. Suitable chromophores, reporter groups, and dye-labeled RNAs include, but are not limited to, fluorescent dyes such as fluorescein and rhodamine, chemiluminescent, electrochemiluminescent, and bioluminescent marker compounds. The design of example linkers conjugating two RNA components are also described in WO 2004/015075.

The linker (e.g., a non-nucleotide loop) can be of any length. In some embodiments, the linker has a length equivalent to about 0-16 nucleotides. In some embodiments, the linker has a length equivalent to about 0-8 nucleotides. In some embodiments, the linker has a length equivalent to about 0-4 nucleotides. In some embodiments, the linker has a length equivalent to about 2 nucleotides. Example linker design is also described in WO2011/008730.

A typical nucleic acid modifying sgRNA comprises (in 5' to 3' direction): a guide sequence, a poly U tract, a first complimentary stretch (the "repeat"), a loop (tetraloop), a second complimentary stretch (the "anti-repeat" being complimentary to the repeat), a stem, and further stem loops and stems and a poly A (often poly U in RNA) tail (terminator). In preferred embodiments, certain aspects of guide architecture are retained, certain aspect of guide architecture cam be modified, for example by addition, subtraction, or substitution of features, whereas certain other aspects of guide architecture are maintained. Preferred locations for engineered sgRNA modifications, including but not limited to insertions, deletions, and substitutions include guide termini and regions of the sgRNA that are exposed when complexed with CRISPR protein and/or target, for example the tetraloop and/or loop2. Certain guide architecture and secondary structure may, as described herein, be utilized or encouraged in guides other than those specifically referred to as sgRNA.

In certain embodiments, guides of the invention comprise, for example are adapted or designed to include, one or more specific binding sites (e.g. comprising an aptamer or aptamer sequences such as MS2 or PP7, for example as described herein) for adaptor proteins. The adaptor proteins may comprise one or more effector domains (e.g. via fusion protein). When such a guide forms a nucleic acid modifying complex (i.e. nucleic acid modifying protein binding to guide and target) the adaptor proteins bind and, the effector domain associated with the adaptor protein is positioned in a spatial orientation which is advantageous for the attributed function to be effective. For example, if the effector domain is a transcription activator (e.g. VP64 or p65), the transcription activator is placed in a spatial orientation which allows it to affect the transcription of the target. Likewise, a transcription repressor (e.g. KRAB) will be advantageously positioned to affect the transcription of the target and a nuclease (e.g. Fok1) will be advantageously positioned to cleave or partially cleave the target. Suitable examples of aptamer are described herein, for example below. Suitable examples of effector domains are also described herein.

The skilled person will understand that modifications to the guide which allow for binding of the adaptor+effector domain but not proper positioning of the adaptor+effector domain (e.g. due to steric hindrance within the three dimensional structure of the nucleic acid modifying complex) are modifications which are not intended if the nucleic acid modifying complex is to be optimally formed or formed in a functional manner. In some embodiments, sub-optimal formation of the nucleic acid modifying complex may be useful. The one or more modified guide may be modified at the tetra loop, the stem loop 1, stem loop 2, or stem loop 3, as described herein, preferably at either the tetra loop or stem loop 2, and most preferably at both the tetra loop and stem loop 2.

The repeat:anti repeat duplex will be apparent from the secondary structure of the sgRNA. It may be typically a first complimentary stretch after (in 5' to 3' direction) the poly U tract and before the tetraloop; and a second complimentary stretch after (in 5' to 3' direction) the tetraloop and before the poly A tract. The first complimentary stretch (the "repeat") is complimentary to the second complimentary stretch (the "anti-repeat"). As such, they Watson-Crick base pair to form a duplex of dsRNA when folded back on one another. As such, the anti-repeat sequence is the complimentary sequence of the repeat and in terms to A-U or C-G base pairing, but also in terms of the fact that the anti-repeat is in the reverse orientation due to the tetraloop.

In an embodiment of the invention, modification of guide architecture comprises replacing bases in stemloop 2. For example, in some embodiments, "actt" ("acuu" in RNA) and "aagt" ("aagu" in RNA) bases in stemloop2 are replaced with "cgcc" and "gcgg". In some embodiments, "actt" and "aagt" bases in stemloop2 are replaced with complimentary GC-rich regions of 4 nucleotides. In some embodiments, the complimentary GC-rich regions of 4 nucleotides are "cgcc" and "gcgg" (both in 5' to 3' direction). In some embodiments, the complimentary GC-rich regions of 4 nucleotides are "gcgg" and "cgcc" (both in 5' to 3' direction). Other combination of C and G in the complimentary GC-rich regions of 4 nucleotides will be apparent including CCCC and GGGG.

In one aspect, the stemloop 2, e.g., "ACTTgtttAAGT" (SEQ ID NO: 3) can be replaced by any "XXXXgttTYYYY", e.g., where XXXX and YYYY represent any complementary sets of nucleotides that together will base pair to each other to create a stem.

In one aspect, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-12 and Y2-12 (wherein X and Y represent any complementary set of nucleotides) may be contemplated. In one aspect, the stem made of the X and Y nucleotides, together with the "gttt," will form a complete hairpin in the overall secondary structure; and this may be advantageous and the amount of base pairs can be any amount that forms a complete hairpin. In one aspect, any complementary X:Y basepairing sequence (e.g., as to length) is tolerated, so long as the secondary structure of the entire sgRNA is preserved. In one aspect, the stem can be a form of X:Y basepairing that does not disrupt the secondary structure of the whole sgRNA in that it has a DR:tracr duplex, and 3 stemloops. In one aspect, the "gttt" tetraloop that connects ACTT and AAGT (or any alternative stem made of X:Y basepairs) can be any sequence of the same length (e.g., 4 basepair) or longer that does not interrupt the overall secondary structure of the sgRNA. In one aspect, the stemloop can be something that further lengthens stemloop2, e.g. can be MS2 aptamer. In one aspect, the stemloop3 "GGCACCGagtCGGTGC" (SEQ ID NO: 4) can likewise take on a "XXXXXXXagtYYYYYYY" form, e.g., wherein X7 and Y7 represent any complementary sets of nucleotides that together will base pair to each other to create a stem. In one aspect, the stem comprises about 7 bp comprising complementary X and Y sequences, although stems of more or fewer basepairs are also contemplated. In one aspect, the stem made of the X and Y nucleotides, together with the "agt", will form a complete hairpin in the overall secondary structure. In one aspect, any complementary X:Y basepairing sequence is tolerated, so long as the secondary structure of the entire sgRNA is preserved. In one aspect, the stem can be a form of X:Y basepairing that doesn't disrupt the secondary structure of the whole sgRNA in that it has a DR:tracr duplex, and 3 stemloops. In one aspect, the "agt" sequence of the stemloop 3 can be extended or be replaced by an aptamer, e.g., a MS2 aptamer or sequence that otherwise generally preserves the architecture of stemloop3. In one aspect for alternative Stemloops 2 and/or 3, each X and Y pair can refer to any basepair. In one aspect, non-Watson Crick basepairing is contemplated, where such pairing otherwise generally preserves the architecture of the stemloop at that position. See herein for further discussion of aptamers.

In one aspect, the DR:tracrRNA duplex can be replaced with the form: gYYYYag(N)NNNNxxxxNNNN(AAN)

uuRRRRu (using standard IUPAC nomenclature for nucleotides), wherein (N) and (AAN) represent part of the bulge in the duplex, and "xxxx" represents a linker sequence. NNNN on the direct repeat can be anything so long as it basepairs with the corresponding NNNN portion of the tracrRNA. In one aspect, the DR:tracrRNA duplex can be connected by a linker of any length (xxxx . . . ), any base composition, as long as it does not alter the overall structure.

In one aspect, the sgRNA structural requirement is to have a duplex and 3 stemloops. In most aspects, the actual sequence requirement for many of the particular base requirements are lax, in that the architecture of the DR:tracrRNA duplex should be preserved, but the sequence that creates the architecture, i.e., the stems, loops, bulges, etc., may be altered.

Aptamers

In general, the guides are modified in a manner that provides specific binding sites (e.g. aptamers) for adaptor proteins comprising one or more effector domains (e.g. via fusion protein) to bind to. The modified guides are modified such that once the guides forms a DNA binding complex (i.e. nucleic acid modifying protein binding to guides and target) the adaptor proteins bind. The effector domain on the adaptor protein is positioned in a spatial orientation which is advantageous for the attributed function to be effective. For example, if the effector domain is a transcription activator (e.g. VP64 or p65), the transcription activator is placed in a spatial orientation which allows it to affect the transcription of the target. Likewise, a transcription repressor (e.g. KRAB) will be advantageously positioned to affect the transcription of the target and a nuclease (e.g. Fok1) will be advantageously positioned to cleave or partially cleave the target.

The skilled person will understand that modifications to the guide which allow for binding of the adaptor+effector domain but not proper positioning of the adaptor+effector domain (e.g. due to steric hindrance within the three dimensional structure of the nucleic acid modifying complex) are modifications which are not intended. The one or more modified guide may be modified at the tetra loop, the stem loop 1, stem loop 2, or stem loop 3, as appropriate. This is described herein, preferably at either the tetra loop or stem loop 2, and most preferably at both the tetra loop and stem loop 2.

As explained herein the effector domains may be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). In some cases it is advantageous that additionally at least one NLS is provided. In some instances, it is advantageous to position the NLS at the N terminus. When more than one effector domain is included, the effector domains may be the same or different.

The guide may be designed to include multiple binding recognition sites (e.g. aptamers) specific to the same or different adaptor protein. The guide may be designed to bind to the promoter region −1000-+1 nucleic acids upstream of the transcription start site (i.e. TSS), preferably −200 nucleic acids. This positioning improves effector domains which affect gene activation (e.g. transcription activators) or gene inhibition (e.g. transcription repressors). The modified guide may be one or more modified guides targeted to one or more target loci (e.g. at least 1 guide, at least 2 guides, at least 5 guides, at least 10 guides, at least 20 guides, at least 30 guides, at least 50 guides) comprised in a composition. The guides may be gRNA or may comprise DNA as described herein.

MS2 and PP7 are examples of suitable aptamers and so their sequences may be incorporated into the guides. Thus, in some embodiments, the guide may comprise aptamer sequences such as MS2 or PP7, capable of binding to a nucleotide-binding protein. The nucleotide-binding protein may be fused to otherwise comprise a effector domain as described hereon. References is made here to Konermann et al. (Konermann et al., "Genome-scale transcription activation by an engineered CRISPR-Cas9 complex," doi: 10.1038/nature14136, incorporated herein by reference).

The adaptor protein may be any number of proteins that binds to an aptamer or recognition site introduced into the modified dead gRNA and which allows proper positioning of one or more effector domains, once the dead gRNA has been incorporated into the nucleic acid modifying complex, to affect the target with the attributed function. As explained in detail in this application such may be coat proteins, preferably bacteriophage coat proteins. The effector domains associated with such adaptor proteins (e.g. in the form of fusion protein) may include, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that the effector domain is a transcription activator or transcription repressor it is advantageous that additionally at least an NLS is provided and preferably at the N terminus. When more than one effector domain is included, the effector domains may be the same or different. The adaptor protein may utilize known linkers to attach such effector domains.

Examples of guide-aptamers-nucleotide-binding protein-effector domain arrangements include:
Guide—MS2 aptamer-MS2 RNA-binding protein-ED; or
Guide—PP7 aptamer-PP7 RNA-binding protein-ED.
where ED is a Effector domain such as VP64 activator, SID4x repressor, Fok1 nuclease, or as otherwise described herein.

One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:
Guide 1—MS2 aptamer-MS2 RNA-binding protein-VP64 activator; and
Guide 2—PP7 aptamer-PP7 RNA-binding protein-SID4x repressor.

The present invention also relates to orthogonal PP7/MS2 gene targeting. In this example, sgRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as Q-beta.

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g. using the Alu repressor (in RNA) that interferes with RNA polymerase II in mammalian cells). The Alu RNA sequence was located: in place of the MS2 RNA sequences as used herein (e.g. at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker).

The use of two different aptamers (distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for example 10 or 20 or 30 and so forth, whilst only one (or at least a minimal number) of nucleic acid modifying proteins to be delivered, as a comparatively small number of nucleic acid modifying proteins can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, whilst the other might be p65, although these are just examples and other transcriptional activators are envisaged. Three or more or even four or more activators (or repressors) may be used, but package size may limit the number being higher than 5 different effector domains. Linkers are preferably used, over a direct fusion to the adaptor protein, where two or more effector domains are associated with the adaptor protein. Suitable linkers might include the GlySer linker.

It is also envisaged that the protein-guide complex as a whole may be associated with two or more effector domains. For example, there may be two or more effector domains associated with the nucleic acid modifying protein, or there may be two or more effector domains associated with the guide (via one or more adaptor proteins), or there may be one or more effector domains associated with the nucleic acid modifying protein and one or more effector domains associated with the guide (via one or more adaptor proteins).

The fusion between the adaptor protein and the activator or repressor may include a linker. For example, GlySer linkers GGGS can be used. They can be used in repeats of 3 ((GGGGS)3) (SEQ ID NO: 5) or 6, 9 or even 12 or more, to provide suitable lengths, as required. Linkers can be used between the DNA binding protein and an effector domain (activator or repressor), or between the nucleic acid binding domain and the effector domain (activator or repressor). The linkers the user to engineer appropriate amounts of "mechanical flexibility".

Dead Guides: Guide RNAs Comprising a Dead Guide Sequence May be Used in the Present INVENTION In one aspect, the invention provides guide sequences which are modified in a manner which allows for formation of the CRISPR complex and successful binding to the target, while at the same time, not allowing for successful nuclease activity (i.e. without nuclease activity/without indel activity). For matters of explanation such modified guide sequences are referred to as "dead guides" or "dead guide sequences". These dead guides or dead guide sequences can be thought of as catalytically inactive or conformationally inactive with regard to nuclease activity. Nuclease activity may be measured using surveyor analysis or deep sequencing as commonly used in the art, preferably surveyor analysis. Similarly, dead guide sequences may not sufficiently engage in productive base pairing with respect to the ability to promote catalytic activity or to distinguish on-target and off-target binding activity. Briefly, the surveyor assay involves purifying and amplifying a CRISPR target site for a gene and forming heteroduplexes with primers amplifying the CRISPR target site. After re-anneal, the products are treated with SURVEYOR nuclease and SURVEYOR enhancer S (Transgenomics) following the manufacturer's recommended protocols, analyzed on gels, and quantified based upon relative band intensities.

Hence, in a related aspect, the invention provides a non-naturally occurring or engineered composition nucleic acid modifying system comprising a functional nucleic acid modifying protein as described herein, and guide RNA (gRNA) wherein the gRNA comprises a dead guide sequence whereby the gRNA is capable of hybridizing to a target sequence such that the nucleic acid modifying system is directed to a genomic locus of interest in a cell without detectable indel activity resultant from nuclease activity of nucleic acid modifying protein of the system as detected by a SURVEYOR assay. For shorthand purposes, a gRNA comprising a dead guide sequence whereby the gRNA is capable of hybridizing to a target sequence such that the nucleic acid modifying system is directed to a genomic locus of interest in a cell without detectable indel activity resultant from nuclease activity of a nucleic acid modifying protein of the system as detected by a SURVEYOR assay is herein termed a "dead gRNA". It is to be understood that any of the gRNAs according to the invention as described herein elsewhere may be used as dead gRNAs/gRNAs comprising a dead guide sequence as described herein below. Any of the methods, products, compositions and uses as described herein elsewhere is equally applicable with the dead gRNAs/gRNAs comprising a dead guide sequence as further detailed below. By means of further guidance, the following particular aspects and embodiments are provided.

The ability of a dead guide sequence to direct sequence-specific binding of a nucleic acid modifying complex (nucleic acid modifying protein and guide) to a target sequence may be assessed by any suitable assay. For example, the components of a nucleic acid modifying system sufficient to form a nucleic acid modifying complex, including the dead guide sequence to be tested, may be provided to a host cell having the corresponding target sequence, such as by transfection with vectors encoding the components of the nucleic acid modifying sequence, followed by an assessment of preferential cleavage within the target sequence, such as by Surveyor assay as described herein. Similarly, cleavage of a target polynucleotide sequence may be evaluated in a test tube by providing the target sequence, components of a nucleic acid modifying complex, including the dead guide sequence to be tested and a control guide sequence different from the test dead guide sequence, and comparing binding or rate of cleavage at the target sequence between the test and control guide sequence reactions. Other assays are possible, and will occur to those skilled in the art. A dead guide sequence may be selected to target any target sequence. In some embodiments, the target sequence is a sequence within a genome of a cell.

As explained further herein, several structural parameters allow for a proper framework to arrive at such dead guides. Dead guide sequences are shorter than respective guide sequences which result in active nucleic acid modifying protein-specific indel formation. Dead guides are 5%, 10%, 20%, 30%, 40%, 50%, shorter than respective guides directed to the same nucleic acid modifying protein leading to active nucleic acid modifying protein-specific indel formation.

As explained below and known in the art, one aspect of gRNA-nucleic acid modifying protein specificity is the direct repeat sequence, which is to be appropriately linked to such guides. In particular, this implies that the direct repeat sequences are designed dependent on the origin of the nucleic acid modifying protein. Thus, structural data available for validated dead guide sequences may be used for designing nucleic acid modifying protein specific equivalents. Structural similarity between, e.g., the orthologous nuclease domains RuvC of two or more Cas9 effector proteins may be used to transfer design equivalent dead guides. Thus, the dead guide herein may be appropriately modified in length and sequence to reflect such Cas9 specific equivalents, allowing for formation of the nucleic acid modifying complex and successful binding to the target, while at the same time, not allowing for successful nuclease activity.

The use of dead guides in the context herein as well as the state of the art provides a surprising and unexpected platform for network biology and/or systems biology in both in vitro, ex vivo, and in vivo applications, allowing for multiplex gene targeting, and in particular bidirectional multiplex gene targeting. Prior to the use of dead guides, addressing multiple targets, for example for activation, repression and/or silencing of gene activity, has been challenging and in some cases not possible. With the use of dead guides, multiple targets, and thus multiple activities, may be addressed, for example, in the same cell, in the same animal, or in the same patient. Such multiplexing may occur at the same time or staggered for a desired timeframe.

For example, the dead guides now allow for the first time to use gRNA as a means for gene targeting, without the consequence of nuclease activity, while at the same time providing directed means for activation or repression. Guide RNA comprising a dead guide may be modified to further include elements in a manner which allow for activation or repression of gene activity, in particular protein adaptors (e.g. aptamers) as described herein elsewhere allowing for functional placement of gene effectors (e.g. activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g. an activator or repressor; dimerized MS2 bacteriophage coat proteins as fusion proteins with an activator or repressor), or a protein which itself binds an effector (e.g. activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional upregulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

Thus, one aspect is a gRNA of the invention which comprises a dead guide, wherein the gRNA further comprises modifications which provide for gene activation or repression, as described herein. The dead gRNA may comprise one or more aptamers. The aptamers may be specific to gene effectors, gene activators or gene repressors. Alternatively, the aptamers may be specific to a protein which in turn is specific to and recruits/binds a specific gene effector, gene activator or gene repressor. If there are multiple sites for activator or repressor recruitment, it is preferred that the sites are specific to either activators or repressors. If there are multiple sites for activator or repressor binding, the sites may be specific to the same activators or same repressors. The sites may also be specific to different activators or different repressors. The gene effectors, gene activators, gene repressors may be present in the form of fusion proteins.

In an embodiment, the dead gRNA as described herein or the Cas9 CRISPR-Cas complex as described herein includes a non-naturally occurring or engineered composition comprising two or more adaptor proteins, wherein each protein is associated with one or more effector domains and wherein the adaptor protein binds to the distinct RNA sequence(s) inserted into the at least one loop of the dead gRNA.

Hence, an aspect provides a non-naturally occurring or engineered composition comprising a guide RNA (gRNA) comprising a dead guide sequence capable of hybridizing to a target sequence in a genomic locus of interest in a cell, wherein the dead guide sequence is as defined herein, a nucleic acid modifying protein comprising at least one or more nuclear localization sequences, wherein the nucleic acid modifying protein optionally comprises at least one mutation wherein at least one loop of the dead gRNA is modified by the insertion of distinct RNA sequence(s) that bind to one or more adaptor proteins, and wherein the adaptor protein is associated with one or more effector domains; or, wherein the dead gRNA is modified to have at least one non-coding functional loop, and wherein the composition comprises two or more adaptor proteins, wherein the each protein is associated with one or more effector domains.

In certain embodiments, the adaptor protein is a fusion protein comprising the effector domain, the fusion protein optionally comprising a linker between the adaptor protein and the effector domain, the linker optionally including a GlySer linker.

In certain embodiments, the at least one loop of the dead gRNA is not modified by the insertion of distinct RNA sequence(s) that bind to the two or more adaptor proteins.

In certain embodiments, the one or more effector domains associated with the adaptor protein is a transcriptional activation domain.

In certain embodiments, the one or more effector domains associated with the adaptor protein is a transcriptional activation domain comprising VP64, p65, MyoD1, HSF1, RTA or SET7/9.

In certain embodiments, the one or more effector domains associated with the adaptor protein is a transcriptional repressor domain.

In certain embodiments, the transcriptional repressor domain is a KRAB domain.

In certain embodiments, the transcriptional repressor domain is a NuE domain, NcoR domain, SID domain or a SID4X domain.

In certain embodiments, at least one of the one or more effector domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity.

In certain embodiments, the DNA cleavage activity is due to a Fok1 nuclease.

In certain embodiments, the dead gRNA is modified so that, after dead gRNA binds the adaptor protein and further binds to the nucleic acid modifying protein and target, the effector domain is in a spatial orientation allowing for the effector domain to function in its attributed function.

In certain embodiments, the at least one loop of the dead gRNA is tetra loop and/or loop2. In certain embodiments, the tetra loop and loop 2 of the dead gRNA are modified by the insertion of the distinct RNA sequence(s).

In certain embodiments, the insertion of distinct RNA sequence(s) that bind to one or more adaptor proteins is an aptamer sequence. In certain embodiments, the aptamer sequence is two or more aptamer sequences specific to the same adaptor protein. In certain embodiments, the aptamer sequence is two or more aptamer sequences specific to different adaptor protein.

In certain embodiments, the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1.

In certain embodiments, the cell is a eukaryotic cell. In certain embodiments, the eukaryotic cell is a mammalian cell, optionally a mouse cell. In certain embodiments, the mammalian cell is a human cell.

In certain embodiments, a first adaptor protein is associated with a p65 domain and a second adaptor protein is associated with a HSF1 domain.

In certain embodiments, the composition comprises a nucleic acid modifying complex having at least three effector domains, at least one of which is associated with the nucleic acid modifying protein and at least two of which are associated with dead gRNA.

In certain embodiments, the composition further comprises a second gRNA, wherein the second gRNA is a live gRNA capable of hybridizing to a second target sequence such that a second nucleic acid modifying system is directed to a second genomic locus of interest in a cell with detectable indel activity at the second genomic locus resultant from nuclease activity of the nucleic acid modifying protein of the system.

In certain embodiments, the composition further comprises a plurality of dead gRNAs and/or a plurality of live gRNAs.

One aspect of the invention is to take advantage of the modularity and customizability of the gRNA scaffold to establish a series of gRNA scaffolds with different binding sites (in particular aptamers) for recruiting distinct types of effectors in an orthogonal manner. Again, for matters of example and illustration of the broader concept, replacement of the MS2 stem-loops with PP7-interacting stem-loops may be used to bind/recruit repressive elements, enabling multiplexed bidirectional transcriptional control. Thus, in general, gRNA comprising a dead guide may be employed to provide for multiplex transcriptional control and preferred bidirectional transcriptional control. This transcriptional control is most preferred of genes. For example, one or more gRNA comprising dead guide(s) may be employed in targeting the activation of one or more target genes. At the same time, one or more gRNA comprising dead guide(s) may be employed in targeting the repression of one or more target genes. Such a sequence may be applied in a variety of different combinations, for example the target genes are first repressed and then at an appropriate period other targets are activated, or select genes are repressed at the same time as select genes are activated, followed by further activation and/or repression. As a result, multiple components of one or more biological systems may advantageously be addressed together.

In an aspect, the invention provides nucleic acid molecule(s) encoding dead gRNA or the nucleic acid modifying complex or the composition as described herein.

In an aspect, the invention provides a vector system comprising: a nucleic acid molecule encoding dead guide RNA as defined herein. In certain embodiments, the vector system further comprises a nucleic acid molecule(s) encoding nucleic acid modifying protein. In certain embodiments, the vector system further comprises a nucleic acid molecule(s) encoding (live) gRNA. In certain embodiments, the nucleic acid molecule or the vector further comprises regulatory element(s) operable in a eukaryotic cell operably linked to the nucleic acid molecule encoding the guide sequence (gRNA) and/or the nucleic acid molecule encoding nucleic acid modifying protein and/or the optional nuclear localization sequence(s).

In another aspect, structural analysis may also be used to study interactions between the dead guide and the active nucleic acid modifying nuclease that enable DNA binding, but no DNA cutting. In this way amino acids or effector domains important for nuclease activity of nucleic acid modifying protein are determined. Modification of such amino acids allows for improved nucleic acid modifying protein used for gene editing.

A further aspect is combining the use of dead guides as explained herein with other applications of DNA modification, as explained herein as well as known in the art. For example, gRNA comprising dead guide(s) for targeted multiplex gene activation or repression or targeted multiplex bidirectional gene activation/repression may be combined with gRNA comprising guides which maintain nuclease activity, as explained herein. Such gRNA comprising guides which maintain nuclease activity may or may not further include modifications which allow for repression of gene activity (e.g. aptamers). Such gRNA comprising guides which maintain nuclease activity may or may not further include modifications which allow for activation of gene activity (e.g. aptamers). In such a manner, a further means for multiplex gene control is introduced (e.g. multiplex gene targeted activation without nuclease activity/without indel activity may be provided at the same time or in combination with gene targeted repression with nuclease activity).

For example, 1) using one or more gRNA (e.g. 1-50, 1-40, 1-30, 1-20, preferably 1-10, more preferably 1-5) comprising dead guide(s) targeted to one or more genes and further modified with appropriate aptamers for the recruitment of gene activators; 2) may be combined with one or more gRNA (e.g. 1-50, 1-40, 1-30, 1-20, preferably 1-10, more preferably 1-5) comprising dead guide(s) targeted to one or more genes and further modified with appropriate aptamers for the recruitment of gene repressors. 1) and/or 2) may then be combined with 3) one or more gRNA (e.g. 1-50, 1-40, 1-30, 1-20, preferably 1-10, more preferably 1-5) targeted to one or more genes. This combination can then be carried out in turn with 1)+2)+3) with 4) one or more gRNA (e.g. 1-50, 1-40, 1-30, 1-20, preferably 1-10, more preferably 1-5) targeted to one or more genes and further modified with appropriate aptamers for the recruitment of gene activators. This combination can then be carried in turn with 1)+2)+3)+4) with 5) one or more gRNA (e.g. 1-50, 1-40, 1-30, 1-20, preferably 1-10, more preferably 1-5) targeted to one or more genes and further modified with appropriate aptamers for the recruitment of gene repressors. As a result various uses and combinations are included in the invention. For example, combination 1)+2); combination 1)+3); combination 2)+3); combination 1)+2)+3); combination 1)+2)+3)+4); combination 1)+3)+4); combination 2)+3)+4); combination 1)+2)+4); combination 1)+2)+3)+4)+5); combination 1)+3)+4)+5); combination 2)+3)+4)+5); combination 1)+2)+4)+5); combination 1)+2)+3)+5); combination 1)+3)+5); combination 2)+3)+5); combination 1)+2)+5).

In an aspect, the invention provides an algorithm for designing, evaluating, or selecting a dead guide RNA targeting sequence (dead guide sequence) for guiding a nucleic acid modifying system to a target gene locus. In particular, it has been determined that dead guide RNA specificity relates to and can be optimized by varying i) GC content and ii) targeting sequence length. In an aspect, the invention provides an algorithm for designing or evaluating a dead guide RNA targeting sequence that minimizes off-target binding or interaction of the dead guide RNA. In an embodiment of the invention, the algorithm for selecting a dead guide RNA targeting sequence for directing a nucleic acid modifying system to a gene locus in an organism comprises a) locating one or more CRISPR motifs in the gene locus, analyzing the 20 nt sequence downstream of each CRISPR motif by i) determining the GC content of the sequence; and ii) determining whether there are off-target matches of the 15 downstream nucleotides nearest to the CRISPR motif in the genome of the organism, and c) selecting the 15 nucleotide sequence for use in a dead guide RNA if the GC content of the sequence is 70% or less and no off-target matches are identified. In an embodiment, the sequence is selected for a targeting sequence if the GC content is 60% or less. In certain embodiments, the sequence is selected for a targeting sequence if the GC content is 55% or less, 50% or less, 45% or less, 40% or less, 35% or less or 30% or less. In an embodiment, two or more sequences of the gene locus are analyzed and the sequence having the lowest GC content, or the next lowest GC content, or the next lowest GC content is selected. In an embodiment, the sequence is selected for a targeting sequence if no off-target matches are identified in the genome of the organism. In an embodiment, the targeting sequence is selected if no off-target matches are identified in regulatory sequences of the genome.

In an aspect, the invention provides a method of selecting a dead guide RNA targeting sequence for directing a functionalized nucleic acid modifying system to a gene locus in an organism, which comprises: a) locating one or more CRISPR motifs in the gene locus; b) analyzing the 20 nt sequence downstream of each CRISPR motif by: i) determining the GC content of the sequence; and ii) determining whether there are off-target matches of the first 15 nt of the sequence in the genome of the organism; c) selecting the sequence for use in a guide RNA if the GC content of the sequence is 70% or less and no off-target matches are identified. In an embodiment, the sequence is selected if the GC content is 50% or less. In an embodiment, the sequence is selected if the GC content is 40% or less. In an embodiment, the sequence is selected if the GC content is 30% or less. In an embodiment, two or more sequences are analyzed and the sequence having the lowest GC content is selected. In an embodiment, off-target matches are determined in regulatory sequences of the organism. In an embodiment, the gene locus is a regulatory region. An aspect provides a dead guide RNA comprising the targeting sequence selected according to the aforementioned methods.

In an aspect, the invention provides a dead guide RNA for targeting a functionalized nucleic acid modifying system to a gene locus in an organism. In an embodiment of the invention, the dead guide RNA comprises a targeting sequence wherein the CG content of the target sequence is 70% or less, and the first 15 nt of the targeting sequence does not match an off-target sequence downstream from a CRISPR motif in the regulatory sequence of another gene locus in the organism. In certain embodiments, the GC content of the targeting sequence 60% or less, 55% or less, 50% or less, 45% or less, 40% or less, 35% or less or 30% or less. In certain embodiments, the GC content of the targeting sequence is from 70% to 60% or from 60% to 50% or from 50% to 40% or from 40% to 30%. In an embodiment, the targeting sequence has the lowest CG content among potential targeting sequences of the locus.

In an embodiment of the invention, the first 15 nt of the dead guide match the target sequence. In another embodiment, first 14 nt of the dead guide match the target sequence. In another embodiment, the first 13 nt of the dead guide match the target sequence. In another embodiment first 12 nt of the dead guide match the target sequence. In another embodiment, first 11 nt of the dead guide match the target sequence. In another embodiment, the first 10 nt of the dead guide match the target sequence. In an embodiment of the invention the first 15 nt of the dead guide does not match an off-target sequence downstream from a CRISPR motif in the regulatory region of another gene locus. In other embodiments, the first 14 nt, or the first 13 nt of the dead guide, or the first 12 nt of the guide, or the first 11 nt of the dead guide, or the first 10 nt of the dead guide, does not match an off-target sequence downstream from a CRISPR motif in the regulatory region of another gene locus. In other embodiments, the first 15 nt, or 14 nt, or 13 nt, or 12 nt, or 11 nt of the dead guide do not match an off-target sequence downstream from a CRISPR motif in the genome.

In certain embodiments, the dead guide RNA includes additional nucleotides at the 3'-end that do not match the target sequence. Thus, a dead guide RNA that includes the first 15 nt, or 14 nt, or 13 nt, or 12 nt, or 11 nt downstream of a CRISPR motif can be extended in length at the 3' end to 12 nt, 13 nt, 14 nt, 15 nt, 16 nt, 17 nt, 18 nt, 19 nt, 20 nt, or longer.

The invention provides a method for directing a nucleic acid modifying system, including but not limited to a dead Cas9 (dCas9) or functionalized nucleic acid modifying system (which may comprise a functionalized nucleic acid modifying protein or functionalized guide) to a gene locus. In an aspect, the invention provides a method for selecting a dead guide RNA targeting sequence and directing a functionalized nucleic acid modifying system to a gene locus in an organism. In an aspect, the invention provides a method for selecting a dead guide RNA targeting sequence and effecting gene regulation of a target gene locus by a functionalized nucleic acid modifying system. In certain embodiments, the method is used to effect target gene regulation while minimizing off-target effects. In an aspect, the invention provides a method for selecting two or more dead guide RNA targeting sequences and effecting gene regulation of two or more target gene loci by a functionalized nucleic acid modifying system. In certain embodiments, the method is used to effect regulation of two or more target gene loci while minimizing off-target effects.

In an aspect, the invention provides a method of selecting a dead guide RNA targeting sequence for directing a functionalized nucleic acid modifying protein to a gene locus in an organism, which comprises: a) locating one or more CRISPR motifs in the gene locus; b) analyzing the sequence downstream of each CRISPR motif by: i) selecting 10 to 15 nt adjacent to the CRISPR motif, ii) determining the GC content of the sequence; and c) selecting the 10 to 15 nt sequence as a targeting sequence for use in a guide RNA if the GC content of the sequence is 40% or more. In an embodiment, the sequence is selected if the GC content is 50% or more. In an embodiment, the sequence is selected if the GC content is 60% or more. In an embodiment, the sequence is selected if the GC content is 70% or more. In an embodiment, two or more sequences are analyzed and the sequence having the highest GC content is selected. In an embodiment, the method further comprises adding nucleotides to the 3' end of the selected sequence which do not match the sequence downstream of the CRISPR motif. An aspect provides a dead guide RNA comprising the targeting sequence selected according to the aforementioned methods.

In an aspect, the invention provides a dead guide RNA for directing a functionalized nucleic acid modifying system to a gene locus in an organism wherein the targeting sequence of the dead guide RNA consists of 10 to 15 nucleotides adjacent to the CRISPR motif of the gene locus, wherein the CG content of the target sequence is 50% or more. In certain embodiments, the dead guide RNA further comprises nucleotides added to the 3' end of the targeting sequence which do not match the sequence downstream of the CRISPR motif of the gene locus.

In an aspect, the invention provides for a single effector to be directed to one or more, or two or more gene loci. In certain embodiments, the effector is associated with one or more domains of a Cas9, and one or more, or two or more selected dead guide RNAs are used to direct the Cas9-associated effector to one or more, or two or more selected target gene loci. In certain embodiments, the effector is associated with one or more, or two or more selected dead guide RNAs, each selected dead guide RNA, when complexed with a nucleic acid modifying protein, causing its associated effector to localize to the dead guide RNA target. One non-limiting example of such nucleic acid modifying systems modulates activity of one or more, or two or more gene loci subject to regulation by the same transcription factor.

In an aspect, the invention provides for two or more effectors to be directed to one or more gene loci. In certain embodiments, two or more dead guide RNAs are employed, each of the two or more effectors being associated with a selected dead guide RNA, with each of the two or more effectors being localized to the selected target of its dead guide RNA. One non-limiting example of such nucleic acid modifying systems modulates activity of one or more, or two or more gene loci subject to regulation by different transcription factors. Thus, in one non-limiting embodiment, two or more transcription factors are localized to different regulatory sequences of a single gene. In another non-limiting embodiment, two or more transcription factors are localized to different regulatory sequences of different genes. In certain embodiments, one transcription factor is an activator. In certain embodiments, one transcription factor is an inhibitor. In certain embodiments, one transcription factor is an activator and another transcription factor is an inhibitor. In certain embodiments, gene loci expressing different components of the same regulatory pathway are regulated. In certain embodiments, gene loci expressing components of different regulatory pathways are regulated.

In an aspect, the invention also provides a method and algorithm for designing and selecting dead guide RNAs that are specific for target DNA cleavage or target binding and gene regulation mediated by a nucleic acid modifying system. In certain embodiments, the nucleic acid modifying system provides orthogonal gene control using an active nucleic acid modifying protein which cleaves target DNA at one gene locus while at the same time binds to and promotes regulation of another gene locus.

In an aspect, the invention provides an method of selecting a dead guide RNA targeting sequence for directing a functionalized nucleic acid modifying protein to a gene locus in an organism, without cleavage, which comprises a) locating one or more CRISPR motifs in the gene locus; b) analyzing the sequence downstream of each CRISPR motif by i) selecting 10 to 15 nt adjacent to the CRISPR motif, ii) determining the GC content of the sequence, and c) selecting the 10 to 15 nt sequence as a targeting sequence for use in a dead guide RNA if the GC content of the sequence is 30% more, 40% or more. In certain embodiments, the GC content of the targeting sequence is 35% or more, 40% or more, 45% or more, 50% or more, 55% or more, 60% or more, 65% or more, or 70% or more. In certain embodiments, the GC content of the targeting sequence is from 30% to 40% or from 40% to 50% or from 50% to 60% or from 60% to 70%. In an embodiment of the invention, two or more sequences in a gene locus are analyzed and the sequence having the highest GC content is selected.

In an embodiment of the invention, the portion of the targeting sequence in which GC content is evaluated is 10 to 15 contiguous nucleotides of the 15 target nucleotides nearest to the PAM. In an embodiment of the invention, the portion of the guide in which GC content is considered is the 10 to 11 nucleotides or 11 to 12 nucleotides or 12 to 13 nucleotides or 13, or 14, or 15 contiguous nucleotides of the 15 nucleotides nearest to the PAM.

In an aspect, the invention further provides an algorithm for identifying dead guide RNAs which promote nucleic acid modifying system gene locus cleavage while avoiding functional activation or inhibition. It is observed that increased GC content in dead guide RNAs of 16 to 20 nucleotides coincides with increased DNA cleavage and reduced functional activation.

It is also demonstrated herein that efficiency of functionalized nucleic acid modifying protein can be increased by addition of nucleotides to the 3' end of a guide RNA which do not match a target sequence downstream of the CRISPR motif. For example, of dead guide RNA 11 to 15 nt in length, shorter guides may be less likely to promote target cleavage, but are also less efficient at promoting nucleic acid modifying system binding and functional control. In certain embodiments, addition of nucleotides that don't match the target sequence to the 3' end of the dead guide RNA increase activation efficiency while not increasing undesired target cleavage. In an aspect, the invention also provides a method and algorithm for identifying improved dead guide RNAs that effectively promote nucleic acid modifying system function in DNA binding and gene regulation while not promoting DNA cleavage. Thus, in certain embodiments, the invention provides a dead guide RNA that includes the first 15 nt, or 14 nt, or 13 nt, or 12 nt, or 11 nt downstream of a CRISPR motif and is extended in length at the 3' end by nucleotides that mismatch the target to 12 nt, 13 nt, 14 nt, 15 nt, 16 nt, 17 nt, 18 nt, 19 nt, 20 nt, or longer.

In an aspect, the invention provides a method for effecting selective orthogonal gene control. As will be appreciated from the disclosure herein, dead guide selection according to the invention, taking into account guide length and GC content, provides effective and selective transcription control by a functional nucleic acid modifying system, for example to regulate transcription of a gene locus by activation or inhibition and minimize off-target effects. Accordingly, by providing effective regulation of individual target loci, the invention also provides effective orthogonal regulation of two or more target loci.

In certain embodiments, orthogonal gene control is by activation or inhibition of two or more target loci. In certain embodiments, orthogonal gene control is by activation or inhibition of one or more target locus and cleavage of one or more target locus.

In one aspect, the invention provides a cell comprising a non-naturally occurring nucleic acid modifying system comprising one or more dead guide RNAs disclosed or made according to a method or algorithm described herein wherein the expression of one or more gene products has been altered. In an embodiment of the invention, the expression in the cell of two or more gene products has been altered. The invention also provides a cell line from such a cell.

In one aspect, the invention provides a multicellular organism comprising one or more cells comprising a non-naturally occurring nucleic acid modifying system comprising one or more dead guide RNAs disclosed or made according to a method or algorithm described herein. In one aspect, the invention provides a product from a cell, cell line, or multicellular organism comprising a non-naturally occurring nucleic acid modifying system comprising one or more dead guide RNAs disclosed or made according to a method or algorithm described herein.

A further aspect of this invention is the use of gRNA comprising dead guide(s) as described herein, optionally in combination with gRNA comprising guide(s) as described herein or in the state of the art, in combination with systems e.g. cells, transgenic animals, transgenic mice, inducible transgenic animals, inducible transgenic mice) which are engineered for either overexpression of nucleic acid modifying protein or preferably knock in nucleic acid modifying protein. As a result a single system (e.g. transgenic animal, cell) can serve as a basis for multiplex gene modifications in systems/network biology. On account of the dead guides, this is now possible in both in vitro, ex vivo, and in vivo.

For example, once the nucleic acid modifying protein is provided for, one or more dead gRNAs may be provided to direct multiplex gene regulation, and preferably multiplex bidirectional gene regulation. The one or more dead gRNAs may be provided in a spatially and temporally appropriate manner if necessary or desired (for example tissue specific induction of nucleic acid modifying protein expression). On account that the transgenic/inducible nucleic acid modifying protein is provided for (e.g. expressed) in the cell, tissue, animal of interest, both gRNAs comprising dead guides or gRNAs comprising guides are equally effective. In the same manner, a further aspect of this invention is the use of gRNA comprising dead guide(s) as described herein, optionally in combination with gRNA comprising guide(s) as described herein or in the state of the art, in combination with systems (e.g. cells, transgenic animals, transgenic mice, inducible transgenic animals, inducible transgenic mice) which are engineered for knockout nucleic acid modifying protein.

As a result, the combination of dead guides as described herein with DNA modification applications described herein and DNA modifications applications known in the art results in a highly efficient and accurate means for multiplex screening of systems (e.g. network biology). Such screening allows, for example, identification of specific combinations of gene activities for identifying genes responsible for diseases (e.g. on/off combinations), in particular gene related diseases. A preferred application of such screening is cancer. In the same manner, screening for treatment for such diseases is included in the invention. Cells or animals may be exposed to aberrant conditions resulting in disease or disease like effects. Candidate compositions may be provided and screened for an effect in the desired multiplex environment. For example a patient's cancer cells may be screened for which gene combinations will cause them to die, and then use this information to establish appropriate therapies.

In one aspect, the invention provides a kit comprising one or more of the components described herein. The kit may include dead guides as described herein with or without guides as described herein.

The structural information provided herein allows for interrogation of dead gRNA interaction with the target DNA and the nucleic acid modifying protein permitting engineering or alteration of dead gRNA structure to optimize functionality of the entire nucleic acid modifying system. For example, loops of the dead gRNA may be extended, without colliding with the nucleic acid modifying protein by the insertion of adaptor proteins that can bind to RNA. These adaptor proteins can further recruit effector proteins or fusions which comprise one or more effector domains.

In some preferred embodiments, the effector domain is a transcriptional activation domain, preferably VP64. In some embodiments, the effector domain is a transcription repression domain, preferably KRAB. In some embodiments, the transcription repression domain is SID, or concatemers of SID (e.g. SID4X). In some embodiments, the effector domain is an epigenetic modifying domain, such that an epigenetic modifying enzyme is provided. In some embodiments, the effector domain is an activation domain, which may be the P65 activation domain.

An aspect of the invention is that the above elements are comprised in a single composition or comprised in individual compositions. These compositions may advantageously be applied to a host to elicit a functional effect on the genomic level.

In general, the dead gRNA are modified in a manner that provides specific binding sites (e.g. aptamers) for adaptor proteins comprising one or more effector domains (e.g. via fusion protein) to bind to. The modified dead gRNA are modified such that once the dead gRNA forms a nucleic acid modifying complex (i.e. nucleic acid modifying protein binding to dead gRNA and target) the adaptor proteins bind and, the effector domain on the adaptor protein is positioned in a spatial orientation which is advantageous for the attributed function to be effective. For example, if the effector domain is a transcription activator (e.g. VP64 or p65), the transcription activator is placed in a spatial orientation which allows it to affect the transcription of the target. Likewise, a transcription repressor will be advantageously positioned to affect the transcription of the target and a nuclease (e.g. Fok1) will be advantageously positioned to cleave or partially cleave the target.

The skilled person will understand that modifications to the dead gRNA which allow for binding of the adaptor+ effector domain but not proper positioning of the adaptor+ effector domain (e.g. due to steric hindrance within the three dimensional structure of the nucleic acid modifying complex) are modifications which are not intended. The one or more modified dead gRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the effector domains may be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). In some cases it is advantageous that additionally at least one NLS is provided. In some instances, it is advantageous to position the NLS at the N terminus. When more than one effector domain is included, the effector domains may be the same or different.

The dead gRNA may be designed to include multiple binding recognition sites (e.g. aptamers) specific to the same or different adaptor protein. The dead gRNA may be designed to bind to the promoter region −1000-+1 nucleic acids upstream of the transcription start site (i.e. TSS), preferably −200 nucleic acids. This positioning improves effector domains which affect gene activation (e.g. transcription activators) or gene inhibition (e.g. transcription repressors). The modified dead gRNA may be one or more modified dead gRNAs targeted to one or more target loci (e.g. at least 1 gRNA, at least 2 gRNA, at least 5 gRNA, at least 10 gRNA, at least 20 gRNA, at least 30 gRNA, at least 50 gRNA) comprised in a composition.

The adaptor protein may be any number of proteins that binds to an aptamer or recognition site introduced into the modified dead gRNA and which allows proper positioning of one or more effector domains, once the dead gRNA has been incorporated into the nucleic acid modifying complex, to affect the target with the attributed function. As explained in detail in this application such may be coat proteins, preferably bacteriophage coat proteins. The effector domains associated with such adaptor proteins (e.g. in the form of fusion protein) may include, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that the effector domain is a transcription activator or transcription repressor it is advantageous that additionally at least an NLS is provided and preferably at the N terminus. When more than one effector domain is included, the effector domains may be the same or different. The adaptor protein may utilize known linkers to attach such effector domains.

Thus, the modified dead gRNA, the (inactivated) nucleic acid modifying protein (with or without effector domains), and the binding protein with one or more effector domains, may each individually be comprised in a composition and administered to a host individually or collectively. Alternatively, these components may be provided in a single composition for administration to a host. Administration to a host may be performed via viral vectors known to the skilled person or described herein for delivery to a host (e.g. lentiviral vector, adenoviral vector, AAV vector). As explained herein, use of different selection markers (e.g. for lentiviral gRNA selection) and concentration of gRNA (e.g. dependent on whether multiple gRNAs are used) may be advantageous for eliciting an improved effect.

On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different effector domains to elicit one or more genomic locus events. The compositions may be applied in a wide variety of methods for screening in libraries in cells and functional modeling in vivo (e.g. gene activation of lincRNA and identification of function; gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible nucleic acid modifying transgenic cell/animals, which are not believed prior to the present invention or application. For example, the target cell comprises nucleic acid modifying protein conditionally or inducibly (e.g. in the form of Cre dependent constructs) and/or the adaptor protein conditionally or inducibly and, on expression of a vector introduced into the target cell, the vector expresses that which induces or gives rise to the condition of nucleic acid modifying protein expression and/or adaptor expression in the target cell. By applying the teaching and compositions of the current invention with the known method of creating a nucleic acid modifying complex, inducible genomic events affected by effector domains are also an aspect of the current invention. One example of this is the creation of a nucleic acid modifying protein knock-in/conditional transgenic animal (e.g. mouse comprising e.g. a Lox-Stop-polyA-Lox (LSL) cassette) and subsequent delivery of one or more compositions providing one or more modified dead gRNA (e.g. −200 nucleotides to TSS of a target gene of interest for gene activation purposes) as described herein (e.g. modified dead gRNA with one or more aptamers recognized by coat proteins, e.g. MS2), one or more adaptor proteins as described herein (MS2 binding protein linked to one or more VP64) and means for inducing the conditional animal (e.g. Cre recombinase for rendering nucleic acid modifying protein expression inducible). Alternatively, the adaptor protein may be provided as a conditional or inducible element with a conditional or inducible nucleic acid modifying protein to provide an effective model for screening purposes, which advantageously only requires minimal design and administration of specific dead gRNAs for a broad number of applications.

In another aspect the dead guides are further modified to improve specificity. Protected dead guides may be synthesized, whereby secondary structure is introduced into the 3' end of the dead guide to improve its specificity. A protected guide RNA (pgRNA) comprises a guide sequence capable of hybridizing to a target sequence in a genomic locus of interest in a cell and a protector strand, wherein the protector strand is optionally complementary to the guide sequence and wherein the guide sequence may in part be hybridizable to the protector strand. The pgRNA optionally includes an extension sequence. The thermodynamics of the pgRNA-target DNA hybridization is determined by the number of bases complementary between the guide RNA and target DNA. By employing 'thermodynamic protection', specificity of dead gRNA can be improved by adding a protector sequence. For example, one method adds a complementary protector strand of varying lengths to the 3' end of the guide sequence within the dead gRNA. As a result, the protector strand is bound to at least a portion of the dead gRNA and provides for a protected gRNA (pgRNA). In turn, the dead gRNA references herein may be easily protected using the described embodiments, resulting in pgRNA. The protector strand can be either a separate RNA transcript or strand or a chimeric version joined to the 3' end of the dead gRNA guide sequence.

Tandem Guides and Uses in a Multiplex (Tandem) Targeting Approach

The inventors have shown that nucleic acid modifying proteins as defined herein can employ more than one RNA guide without losing activity. This enables the use of the nucleic acid modifying proteins, systems or complexes as defined herein for targeting multiple DNA targets, genes or gene loci, with a single enzyme, system or complex as defined herein. The guide RNAs may be tandemly arranged, optionally separated by a nucleotide sequence such as a direct repeat as defined herein. The position of the different guide RNAs is the tandem does not influence the activity. It is noted that the terms "nucleic acid modifying system" and "nucleic acid modifying complex" are used interchangeably. Also the terms "protein" or "nucleic acid modifying protein" can be used interchangeably. In preferred embodiments, said nucleic acid modifying protein comprises one or more domains of a Cas9, or one or more domains of any one of the modified or mutated variants thereof described herein elsewhere.

In one aspect, the invention provides a non-naturally occurring or engineered nucleic acid modifying protein comprising one or more domains of a CRISPR enzyme, preferably a class 2 CRISPR enzyme, preferably a Type V or VI CRISPR enzyme as described herein, such as without limitation Cas9 as described herein elsewhere, used for tandem or multiplex targeting. It is to be understood that the nucleic acid modifying protein nucleic acid modifying enzymes, complexes, or systems according to the invention as described herein elsewhere may be used in such an approach. Any of the methods, products, compositions and uses as described herein elsewhere are equally applicable with the multiplex or tandem targeting approach further detailed below. By means of further guidance, the following particular aspects and embodiments are provided.

In one aspect, the invention provides for the use of a nucleic acid modifying protein, complex or system as defined herein for targeting multiple gene loci. In one embodiment, this can be established by using multiple (tandem or multiplex) guide RNA (gRNA) sequences.

In one aspect, the invention provides methods for using one or more elements of a nucleic acid modifying protein, complex or system as defined herein for tandem or multiplex targeting, wherein said nucleic acid modifying system comprises multiple guide RNA sequences. Preferably, said gRNA sequences are separated by a nucleotide sequence, such as a direct repeat as defined herein elsewhere.

The nucleic acid modifying protein, system or complex as defined herein provides an effective means for modifying multiple target polynucleotides. The nucleic acid modifying protein, system or complex as defined herein has a wide variety of utility including modifying (e.g., deleting, inserting, translocating, inactivating, activating) one or more target polynucleotides in a multiplicity of cell types. As such the nucleic acid modifying protein, system or complex as defined herein of the invention has a broad spectrum of applications in, e.g., gene therapy, drug screening, disease diagnosis, and prognosis, including targeting multiple gene loci within a single nucleic acid modifying system.

In one aspect, the invention provides a nucleic acid modifying protein, system or complex as defined herein, i.e. a nucleic acid modifying complex having a nucleic acid modifying protein having at least one destabilization domain associated therewith, and multiple guide RNAs that target multiple nucleic acid molecules such as DNA molecules, whereby each of said multiple guide RNAs specifically targets its corresponding nucleic acid molecule, e.g., DNA molecule. Each nucleic acid molecule target, e.g., DNA molecule can encode a gene product or encompass a gene locus. Using multiple guide RNAs hence enables the targeting of multiple gene loci or multiple genes. In some embodiments the nucleic acid modifying protein may cleave the DNA molecule encoding the gene product. In some embodiments expression of the gene product is altered. The nucleic acid modifying protein and the guide RNAs do not naturally occur together. The invention comprehends the guide RNAs comprising tandemly arranged guide sequences. The invention further comprehends coding sequences for the DNA binding protein being codon optimized for expression in a eukaryotic cell. In a preferred embodiment the eukaryotic cell is a mammalian cell, a plant cell or a yeast cell and in a more preferred embodiment the mammalian cell is a human cell. Expression of the gene product may be decreased. The nucleic acid modifying protein may form part of a nucleic acid modifying system or complex, which further comprises tandemly arranged guide RNAs (gRNAs) comprising a series of 2, 3, 4, 5, 6, 7, 8, 9, 10, 15, 25, 25, 30, or more than 30 guide sequences, each capable of specifically hybridizing to a target sequence in a genomic locus of interest in a cell. In some embodiments, the functional nucleic acid modifying system or complex binds to the multiple target sequences. In some embodiments, the functional nucleic acid modifying system or complex may edit the multiple target sequences, e.g., the target sequences may comprise a genomic locus, and in some embodiments there may be an alteration of gene expression. In some embodiments, the functional nucleic acid modifying system or complex may comprise further effector domains. In some embodiments, the invention provides a method for altering or modifying expression of multiple gene products. The method may comprise introducing into a cell containing said target nucleic acids, e.g., DNA molecules, or containing and expressing target nucleic acid, e.g., DNA molecules; for instance, the target nucleic acids may encode gene products or provide for expression of gene products (e.g., regulatory sequences).

In preferred embodiments the nucleic acid modifying protein used for multiplex targeting comprises one or more domains of a Cas9, or the nucleic acid modifying system or complex comprises one or more domains of a Cas9. In some embodiments, the nucleic acid modifying protein used for multiplex targeting comprises one or more domains of AsCas9, or the nucleic acid modifying system or complex used for multiplex targeting comprises one or more domains of an AsCas9. In some embodiments, the nucleic acid modifying protein comprises one or more domains of an LbCas9, or the nucleic acid modifying system or complex comprises one or more domains of LbCas9. In some embodiments, the nucleic acid modifying protein used for multiplex targeting cleaves both strands of DNA to produce a double strand break (DSB). In some embodiments, the nucleic acid modifying protein used for multiplex targeting is a nickase. In some embodiments, the nucleic acid modifying protein used for multiplex targeting is a dual nickase. In some embodiments, the nucleic acid modifying protein used for multiplex targeting comprises one of more domains of a Cas9 enzyme such as a DD Cas9 enzyme as defined herein elsewhere.

In some general embodiments, the nucleic acid modifying protein used for multiplex targeting comprises and/or is associated with one or more effector domains. In some more specific embodiments, the nucleic acid modifying protein used for multiplex targeting comprises one or more domains of a deadCas9 as defined herein elsewhere.

In an aspect, the present invention provides a means for delivering the nucleic acid modifying protein, system or complex for use in multiple targeting as defined herein or the polynucleotides defined herein. Non-limiting examples of such delivery means are e.g. particle(s) delivering component(s) of the complex, vector(s) comprising the polynucleotide(s) discussed herein (e.g., encoding the nucleic acid modifying protein, providing the nucleotides encoding the nucleic acid modifying complex). In some embodiments, the vector may be a plasmid or a viral vector such as AAV, or lentivirus. Transient transfection with plasmids, e.g., into HEK cells may be advantageous, especially given the size limitations of AAV and that while Cas9 fits into AAV, one may reach an upper limit with additional guide RNAs.

Also provided is a model that constitutively expresses the nucleic acid modifying protein, complex or system as used herein for use in multiplex targeting. The organism may be transgenic and may have been transfected with the present vectors or may be the offspring of an organism so transfected. In a further aspect, the present invention provides compositions comprising the nucleic acid modifying protein, system and complex as defined herein or the polynucleotides or vectors described herein. Also provides are nucleic acid modifying systems or complexes comprising multiple guide RNAs, preferably in a tandemly arranged format. Said different guide RNAs may be separated by nucleotide sequences such as direct repeats.

Also provided is a method of treating a subject, e.g., a subject in need thereof, comprising inducing gene editing by transforming the subject with the polynucleotide encoding the nucleic acid modifying system or complex or any of polynucleotides or vectors described herein and administering them to the subject. A suitable repair template may also be provided, for example delivered by a vector comprising said repair template. Also provided is a method of treating a subject, e.g., a subject in need thereof, comprising inducing transcriptional activation or repression of multiple target gene loci by transforming the subject with the polynucleotides or vectors described herein, wherein said polynucleotide or vector encodes or comprises the nucleic acid modifying protein, complex or system comprising multiple guide RNAs, preferably tandemly arranged. Where any treatment is occurring ex vivo, for example in a cell culture, then it will be appreciated that the term 'subject' may be replaced by the phrase "cell or cell culture."

Compositions comprising nucleic acid modifying protein, complex or system comprising multiple guide RNAs, preferably tandemly arranged, or the polynucleotide or vector encoding or comprising said nucleic acid modifying protein, complex or system comprising multiple guide RNAs, preferably tandemly arranged, for use in the methods of treatment as defined herein elsewhere are also provided. A kit of parts may be provided including such compositions. Use of said composition in the manufacture of a medicament for such methods of treatment are also provided. Use of a nucleic acid modifying system in screening is also provided by the present invention, e.g., gain of function screens. Cells which are artificially forced to overexpress a gene are able to down regulate the gene over time (re-establishing equilibrium) e.g. by negative feedback loops. By the time the screen starts the unregulated gene might be reduced again. Using an inducible nucleic acid modifying activator allows one to induce transcription right before the screen and therefore minimizes the chance of false negative hits. Accordingly, by use of the instant invention in screening, e.g., gain of function screens, the chance of false negative results may be minimized.

In one aspect, the invention provides an engineered, non-naturally occurring nucleic acid modifying system comprising a nucleic acid modifying protein and multiple guide RNAs that each specifically target a DNA molecule encoding a gene product in a cell, whereby the multiple guide RNAs each target their specific DNA molecule encoding the gene product and the nucleic acid modifying protein cleaves the target DNA molecule encoding the gene product, whereby expression of the gene product is altered; and, wherein the nucleic acid modifying protein and the guide RNAs do not naturally occur together. The invention comprehends the multiple guide RNAs comprising multiple guide sequences, preferably separated by a nucleotide sequence such as a direct repeat and optionally fused to a tracr sequence. In an embodiment of the invention the nucleic acid modifying protein comprises one or more domains of a type V or VI CRISPR-Cas protein, and in a more preferred embodiment the nucleic acid modifying protein comprises one or more domains of a Cas9 protein. The invention further comprehends a nucleic acid modifying protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to the multiple nucleic acid modifying system guide RNAs that each specifically target a DNA molecule encoding a gene product and a second regulatory element operably linked coding for a nucleic acid modifying protein. Both regulatory elements may be located on the same vector or on different vectors of the system. The multiple guide RNAs target the multiple DNA molecules encoding the multiple gene products in a cell and the nucleic acid modifying protein may cleave the multiple DNA molecules encoding the gene products (it may cleave one or both strands or have substantially no nuclease activity), whereby expression of the multiple gene products is altered; and, wherein the nucleic acid modifying protein and the multiple guide RNAs do not naturally occur together. In a preferred embodiment the nucleic acid modifying protein comprises one or more domains of a Cas9 protein, optionally codon optimized for expression in a eukaryotic cell. In a preferred embodiment the eukaryotic cell is a mammalian cell, a plant cell or a yeast cell and in a more preferred embodiment the mammalian cell is a human cell. In a further embodiment of the invention, the expression of each of the multiple gene products is altered, preferably decreased.

In one aspect, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the nucleic acid modifying complex to the one or more target sequence(s) in a eukaryotic cell, wherein the nucleic acid modifying complex comprises a nucleic acid modifying protein complexed with the one or more guide sequence(s) that is hybridized to the one or more target sequence(s); and (b) a second regulatory element operably linked to protein-coding sequence encoding said nucleic acid modifying protein, preferably comprising at least one nuclear localization sequence and/or at least one NES; wherein components (a) and (b) are located on the same or different vectors of the system. Where applicable, a tracr sequence may also be provided. In some embodiments, component (a) further comprises two or more guide sequences operably linked to the first regulatory element, wherein when expressed, each of the two or more guide sequences direct sequence specific binding of a nucleic acid modifying complex to a different target sequence in a eukaryotic cell. In some embodiments, the nucleic acid modifying complex comprises one or more nuclear localization sequences and/or one or more NES of sufficient strength to drive accumulation of said nucleic acid modifying complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

Recombinant expression vectors can comprise the polynucleotides encoding the nucleic acid modifying protein, system or complex for use in multiple targeting as defined herein in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

In some embodiments, a host cell is transiently or non-transiently transfected with one or more vectors comprising the polynucleotides encoding the nucleic acid modifying protein, system or complex for use in multiple targeting as defined herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art and exemplified herein elsewhere. Cell lines are available from a variety of sources known to those with skill in the art (see, e.g., the American Type Culture Collection (ATCC) (Manassas, Va.)). In some embodiments, a cell transfected with one or more vectors comprising the polynucleotides encoding the nucleic acid modifying protein, system or complex for use in multiple targeting as defined herein is used to establish a new cell line comprising one or more vector-derived sequences. In some embodiments, a cell transiently transfected with the components of a nucleic acid modifying system or complex for use in multiple targeting as described herein (such as by transient transfection of one or more vectors, or transfection with RNA), and modified through the activity of a nucleic acid modifying system or complex, is used to establish a new cell line comprising cells containing the modification but lacking any other exogenous sequence. In some embodiments, cells transiently or non-transiently transfected with one or more vectors comprising the polynucleotides encoding the nucleic acid modifying protein, system or complex for use in multiple targeting as defined herein, or cell lines derived from such cells are used in assessing one or more test compounds.

The term "regulatory element" is as defined herein elsewhere.

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a direct repeat sequence and one or more insertion sites for inserting one or more guide RNA sequences up- or downstream (whichever applicable) of the direct repeat sequence, wherein when expressed, the guide sequence(s) direct(s) sequence-specific binding of the nucleic acid modifying complex to the respective target sequence(s) in a eukaryotic cell, wherein the nucleic acid modifying complex comprises a nucleic acid modifying protein complexed with the one or more guide sequence(s) that is hybridized to the respective target sequence(s); and/or (b) a second regulatory element operably linked to an enzyme-coding sequence encoding said nucleic acid modifying protein comprising preferably at least one nuclear localization sequence and/or NES. In some embodiments, the host cell comprises components (a) and (b). Where applicable, a tracr sequence may also be provided. In some embodiments, component (a), component (b), or components (a) and (b) are stably integrated into a genome of the host eukaryotic cell. In some embodiments, component (a) further comprises two or more guide sequences operably linked to the first regulatory element, and optionally separated by a direct repeat, wherein when expressed, each of the two or more guide sequences direct sequence specific binding of a nucleic acid modifying complex to a different target sequence in a eukaryotic cell. In some embodiments, the nucleic acid modifying protein comprises one or more nuclear localization sequences and/or nuclear export sequences or NES of sufficient strength to drive accumulation of said nucleic acid modifying protein in a detectable amount in and/or out of the nucleus of a eukaryotic cell.

In some embodiments, the nucleic acid modifying protein comprises one or more domains of a Cas enzyme that is a type V or VI CRISPR system enzyme. In some embodiments, the Cas enzyme is a Cas9 enzyme. In some embodiments, the Cas9 enzyme is derived from *Francisella tularensis* 1, *Francisella tularensis* subsp. *novicida*, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, Candidatus Methanoplasma *termitum*, *Eubacterium eligens*, *Moraxella bovoculi* 237, *Leptospira inadai*, Lachnospiraceae bacterium ND2006, *Porphyromonas crevioricanis*

3, *Prevotella disiens*, or *Porphyromonas macacae* Cas9, and may include further alterations or mutations of the Cas9 as defined herein elsewhere, and can be a chimeric Cas9. In some embodiments, the Cas9 enzyme is codon-optimized for expression in a eukaryotic cell. In some embodiments, the CRISPR enzyme directs cleavage of one or two strands at the location of the target sequence. In some embodiments, the first regulatory element is a polymerase III promoter. In some embodiments, the second regulatory element is a polymerase II promoter. In some embodiments, the one or more guide sequence(s) is (are each) at least 16, 17, 18, 19, 20, 25 nucleotides, or between 16-30, or between 16-25, or between 16-20 nucleotides in length. When multiple guide RNAs are used, they are preferably separated by a direct repeat sequence. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal, for example a mammal. Also, the organism may be an arthropod such as an insect. The organism also may be a plant. Further, the organism may be a fungus.

In one aspect, the invention provides a kit comprising one or more of the components described herein. In some embodiments, the kit comprises a vector system and instructions for using the kit. In some embodiments, the vector system comprises (a) a first regulatory element operably linked to a direct repeat sequence and one or more insertion sites for inserting one or more guide sequences up- or downstream (whichever applicable) of the direct repeat sequence, wherein when expressed, the guide sequence directs sequence-specific binding of a nucleic acid modifying complex to a target sequence in a eukaryotic cell, wherein the nucleic acid modifying complex comprises a nucleic acid modifying protein comprising a nucleic acid binding protein complexed with the guide sequence that is hybridized to the target sequence; and/or (b) a second regulatory element operably linked to an protein-coding sequence encoding said nucleic acid modifying protein comprising a nuclear localization sequence. Where applicable, a tracr sequence may also be provided. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a nucleic acid modifying complex to a different target sequence in a eukaryotic cell. In some embodiments, the nucleic acid modifying protein comprises one or more nuclear localization sequences of sufficient strength to drive accumulation of said nucleic acid modifying protein in a detectable amount in the nucleus of a eukaryotic cell. In some embodiments, the nucleic acid modifying protein comprises one or more domains of a type V or VI CRISPR system enzyme. In some embodiments, the CRISPR enzyme is a Cas9 enzyme. In some embodiments, the Cas9 enzyme is derived from *Francisella tularensis* 1, *Francisella tularensis* subsp. *novicida*, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, Candidatus Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens*, or *Porphyromonas macacae* Cas9 (e.g., modified to have or be associated with at least one DD), and may include further alteration or mutation of the Cas9, and can be a chimeric Cas9. In some embodiments, the DD-CRISPR enzyme is codon-optimized for expression in a eukaryotic cell. In some embodiments, the DD-CRISPR enzyme directs cleavage of one or two strands at the location of the target sequence. In some embodiments, the DD-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 16, 17, 18, 19, 20, 25 nucleotides, or between 16-30, or between 16-25, or between 16-20 nucleotides in length.

In one aspect, the invention provides a method of modifying multiple target polynucleotides in a host cell such as a eukaryotic cell. In some embodiments, the method comprises allowing a nucleic acid modifying complex to bind to multiple target polynucleotides, e.g., to effect cleavage of said multiple target polynucleotides, thereby modifying multiple target polynucleotides, wherein the nucleic acid modifying complex comprises a nucleic acid modifying protein complexed with multiple guide sequences each of the being hybridized to a specific target sequence within said target polynucleotide, wherein said multiple guide sequences are linked to a direct repeat sequence. Where applicable, a tracr sequence may also be provided (e.g. to provide a single guide RNA, sgRNA). In some embodiments, said cleavage comprises cleaving one or two strands at the location of each of the target sequence by said nucleic acid modifying protein. In some embodiments, said cleavage results in decreased transcription of the multiple target genes. In some embodiments, the method further comprises repairing one or more of said cleaved target polynucleotide by homologous recombination with an exogenous template polynucleotide, wherein said repair results in a mutation comprising an insertion, deletion, or substitution of one or more nucleotides of one or more of said target polynucleotides. In some embodiments, said mutation results in one or more amino acid changes in a protein expressed from a gene comprising one or more of the target sequence(s). In some embodiments, the method further comprises delivering one or more vectors to said eukaryotic cell, wherein the one or more vectors drive expression of one or more of: the nucleic acid modifying protein and the multiple guide RNA sequence linked to a direct repeat sequence. Where applicable, a tracr sequence may also be provided. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of multiple polynucleotides in a eukaryotic cell. In some embodiments, the method comprises allowing a nucleic acid modifying complex to bind to multiple polynucleotides such that said binding results in increased or decreased expression of said polynucleotides; wherein the nucleic acid modifying complex comprises a nucleic acid modifying protein complexed with multiple guide sequences each specifically hybridized to its own target sequence within said polynucleotide, wherein said guide sequences are linked to a direct repeat sequence. Where applicable, a tracr sequence may also be provided. In some embodiments, the method further comprises delivering one or more vectors to said eukaryotic cells, wherein the one or more vectors drive expression of one or more of: the nucleic acid modifying protein and the multiple guide sequences linked to the direct repeat sequences. Where applicable, a tracr sequence may also be provided.

In one aspect, the invention provides a recombinant polynucleotide comprising multiple guide RNA sequences up- or downstream (whichever applicable) of a direct repeat sequence, wherein each of the guide sequences when expressed directs sequence-specific binding of a nucleic acid modifying complex to its corresponding target sequence present in a eukaryotic cell. In some embodiments, the target sequence is a viral sequence present in a eukaryotic cell. Where applicable, a tracr sequence may also be provided. In some embodiments, the target sequence is a proto-oncogene or an oncogene.

Aspects of the invention encompass a non-naturally occurring or engineered composition that may comprise a guide RNA (gRNA) comprising a guide sequence capable of hybridizing to a target sequence in a genomic locus of interest in a cell and a nucleic acid modifying protein as defined herein that may comprise at least one or more nuclear localization sequences.

An aspect of the invention encompasses methods of modifying a genomic locus of interest to change gene expression in a cell by introducing into the cell any of the compositions described herein.

An aspect of the invention is that the above elements are comprised in a single composition or comprised in individual compositions. These compositions may advantageously be applied to a host to elicit a functional effect on the genomic level.

As used herein, the term "guide RNA" or "gRNA" has the leaning as used herein elsewhere and comprises any polynucleotide sequence having sufficient complementarity with a target nucleic acid sequence to hybridize with the target nucleic acid sequence and direct sequence-specific binding of a nucleic acid-targeting complex to the target nucleic acid sequence. Each gRNA may be designed to include multiple binding recognition sites (e.g., aptamers) specific to the same or different adaptor protein. Each gRNA may be designed to bind to the promoter region −1000−+1 nucleic acids upstream of the transcription start site (i.e. TSS), preferably −200 nucleic acids. This positioning improves effector domains which affect gene activation (e.g., transcription activators) or gene inhibition (e.g., transcription repressors). The modified gRNA may be one or more modified gRNAs targeted to one or more target loci (e.g., at least 1 gRNA, at least 2 gRNA, at least 5 gRNA, at least 10 gRNA, at least 20 gRNA, at least 30 g RNA, at least 50 gRNA) comprised in a composition. Said multiple gRNA sequences can be tandemly arranged and are preferably separated by a direct repeat.

Thus, gRNA, the nucleic acid modifying protein as defined herein may each individually be comprised in a composition and administered to a host individually or collectively. Alternatively, these components may be provided in a single composition for administration to a host. Administration to a host may be performed via viral vectors known to the skilled person or described herein for delivery to a host (e.g., lentiviral vector, adenoviral vector, AAV vector). As explained herein, use of different selection markers (e.g., for lentiviral sgRNA selection) and concentration of gRNA (e.g., dependent on whether multiple gRNAs are used) may be advantageous for eliciting an improved effect. On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different effector domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

In certain embodiments, effector domains are linked directly to guides. For example, a SNAP-tag is an engineered methyltransferase that can be reacted with guides that carry 06-benzylguanine derivatives.

The current invention comprehends the use of the compositions of the current invention to establish and utilize conditional or inducible nucleic acid modifying transgenic cell/animals; see, e.g., Platt et al., Cell (2014), 159(2): 440-455, or PCT patent publications cited herein, such as WO 2014/093622 (PCT/US2013/074667). For example, cells or animals such as non-human animals, e.g., vertebrates or mammals, such as rodents, e.g., mice, rats, or other laboratory or field animals, e.g., cats, dogs, sheep, etc., may be 'knock-in' whereby the animal conditionally or inducibly expresses nucleic acid modifying protein akin to Platt et al. The target cell or animal thus comprises the nucleic acid modifying protein comprising one or more domains of a Cas protein conditionally or inducibly (e.g., in the form of Cre dependent constructs), on expression of a vector introduced into the target cell, the vector expresses that which induces or gives rise to the condition of the nucleic acid modifying protein expression in the target cell. By applying the teaching and compositions as defined herein with the known method of creating a nucleic acid modifying complex, inducible genomic events are also an aspect of the current invention. Examples of such inducible events have been described herein elsewhere.

In some embodiments, phenotypic alteration is preferably the result of genome modification when a genetic disease is targeted, especially in methods of therapy and preferably where a repair template is provided to correct or alter the phenotype.

In some embodiments diseases that may be targeted include those concerned with disease-causing splice defects.

In some embodiments, cellular targets include Hemopoietic Stem/Progenitor Cells (CD34+); Human T cells; and Eye (retinal cells)—for example photoreceptor precursor cells.

In some embodiments Gene targets include: Human Beta Globin—HBB (for treating Sickle Cell Anemia, including by stimulating gene-conversion (using closely related HBD gene as an endogenous template)); CD3 (T-Cells); and CEP920—retina (eye).

In some embodiments disease targets also include: cancer; Sickle Cell Anemia (based on a point mutation); HBV, HIV;

Beta-Thalassemia; and ophthalmic or ocular disease—for example Leber Congenital Amaurosis (LCA)-causing Splice Defect.

In some embodiments delivery methods include: Cationic Lipid Mediated "direct" delivery of Enzyme-Guide complex (RiboNucleoProtein) and electroporation of plasmid DNA.

Methods, products and uses described herein may be used for non-therapeutic purposes. Furthermore, any of the methods described herein may be applied in vitro and ex vivo.

In an aspect, provided is a non-naturally occurring or engineered composition comprising:
I. two or more nucleic acid modifying system polynucleotide sequences comprising
  (a) a first guide sequence capable of hybridizing to a first target sequence in a polynucleotide locus,
  (b) a second guide sequence capable of hybridizing to a second target sequence in a polynucleotide locus,
  (c) a direct repeat sequence,
  and
II. a nucleic acid modifying protein or a second polynucleotide sequence encoding it,
wherein when transcribed, the first and the second guide sequences direct sequence-specific binding of a first and a second nucleic acid modifying complex to the first and second target sequences respectively,
wherein the first nucleic acid modifying complex comprises the nucleic acid modifying protein comprising a nucleic acid binding protein complexed with the first guide sequence that is hybridizable to the first target sequence,
wherein the second nucleic acid modifying complex comprises the nucleic acid modifying protein complexed with the second guide sequence that is hybridizable to the second target sequence, and
wherein the first guide sequence directs cleavage of one strand of the DNA duplex near the first target sequence and the second guide sequence directs cleavage of the other strand near the second target sequence inducing a double strand break, thereby modifying the organism or the non-human or non-animal organism. Similarly, compositions comprising more than two guide RNAs can be envisaged e.g. each specific for one target, and arranged tandemly in the composition or nucleic acid modifying system or complex as described herein.

In another embodiment, the nucleic acid modifying protein is delivered into the cell as a protein. In another and particularly preferred embodiment, the nucleic acid modifying protein is delivered into the cell as a protein or as a nucleotide sequence encoding it. Delivery to the cell as a protein may include delivery of a Ribonucleoprotein (RNP) complex, where the protein is complexed with the multiple guides.

In an aspect, host cells and cell lines modified by or comprising the compositions, systems or modified enzymes of present invention are provided, including stem cells, and progeny thereof.

In an aspect, methods of cellular therapy are provided, where, for example, a single cell or a population of cells is sampled or cultured, wherein that cell or cells is or has been modified ex vivo as described herein, and is then re-introduced (sampled cells) or introduced (cultured cells) into the organism. Stem cells, whether embryonic or induce pluripotent or totipotent stem cells, are also particularly preferred in this regard. But, of course, in vivo embodiments are also envisaged.

Inventive methods can further comprise delivery of templates, such as repair templates, which may be dsODN or ssODN, see below. Delivery of templates may be via the cotemporaneous or separate from delivery of any or all the nucleic acid modifying protein or guide RNAs and via the same delivery mechanism or different. In some embodiments, it is preferred that the template is delivered together with the guide RNAs and, preferably, also the nucleic acid modifying protein. An example may be an AAV vector where the nucleic acid modifying protein comprises one or more domains of a CRISPR Cas protein, which is AsCas9 or LbCas9.

Inventive methods can further comprise: (a) delivering to the cell a double-stranded oligodeoxynucleotide (dsODN) comprising overhangs complimentary to the overhangs created by said double strand break, wherein said dsODN is integrated into the locus of interest; or—(b) delivering to the cell a single-stranded oligodeoxynucleotide (ssODN), wherein said ssODN acts as a template for homology directed repair of said double strand break. Inventive methods can be for the prevention or treatment of disease in an individual, optionally wherein said disease is caused by a defect in said locus of interest. Inventive methods can be conducted in vivo in the individual or ex vivo on a cell taken from the individual, optionally wherein said cell is returned to the individual.

The invention also comprehends products obtained from using nucleic acid modifying protein or nucleic acid modifying enzyme or nucleic acid modifying protein comprising a nucleic acid binding domain, which comprises one or more domains of a Cas9 enzyme or nucleic acid modifying system or nucleic acid modifying complex for use in tandem or multiple targeting as defined herein.

Escorted Guides for the Nucleic Acid Modifying System According to the Invention In one aspect the invention provides escorted nucleic acid modifying systems or complexes, especially such a system involving an escorted nucleic acid modifying system guide. By "escorted" is meant that the nucleic acid modifying system or complex or guide is delivered to a selected time or place within a cell, so that activity of the nucleic acid modifying system or complex or guide is spatially or temporally controlled. For example, the activity and destination of the nucleic acid modifying system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted nucleic acid modifying systems or complexes have a gRNA with a functional structure designed to improve gRNA structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7

(2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, provided herein is a gRNA modified, e.g., by one or more aptamer(s) designed to improve gRNA delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to a selected effector. The invention accordingly comprehends an gRNA that responds to normal or pathological physiological conditions, including without limitation pH, hypoxia, O2 concentration, temperature, protein concentration, enzymatic concentration, lipid structure, light exposure, mechanical disruption (e.g. ultrasound waves), magnetic fields, electric fields, or electromagnetic radiation.

An aspect of the invention provides non-naturally occurring or engineered composition comprising an escorted guide RNA (egRNA) comprising:

an RNA guide sequence capable of hybridizing to a target sequence in a genomic locus of interest in a cell; and,
an escort RNA aptamer sequence, wherein the escort aptamer has binding affinity for an aptamer ligand on or in the cell, or the escort aptamer is responsive to a localized aptamer effector on or in the cell, wherein the presence of the aptamer ligand or effector on or in the cell is spatially or temporally restricted.

The escort aptamer may for example change conformation in response to an interaction with the aptamer ligand or effector in the cell.

The escort aptamer may have specific binding affinity for the aptamer ligand.

The aptamer ligand may be localized in a location or compartment of the cell, for example on or in a membrane of the cell. Binding of the escort aptamer to the aptamer ligand may accordingly direct the egRNA to a location of interest in the cell, such as the interior of the cell by way of binding to an aptamer ligand that is a cell surface ligand. In this way, a variety of spatially restricted locations within the cell may be targeted, such as the cell nucleus or mitochondria.

Once intended alterations have been introduced, such as by editing intended copies of a gene in the genome of a cell, continued nucleic acid modifying protein expression in that cell is no longer necessary. Indeed, sustained expression would be undesirable in certain casein case of off-target effects at unintended genomic sites, etc. Thus time-limited expression would be useful. Inducible expression offers one approach, but in addition Applicants have engineered a Self-Inactivating nucleic acid modifying system that relies on the use of a non-coding guide target sequence within the nucleic acid modifying vector itself. Thus, after expression begins, the nucleic acid modifying system will lead to its own destruction, but before destruction is complete it will have time to edit the genomic copies of the target gene (which, with a normal point mutation in a diploid cell, requires at most two edits). Simply, the self inactivating nucleic acid modifying system includes additional RNA (i.e., guide RNA) that targets the coding sequence for the nucleic acid modifying protein itself or that targets one or more non-coding guide target sequences complementary to unique sequences present in one or more of the following: (a) within the promoter driving expression of the non-coding RNA elements, (b) within the promoter driving expression of the nucleic acid modifying protein gene, (c) within 100 bp of the ATG translational start codon in the nucleic acid modifying protein coding sequence, (d) within the inverted terminal repeat (iTR) of a viral delivery vector, e.g., in an AAV genome.

The egRNA may include an RNA aptamer linking sequence, operably linking the escort RNA sequence to the RNA guide sequence.

In embodiments, the egRNA may include one or more photolabile bonds or non-naturally occurring residues.

In one aspect, the escort RNA aptamer sequence may be complementary to a target miRNA, which may or may not be present within a cell, so that only when the target miRNA is present is there binding of the escort RNA aptamer sequence to the target miRNA which results in cleavage of the egRNA by an RNA-induced silencing complex (RISC) within the cell.

In embodiments, the escort RNA aptamer sequence may for example be from 10 to 200 nucleotides in length, and the egRNA may include more than one escort RNA aptamer sequence.

It is to be understood that any of the RNA guide sequences as described herein elsewhere can be used in the egRNA described herein. In certain embodiments of the invention, the guide RNA or mature crRNA comprises, consists essentially of, or consists of a direct repeat sequence and a guide sequence or spacer sequence. In certain embodiments, the guide RNA or mature crRNA comprises, consists essentially of, or consists of a direct repeat sequence linked to a guide sequence or spacer sequence. In certain embodiments the guide RNA or mature crRNA comprises 19 nts of partial direct repeat followed by 23-25 nt of guide sequence or spacer sequence. In certain embodiments, the effector protein is a nucleic acid modifying protein comprising one or more domains of a FnCas9 effector protein and requires at least 16 nt of guide sequence to achieve detectable DNA cleavage and a minimum of 17 nt of guide sequence to achieve efficient DNA cleavage in vitro. In certain embodiments, the direct repeat sequence is located upstream (i.e., 5') from the guide sequence or spacer sequence. In a preferred embodiment the seed sequence (i.e. the sequence essential critical for recognition and/or hybridization to the sequence at the target locus) of the FnCas9 guide RNA is approximately within the first 5 nt on the 5' end of the guide sequence or spacer sequence.

The egRNA may be included in a non-naturally occurring or engineered nucleic acid modifying complex composition, together with a nucleic acid modifying protein which may include at least one mutation, for example a mutation so that the nucleic acid modifying protein has no more than 5% of the nuclease activity of a nucleic acid modifying protein not having the at least one mutation, for example having a diminished nuclease activity of at least 97%, or 100% as compared with the nucleic acid modifying protein not having the at least one mutation. The nucleic acid modifying protein may also include one or more nuclear localization sequences. Mutated nucleic acid modifying protein having modulated activity such as diminished nuclease activity are described herein elsewhere.

The engineered nucleic acid modifying composition may be provided in a cell, such as a eukaryotic cell, a mammalian cell, or a human cell.

In embodiments, the compositions described herein comprise a nucleic acid modifying complex having at least three effector domains, at least one of which is associated with nucleic acid modifying protein and at least two of which are associated with egRNA.

The compositions described herein may be used to introduce a genomic locus event in a host cell, such as an eukaryotic cell, in particular a mammalian cell, or a non-human eukaryote, in particular a non-human mammal such as a mouse, in vivo. The genomic locus event may comprise affecting gene activation, gene inhibition, or cleavage in a locus. The compositions described herein may also be used to modify a genomic locus of interest to change gene expression in a cell. Methods of introducing a genomic locus event in a host cell using the nucleic acid modifying protein provided herein are described herein in detail elsewhere. Delivery of the composition may for example be by way of delivery of a nucleic acid molecule(s) coding for the composition, which nucleic acid molecule(s) is operatively linked to regulatory sequence(s), and expression of the nucleic acid molecule(s) in vivo, for example by way of a lentivirus, an adenovirus, or an AAV.

The present invention provides compositions and methods by which gRNA-mediated gene editing activity can be adapted. The invention provides gRNA secondary structures that improve cutting efficiency by increasing gRNA and/or increasing the amount of RNA delivered into the cell. The gRNA may include light labile or inducible nucleotides.

To increase the effectiveness of gRNA, for example gRNA delivered with viral or non-viral technologies, Applicants added secondary structures into the gRNA that enhance its stability and improve gene editing. Separately, to overcome the lack of effective delivery, Applicants modified gRNAs with cell penetrating RNA aptamers; the aptamers bind to cell surface receptors and promote the entry of gRNAs into cells. Notably, the cell-penetrating aptamers can be designed to target specific cell receptors, in order to mediate cell-specific delivery. Applicants also have created guides that are inducible. In an embodiment the binding of the nucleic acid binding domain to a target nucleic acid is inducible. In an embodiment, the target nucleic acid comprises chromosomal DNA, mitochondrial DNA, viral DNA or RNA, bacterial DNA, or fungal DNA.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm2. In a preferred embodiment, a stimulation paradigm of as low as 0.25 sec every 15 sec should result in maximal activation.

Cells involved in the practice of the present invention may be a prokaryotic cell or a eukaryotic cell, advantageously an animal cell a plant cell or a yeast cell, more advantageously a mammalian cell.

The chemical or energy sensitive guide may undergo a conformational change upon induction by the binding of a chemical source or by the energy allowing it act as a guide and have the nucleic acid modifying system or complex function. The invention can involve applying the chemical source or energy so as to have the guide function and the nucleic acid modifying system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

Another system contemplated by the present invention is a chemical inducible system based on change in sub-cellular localization. Applicants also developed a system in which the polypeptide include a nucleic acid binding domain comprising at least five or more Transcription activator-like effector (TALE) monomers and at least one or more half-monomers specifically ordered to target the genomic locus of interest linked to at least one or more effector domains are further linked to a chemical or energy sensitive protein. This protein will lead to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus) and result in activation or repression of target gene expression.

This type of system could also be used to induce the cleavage of a genomic locus of interest in a cell when the effector domain is a nuclease.

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www-.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the nucleic acid modifying complex or system, and the binding will induce the change of sub-cellular localization of the polypeptide, leading to the entire polypeptide entering the nucleus of cells. Once inside the nucleus, the guide protein and the other components of the nucleic acid modifying complex will be active and modulating target gene expression in cells.

This type of system could also be used to induce the cleavage of a genomic locus of interest in a cell; and, in this regard, it is noted that the nucleic acid modifying protein is a nuclease. The light could be generated with a laser or other forms of energy sources. The heat could be generated by raise of temperature results from an energy source, or from nanoparticles that release heat after absorbing energy from an energy source delivered in the form of radio-wave.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

The rapid transcriptional response and endogenous targeting of the instant invention make for an ideal system for the study of transcriptional dynamics. For example, the instant invention may be used to study the dynamics of variant production upon induced expression of a target gene. On the other end of the transcription cycle, mRNA degradation studies are often performed in response to a strong extracellular stimulus, causing expression level changes in a plethora of genes. The instant invention may be utilized to reversibly induce transcription of an endogenous target, after which point stimulation may be stopped and the degradation kinetics of the unique target may be tracked.

The temporal precision of the instant invention may provide the power to time genetic regulation in concert with experimental interventions. For example, targets with suspected involvement in long-term potentiation (LTP) may be modulated in organotypic or dissociated neuronal cultures, but only during stimulus to induce LTP, so as to avoid interfering with the normal development of the cells. Similarly, in cellular models exhibiting disease phenotypes, targets suspected to be involved in the effectiveness of a particular therapy may be modulated only during treatment. Conversely, genetic targets may be modulated only during a pathological stimulus. Any number of experiments in which timing of genetic cues to external experimental stimuli is of relevance may potentially benefit from the utility of the instant invention.

The in vivo context offers equally rich opportunities for the instant invention to control gene expression. Photoinducibility provides the potential for spatial precision. Taking advantage of the development of optrode technology, a stimulating fiber optic lead may be placed in a precise brain region. Stimulation region size may then be tuned by light intensity. This may be done in conjunction with the delivery of the nucleic acid modifying system or complex of the invention, or, in the case of transgenic nucleic acid modifying protein expressing animals, guide RNA of the invention may be delivered and the optrode technology can allow for the modulation of gene expression in precise brain regions. A transparent nucleic acid modifying protein expressing organism, can have guide RNA of the invention administered to it and then there can be extremely precise laser induced local gene expression changes.

A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types may be found at the American Type Culture Collection (ATCC) or the European Collection of Cell Cultures (ECACC). Culture media may be supplemented with amino acids such as L-glutamine, salts, anti-fungal or anti-bacterial agents such as Fungizone®, penicillin-streptomycin, animal serum, and the like. The cell culture medium may optionally be serum-free.

The invention may also offer valuable temporal precision in vivo. The invention may be used to alter gene expression during a particular stage of development. The invention may be used to time a genetic cue to a particular experimental window. For example, genes implicated in learning may be overexpressed or repressed only during the learning stimulus in a precise region of the intact rodent or primate brain. Further, the invention may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the invention, they highlight some of the areas in which the invention may be a powerful technology.

Protected Guides: Enzymes According to the Invention can be Used in Combination with Protected Guide RNAs In one aspect, an object of the current invention is to further enhance the specificity of nucleic acid modifying protein given individual guide RNAs through thermodynamic tuning of the binding specificity of the guide RNA to target DNA. This is a general approach of introducing mismatches, elongation or truncation of the guide sequence to increase/decrease the number of complimentary bases vs. mismatched bases shared between a genomic target and its potential off-target loci, in order to give thermodynamic advantage to targeted genomic loci over genomic off-targets.

In one aspect, the invention provides for the guide sequence being modified by secondary structure to increase the specificity of the nucleic acid modifying system and whereby the secondary structure can protect against exonuclease activity and allow for 3' additions to the guide sequence.

In one aspect, the invention provides for hybridizing a "protector RNA" to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target DNA binding to the mismatched base pairs at the 3' end. In embodiments of the invention, additional sequences comprising an extended length may also be present.

Guide RNA (gRNA) extensions matching the genomic target provide gRNA protection and enhance specificity. Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region. Thermodynamic prediction can be used to predict completely matching or partially matching guide extensions that result in protected gRNA states. This extends the concept of protected gRNAs to interaction between X and Z, where X will generally be of length 17-20nt and Z is of length 1-30nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and EL are used interchangeably to correspond to the term extended length (ExL) which represents the number of nucleotides by which the target sequence is extended.

An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence.

An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence.

Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

In one aspect, the invention provides for enhanced nucleic acid modifying protein specificity wherein the double stranded 3' end of the protected guide RNA (pgRNA) allows for two possible outcomes: (1) the guide RNA-protector RNA to guide RNA-target DNA strand exchange will occur and the guide will fully bind the target, or (2) the guide RNA will fail to fully bind the target and because nucleic acid modifying protein target cleavage is a multiple step kinetic reaction that requires guide RNA:target DNA binding to activate protein-catalyzed DSBs, wherein protein cleavage does not occur if the guide RNA does not properly bind. According to particular embodiments, the protected guide RNA improves specificity of target binding as compared to a unprotected guide system. According to particular embodiments the protected modified guide RNA improves stability as compared to an unmodified guide system. According to particular embodiments the protector sequence has a length between 3 and 120 nucleotides and comprises 3 or more contiguous nucleotides complementary to another sequence of guide or protector. According to particular embodiments, the protector sequence forms a hairpin. According to particular embodiments the guide RNA further comprises a protected sequence and an exposed sequence. According to particular embodiments the exposed sequence is 1 to 19 nucleotides. More particularly, the exposed sequence is at least 75%, at least 90% or about 100% complementary to the target sequence. According to particular embodiments the guide sequence is at least 90% or about 100% complementary to the protector strand. According to particular embodiments the guide sequence is at least 75%, at least 90% or about 100% complementary to the target sequence. According to particular embodiments, the guide RNA further comprises an extension sequence. More particularly, the extension sequence is operably linked to the 3' end of the protected guide sequence, and optionally directly linked to the 3' end of the protected guide sequence. According to particular embodiments the extension sequence is 1-12 nucleotides. According to particular embodiments the extension sequence is operably linked to the guide sequence at the 3' end of the protected guide sequence and the 5' end of the protector strand and optionally directly linked to the 3' end of the protected guide sequence and the 3' end of the protector strand, wherein the extension sequence is a linking sequence between the protected sequence and the protector strand. According to particular embodiments the extension sequence is 100% not complementary to the protector strand, optionally at least 95%, at least 90%, at least 80%, at least 70%, at least 60%, or at least 50% not complementary to the protector strand. According to particular embodiments the guide sequence further comprises mismatches appended to the end of the guide sequence, wherein the mismatches thermodynamically optimize specificity.

In one aspect, the invention provides an engineered, non-naturally occurring nucleic acid modifying system comprising a nucleic acid modifying protein and a protected guide RNA that targets a DNA molecule encoding a gene product in a cell, whereby the protected guide RNA targets the DNA molecule encoding the gene product and the nucleic acid modifying protein cleaves the DNA molecule encoding the gene product, whereby expression of the gene product is altered; and, wherein the nucleic acid modifying protein and the protected guide RNA do not naturally occur together. The invention comprehends the protected guide RNA comprising a guide sequence fused 3' to a direct repeat sequence. The invention further comprehends the nucleic acid modifying protein being codon optimized for expression in a Eukaryotic cell. In a preferred embodiment the Eukaryotic cell is a mammalian cell, a plant cell or a yeast cell and in a more preferred embodiment the mammalian cell is a human cell. In a further embodiment of the invention, the expression of the gene product is decreased. In some embodiments, the nucleic acid modifying protein comprises one or more domains of a *Acidaminococcus* sp. BV3L6, Lachnospiraceae bacterium or *Francisella* Novicida Cas9, and may include mutated Cas9 derived from these organisms. The protein may comprise one or more domains of a Cas9 homolog or ortholog. In some embodiments, the nucleotide sequence encoding the nucleic acid modifying protein is codon-optimized for expression in a eukaryotic cell. In some embodiments, the nucleic acid modifying protein directs cleavage of one or two strands at the location of the target sequence. In some embodiments, the first regulatory element is a polymerase III promoter. In some embodiments, the second regulatory element is a polymerase II promoter. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a direct repeat sequence and one or more insertion sites for inserting one or more guide sequences downstream of the direct repeat sequence, wherein when expressed, the guide sequence directs sequence-specific binding of a nucleic acid modifying complex to a target sequence in a eukaryotic cell, wherein the nucleic acid modifying complex comprises a nucleic acid modifying protein complexed with the guide RNA comprising the guide sequence that is hybridized to the target sequence and/or (b) a second regulatory element operably linked to an protein-coding sequence encoding said nucleic acid modifying protein comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises two or more guide sequences operably linked to the first regulatory element, wherein when expressed, each of the two or more guide sequences direct sequence specific binding of a nucleic acid modifying complex to a different target sequence in a eukaryotic cell. In some embodiments, the nucleic acid modifying protein directs cleavage of one or two strands at the location of the target sequence. In some embodiments, the nucleic acid modifying protein lacks DNA strand cleavage activity. In some embodiments, the first regulatory element is a polymerase III promoter. In some embodiments, the second regulatory element is a polymerase II promoter.

In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant or a yeast. Further, the organism may be a fungus.

In one aspect, the invention provides a kit comprising one or more of the components described herein above. In some embodiments, the kit comprises a vector system and instructions for using the kit. In some embodiments, the vector system comprises (a) a first regulatory element operably linked to a direct repeat sequence and one or more insertion sites for inserting one or more guide sequences downstream of the direct repeat sequence, wherein when expressed, the guide sequence directs sequence-specific binding of a nucleic acid modifying complex to a target sequence in a eukaryotic cell, wherein the nucleic acid modifying complex comprises a nucleic acid modifying protein complexed with the protected guide RNA comprising the guide sequence that is hybridized to the target sequence and/or (b) a second regulatory element operably linked to an enzyme-coding sequence encoding said nucleic acid modifying protein comprising a nuclear localization sequence. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a nucleic acid modifying complex to a different target sequence in a eukaryotic cell. In some embodiments, the nucleic acid modifying protein comprises one or more nuclear localization sequences of sufficient strength to drive accumulation of said nucleic acid modifying protein in a detectable amount in the nucleus of a eukaryotic cell. In some embodiments, the nucleic acid modifying protein comprises one or more domains of a *Acidaminococcus* sp. BV3L6, Lachnospiraceae bacterium MA2020 or *Francisella tularensis* 1 Novicida Cas9 or mutated Cas9 derived from these organisms. The nucleic acid modifying protein may comprise one or more domains from a Cas9 homolog or ortholog. In some embodiments, the nucleic acid modifying protein is codon-optimized for expression in a eukaryotic cell. In some embodiments, the nucleic acid modifying protein directs cleavage of one or two strands at the location of the target sequence. In some embodiments, the nucleic acid modifying protein lacks DNA strand cleavage activity. In some embodiments, the first regulatory element is a polymerase III promoter. In some embodiments, the second regulatory element is a polymerase II promoter.

In one aspect, the invention provides a method of modifying a target polynucleotide in a eukaryotic cell. In some embodiments, the method comprises allowing a nucleic acid modifying complex to bind to the target polynucleotide to effect cleavage of said target polynucleotide thereby modifying the target polynucleotide, wherein the nucleic acid modifying complex comprises a nucleic acid modifying protein complexed with protected guide RNA comprising a guide sequence hybridized to a target sequence within said target polynucleotide. In some embodiments, said cleavage comprises cleaving one or two strands at the location of the target sequence by said nucleic acid modifying protein. In some embodiments, said cleavage results in decreased transcription of a target gene. In some embodiments, the method further comprises repairing said cleaved target polynucleotide by non-homologous end joining (NHEJ)-based gene insertion mechanisms, more particularly with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the nucleic acid modifying protein, the protected guide RNA comprising the guide sequence linked to direct repeat sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a nucleic acid modifying complex to bind to the polynucleotide such that said binding results in increased or decreased expression of said polynucleotide; wherein the CRISPR complex comprises a nucleic acid modifying protein complexed with a protected guide RNA comprising a guide sequence hybridized to a target sequence within said polynucleotide. In some embodiments, the method further comprises delivering one or more vectors to said eukaryotic cells, wherein the one or more vectors drive expression of one or more of: the nucleic acid modifying protein and the protected guide RNA.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a nucleic acid modifying protein and a protected guide RNA comprising a guide sequence linked to a direct repeat sequence; and (b) allowing a nucleic acid modifying complex to bind to a target polynucleotide to effect cleavage of the target polynucleotide within said disease gene, wherein the nucleic acid modifying complex comprises the nucleic acid modifying protein complexed with the guide RNA comprising the sequence that is hybridized to the target sequence within the target polynucleotide, thereby generating a model eukaryotic cell comprising a mutated disease gene. In some embodiments, said cleavage comprises cleaving one or two strands at the location of the target sequence by said nucleic acid modifying protein. In some embodiments, said cleavage results in decreased transcription of a target gene. In some embodiments, the method further comprises repairing said cleaved target polynucleotide by non-homologous end joining (NHEJ)-based gene insertion mechanisms with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a protected guide sequence downstream of a direct repeat sequence, wherein the protected guide sequence when expressed directs sequence-specific binding of a nucleic acid modifying complex to a corresponding target sequence present in a eukaryotic cell. In some embodiments, the target sequence is a viral sequence present in a eukaryotic cell. In some embodiments, the target sequence is a proto-oncogene or an oncogene.

In one aspect, the invention provides for a method of selecting one or more cell(s) by introducing one or more mutations in a gene in the one or more cell (s), the method comprising: introducing one or more vectors into the cell (s), wherein the one or more vectors drive expression of one or more of: a nucleic acid modifying protein, a protected guide RNA comprising a guide sequence, and an editing template; wherein the editing template comprises the one or more mutations that abolish nucleic acid modifying protein cleavage; allowing non-homologous end joining (NHEJ)-based gene insertion mechanisms of the editing template with the target polynucleotide in the cell(s) to be selected; allowing a nucleic acid modifying complex to bind to a target polynucleotide to effect cleavage of the target polynucleotide within said gene, wherein the nucleic acid modifying complex comprises the nucleic acid modifying protein complexed with the protected guide RNA comprising a guide sequence that is hybridized to the target sequence within the target polynucleotide, wherein binding of the nucleic acid modifying complex to the target polynucleotide induces cell death, thereby allowing one or more cell(s) in which one or more mutations have been introduced to be selected. In a preferred embodiment of the invention, the cell to be selected may be a eukaryotic cell. Aspects of the invention allow for selection of specific cells without requiring a selection marker or a two-step process that may include a counter-selection system.

With respect to mutations of the nucleic acid modifying protein, when the protein does not comprise one or more domains of FnCas9, mutations may be as described herein elsewhere; conservative substitution for any of the replacement amino acids is also envisaged. In an aspect the invention provides as to any or each or all embodiments herein-discussed wherein the CRISPR enzyme comprises at least one or more, or at least two or more mutations, wherein the at least one or more mutation or the at least two or more mutations are selected from those described herein elsewhere.

In a further aspect, the invention involves a computer-assisted method for identifying or designing potential compounds to fit within or bind to nucleic acid modifying system or a functional portion thereof or vice versa (a computer-assisted method for identifying or designing potential nucleic acid modifying systems or a functional portion thereof for binding to desired compounds) or a computer-assisted method for identifying or designing potential nucleic acid modifying systems (e.g., with regard to predicting areas of the nucleic acid modifying system to be able to be manipulated—for instance, based on crystal structure data or based on data of Cas9 orthologs, or with respect to where a functional group such as an activator or repressor can be attached to the CRISPR-Cas9 system, or as to Cas9 truncations or as to designing nickases), said method comprising: using a computer system, e.g., a programmed computer comprising a processor, a data storage system, an input device, and an output device, the steps of:

(a) inputting into the programmed computer through said input device data comprising the three-dimensional co-ordinates of a subset of the atoms from or pertaining to the CRISPR-Cas9 crystal structure, e.g., in the CRISPR-Cas9 system binding domain or alternatively or additionally in domains that vary based on variance among Cas9 orthologs or as to Cas9s or as to nickases or as to functional groups, optionally with structural information from CRISPR-Cas9 system complex(es), thereby generating a data set;

(b) comparing, using said processor, said data set to a computer database of structures stored in said computer data storage system, e.g., structures of compounds that bind or putatively bind or that are desired to bind to a CRISPR-Cas9 system or as to Cas9 orthologs (e.g., as Cas9s or as to domains or regions that vary amongst Cas9 orthologs) or as to the CRISPR-Cas9 crystal structure or as to nickases or as to functional groups;

(c) selecting from said database, using computer methods, structure(s)—e.g., CRISPR-Cas9 structures that may bind to desired structures, desired structures that may bind to certain CRISPR-Cas9 structures, portions of the CRISPR-Cas9 system that may be manipulated, e.g., based on data from other portions of the CRISPR-Cas9 crystal structure and/or from Cas9 orthologs, truncated Cas9s, novel nickases or particular functional groups, or positions for attaching functional groups or functional-group-CRISPR-Cas9 systems;

(d) constructing, using computer methods, a model of the selected structure(s); and (e) outputting to said output device the selected structure (s);

and optionally synthesizing one or more of the selected structure(s);

and further optionally testing said synthesized selected structure(s) as or in a nucleic acid modifying system;

or, said method comprising: providing the co-ordinates of at least two atoms of the CRISPR-Cas9 crystal structure, e.g., at least two atoms of the herein Crystal Structure Table of the CRISPR-Cas9 crystal structure or co-ordinates of at least a sub-domain of the CRISPR-Cas9 crystal structure ("selected co-ordinates"), providing the structure of a candidate comprising a binding molecule or of portions of the CRISPR-Cas9 system that may be manipulated, e.g., based on data from other portions of the CRISPR-Cas9 crystal structure and/or from Cas9 orthologs, or the structure of functional groups, and fitting the structure of the candidate to the selected co-ordinates, to thereby obtain product data comprising CRISPR-Cas9 structures that may bind to desired structures, desired structures that may bind to certain CRISPR-Cas9 structures, portions of the CRISPR-Cas9 system that may be manipulated, truncated Cas9s, novel nickases, or particular functional groups, or positions for attaching functional groups or functional-group-CRISPR-Cas9 systems, with output thereof, and optionally synthesizing compound(s) from said product data and further optionally comprising testing said synthesized compound(s) as or in a nucleic acid modifying system.

The testing can comprise analyzing the nucleic acid modifying system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (e.g. POWERPOINT), internet, email, documentary communication such as a computer program (e.g. WORD) document and the like. Accordingly, the invention also comprehends computer readable media containing: atomic co-ordinate data according to the herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The computer readable media can also contain any data of the foregoing methods. The invention further comprehends methods a computer system for generating or performing rational design as in the foregoing methods containing either: atomic co-ordinate data according to herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The invention further comprehends a method of doing business comprising providing to a user the computer system or the media or the three dimensional structure of CRISPR-Cas9 or at least one sub-domain thereof, or structure factor data for CRISPR-Cas9, said structure set forth in and said structure factor data being derivable from the atomic co-ordinate data of herein-referenced Crystal Structure, or the herein computer media or a herein data transmission.

A "binding site" or an "active site" comprises or consists essentially of or consists of a site (such as an atom, a functional group of an amino acid residue or a plurality of such atoms and/or groups) in a binding cavity or region, which may bind to a compound such as a nucleic acid molecule, which is/are involved in binding.

By "fitting", is meant determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further By "root mean square (or rms) deviation", we mean the square root of the arithmetic mean of the squares of the deviations from the mean.

By a "computer system", is meant the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data.

The data storage means may be RAM or means for accessing computer readable media of the invention. Examples of such systems are computer and tablet devices running Unix, Windows or Apple operating systems.

By "computer readable media", is meant any medium or media, which can be read and accessed directly or indirectly by a computer e.g., so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; thumb drive devices; cloud storage devices and hybrids of these categories such as magnetic/optical storage media.

The invention comprehends the use of the protected guides described herein above in the optimized functional nucleic acid modifying systems described herein.

Targeting and Delivery

With regard to targeting moieties, mention is made of Deshpande et al, "Current trends in the use of liposomes for tumor targeting," Nanomedicine (Lond). 8(9), doi:10.2217/nnm.13.118 (2013), and the documents it cites, all of which are incorporated herein by reference. Mention is also made of WO/2016/027264, and the documents it cites, all of which are incorporated herein by reference. And mention is made of Lorenzer et al, "Going beyond the liver: Progress and challenges of targeted delivery of siRNA therapeutics," Journal of Controlled Release, 203: 1-15 (2015), and the documents it cites, all of which are incorporated herein by reference.

An actively targeting lipid particle or nanoparticle or liposome or lipid bilayer delivery system (generally as to embodiments of the invention, "lipid entity of the invention" delivery systems) are prepared by conjugating targeting moieties, including small molecule ligands, peptides and monoclonal antibodies, on the lipid or liposomal surface; for example, certain receptors, such as folate and transferrin (Tf) receptors (TfR), are overexpressed on many cancer cells and have been used to make liposomes tumor cell specific. Liposomes that accumulate in the tumor microenvironment can be subsequently endocytosed into the cells by interacting with specific cell surface receptors. To efficiently target liposomes to cells, such as cancer cells, it is useful that the targeting moiety have an affinity for a cell surface receptor and to link the targeting moiety in sufficient quantities to have optimum affinity for the cell surface receptors; and determining these aspects are within the ambit of the skilled artisan. In the field of active targeting, there are a number of cell-, e.g., tumor-, specific targeting ligands.

Also as to active targeting, with regard to targeting cell surface receptors such as cancer cell surface receptors, targeting ligands on liposomes can provide attachment of liposomes to cells, e.g., vascular cells, via a noninternalizing epitope; and, this can increase the extracellular concentration of that which is being delivered, thereby increasing the amount delivered to the target cells. A strategy to target cell surface receptors, such as cell surface receptors on cancer cells, such as overexpressed cell surface receptors on cancer cells, is to use receptor-specific ligands or antibodies. Many cancer cell types display upregulation of tumor-specific receptors. For example, TfRs and folate receptors (FRs) are greatly overexpressed by many tumor cell types in response to their increased metabolic demand. Folic acid can be used as a targeting ligand for specialized delivery owing to its ease of conjugation to nanocarriers, its high affinity for FRs and the relatively low frequency of FRs, in normal tissues as compared with their overexpression in activated macrophages and cancer cells, e.g., certain ovarian, breast, lung, colon, kidney and brain tumors. Overexpression of FR on macrophages is an indication of inflammatory diseases, such as psoriasis, Crohn's disease, rheumatoid arthritis and atherosclerosis; accordingly, folate-mediated targeting of the invention can also be used for studying, addressing or treating inflammatory disorders, as well as cancers. Folate-linked lipid particles or nanoparticles or liposomes or lipid bylayers of the invention ("lipid entity of the invention") deliver their cargo intracellularly through receptor-mediated endocytosis. Intracellular trafficking can be directed to acidic compartments that facilitate cargo release, and, most importantly, release of the cargo can be altered or delayed until it reaches the cytoplasm or vicinity of target organelles. Delivery of cargo using a lipid entity of the invention having a targeting moiety, such as a folate-linked lipid entity of the invention, can be superior to nontargeted lipid entity of the invention. The attachment of folate directly to the lipid head groups may not be favorable for intracellular delivery of folate-conjugated lipid entity of the invention, since they may not bind as efficiently to cells as folate attached to the lipid entity of the invention surface by a spacer, which may can enter cancer cells more efficiently. A lipid entity of the invention coupled to folate can be used for the delivery of complexes of lipid, e.g., liposome, e.g., anionic liposome and virus or capsid or envelope or virus outer protein, such as those herein discussed such as adenoviruses or AAV. Tf is a monomeric serum glycoprotein of approximately 80 KDa involved in the transport of iron throughout the body. Tf binds to the TfR and translocates into cells via receptor-mediated endocytosis. The expression of TfR can be higher in certain cells, such as tumor cells (as compared with normal cells and is associated with the increased iron demand in rapidly proliferating cancer cells. Accordingly, the invention comprehends a TfR-targeted lipid entity of the invention, e.g., as to liver cells, liver cancer, breast cells such as breast cancer cells, colon such as colon cancer cells, ovarian cells such as ovarian cancer cells, head, neck and lung cells, such as head, neck and non-small-cell lung cancer cells, cells of the mouth such as oral tumor cells.

Also as to active targeting, a lipid entity of the invention can be multifunctional, i.e., employ more than one targeting moiety such as CPP, along with Tf; a bifunctional system; e.g., a combination of Tf and poly-L-arginine which can provide transport across the endothelium of the blood-brain barrier. EGFR is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer. The invention comprehends EGFR-targeted monoclonal antibody(ies) linked to a lipid entity of the invention. HER-2 is often overexpressed in patients with breast cancer, and is also associated with lung, bladder, prostate, brain and stomach cancers. HER-2, encoded by the ERBB2 gene. The invention comprehends a HER-2-targeting lipid entity of the invention, e.g., an anti-HER-2-antibody (or binding fragment thereof)-lipid entity of the invention, a HER-2-targeting-PEGylated lipid entity of the invention (e.g., having an anti-HER-2-antibody or binding fragment thereof), a HER-2-targeting-maleimide-PEG polymer-lipid entity of the invention (e.g., having an anti-HER-2-antibody or binding fragment thereof). Upon cellular association, the receptor-antibody complex can be internalized by formation of an endosome for delivery to the cytoplasm. With respect to receptor-mediated targeting, the skilled artisan takes into consideration ligand/target affinity and the quantity of receptors on the cell surface, and that PEGylation can act as a barrier against interaction with receptors. The use of antibody-lipid entity of the invention targeting can be advantageous. Multivalent presentation of targeting moieties can also increase the uptake and signaling properties of antibody fragments. In practice of the invention, the skilled person takes into account ligand density (e.g., high ligand densities on a lipid entity of the invention may be advantageous for increased binding to target cells). Preventing early by macrophages can be addressed with a sterically stabilized lipid entity of the invention and linking ligands to the terminus of molecules such as PEG, which is anchored in the lipid entity of the invention (e.g., lipid particle or nanoparticle or liposome or lipid bylayer). The microenvironment of a cell mass such as a tumor microenvironment can be targeted; for instance, it may be advantageous to target cell mass vasculature, such as the tumor vasculature microenvironment. Thus, the invention comprehends targeting VEGF. VEGF and its receptors are well-known proangiogenic molecules and are well-characterized targets for antiangiogenic therapy. Many small-molecule inhibitors of receptor tyrosine kinases, such as VEGFRs or basic FGFRs, have been developed as anticancer agents and the invention comprehends coupling any one or more of these peptides to a lipid entity of the invention, e.g., phage IVO peptide(s) (e.g., via or with a PEG terminus), tumor-homing peptide APRPG (SEQ ID NO: 14) such as APRPG-PEG-modified (SEQ ID NO: 15). VCAM, the vascular endothelium plays a key role in the pathogenesis of inflammation, thrombosis and atherosclerosis. CAMs are involved in inflammatory disorders, including cancer, and are a logical target, E- and P-selectins, VCAM-1 and ICAMs. Can be used to target a lipid entity of the invention, e.g., with PEGylation. Matrix metalloproteases (MMPs) belong to the family of zinc-dependent endopeptidases. They are involved in tissue remodeling, tumor invasiveness, resistance to apoptosis and metastasis. There are four MMP inhibitors called TIMP1-4, which determine the balance between tumor growth inhibition and metastasis; a protein involved in the angiogenesis of tumor vessels is MT1-MMP, expressed on newly formed vessels and tumor tissues. The proteolytic activity of MT1-MMP cleaves proteins, such as fibronectin, elastin, collagen and laminin, at the plasma membrane and activates soluble MMPs, such as MMP-2, which degrades the matrix. An antibody or fragment thereof such as a Fab' fragment can be used in the practice of the invention such as for an antihuman MT1-MMP monoclonal antibody linked to a lipid entity of the invention, e.g., via a spacer such as a PEG spacer. αβ-integrins or integrins are a group of transmembrane glycoprotein receptors that mediate attachment between a cell and its surrounding tissues or extracellular matrix. Integrins contain two distinct chains (heterodimers) called α- and β-subunits. The tumor tissue-specific expression of integrin receptors can be utilized for targeted delivery in the invention, e.g., whereby the targeting moiety can be an RGD peptide such as a cyclic RGD. Aptamers are ssDNA or RNA oligonucleotides that impart high affinity and specific recognition of the target molecules by electrostatic interactions, hydrogen bonding and hydrophobic interactions as opposed to the Watson-Crick base pairing, which is typical for the bonding interactions of oligonucleotides. Aptamers as a targeting moiety can have advantages over antibodies: aptamers can demonstrate higher target antigen recognition as compared with antibodies; aptamers can be more stable and smaller in size as compared with antibodies; aptamers can be easily synthesized and chemically modified for molecular conjugation; and aptamers can be changed in sequence for improved selectivity and can be developed to recognize poorly immunogenic targets. Such moieties as a sgc8 aptamer can be used as a targeting moiety (e.g., via covalent linking to the lipid entity of the invention, e.g., via a spacer, such as a PEG spacer). The targeting moiety can be stimuli-sensitive, e.g., sensitive to an externally applied stimuli, such as magnetic fields, ultrasound or light; and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of the particular environment or microenvironment such as an endocytic vacuole or the acidotic tumor mass. pH-sensitive copolymers can also be incorporated in embodiments of the invention can provide shielding; diortho esters, vinyl esters, cysteine-cleavable lipopolymers, double esters and hydrazones are a few examples of pH-sensitive bonds that are quite stable at pH 7.5, but are hydrolyzed relatively rapidly at pH 6 and below, e.g., a terminally alkylated copolymer of N-isopropylacrylamide and methacrylic acid that copolymer facilitates destabilization of a lipid entity of the invention and release in compartments with decreased pH value; or, the invention comprehends ionic polymers for generation of a pH-responsive lipid entity of the invention (e.g., poly(methacrylic acid), poly(diethylaminoethyl methacrylate), poly(acrylamide) and poly(acrylic acid)). Temperature-triggered delivery is also within the ambit of the invention. Many pathological areas, such as inflamed tissues and tumors, show a distinctive hyperthermia compared with normal tissues. Utilizing this hyperthermia is an attractive strategy in cancer therapy since hyperthermia is associated with increased tumor permeability and enhanced uptake. This technique involves local heating of the site to increase microvascular pore size and blood flow, which, in turn, can result in an increased extravasation of embodiments of the invention. Temperature-sensitive lipid entity of the invention can be prepared from thermosensitive lipids or polymers with a low critical solution temperature. Above the low critical solution temperature (e.g., at site such as tumor site or inflamed tissue site), the polymer precipitates, disrupting the liposomes to release. Lipids with a specific gel-to-liquid phase transition temperature are used to prepare these lipid entities of the invention; and a lipid for a thermosensitive embodiment can be dipalmitoylphosphatidylcholine. Thermosensitive polymers can also facilitate destabilization followed by release, and a useful thermosensitive polymer is poly (N-isopropylacrylamide). Another temperature triggered system can employ lysolipid temperature-sensitive liposomes. The invention also comprehends redox-triggered delivery: The difference in redox potential between normal and inflamed or tumor tissues, and between the intra- and extra-cellular environments has been exploited for delivery; e.g., GSH is a reducing agent abundant in cells, especially in the cytosol, mitochondria and nucleus. The GSH concentrations in blood and extracellular matrix are just one out of 100 to one out of 1000 of the intracellular concentration, respectively. This high redox potential difference caused by GSH, cysteine and other reducing agents can break the reducible bonds, destabilize a lipid entity of the invention and result in release of payload. The disulfide bond can be used as the cleavable/reversible linker in a lipid entity of the invention, because it causes sensitivity to redox owing to the disulfide-to-thiol reduction reaction; a lipid entity of the invention can be made reduction sensitive by using two (e.g., two forms of a disulfide-conjugated multifunctional lipid as cleavage of the disulfide bond (e.g., via tris(2-carboxyethyl)phosphine, dithiothreitol, L-cysteine or GSH), can cause removal of the hydrophilic head group of the conjugate and alter the membrane organization leading to release of payload. Calcein release from reduction-sensitive lipid entity of the invention containing a disulfide conjugate can be more useful than a reduction-insensitive embodiment. Enzymes can also be used as a trigger to release payload. Enzymes, including MMPs (e.g. MMP2), phospholipase A2, alkaline phosphatase, transglutaminase or phosphatidylinositol-specific phospholipase C, have been found to be overexpressed in certain tissues, e.g., tumor tissues. In the presence of these enzymes, specially engineered enzyme-sensitive lipid entity of the invention can be disrupted and release the payload. an MMP2-cleavable octapeptide (Gly-Pro-Leu-Gly-Ile-Ala-Gly-Gln (SEQ ID NO: 16)) can be incorporated into a linker, and can have antibody targeting, e.g., antibody 2C5. The invention also comprehends light-or energy-triggered delivery, e.g., the lipid entity of the invention can be light-sensitive, such that light or energy can facilitate structural and conformational changes, which lead to direct interaction of the lipid entity of the invention with the target cells via membrane fusion, photo-isomerism, photofragmentation or photopolymerization; such a moiety therefor can be benzoporphyrin photosensitizer. Ultrasound can be a form of energy to trigger delivery; a lipid entity of the invention with a small quantity of particular gas, including air or perfluorinated hydrocarbon can be triggered to release with ultrasound, e.g., low-frequency ultrasound (LFUS). Magnetic delivery: A lipid entity of the invention can be magnetized by incorporation of magnetites, such as Fe3O4 or γ-Fe2O3, e.g., those that are less than 10 nm in size. Targeted delivery can be then by exposure to a magnetic field.

Also as to active targeting, the invention also comprehends intracellular delivery. Since liposomes follow the endocytic pathway, they are entrapped in the endosomes (pH 6.5-6) and subsequently fuse with lysosomes (pH<5), where they undergo degradation that results in a lower therapeutic potential. The low endosomal pH can be taken advantage of to escape degradation. Fusogenic lipids or peptides, which destabilize the endosomal membrane after the conformational transition/activation at a lowered pH. Amines are protonated at an acidic pH and cause endosomal swelling and rupture by a buffer effect Unsaturated dioleoylphosphatidylethanolamine (DOPE) readily adopts an inverted hexagonal shape at a low pH, which causes fusion of liposomes to the endosomal membrane. This process destabilizes a lipid entity containing DOPE and releases the cargo into the cytoplasm; fusogenic lipid GALA, cholesteryl-GALA and PEG-GALA may show a highly efficient endosomal release; a pore-forming protein listeriolysin O may provide an endosomal escape mechanism; and, histidine-rich peptides have the ability to fuse with the endosomal membrane, resulting in pore formation, and can buffer the proton pump causing membrane lysis.

Also as to active targeting, cell-penetrating peptides (CPPs) facilitate uptake of macromolecules through cellular membranes and, thus, enhance the delivery of CPP-modified molecules inside the cell. CPPs can be split into two classes: amphipathic helical peptides, such as transportan and MAP, where lysine residues are major contributors to the positive charge; and Arg-rich peptides, such as TATp, Antennapedia or penetratin. TATp is a transcription-activating factor with 86 amino acids that contains a highly basic (two Lys and six Arg among nine residues) protein transduction domain, which brings about nuclear localization and RNA binding.

Other CPPs that have been used for the modification of liposomes include the following: the minimal protein transduction domain of Antennapedia, a *Drosophila* homeoprotein, called penetratin, which is a 16-mer peptide (residues 43-58) present in the third helix of the homeodomain; a 27-amino acid-long chimeric CPP, containing the peptide sequence from the amino terminus of the neuropeptide galanin bound via the Lys residue, mastoparan, a wasp venom peptide; VP22, a major structural component of HSV-1 facilitating intracellular transport and transportan (18-mer) amphipathic model peptide that translocates plasma membranes of mast cells and endothelial cells by both energy-dependent and -independent mechanisms. The invention comprehends a lipid entity of the invention modified with CPP(s), for intracellular delivery that may proceed via energy dependent macropinocytosis followed by endosomal escape. The invention further comprehends organelle-specific targeting. A lipid entity of the invention surface-functionalized with the triphenylphosphonium (TPP) moiety or a lipid entity of the invention with a lipophilic cation, rhodamine 123 can be effective in delivery of cargo to mitochondria. DOPE/sphingomyelin/stearyl-octa-arginine can delivers cargos to the mitochondrial interior via membrane fusion. A lipid entity of the invention surface modified with a lysosomotropic ligand, octadecyl rhodamine B can deliver cargo to lysosomes. Ceramides are useful in inducing lysosomal membrane permeabilization; the invention comprehends intracellular delivery of a lipid entity of the invention having a ceramide. The invention further comprehends a lipid entity of the invention targeting the nucleus, e.g., via a DNA-intercalating moiety. The invention also comprehends multifunctional liposomes for targeting, i.e., attaching more than one functional group to the surface of the lipid entity of the invention, for instance to enhances accumulation in a desired site and/or promotes organelle-specific delivery and/or target a particular type of cell and/or respond to the local stimuli such as temperature (e.g., elevated), pH (e.g., decreased), respond to externally applied stimuli such as a magnetic field, light, energy, heat or ultrasound and/or promote intracellular delivery of the cargo. All of these are considered actively targeting moieties.

An embodiment of the invention includes the particle delivery system comprising an actively targeting lipid particle or nanoparticle or liposome or lipid bylayer delivery system; or comprising a lipid particle or nanoparticle or liposome or lipid bylayer comprising a targeting moiety whereby there is active targeting or wherein the targeting moiety is an actively targeting moiety. A targeting moiety can be one or more targeting moieties, and a targeting moiety can be for any desired type of targeting such as, e.g., to target a cell such as any herein-mentioned; or to target an organelle such as any herein-mentioned; or for targeting a response such as to a physical condition such as heat, energy, ultrasound, light, pH, chemical such as enzymatic, or magnetic stimuli; or to target to achieve a particular outcome such as delivery of payload to a particular location, such as by cell penetration.

It should be understood that as to each possible targeting or active targeting moiety herein-discussed, there is an aspect of the invention wherein the delivery system comprises such a targeting or active targeting moiety. Likewise, the following table provides exemplary targeting moieties that can be used in the practice of the invention an as to each an aspect of the invention provides a delivery system that comprises such a targeting moiety.

| Targeting Moiety | Target Molecule | Target Cell or Tissue |
| --- | --- | --- |
| folate | folate receptor | cancer cells |
| transferrin | transferrin receptor | cancer cells |
| Antibody CC52 | rat CC531 | rat colon adenocarcinoma CC531 |
| anti- HER2 antibody | HER2 | HER2 -overexpressing tumors |
| anti-GD2 | GD2 | neuroblastoma, melanoma |
| anti-EGFR | EGFR | tumor cells overexpressing EGFR |
| pH-dependent fusogenic peptide diINF-7 | | ovarian carcinoma |
| anti-VEGFR | VEGF Receptor | tumor vasculature |
| anti-CD19 | CD19 (B cell marker) | leukemia, lymphoma |
| cell-penetrating peptide | | blood-brain barrier |
| cyclic arginine-glycine-aspartic acid-tyrosine-cysteine peptide (c(RGDyC)-LP) (SEQ ID NO: 17) | $\alpha v \beta 3$ | glioblastoma cells, human umbilical vein endothelial cells, tumor angiogenesis |
| ASSHN (SEQ ID NO: 18) peptide | | endothelial progenitor cells; anti-cancer |
| PR_b peptide | $\alpha_5\beta_1$ integrin | cancer cells |
| AG86 peptide | $\alpha_6\beta_4$ integrin | cancer cells |
| KCCYSL (SEQ ID NO: 19) (P6.1 peptide) | HER-2 receptor | cancer cells |
| affinity peptide LN (YEVGHRC) (SEQ ID NO: 20) | Aminopeptidase N (APN/CD13) | APN-positive tumor |
| synthetic somatostatin analogue | Somatostatin receptor 2 (SSTR2) | breast cancer |
| anti-CD20 monoclonal antibody | B-lymphocytes | B cell lymphoma |

Thus, in an embodiment of the particle delivery system, the targeting moiety comprises a receptor ligand, such as, for example, hyaluronic acid for CD44 receptor, galactose for hepatocytes, or antibody or fragment thereof such as a binding antibody fragment against a desired surface receptor, and as to each of a targeting moiety comprising a receptor ligand, or an antibody or fragment thereof such as a binding fragment thereof, such as against a desired surface receptor, there is an aspect of the invention wherein the delivery system comprises a targeting moiety comprising a receptor ligand, or an antibody or fragment thereof such as a binding fragment thereof, such as against a desired surface receptor, or hyaluronic acid for CD44 receptor, galactose for hepatocytes (see, e.g., Surace et al, "Lipoplexes targeting the CD44 hyaluronic acid receptor for efficient transfection of breast cancer cells," J. Mol Pharm 6(4):1062-73; doi: 10.1021/mp800215d (2009); Sonoke et al, "Galactose-modified cationic liposomes as a liver-targeting delivery system for small interfering RNA," Biol Pharm Bull. 34(8): 1338-42 (2011); Torchilin, "Antibody-modified liposomes for cancer chemotherapy," Expert Opin. Drug Deliv. 5 (9), 1003-1025 (2008); Manjappa et al, "Antibody derivatization and conjugation strategies: application in preparation of stealth immunoliposome to target chemotherapeutics to tumor," J. Control. Release 150 (1), 2-22 (2011); Sofou S "Antibody-targeted liposomes in cancer therapy and imaging," Expert Opin. Drug Deliv. 5 (2): 189-204 (2008); Gao J et al, "Antibody-targeted immunoliposomes for cancer treatment," Mini. Rev. Med. Chem. 13(14): 2026-2035 (2013); Molavi et al, "Anti-CD30 antibody conjugated liposomal doxorubicin with significantly improved therapeutic efficacy against anaplastic large cell lymphoma," Biomaterials 34(34):8718-25 (2013), each of which and the documents cited therein are hereby incorporated herein by reference).

Moreover, in view of the teachings herein the skilled artisan can readily select and apply a desired targeting moiety in the practice of the invention as to a lipid entity of the invention. The invention comprehends an embodiment wherein the delivery system comprises a lipid entity having a targeting moiety.

In an embodiment of the particle delivery system, the protein comprises a nucleic acid modifying protein.

In some embodiments a non-capsid protein or protein that is not a virus outer protein or a virus envelope (sometimes herein shorthanded as "non-capsid protein"), such as a nucleic acid modifying protein, can have one or more functional moiety(ies) thereon, such as a moiety for targeting or locating, such as an NLS or NES, or an activator or repressor.

In an embodiment of the particle delivery system, a nucleic acid modifying protein can comprise a tag.

In an aspect, the invention provides a virus particle comprising a capsid or outer protein having one or more hybrid virus capsid or outer proteins comprising the virus capsid or outer protein attached to at least a portion of a non-capsid protein or a nucleic acid modifying protein.

In an aspect, the invention provides an in vitro method of delivery comprising contacting the particle delivery system with a cell, optionally a eukaryotic cell, whereby there is delivery into the cell of constituents of the delivery system.

In an aspect, the invention provides an in vitro, a research or study method of delivery comprising contacting the particle delivery system with a cell, optionally a eukaryotic cell, whereby there is delivery into the cell of constituents of the delivery system, obtaining data or results from the contacting, and transmitting the data or results.

In an aspect, the invention provides a cell from or of an in vitro method of delivery, wherein the method comprises contacting the particle delivery system with a cell, optionally a eukaryotic cell, whereby there is delivery into the cell of constituents of the delivery system, and optionally obtaining data or results from the contacting, and transmitting the data or results.

In an aspect, the invention provides a cell from or of an in vitro method of delivery, wherein the method comprises contacting the particle delivery system with a cell, optionally a eukaryotic cell, whereby there is delivery into the cell of constituents of the delivery system, and optionally obtaining data or results from the contacting, and transmitting the data or results; and wherein the cell product is altered compared to the cell not contacted with the delivery system, for example altered from that which would have been wild type of the cell but for the contacting.

In an embodiment, the cell product is non-human or animal.

In one aspect, the invention provides a particle delivery system comprising a composite virus particle, wherein the composite virus particle comprises a lipid, a virus capsid protein, and at least a portion of a non-capsid protein or peptide. The non-capsid peptide or protein can have a molecular weight of up to one megadalton.

In one embodiment, the particle delivery system comprises a virus particle adsorbed to a liposome or lipid particle or nanoparticle. In one embodiment, a virus is adsorbed to a liposome or lipid particle or nanoparticle either through electrostatic interactions, or is covalently linked through a linker. The lipid particle or nanoparticles (1 mg/ml) dissolved in either sodium acetate buffer (pH 5.2) or pure H2O (pH 7) are positively charged. The isoelectropoint of most viruses is in the range of 3.5-7. They have a negatively charged surface in either sodium acetate buffer (pH 5.2) or pure H2O. The electrostatic interaction between the virus and the liposome or synthetic lipid nanoparticle is the most significant factor driving adsorption. By modifying the charge density of the lipid nanoparticle, e.g. inclusion of neutral lipids into the lipid nanoparticle, it is possible to modulate the interaction between the lipid nanoparticle and the virus, hence modulating the assembly. In one embodiment, the liposome comprises a cationic lipid.

In one embodiment, the liposome of the particle delivery system comprises a CRISPR system component.

In one aspect, the invention provides a delivery system comprising one or more hybrid virus capsid proteins in combination with a lipid particle, wherein the hybrid virus capsid protein comprises at least a portion of a virus capsid protein attached to at least a portion of a non-capsid protein.

In one embodiment, the virus capsid protein of the delivery system is attached to a surface of the lipid particle. When the lipid particle is a bilayer, e.g., a liposome, the lipid particle comprises an exterior hydrophilic surface and an interior hydrophilic surface. In one embodiment, the virus capsid protein is attached to a surface of the lipid particle by an electrostatic interaction or by hydrophobic interaction.

In one embodiment, the particle delivery system has a diameter of 50-1000 nm, preferably 100-1000 nm.

In one embodiment, the particle delivery system comprises a non-capsid protein or peptide, wherein the non-capsid protein or peptide has a molecular weight of up to a megadalton. In one embodiment, the non-capsid protein or peptide has a molecular weight in the range of 110 to 160 kDa, 160 to 200 kDa, 200 to 250 kDa, 250 to 300 kDa, 300 to 400 kDa, or 400 to 500 kDa.

In one embodiment, the delivery system comprises a non-capsid protein or peptide, wherein the protein or peptide comprises a nucleic acid modifying protein. In one embodiment, the nucleic acid modifying protein comprises one or more domains of a Cas9, a Cpf1 or a C2c2/Cas13a.

In one embodiment, a composite virus particle of the delivery system comprises a lipid, wherein the lipid comprises at least one cationic lipid.

In one embodiment, the delivery system comprises a lipid particle, wherein the lipid particle comprises at least one cationic lipid.

In one embodiment, a particle of the delivery system comprises a lipid layer, wherein the lipid layer comprises at least one cationic lipid.

As used herein, a "composite virus particle" means a virus particle that includes, at a minimum, at least a portion of a virus capsid protein, one or more lipids and a non-capsid protein or peptide. The lipid can be part of a liposome and the virus particle can be adsorbed to the liposome. In certain embodiments, the virus particle is attached to the lipid directly. Alternatively, the virus particle is attached to the lipid via a linker moiety. As used herein, "at least a portion of" means at least 50%, for example, 50%, 55%, 60%, 65%, 70%, 75%, 80%, 85%, 90% or 99%. "At least a portion of", as it refers to a virus capsid protein or a non-capsid protein, means of a length that is sufficient to allow the two proteins to attach, either directly or via a linker. "At least a portion of", as it refers to an outer protein or a non-capsid protein, means of a length that is sufficient to allow the two proteins to attach, either directly or via a linker. As used herein, a "lipid particle" is a particle comprised of lipid molecules. As used herein, a "lipid layer" means a layer of lipid molecules arranged side-by-side, preferably with charged groups aligned to one surface. For example, a biological membrane typically comprises two lipid layers, with hydrophobic regions arranged tail-to-tail, and charged regions exposed to an aqueous environment. Using a linker to covalently attach the skilled person from knowledge in the art and this disclosure can obtain 5-100% virus or capsid or virus outer protein or envelope attached to non-capsid or non-virus outer protein or non-envelope protein.

The lipid, lipid particle, or lipid bylayer or lipid entity of the invention can be prepared by methods well known in the art. See Wang et al., ACS Synthetic Biology, 1, 403-07 (2012); Wang et al., PNAS, 113(11) 2868-2873 (2016); Manoharan, et al., WO 2008/042973; Zugates et al., U.S. Pat. No. 8,071,082; Xu et al., WO 2014/186366 A1 (US20160082126). Xu et provides a way to make a nanocomplex for the delivery of saporin wherein the nanocomplex comprising saporin and a lipid-like compound, and wherein the nanocomplex has a particle size of 50 nm to 1000 nm; the saporin binds to the lipid-like compound via non-covalent interaction or covalent bonding; and the lipid-like compound has a hydrophilic moiety, a hydrophobic moiety, and a linker joining the hydrophilic moiety and the hydrophobic moiety, the hydrophilic moiety being optionally charged and the hydrophobic moiety having 8 to 24 carbon atoms. Xu et al., WO 2014/186348 (US20160129120) provides examples of nanocomplexes of modified peptides or proteins comprising a cationic delivery agent and an anionic pharmaceutical agent, wherein the nanocomplex has a particle size of 50 to 1000 nm, the cationic delivery agent binds to the anionic pharmaceutical agent, and the anionic pharmaceutical agent is a modified peptide or protein formed of a peptide and a protein and an added chemical moiety that contains an anionic group. The added chemical moiety is linked to the peptide or protein via an amide group, an ester group, an ether group, a thioether group, a disulfide group, a hydrazone group, a sulfenate ester group, an amidine group, a urea group, a carbamate group, an imidoester group, or a carbonate group. More particularly these documents provide examples of lipid or lipid-like compounds that can be used to make the particle delivery system of the present invention, including compounds of the formula B1-K1-A-K2-B2, in which A, the hydrophilic moiety, is

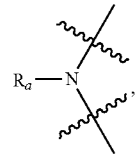

,

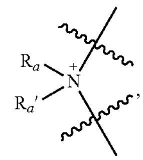

,

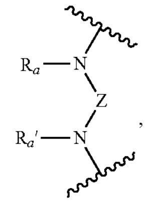

,

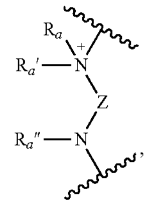

, or

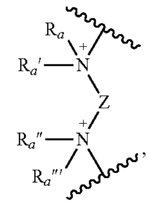

, each of $R_a$, $R_a'$, $R_a''$, and $R_a'''$, independently, being a $C_1$-$C_{20}$ monovalent aliphatic radical, a $C_1$-$C_{20}$ monovalent heteroaliphatic radical, a monovalent aryl radical, or a monovalent heteroaryl radical; and Z being a $C_1$-$C_{20}$ bivalent aliphatic radical, a $C_1$-$C_{20}$ bivalent heteroaliphatic radical, a bivalent aryl radical, or a bivalent heteroaryl radical; each of $B_1$, the hydrophobic moiety, and $B_2$, also the hydrophobic moiety, independently, is a $C_{12-20}$ aliphatic radical or a $C_{12-20}$ heteroaliphatic radical; and each of $K_1$, the linker, and $K_2$, also the linker, independently, is O, S, Si, $C_1$-$C_6$ alkylene

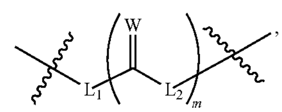

,

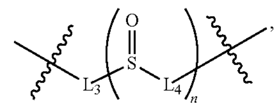

,

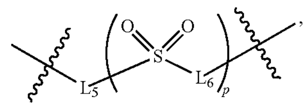

,

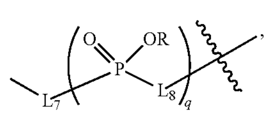

, or

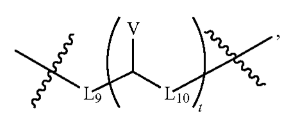

, in which each of m, n, p, q, and t, independently, is 1-6; W is O, S, or $NR_C$; each of $L_1$, $L_3$, $L_5$, $L_7$, and $L_9$, independently, is a bond, O, S, or $NR_d$; each of L2, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical and specific compounds:

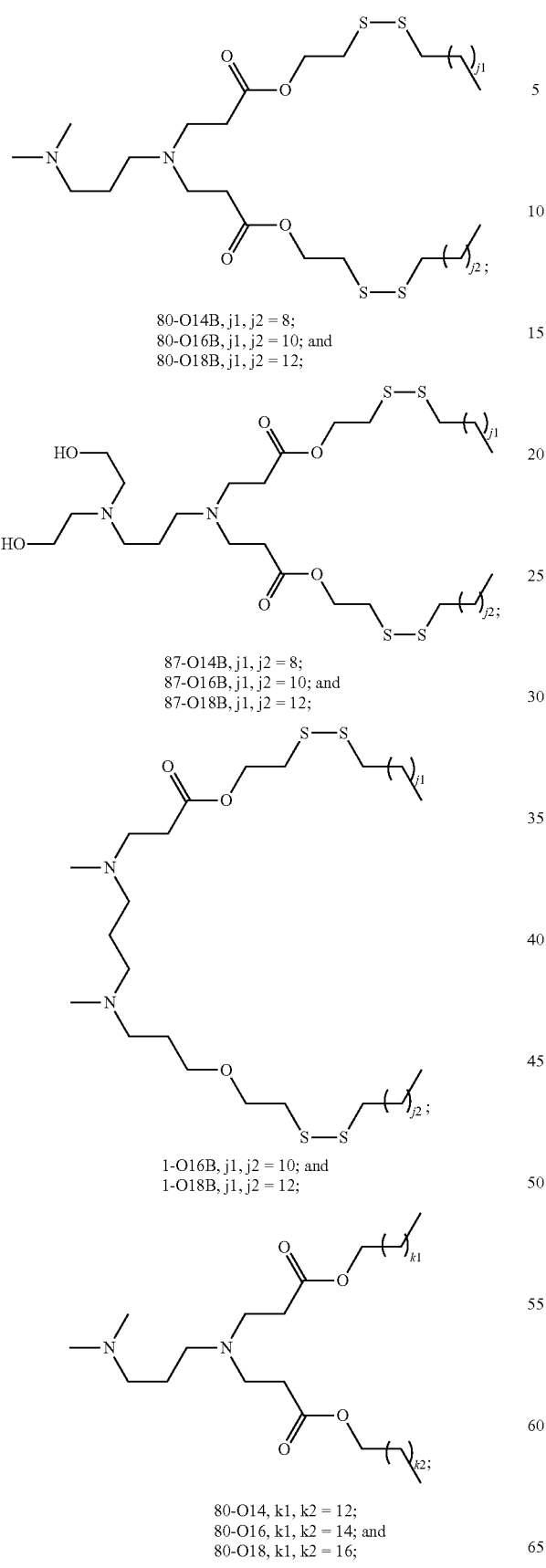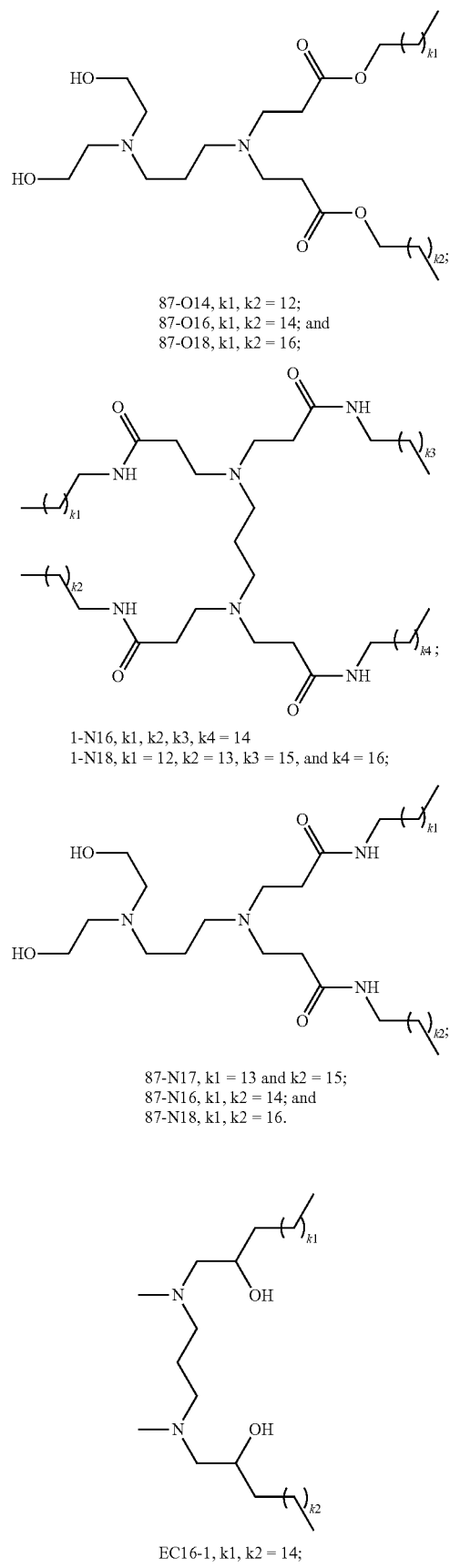

-continued

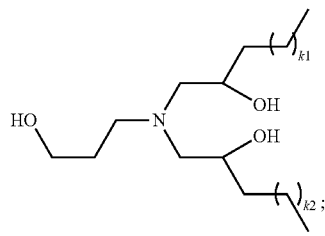

EC16-3, k1, k2 = 14

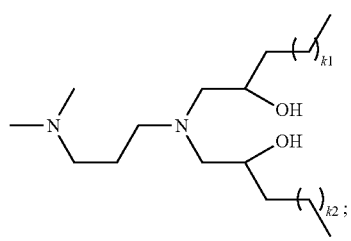

EC16-12, k1, k2 = 14

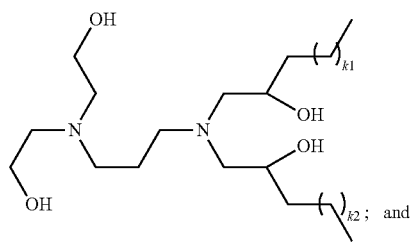

EC16-14, k1, k2 = 14

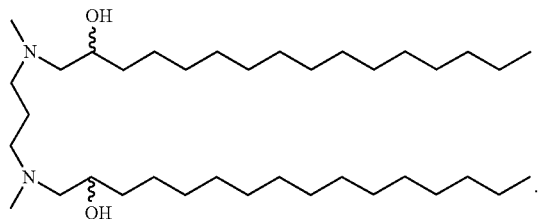

EC16-63

Additional examples of cationic lipid that can be used to make the particle delivery system of the invention can be found in US20150140070, wherein the cationic lipid has the formula

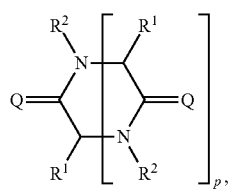

wherein p is an integer between 1 and 9, inclusive; each instance of Q is independently O, S, or $NR^Q$; $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii) or (iii); each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, $-OR^{A1}$, $-N(R^{A1})_2$, $-SR^{A1}$, or a group of formula:

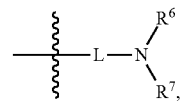

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii); each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{A1}$ groups, together with the nitrogen atom to which they are attached, are joined to form an optionally substituted heterocyclic or optionally substituted heteroaryl ring; each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); Formulae (i), (ii), and (iii) are:

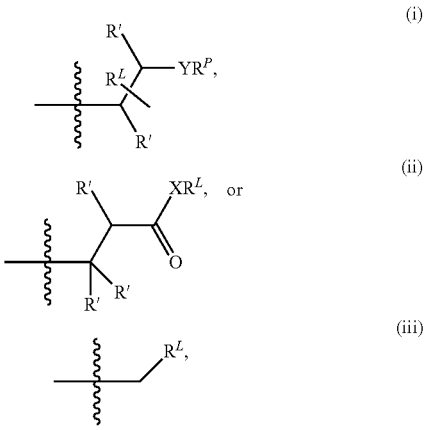

each instance of R' is independently hydrogen or optionally substituted alkyl; X is O, S, or $NR^X$; $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; Y is O, S, or $NR^Y$; $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; R is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; $R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer; provided that at least one instance of $R^Q$, $R^2$, $R^6$, or $R^7$ is a group of the formula (i), (ii), or (iii); in Liu et al., (US 20160200779, US 20150118216, US 20150071903, and US 20150071903), which provide examples of cationic lipids to include polyethylenimine, polyamidoamine (PAMAM) starburst dendrimers, Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif). Exemplary cationic liposomes can be made from N-[1-(2,3-dioleoyloxy)-propyl]-N,N,N-trimethylammonium chloride (DOTMA), N-[1-(2,3-dioleoyloxy)-propyl]-N,N,N-trimethylammonium methylsulfate (DOTAP), 3.beta.-[N—(N',N'-dimethylaminoethane)carbamoyl]cholesterol (DC-Chol), 2,3,-dioleyloxy-N-[2 (sperminecarboxamido)ethyl]-N,N-dimethyl-1-propanamin-ium trifluoroacetate (DOSPA), 1,2-dimyristyloxypropyl-3-dimethyl-hydroxyethyl ammonium bromide; and dimethyldioctadecylammonium bromide (DDAB); in WO2013/093648 which provides cationic lipids of formula

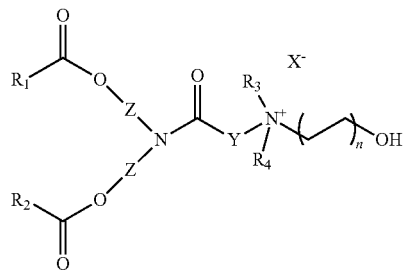

in which Z=an alkyl linker, $C_2$-$C_4$ alkyl, Y=an alkyl linker, $C_1$-$C_6$ alkyl, $R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$-$C_{18}$alkyl, $C_{13}$-$C_{17}$alkyl, $C_{13}$alkyl, $C_{10}$-$C_{30}$alkenyl, $C_{10}$-$C_{20}$alkenyl. $C_{12}$-$C_{18}$alkenyl, $C_{13}$-$C_{17}$alkenyl, $C_{17}$alkenyl; R3 and R4 are each independently hydrogen, $C_1$-$C_6$ alkyl, or —$CH_2CH_2OH$, $C_1$-$C_6$ alkyl, $C_1$-$C_3$alkyl; n is 1-6; and X is a counterion, including any nitrogen counterion, as that term is readily understood in the art, and specific cationic lipids including

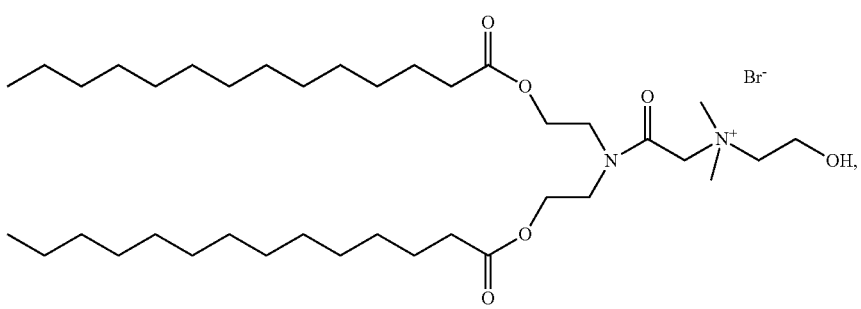

("HEDC")

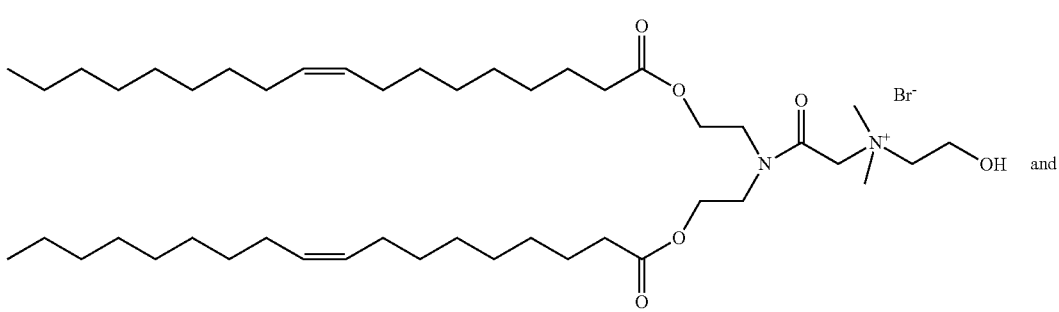

("HEDODC")

and

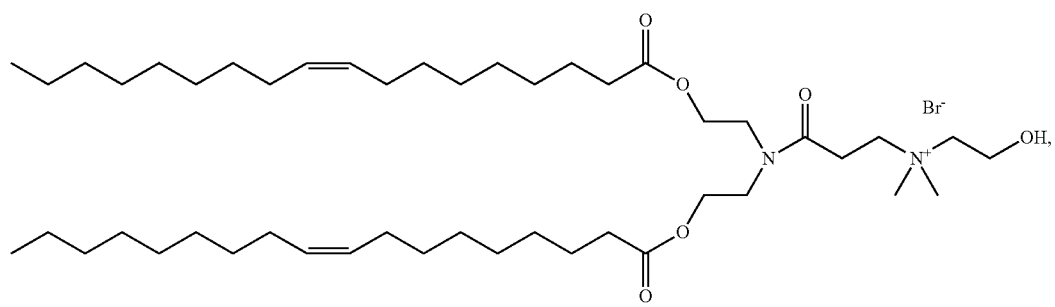

("HE-Et-DODC")

WO2013/093648 also provides examples of other cationic charged lipids at physiological pH including N,N-dioleyl-N,N-dimethylammonium chloride (DODAC), N,N-distearyl-N,N-dimethylammonium bromide (DDAB); N-(1,2-dimyristyloxyprop-3-yl)-N,N-dimethyl-N-hydroxyethylammonium bromide (DMRIE) and dioctadecylamidoglycyl carboxyspermidine (DOGS); in US 20160257951, which provides cationic lipids with a general formula

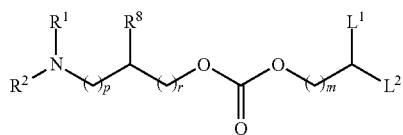

or a pharmacologically acceptable salt thereof, wherein $R^1$ and $R^2$ are each independently a hydrogen atom, a $C_1$-$C_6$ alkyl group optionally substituted with one or more substituents selected from substituent group α, a $C_2$-$C_6$ alkenyl group optionally substituted with one or more substituents selected from substituent group α, a $C_2$-$C_6$ alkynyl group optionally substituted with one or more substituents selected from substituent group α, or a $C_3$-$C_7$ cycloalkyl group optionally substituted with one or more substituents selected from substituent group α, or $R^1$ and $R^2$ form a 3- to 10-membered heterocyclic ring together with the nitrogen atom bonded thereto, wherein the heterocyclic ring is optionally substituted with one or more substituents selected from substituent group α and optionally contains one or more atoms selected from a nitrogen atom, an oxygen atom, and a sulfur atom, in addition to the nitrogen atom bonded to $R^1$ and $R^2$, as atoms constituting the heterocyclic ring; $R^8$ is a hydrogen atom or a $C_1$-$C_6$ alkyl group optionally substituted with one or more substituents selected from substituent group α; or $R^1$ and $R^8$ together are the group —$(CH_2)_q$—; substituent group α consists of a halogen atom, an oxo group, a hydroxy group, a sulfanyl group, an amino group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_6$ alkylamino group, and a $C_1$-$C_7$ alkanoyl group; $L^1$ is a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, or a ($C_1$-$C_{10}$ alkyl)-$(Q)_k$-($C_1$-$C_{10}$ alkyl) group optionally substituted with one or more substituents selected from substituent group β1; $L^2$ is independently of $L^1$, a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, a ($C_1$-$C_{10}$ alkyl)-$(Q)_k$-($C_1$-$C_{10}$ alkyl) group optionally substituted with having one or more substituents selected from substituent group β1, a ($C_{10}$-$C_{24}$ alkoxy)methyl group optionally substituted with one or more substituents selected from substituent group β1, a ($C_{10}$-$C_{24}$ alkenyl)oxymethyl group optionally substituted with one or more substituents selected from substituent group β1, a ($C_3$-$C_{24}$ alkynyl)oxymethyl group optionally substituted with one or more substituents selected from substituent group β1, or a ($C_1$-$C_{10}$ alkyl)-$(Q)_k$-($C_1$-$C_{10}$ alkoxy)methyl group optionally substituted with one or more substituents selected from substituent group β1; substituent group β1 consists of a halogen atom, an oxo group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_7$ alkanoyl group, a $C_1$-$C_7$ alkanoyloxy group, a $C_3$-$C_7$ alkoxyalkoxy group, a ($C_1$-$C_6$ alkoxy)carbonyl group, a ($C_1$-$C_6$ alkoxy)carboxyl group, a ($C_1$-$C_6$ alkoxy)carbamoyl group, and a ($C_1$-$C_6$ alkylamino)carboxyl group; Q is a group of formula:

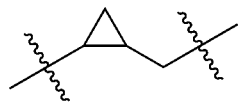 [SMILES: *CC1CC1*]

when $L^1$ and $L^2$ are each substituted with one or more substituents selected from substituent group β1 and substituent group β1 is a $C_1$-$C_6$ alkyl group, a $C_1$-$C_6$ alkoxy group, a $C_1$-$C_6$ alkylsulfanyl group, a $C_1$-$C_7$ alkanoyl group, or a $C_1$-$C_7$ alkanoyloxy group, the substituent or substituents selected from substituent group β1 in $L^1$ and the substituent or substituents selected from substituent group β31 in $L^2$ optionally bind to each other to form a cyclic structure; k is 1, 2, 3, 4, 5, 6, or 7; m is 0 or 1; p is 0, 1, or 2; q is 1, 2, 3, or 4; and r is 0, 1, 2, or 3, provided that p+r is 2 or larger, or q+r is 2 or larger, and specific cationic lipids including

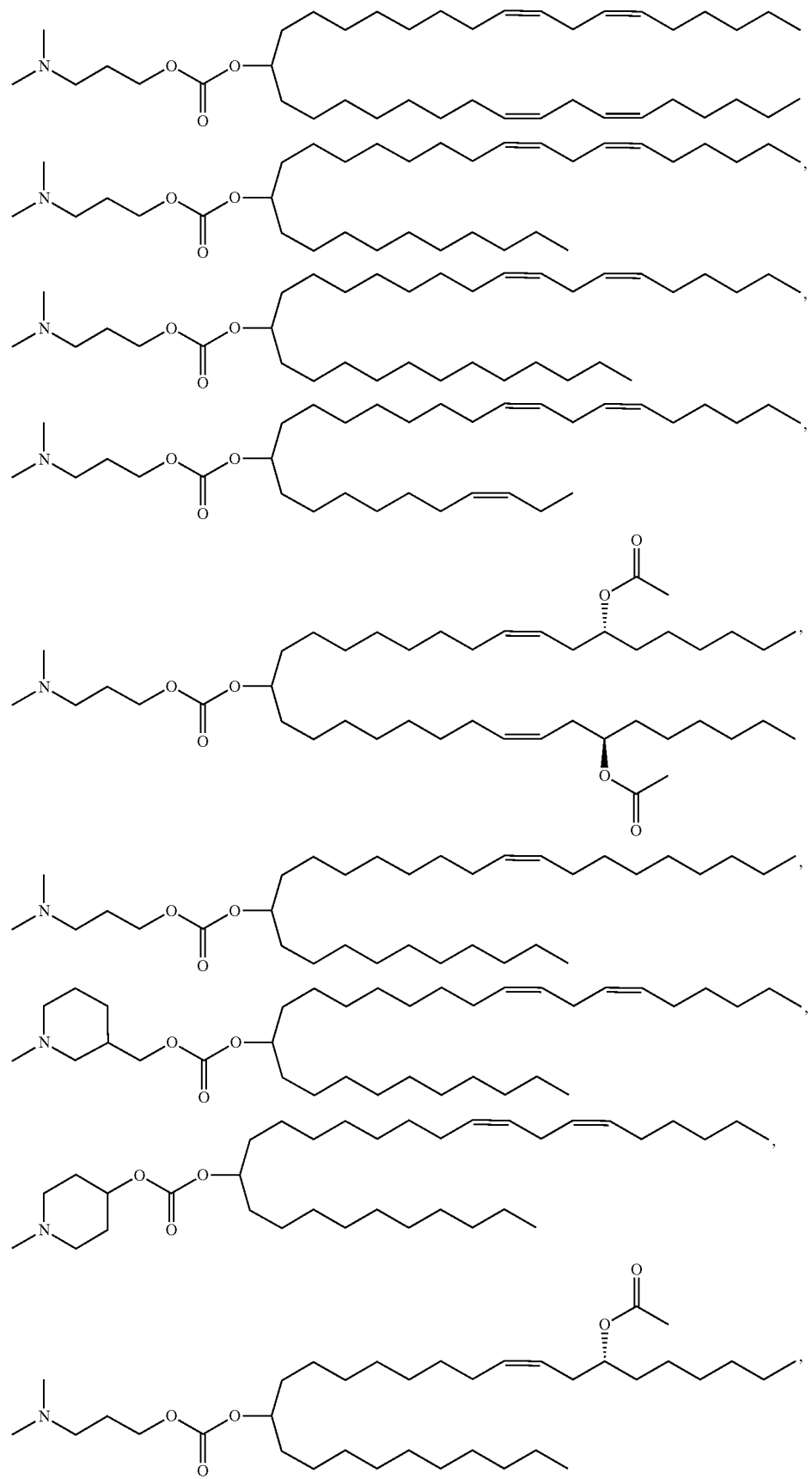

-continued

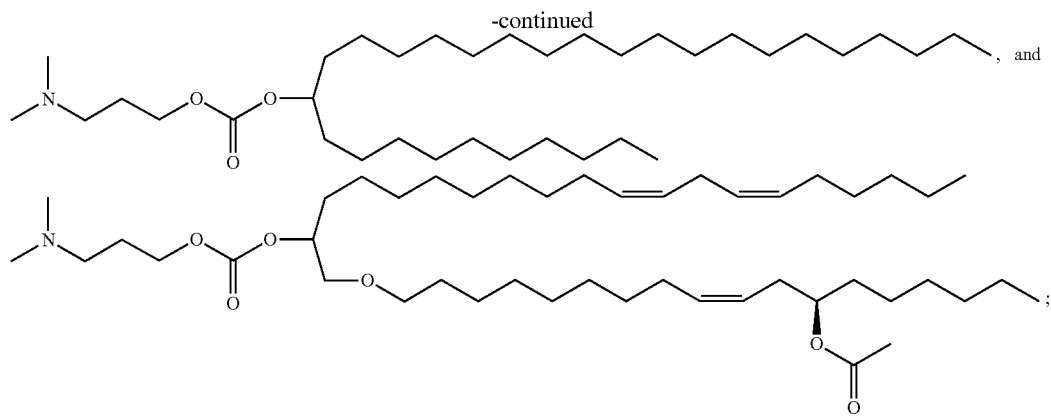

and in US 20160244761, which provides cationic lipids that include 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), 1,2-di-.gamma.-linolenyloxy-N,N-dimethylaminopropane (.gamma.-DLenDMA), 1,2-dilinoleyloxy-keto-N,N-dimethyl-3-aminopropane (DLin-K-DMA), 1,2-dilinoleyl-4-(2-dimethylaminoethyl)-[1,3]-dioxolane (DLin-K-C2-DMA) (also known as DLin-C2K-DMA, XTC2, and C2K), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 1,2-dilinolenyloxy-4-(2-dimethylaminoethyl)-[1,3]-dioxolane (DLen-C2K-DMA), 1,2-di-.gamma.-linolenyloxy-4-(2-dimethylaminoethyl)-[1,3]-dioxolane (.gamma.-DLen-C2K-DMA), dilinoleylmethyl-3-dimethylaminopropionate (DLin-M-C2-DMA) (also known as MC2), (6Z,9Z,28Z,31Z)-heptatriaconta-6,9,28,31-tetraen-19-yl 4-(dimethylamino) butanoate (DLin-M-C3-DMA) (also known as MC3) and 3-(dilinoleylmethoxy)-N,N-dimethylpropan-1-amine (DLin-MP-DMA) (also known as 1-Bl 1).

In one embodiment, the lipid compound is preferably a bio-reducible material, e.g., a bio-reducible polymer and a bio-reducible lipid-like compound.

In embodiment, the lipid compound comprises a hydrophilic head, and a hydrophobic tail, and optionally a linker.

In one embodiment, the hydrophilic head contains one or more hydrophilic functional groups, e.g., hydroxyl, carboxyl, amino, sulfhydryl, phosphate, amide, ester, ether, carbamate, carbonate, carbamide and phosphodiester. These groups can form hydrogen bonds and are optionally positively or negatively charged, in particular at physiological conditions such as physiological pH.

In one embodiment, the hydrophobic tail is a saturated or unsaturated, linear or branched, acyclic or cyclic, aromatic or nonaromatic hydrocarbon moiety, wherein the saturated or unsaturated, linear or branched, acyclic or cyclic, aromatic or nonaromatic hydrocarbon moiety optionally contains a disulfide bond and/or 8-24 carbon atoms. One or more of the carbon atoms can be replaced with a heteroatom, such as N, O, P, B, S, Si, Sb, Al, Sn, As, Se, and Ge. The lipid or lipid-like compounds containing disulfide bond can be bioreducible.

In one embodiment, the linker of the lipid or lipid-like compound links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate phosphate, phosphite, sulfate, sulfite, and thiosulfate.

The lipid or lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

In one embodiment, the lipid, lipid particle or lipid layer of the delivery system further comprises a wild-type capsid protein.

In one embodiment, a weight ratio of hybrid capsid protein to wild-type capsid protein is from 1:10 to 1:1, for example, 1:1, 1:2, 1:3, 1:4, 1:5, 1:6, 1:7, 1:8, 1:9 and 1:10.

In one embodiment, the virus of the delivery system is an Adenoviridae or a Parvoviridae or a Rhabdoviridae or an enveloped virus having a glycoprotein protein. In one embodiment, the virus is an adeno-associated virus (AAV) or an adenovirus or a VSV or a rabies virus. In one embodiment, the virus is a retrovirus or a lentivirus. In one embodiment, the virus is murine leukemia virus (MuMLV).

In one embodiment, the virus capsid protein of the delivery system comprises VP1, VP2 or VP3.

In one embodiment, the virus capsid protein of the delivery system is VP3, and the non-capsid protein is inserted into or tethered or connected to VP3 loop 3 or loop 6.

In one embodiment, the virus of the delivery system is delivered to the interior of a cell.

In one embodiment, the virus capsid protein and the non-capsid protein are capable of dissociating after delivery into a cell.

In one aspect of the delivery system, the virus capsid protein is attached to the non-capsid protein by a linker. In one embodiment, the linker comprises amino acids. In one embodiment, the linker is a chemical linker. In another embodiment, the linker is cleavable or biodegradable. In one embodiment, the linker comprises (GGGGS) (SEQ ID NO: 10) with repeats from 1-3, ENLYFQG (SEQ ID NO:11), or a disulfide.

In one embodiment of the delivery system, each terminus of the non-capsid protein is attached to the capsid protein by a linker moiety.

In one embodiment, the non-capsid protein is attached to the exterior portion of the virus capsid protein. As used herein, "exterior portion" as it refers to a virus capsid protein means the outer surface of the virus capsid protein when it is in a formed virus capsid.

In one embodiment, the non-capsid protein is attached to the interior portion of the capsid protein or is encapsulated within the lipid particle. As used herein, "interior portion" as it refers to a virus capsid protein means the inner surface of the virus capsid protein when it is in a formed virus capsid. In one embodiment, the virus capsid protein and the non-capsid protein are a fusion protein.

In one embodiment, the fusion protein is attached to the surface of the lipid particle.

In one embodiment, the non-capsid protein is attached to the virus capsid protein prior to formation of the capsid.

In one embodiment, the non-capsid protein is attached to the virus capsid protein after formation of the capsid.

In one embodiment, the non-capsid protein comprises a targeting moiety.

In one embodiment, the targeting moiety comprises a receptor ligand.

In an embodiment, the non-capsid protein comprises a tag.

In an embodiment, the non-capsid protein comprises one or more heterologous nuclear localization signals(s) (NLSs).

In an embodiment, the protein or peptide comprises a Type II CRISPR protein or a Type VI CRISPR protein.

In an embodiment, the delivery system further comprises guide RNS, optionally complexed with the CRISPR protein.

In an embodiment, the delivery system comprises a protease or nucleic acid molecule(s) encoding a protease that is expressed, whereby the protease cleaves the linker. In certain embodiments, there is protease expression, linker cleavage, and dissociation of payload from capsid in the absence of productive virus replication.

In an aspect, the invention provides a delivery system comprising a first hybrid virus capsid protein and a second hybrid virus capsid protein, wherein the first hybrid virus capsid protein comprises a virus capsid protein attached to a first part of a protein, and wherein the second hybrid virus capsid protein comprises a second virus capsid protein attached to a second part of the protein, wherein the first part of the protein and the second part of the protein are capable of associating to form a functional protein.

In an aspect, the invention provides a delivery system comprising a first hybrid virus capsid protein and a second hybrid virus capsid protein, wherein the first hybrid virus capsid protein comprises a virus capsid protein attached to a first part of a CRISPR protein, and wherein the second hybrid virus capsid protein comprises a second virus capsid protein attached to a second part of a CRISPR protein, wherein the first part of the CRISPR protein and the second part of the CRISPR protein are capable of associating to form a functional CRISPR protein.

In an embodiment of the delivery system, the first hybrid virus capsid protein and the second virus capsid protein are on the surface of the same virus particle.

In an embodiment of the delivery system, the first hybrid virus capsule protein is located at the interior of a first virus particle and the second hybrid virus capsid protein is located at the interior of a second virus particle.

In an embodiment of the delivery system, the first part of the protein or CRISPR protein is linked to a first member of a ligand pair, and the second part of the protein or CRISPR protein is linked to a second member of a ligand pair, wherein the first part of the ligand pair binds to the second part of the ligand pair in a cell. In an embodiment, the binding of the first part of the ligand pair to the second part of the ligand pair is inducible.

In an embodiment of the delivery system, either or both of the first part of the protein or CRISPR protein and the second part of the protein or CRISPR protein comprise one or more NLSs.

In an embodiment of the delivery system, either or both of the first part of the protein or CRISPR protein and the second part of the protein or CRISPR protein comprise one or more nuclear export signals (NESs).

In one aspect, the invention provides a delivery system for a non-naturally occurring or engineered CRISPR system, component, protein or complex. The delivery system comprises a non-naturally occurring or engineered CRISPR system, component, protein or complex, associated with a virus structural component and a lipid component. The delivery system can further comprise a targeting molecule, for example a targeting molecule that preferentially guides the delivery system to a cell type or interest, or a cell expressing a target protein of interest. The targeting molecule may be associated with or attached to the virus component or the lipid component. In certain embodiments, the virus component preferentially guides the delivery system to the target of interest.

In certain embodiments, the virus structural component comprises one or more capsid proteins including an entire capsid. In certain embodiments, such as wherein a viral capsid comprises multiple copies of different proteins, the delivery system can provide one or more of the same protein or a mixture of such proteins. For example, AAV comprises 3 capsid proteins, VP1, VP2, and VP3, thus delivery systems of the invention can comprise one or more of VP1, and/or one or more of VP2, and/or one or more of VP3. Accordingly, the present invention is applicable to a virus within the family Adenoviridae, such as Atadenovirus, e.g., Ovine atadenovirus D, Aviadenovirus, e.g., Fowl aviadenovirus A, Ichtadenovirus, e.g., Sturgeon ichtadenovirus A, Mastadenovirus (which includes adenoviruses such as all human adenoviruses), e.g., Human mastadenovirus C, and Siadenovirus, e.g., Frog siadenovirus A. Thus, a virus of within the family Adenoviridae is contemplated as within the invention with discussion herein as to adenovirus applicable to other family members. Target-specific AAV capsid variants can be used or selected. Non-limiting examples include capsid variants selected to bind to chronic myelogenous leukemia cells, human CD34 PBPC cells, breast cancer cells, cells of lung, heart, dermal fibroblasts, melanoma cells, stem cell, glioblastoma cells, coronary artery endothelial cells and keratinocytes. See, e.g., Buning et al, 2015, Current Opinion in Pharmacology 24, 94-104. From teachings herein and knowledge in the art as to modifications of adenovirus (see, e.g., U.S. Pat. Nos. 9,410,129, 7,344,872, 7,256,036, 6,911,199, 6,740,525; Matthews, "Capsid-Incorporation of Antigens into Adenovirus Capsid Proteins for a Vaccine Approach," Mol Pharm, 8(1): 3-11 (2011)), as well as regarding modifications of AAV, the skilled person can readily obtain a modified adenovirus that has a large payload protein or a CRISPR-protein, despite that heretofore it was not expected that such a large protein could be provided on an adenovirus. And as to the viruses related to adenovirus mentioned herein, as well as to the viruses related to AAV mentioned herein, the teachings herein as to modifying adenovirus and AAV, respectively, can be applied to those viruses without undue experimentation from this disclosure and the knowledge in the art.

In an embodiment of the invention, the delivery system comprises a virus protein or particle adsorbed to a lipid component, such as, for example, a liposome. In certain embodiments, a CRISPR system, component, protein or complex is associated with the virus protein or particle. In certain embodiments, a CRISPR system, component, protein or complex is associated with the lipid component. In certain embodiments, one CRISPR system, component, protein or complex is associated with the virus protein or particle, and a second CRISPR system, component, protein, or complex is associated with the lipid component. As used herein, associated with includes, but is not limited to, linked to, adhered to, adsorbed to, enclosed in, enclosed in or within, mixed with, and the like. In certain embodiments, the virus component and the lipid component are mixed, including but not limited to the virus component dissolved in or inserted in a lipid bilayer. In certain embodiments, the virus component and the lipid component are associated but separate, including but not limited a virus protein or particle adsorbed or adhered to a liposome. In embodiments of the invention that further comprise a targeting molecule, the targeting molecule can be associated with a virus component, a lipid component, or a virus component and a lipid component.

In another aspect, the invention provides a non-naturally occurring or engineered CRISPR protein associated with Adeno Associated Virus (AAV), e.g., an AAV comprising a CRISPR protein as a fusion, with or without a linker, to or with an AAV capsid protein such as VP1, VP2, and/or VP3; and, for shorthand purposes, such a non-naturally occurring or engineered CRISPR protein is herein termed a "AAV-CRISPR protein" More in particular, modifying the knowledge in the art, e.g., Rybniker et al., "Incorporation of Antigens into Viral Capsids Augments Immunogenicity of Adeno-Associated Virus Vector-Based Vaccines," J Virol. December 2012; 86(24): 13800-13804, Lux K, et al. 2005. Green fluorescent protein-tagged adeno-associated virus particles allow the study of cytosolic and nuclear trafficking. J. Virol. 79:11776-11787, Munch R C, et al. 2012. "Displaying high-affinity ligands on adeno-associated viral vectors enables tumor cell-specific and safe gene transfer." Mol. Ther. [Epub ahead of print.] doi:10.1038/mt.2012.186 and Warrington K H, Jr, et al. 2004. Adeno-associated virus type 2 VP2 capsid protein is nonessential and can tolerate large peptide insertions at its N terminus. J. Virol. 78:6595-6609, each incorporated herein by reference, one can obtain a modified AAV capsid of the invention. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3). One can modify the cap gene to have expressed at a desired location a non-capsid protein advantageously a large payload protein, such as a CRISPR-protein. Likewise, these can be fusions, with the protein, e.g., large payload protein such as a CRISPR-protein fused in a manner analogous to prior art fusions. See, e.g., US Patent Publication 20090215879; Nance et al., "Perspective on Adeno-Associated Virus Capsid Modification for Duchenne Muscular Dystrophy Gene Therapy," Hum Gene Ther. 26(12):786-800 (2015) and documents cited therein, incorporated herein by reference. The skilled person, from this disclosure and the knowledge in the art can make and use modified AAV or AAV capsid as in the herein invention, and through this disclosure one knows now that large payload proteins can be fused to the AAV capsid. Applicants provide AAV capsid-CRISPR protein (e.g., Cas, Cas9, dCas9, Cpf1, Cas13a, Cas13b) fusions and those AAV-capsid CRISPR protein (e.g., Cas, Cas9) fusions can be a recombinant AAV that contains nucleic acid molecule(s) encoding or providing CRISPR-Cas or CRISPR system or complex RNA guide(s), whereby the CRISPR protein (e.g., Cas, Cas9) fusion delivers a CRISPR-Cas or CRISPR system complex (e.g., the CRISPR protein or Cas or Cas9 is provided by the fusion, e.g., VP1, VP2, pr VP3 fusion, and the guide RNA is provided by the coding of the recombinant virus, whereby in vivo, in a cell, the CRISPR-Cas or CRISPR system is assembled from the nucleic acid molecule(s) of the recombinant providing the guide RNA and the outer surface of the virus providing the CRISPR-Enzyme or Cas or Cas9. Such as complex may herein be termed an "AAV-CRISPR system" or an "AAV-CRISPR-Cas" or "AAV-CRISPR complex" or "AAV-CRISPR-Cas complex." Accordingly, the instant invention is also applicable to a virus in the genus Dependoparvovirus or in the family Parvoviridae, for instance, AAV, or a virus of Amdoparvovirus, e.g., Carnivore amdoparvovirus 1, a virus of Aveparvovirus, e.g., Galliform aveparvovirus 1, a virus of Bocaparvovirus, e.g., Ungulate bocaparvovirus 1, a virus of Copiparvovirus, e.g., Ungulate copiparvovirus 1, a virus of Dependoparvovirus, e.g., Adeno-associated dependoparvovirus A, a virus of Erythroparvovirus, e.g., Primate erythroparvovirus 1, a virus of Protoparvovirus, e.g., Rodent protoparvovirus 1, a virus of Tetraparvovirus, e.g., Primate tetraparvovirus 1. Thus, a virus of within the family Parvoviridae or the genus Dependoparvovirus or any of the other foregoing genera within Parvoviridae is contemplated as within the invention with discussion herein as to AAV applicable to such other viruses.

In one aspect, the invention provides a non-naturally occurring or engineered composition comprising a CRISPR enzyme which is part of or tethered to a AAV capsid domain, i.e., VP1, VP2, or VP3 domain of Adeno-Associated Virus (AAV) capsid. In some embodiments, part of or tethered to a AAV capsid domain includes associated with associated with a AAV capsid domain. In some embodiments, the CRISPR enzyme may be fused to the AAV capsid domain. In some embodiments, the fusion may be to the N-terminal end of the AAV capsid domain. As such, in some embodiments, the C-terminal end of the CRISPR enzyme is fused to the N-terminal end of the AAV capsid domain. In some embodiments, an NLS and/or a linker (such as a GlySer linker) may be positioned between the C-terminal end of the CRISPR enzyme and the N-terminal end of the AAV capsid domain. In some embodiments, the fusion may be to the C-terminal end of the AAV capsid domain. In some embodiments, this is not preferred due to the fact that the VP1, VP2 and VP3 domains of AAV are alternative splices of the same RNA and so a C-terminal fusion may affect all three domains. In some embodiments, the AAV capsid domain is truncated. In some embodiments, some or all of the AAV capsid domain is removed. In some embodiments, some of the AAV capsid domain is removed and replaced with a linker (such as a GlySer linker), typically leaving the N-terminal and C-terminal ends of the AAV capsid domain intact, such as the first 2, 5 or 10 amino acids. In this way, the internal (non-terminal) portion of the VP3 domain may be replaced with a linker. It is particularly preferred that the linker is fused to the CRISPR protein. A branched linker may be used, with the CRISPR protein fused to the end of one of the braches. This allows for some degree of spatial separation between the capsid and the CRISPR protein. In this way, the CRISPR protein is part of (or fused to) the AAV capsid domain.

Alternatively, the CRISPR enzyme may be fused in frame within, i.e. internal to, the AAV capsid domain. Thus in some embodiments, the AAV capsid domain again preferably retains its N-terminal and C-terminal ends. In this case, a linker is preferred, in some embodiments, either at one or both ends of the CRISPR enzyme. In this way, the CRISPR enzyme is again part of (or fused to) the AAV capsid domain. In certain embodiments, the positioning of the CRISPR enzyme is such that the CRISPR enzyme is at the external surface of the viral capsid once formed. In one aspect, the invention provides a non-naturally occurring or engineered composition comprising a CRISPR enzyme associated with a AAV capsid domain of Adeno-Associated Virus (AAV) capsid. Here, associated may mean in some embodiments fused, or in some embodiments bound to, or in some embodiments tethered to. The CRISPR protein may, in some embodiments, be tethered to the VP1, VP2, or VP3 domain. This may be via a connector protein or tethering system such as the biotin-streptavidin system. In one example, a biotinylation sequence (15 amino acids) could therefore be fused to the CRISPR protein. When a fusion of the AAV capsid domain, especially the N-terminus of the AAV AAV capsid domain, with streptavidin is also provided, the two will therefore associate with very high affinity. Thus, in some embodiments, provided is a composition or system comprising a CRISPR protein-biotin fusion and a streptavidin-AAV capsid domain arrangement, such as a fusion. The CRISPR protein-biotin and streptavidin-AAV capsid domain forms a single complex when the two parts are brought together. NLSs may also be incorporated between the CRISPR protein and the biotin; and/or between the streptavidin and the AAV capsid domain.

An alternative tether may be to fuse or otherwise associate the AAV capsid domain to an adaptor protein which binds to or recognizes to a corresponding RNA sequence or motif. In some embodiments, the adaptor is or comprises a binding protein which recognizes and binds (or is bound by) an RNA sequence specific for said binding protein. In some embodiments, a preferred example is the MS2 (see Konermann et al. December 2014, cited infra, incorporated herein by reference) binding protein which recognizes and binds (or is bound by) an RNA sequence specific for the MS2 protein.

With the AAV capsid domain associated with the adaptor protein, the CRISPR protein may, in some embodiments, be tethered to the adaptor protein of the AAV capsid domain. The CRISPR protein may, in some embodiments, be tethered to the adaptor protein of the AAV capsid domain via the CRISPR enzyme being in a complex with a modified guide, see Konermann et al. The modified guide is, in some embodiments, a sgRNA. In some embodiments, the modified guide comprises a distinct RNA sequence; see, e.g., PCT/US14/70175, incorporated herein by reference.

In some embodiments, distinct RNA sequence is an aptamer. Thus, corresponding aptamer-adaptor protein systems are preferred. One or more effector domains may also be associated with the adaptor protein. An example of a preferred arrangement would be:

[AAV AAV capsid domain-adaptor protein]-[modified guide-CRISPR protein]

In certain embodiments, the positioning of the CRISPR protein is such that the CRISPR protein is at the internal surface of the viral capsid once formed. In one aspect, the invention provides a non-naturally occurring or engineered composition comprising a CRISPR protein associated with an internal surface of an AAV capsid domain. Here again, associated may mean in some embodiments fused, or in some embodiments bound to, or in some embodiments tethered to. The CRISPR protein may, in some embodiments, be tethered to the VP1, VP2, or VP3 domain such that it locates to the internal surface of the viral capsid once formed. This may be via a connector protein or tethering system such as the biotin-streptavidin system as described above.

When the CRISPR protein fusion is designed so as to position the CRISPR protein at the internal surface of the capsid once formed, the CRISPR protein will fill most or all of internal volume of the capsid. Alternatively the CRISPR protein may be modified or divided so as to occupy a less of the capsid internal volume. Accordingly, in certain embodiments, the invention provides a CRISRP protein divided in two portions, one portion comprises in one viral particle or capsid and the second portion comprised in a second viral particle or capsid. In certain embodiments, by splitting the CRISPR protein in two portions, space is made available to link one or more heterologous domains to one or both CRISPR protein portions.

Split CRISPR proteins are set forth herein and in documents incorporated herein by reference in further detail herein. In certain embodiments, each part of a split CRISRP proteins are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In general, according to the invention, CRISPR proteins may preferably split between domains, leaving domains intact. Preferred, non-limiting examples of such CRISPR proteins include, without limitation, Cas9, Cpf1, C2c2, Cas13a, Cas13b, and orthologues. Preferred, non-limiting examples of split points include, with reference to SpCas9: a split position between 202A/2035; a split position between 255F/256D; a split position between 310E/311I; a split position between 534R/535K; a split position between 572E/573C; a split position between 7135/714G; a split position between 1003L/104E; a split position between 1054G/1055E; a split position between 1114N/1115S; a split position between 1152K/1153S; a split position between 1245K/1246G; or a split between 1098 and 1099.

In some embodiments, any AAV serotype is preferred. In some embodiments, the VP2 domain associated with the CRISPR enzyme is an AAV serotype 2 VP2 domain. In some embodiments, the VP2 domain associated with the CRISPR enzyme is an AAV serotype 8 VP2 domain. The serotype can be a mixed serotype as is known in the art. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |

| Cell Line | AAV-1 | AAV-2 | AAV-3 | AAV-4 | AAV-5 | AAV-6 | AAV-8 | AAV-9 |
|---|---|---|---|---|---|---|---|---|
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

The CRISPR enzyme may form part of a CRISPR-Cas system, which further comprises a guide RNA (sgRNA) comprising a guide sequence capable of hybridizing to a target sequence in a genomic locus of interest in a cell. In some embodiments, the functional CRISPR-Cas system binds to the target sequence. In some embodiments, the functional CRISPR-Cas system may edit the genomic locus to alter gene expression. In some embodiments, the functional CRISPR-Cas system may comprise further effector domains.

In some embodiments, the CRISPR enzyme is a Cas9. In some embodiments, the CRISPR enzyme is an Sp Cas9. In some embodiments, the CRISPR enzyme is an Sa Cas9. In some embodiments, the CRISPR enzyme is an St or Fn Cas9, although other orthologs are envisaged. Sp and Sa Cas9s are particularly preferred, in some embodiments.

In some embodiments, the CRISPR enzyme is external to the capsid or virus particle. In the sense that it is not inside the capsid (enveloped or encompassed with the capsid) but is externally exposed so that it can contact the target genomic DNA). In some embodiments, the CRISPR enzyme cleaves both strands of DNA to produce a double strand break (DSB). In some embodiments, the CRISPR enzyme is a nickase. In some embodiments, the CRISPR enzyme is a dual nickase. In some embodiments, the CRISPR enzyme is a deadCas9. In some general embodiments, the CRISPR enzyme is associated with one or more effector domains. In some more specific embodiments, the CRISPR enzyme is a deadCas9 and is associated with one or more effector domains. In some embodiments, the CRISPR enzyme comprises a Rec2 or HD2 truncation. In some embodiments, the CRISPR enzyme is associated with the AAV VP2 domain by way of a fusion protein. In some embodiments, the CRISPR enzyme is fused to Destabilization Domain (DD). In other words, the DD may be associated with the CRISPR enzyme by fusion with said CRISPR enzyme. The AAV can then, by way of nucleic acid molecule(s) deliver the stabilizing ligand (or such can be otherwise delivered) In some embodiments, the enzyme may be considered to be a modified CRISPR enzyme, wherein the CRISPR enzyme is fused to at least one destabilization domain (DD) and VP2. In some embodiments, the association may be considered to be a modification of the VP2 domain. Where reference is made herein to a modified VP2 domain, then this will be understood to include any association discussed herein of the VP2 domain and the CRISPR enzyme. In some embodiments, the AAV VP2 domain may be associated (or tethered) to the CRISPR enzyme via a connector protein, for example using a system such as the streptavidin-biotin system. As such, provided is a fusion of a CRISPR enzyme with a connector protein specific for a high affinity ligand for that connector, whereas the AAV VP2 domain is bound to said high affinity ligand. For example, streptavidin may be the connector fused to the CRISPR enzyme, while biotin may be bound to the AAV VP2 domain. Upon co-localization, the streptavidin will bind to the biotin, thus connecting the CRISPR enzyme to the AAV VP2 domain. The reverse arrangement is also possible. In some embodiments, a biotinylation sequence (15 amino acids) could therefore be fused to the AAV VP2 domain, especially the N-terminus of the AAV VP2 domain. A fusion of the CRISPR enzyme with streptavidin is also preferred, in some embodiments. In some embodiments, the biotinylated AAV capsids with streptavidin-CRISPR enzyme are assembled in vitro. This way the AAV capsids should assemble in a straightforward manner and the CRISPR enzyme-streptavidin fusion can be added after assembly of the capsid. In other embodiments a biotinylation sequence (15 amino acids) could therefore be fused to the CRISPR enzyme, together with a fusion of the AAV VP2 domain, especially the N-terminus of the AAV VP2 domain, with streptavidin. For simplicity, a fusion of the CRISPR enzyme and the AAV VP2 domain is preferred in some embodiments. In some embodiments, the fusion may be to the N-terminal end of the CRISPR enzyme. In other words, in some embodiments, the AAV and CRISPR enzyme are associated via fusion. In some embodiments, the AAV and CRISPR enzyme are associated via fusion including a linker. Suitable linkers are discussed herein, but include Gly Ser linkers. Fusion to the N-term of AAV VP2 domain is preferred, in some embodiments. In some embodiments, the CRISPR enzyme comprises at least one Nuclear Localization Signal (NLS). In an aspect, the present invention provides a polynucleotide encoding the present CRISPR enzyme and associated AAV VP2 domain.

Viral delivery vectors, for example modified viral delivery vectors, are hereby provided. While the AAV may advantageously be a vehicle for providing RNA of the CRISPR-Cas Complex or CRISPR system, another vector may also deliver that RNA, and such other vectors are also herein discussed. In one aspect, the invention provides a non-naturally occurring modified AAV having a VP2-CRISPR enzyme capsid protein, wherein the CRISPR enzyme is part of or tethered to the VP2 domain. In some preferred embodiments, the CRISPR enzyme is fused to the VP2 domain so that, in another aspect, the invention provides a non-naturally occurring modified AAV having a VP2-CRISPR enzyme fusion capsid protein. The following embodiments apply equally to either modified AAV aspect, unless otherwise apparent. Thus, reference herein to a VP2-CRISPR enzyme capsid protein may also include a VP2-CRISPR enzyme fusion capsid protein. In some embodiments, the VP2-CRISPR enzyme capsid protein further comprises a linker. In some embodiments, the VP2-CRISPR enzyme capsid protein further comprises a linker, whereby the VP2-CRISPR enzyme is distanced from the remainder of the AAV. In some embodiments, the VP2-CRISPR enzyme capsid protein further comprises at least one protein complex, e.g., CRISPR complex, such as CRISPR-Cas9 complex guide RNA that targets a particular DNA, TALE, etc. A CRISPR complex, such as CRISPR-Cas system comprising the VP2-CRISPR enzyme capsid protein and at least one CRISPR complex, such as CRISPR-Cas9 complex guide RNA that targets a particular DNA, is also provided in one aspect. In general, in some embodiments, the AAV further comprises a repair template. It will be appreciated that comprises here may mean encompassed thin the viral capsid or that the virus encodes the comprised protein. In some embodiments, one or more, preferably two or more guide RNAs, may be comprised/encompassed within the AAV vector. Two may be preferred, in some embodiments, as it allows for multiplexing or dual nickase approaches. Particularly for multiplexing, two or more guides may be used. In fact, in some embodiments, three or more, four or more, five or more, or even six or more guide RNAs may be comprised/encompassed within the AAV. More space has been freed up within the AAV by virtue of the fact that the AAV no longer needs to comprise/encompass the CRISPR enzyme. In each of these instances, a repair template may also be provided comprised/encompassed within the AAV. In some embodiments, the repair template corresponds to or includes the DNA target.

In a further aspect, the present invention provides compositions comprising the CRISPR enzyme and associated AAV VP2 domain or the polynucleotides or vectors described herein. Also provides are CRISPR-Cas systems comprising guide RNAs.

Also provided is a method of treating a subject in need thereof, comprising inducing gene editing by transforming the subject with the polynucleotide encoding the system or any of the present vectors. A suitable repair template may also be provided, for example delivered by a vector comprising said repair template. In some embodiments, a single vector provides the CRISPR enzyme through (association with the viral capsid) and at least one of: guide RNA; and/or a repair template. Also provided is a method of treating a subject in need thereof, comprising inducing transcriptional activation or repression by transforming the subject with the polynucleotide encoding the present system or any of the present vectors, wherein said polynucleotide or vector encodes or comprises the catalytically inactive CRISPR enzyme and one or more associated effector domains. Compositions comprising the present system for use in said method of treatment are also provided. A kit of parts may be provided including such compositions. Use of the present system in the manufacture of a medicament for such methods of treatment are also provided.

Also provided is a pharmaceutical composition comprising the CRISPR enzyme which is part of or tethered to a VP2 domain of Adeno-Associated Virus (AAV) capsid; or the non-naturally occurring modified AAV; or a polynucleotide encoding them.

Also provided is a complex of the CRISPR enzyme with a guideRNA, such as sgRNA. The complex may further include the target DNA.

A split CRISPR enzyme, most preferably Cas9, approach may be used. The so-called 'split Cas9' approach Split Cas9 allows for the following. The Cas9 is split into two pieces and each of these are fused to one half of a dimer. Upon dimerization, the two parts of the Cas9 are brought together and the reconstituted Cas9 has been shown to be functional. Thus, one part of the split Cas9 may be associated with one VP2 domain and second part of the split Cas9 may be associated with another VP2 domain. The two VP2 domains may be in the same or different capsid. In other words, the split parts of the Cas9 could be on the same virus particle or on different virus particles.

In some embodiments, one or more effector domains may be associated with or tethered to CRISPR enzyme and/or may be associated with or tethered to modified guides via adaptor proteins. These can be used irrespective of the fact that the CRISPR enzyme may also be tethered to a virus outer protein or capsid or envelope, such as a VP2 domain or a capsid, via modified guides with aptamer RAN sequences that recognize correspond adaptor proteins.

In some embodiments, one or more effector domains comprise a transcriptional activator, repressor, a recombinase, a transposase, a histone remodeler, a demethylase, a DNA methyltransferase, a cryptochrome, a light inducible/controllable domain, a chemically inducible/controllable domain, an epigenetic modifying domain, or a combination thereof. Advantageously, the effector domain comprises an activator, repressor or nuclease.

In some embodiments, an effector domain can have methylase activity, demethylase activity, transcription activation activity, transcription repression activity, transcription release factor activity, histone modification activity, RNA cleavage activity or nucleic acid binding activity, or activity that a domain identified herein has.

Examples of activators include P65, a tetramer of the herpes simplex activation domain VP16, termed VP64, optimized use of VP64 for activation through modification of both the sgRNA design and addition of additional helper molecules, MS2, P65 and HSF1 in the system called the synergistic activation mediator (SAM) (Konermann et al, "Genome-scale transcriptional activation by an engineered CRISPR-Cas9 complex," Nature 517(7536):583-8 (2015)); and examples of repressors include the KRAB (Kruppel-associated box) domain of Kox1 or SID domain (e.g. SID4X); and an example of a nuclease or nuclease domain suitable for a effector domain comprises Fok1.

Suitable effector domains for use in practice of the invention, such as activators, repressors or nucleases are also discussed in documents incorporated herein by reference, including the patents and patent publications herein-cited and incorporated herein by reference regarding general information on CRISPR-Cas Systems.

In some embodiments, the CRISPR enzyme comprises or consists essentially of or consists of a localization signal as, or as part of, the linker between the CRISPR enzyme and the AAV capsid, e.g., VP2. HA or Flag tags are also within the ambit of the invention as linkers as well as Glycine Serine linkers as short as GS up to (GGGGS)3 (SEQ ID NO: 5). In this regard it is mentioned that tags that can be used in embodiments of the invention include affinity tags, such as chitin binding protein (CBP), maltose binding protein (MBP), glutathione-S-transferase (GST), poly(His) tag; solubilization tags such as thioredoxin (TRX) and poly (NANP), MBP, and GST; chromatography tags such as those consisting of polyanionic amino acids, such as FLAG-tag; epitope tags such as V5-tag, Myc-tag, HA-tag and NE-tag; fluorescence tags, such as GFP and mCherry; protein tags that may allow specific enzymatic modification (such as biotinylation by biotin ligase) or chemical modification (such as reaction with FlAsH-EDT2 for fluorescence imaging).

Also provided is a method of treating a subject, e.g., a subject in need thereof, comprising inducing gene editing by transforming the subject with the AAV-CRISPR enzyme advantageously encoding and expressing in vivo the remaining portions of the CRISPR system (e.g., RNA, guides). A suitable repair template may also be provided, for example delivered by a vector comprising said repair template. Also provided is a method of treating a subject, e.g., a subject in need thereof, comprising inducing transcriptional activation or repression by transforming the subject with the AAV-CRISPR enzyme advantageously encoding and expressing in vivo the remaining portions of the CRISPR system (e.g., RNA, guides); advantageously in some embodiments the CRISPR enzyme is a catalytically inactive CRISPR enzyme and comprises one or more associated effector domains. Where any treatment is occurring ex vivo, for example in a cell culture, then it will be appreciated that the term 'subject' may be replaced by the phrase "cell or cell culture."

Compositions comprising the present system for use in said method of treatment are also provided. A kit of parts may be provided including such compositions. Use of the present system in the manufacture of a medicament for such methods of treatment are also provided. Use of the present system in screening is also provided by the present invention, e.g., gain of function screens. Cells which are artificially forced to overexpress a gene are able to down regulate the gene over time (re-establishing equilibrium) e.g. by negative feedback loops. By the time the screen starts the unregulated gene might be reduced again.

In one aspect, the invention provides an engineered, non-naturally occurring CRISPR-Cas system comprising a AAV-Cas protein and a guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cas9 protein. The invention further comprehends the coding for the Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to a CRISPR-Cas system guide RNA that targets a DNA molecule encoding a gene product and an AAV-Cas protein. The components may be located on same or different vectors of the system, or may be the same vector whereby the AAV-Cas protein also delivers the RNA of the CRISPR system. The guide RNA targets the DNA molecule encoding the gene product in a cell and the AAV-Cas protein may cleaves the DNA molecule encoding the gene product (it may cleave one or both strands or have substantially no nuclease activity), whereby expression of the gene product is altered; and, wherein the AAV-Cas protein and the guide RNA do not naturally occur together. The invention comprehends the guide RNA comprising a guide sequence fused to a tracr sequence. In an embodiment of the invention the AAV-Cas protein is a type II AAV-CRISPR-Cas protein and in a preferred embodiment the AAV-Cas protein is an AAV-Cas9 protein. The invention further comprehends the coding for the AAV-Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of an AAV-CRISPR complex to a target sequence in a eukaryotic cell, wherein the CRISPR complex comprises an AAV-CRISPR enzyme complexed with (1) the guide sequence that is hybridized to the target sequence, and (2) the tracr mate sequence that is hybridized to the tracr sequence; and (b) said AAV-CRISPR enzyme comprising at least one nuclear localization sequence and/or at least one NES; wherein components (a) and (b) are located on or in the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of an AAV-CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publicly and commercially available alignment algorithms and programs such as, but not limited to, ClustalW, Smith-Waterman in matlab, Bowtie, Geneious, Biopython and SeqMan. In some embodiments, the AAV-CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for AAV-CRISPR complex activity in eukaryotes, but that including such sequences enhances activity of the system, especially as to targeting nucleic acid molecules in the nucleus and/or having molecules exit the nucleus. In some embodiments, the AAV-CRISPR enzyme is a type II AAV-CRISPR system enzyme. In some embodiments, the AAV-CRISPR enzyme is an AAV-Cas9 enzyme. In some embodiments, the AAV-Cas9 enzyme is derived from S. pneumoniae, S. pyogenes, S. thermophiles, F. novicida or S. aureus Cas9 (e.g., a Cas9 of one of these organisms modified to have or be associated with at least one AAV), and may include further mutations or alterations or be a chimeric Cas9. The enzyme may be a AAV-Cas9 homolog or ortholog. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Again, the RNA of the CRISPR System, while advantageously delivered via the AAV-CRISPR enzyme can also be delivered separately, e.g. via a separate vector.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In one aspect, the invention provides an AAV-CRISPR enzyme comprising one or more nuclear localization sequences and/or NES. In some embodiments, said AAV-CRISPR enzyme includes a regulatory element that drives transcription of component(s) of the CRISPR system (e.g., RNA, such as guide RNA and/or HR template nucleic acid molecule) in a eukaryotic cell such that said AAV-CRISPR enzyme delivers the CRISPR system accumulates in a detectable amount in the nucleus of the eukaryotic cell and/or is exported from the nucleus. In some embodiments, the regulatory element is a polymerase II promoter. In some embodiments, the AAV-CRISPR enzyme is a type II AAV-CRISPR system enzyme. In some embodiments, the AAV-CRISPR enzyme is a AAV-Cas9 enzyme. In some embodiments, the AAV-Cas9 enzyme is derived from *S. pneumoniae, S. pyogenes, S. thermophilus, F. novicida* or *S. aureus* Cas9 (e.g., modified to have or be associated with at least one AAV), and may include further alteration or mutation of the Cas9, and can be a chimeric Cas9. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity).

In one aspect, the invention provides an AAV-CRISPR enzyme comprising one or more nuclear localization sequences of sufficient strength to drive accumulation of said AAV-CRISPR enzyme in a detectable amount in the nucleus of a eukaryotic cell. In some embodiments, the AAV-CRISPR enzyme is a type II AAV-CRISPR system enzyme. In some embodiments, the AAV-CRISPR enzyme is an AAV-Cas9 enzyme. In some embodiments, the AAV-Cas9 enzyme is derived from *S. pneumoniae, S. pyogenes, S. thermophilus, F. novicida* or *S. aureus* Cas9 (e.g., modified to have or be associated with at least one AAV), and may include further alteration or mutation of the Cas9, and can be a chimeric Cas9. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity).

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of an AAV-CRISPR complex to a target sequence in a eukaryotic cell, wherein the AAV-CRISPR complex comprises an AAV-CRISPR enzyme complexed with (1) the guide sequence that is hybridized to the target sequence, and (2) the tracr mate sequence that is hybridized to the tracr sequence; and/or (b) a said AAV-CRISPR enzyme optionally comprising at least one nuclear localization sequence and/or NES. In some embodiments, the host cell comprises components (a) and (b). In some embodiments, component (a), component (b), or components (a) and (b) are stably integrated into a genome of the host eukaryotic cell. In some embodiments, component (b) includes or contains component (a). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of an AAV-CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the AAV-CRISPR enzyme comprises one or more nuclear localization sequences and/or nuclear export sequences of sufficient strength to drive accumulation of said CRISPR enzyme in a detectable amount in of the nucleus of a eukaryotic cell. In some embodiments, the AAV-CRISPR enzyme is a type II CRISPR system enzyme. In some embodiments, the CRISPR enzyme is a Cas9 enzyme. In some embodiments, the AAV-Cas9 enzyme is derived from S. pneumoniae, S. pyogenes, S. thermophilus, F. novicida or S. aureus Cas9 (e.g., modified to have or be associated with at least one AAV), and may include further alteration or mutation of the Cas9, and can be a chimeric Cas9. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal, for example a mammal. Also, the organism may be an arthropod such as an insect. The organism also may be a plant. Further, the organism may be a fungus. Advantageously the organism is a host of AAV.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) said AAV-CRISPR enzyme optionally comprising a nuclear localization sequence. In some embodiments, the kit comprises components (a) and (b) located on or in the same or different vectors of the system, e.g., (a) can be contained in (b). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is derived from S. pneumoniae, S. pyogenes, S. thermophilus, F. novicida or S. aureus Cas9 (e.g., modified to have or be associated with at least one AAV), and may include further alteration or mutation of the Cas9, and can be a chimeric Cas9. In some embodiments, the coding for the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modifying a target polynucleotide in a eukaryotic cell. In some embodiments, the method comprises allowing an AAV-CRISPR complex to bind to the target polynucleotide, e.g., to effect cleavage of said target polynucleotide, thereby modifying the target polynucleotide, wherein the AAV-CRISPR complex comprises a AAV-CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said AAV-CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein one or more vectors comprise the AAV-CRISPR enzyme and one or more vectors drive expression of one or more of: the guide sequence linked to the tracr mate sequence, and the tracr sequence. In some embodiments, said AAV-CRISPR enzyme drive expression of one or more of: the guide sequence linked to the tracr mate sequence, and the tracr sequence. In some embodiments such AAV-CRISPR enzyme are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing an AAV-CRISPR complex to bind to the polynucleotide such that said binding results in increased or decreased expression of said polynucleotide; wherein the AAV-CRISPR complex comprises an AAV-CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors are the AAV-CRISPR enzyme and/or drive expression of one or more of: the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors comprise the AAV-CRISPR enzyme and/or drive expression of one or more of: a guide sequence linked to a tracr mate sequence, and a tracr sequence; and (b) allowing an AAV-CRISPR complex to bind to a target polynucleotide, e.g., to effect cleavage of the target polynucleotide within said disease gene, wherein the AAV-CRISPR complex comprises the AAV-CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. Thus, in some embodiments the AAV-CRISPR enzyme contains nucleic acid molecules for and drives expression of one or more of: a guide sequence linked to a tracr mate sequence, and a tracr sequence and/or a Homologous Recombination template and/or a stabilizing ligand if the CRISPR enzyme has a destabilization domain. In some embodiments, said cleavage comprises cleaving one or two strands at the location of the target sequence by said AAV-CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of an AAV-CRISPR complex to a corresponding target sequence present in a eukaryotic cell. The polynucleotide can be carried within and expressed in vivo from the AAV-CRISPR enzyme. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors comprise an AAV-CRISPR enzyme and/or drive expression of one or more of: a guide sequence linked to a tracr mate sequence, a tracr sequence, and an editing template; wherein, for example that which is being expressed is within and expressed in vivo by the AAV-CRISPR enzyme and/or the editing template comprises the one or more mutations that abolish AAV-CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the AAV-CRISPR complex comprises the AAV-CRISPR enzyme complexed with (1) the guide sequence that is hybridized to the target sequence within the target polynucleotide, and (2) the tracr mate sequence that is hybridized to the tracr sequence, wherein binding of the AAV-CRISPR complex to the target polynucleotide induces cell death, thereby allowing one or more cell(s) in which one or more mutations have been introduced to be selected. In a preferred embodiment, the AAV-CRISPR enzyme is AAV-Cas9. In another aspect of the invention the cell to be selected may be a eukaryotic cell. Aspects of the invention allow for selection of specific cells without requiring a selection marker or a two-step process that may include a counter-selection system. The cell(s) may be prokaryotic or eukaryotic cells.

With respect to mutations of the AAV-CRISPR enzyme, when the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. In an aspect the invention provides as to any or each or all embodiments herein-discussed wherein the AAV-CRISPR enzyme comprises at least one or more, or at least two or more mutations, wherein the at least one or more mutation or the at least two or more mutations is as to D10, E762, H840, N854, N863, or D986 according to SpCas9 protein, e.g., D10A, E762A, H840A, N854A, N863A and/or D986A as to SpCas9, or N580 according to SaCas9, e.g., N580A as to SaCas9, or any corresponding mutation(s) in a Cas9 of an ortholog to Sp or Sa, or the CRISPR enzyme comprises at least one mutation wherein at least H840 or N863A as to Sp Cas9 or N580A as to Sa Cas9 is mutated; e.g., wherein the CRISPR enzyme comprises H840A, or D10A and H840A, or D10A and N863A, according to SpCas9 protein, or any corresponding mutation(s) in a Cas9 of an ortholog to Sp protein or Sa protein.

Aspects of the invention encompass a non-naturally occurring or engineered composition that may comprise a guide RNA (sgRNA) comprising a guide sequence capable of hybridizing to a target sequence in a genomic locus of interest in a cell and an AAV-CRISPR enzyme that may comprise at least one or more nuclear localization sequences, wherein the AAV-CRISPR enzyme comprises one or two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous effector domains. In an embodiment of the invention the AAV-CRISPR enzyme comprises one or two or more mutations in a residue selected from the group comprising, consisting essentially of, or consisting of D10, E762, H840, N854, N863, or D986. In a further embodiment the AAV-CRISPR enzyme comprises one or two or more mutations selected from the group comprising D10A, E762A, H840A, N854A, N863A or D986A. In another embodiment, the effector domain comprise, consist essentially of a transcriptional activation domain, e.g., VP64. In another embodiment, the effector domain comprise, consist essentially of a transcriptional repressor domain, e.g., KRAB domain, SID domain or a SID4X domain. In embodiments of the invention, the one or more heterologous effector domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In another embodiment, the at least one loop of the sgRNA is tetraloop and/or loop2. An aspect of the invention encompasses methods of modifying a genomic locus of interest to change gene expression in a cell by introducing into the cell any of the compositions described herein. An aspect of the invention is that the above elements are comprised in a single composition or comprised in individual compositions, e.g., the AAV-CRISPR enzyme delivers the enzyme as discussed as well as the guide. These compositions may advantageously be applied to a host to elicit a functional effect on the genomic level. In general, the sgRNA are modified in a manner that provides specific binding sites (e.g., aptamers) for adapter proteins comprising one or more effector domains (e.g., via fusion protein) to bind to. The modified sgRNA are modified such that once the sgRNA forms an AAV-CRISPR complex (i.e. AAV-CRISPR enzyme binding to sgRNA and target) the adapter proteins bind and, the effector domain on the adapter protein is positioned in a spatial orientation which is advantageous for the attributed function to be effective. For example, if the effector domain comprises, consists essentially of or consists of a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target. Again, the AAV-CRISPR enzyme can deliver both the enzyme and the modified guide. The skilled person will understand that modifications to the sgRNA which allow for binding of the adapter+effector domain but not proper positioning of the adapter+effector domain (e.g., due to steric hindrance within the three dimensional structure of the CRISPR complex) are modifications which are not intended. The one or more modified sgRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the effector domains may be, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). In some cases it is advantageous that additionally at least one NLS is provided. In some instances, it is advantageous to position the NLS at the N terminus. When more than one effector domain is included, the effector domains may be the same or different.

The sgRNA may be designed to include multiple binding recognition sites (e.g., aptamers) specific to the same or different adapter protein. The sgRNA may be designed to bind to the promoter region −1000-+1 nucleic acids upstream of the transcription start site (i.e. TSS), preferably −200 nucleic acids. This positioning improves effector domains which affect gene activation (e.g., transcription activators) or gene inhibition (e.g., transcription repressors). The modified sgRNA may be one or more modified sgRNAs targeted to one or more target loci (e.g., at least 1 sgRNA, at least 2 sgRNA, at least 5 sgRNA, at least 10 sgRNA, at least 20 sgRNA, at least 30 sg RNA, at least 50 sgRNA) comprised in a composition.

Further, the AAV-CRISPR enzyme with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a AAV-Cas9 enzyme or AAV-CRISPR enzyme having advantageously about 0% of the nuclease activity of the non-mutated or wild type Cas9 enzyme or CRISPR enzyme, or no more than about 3% or about 5% or about 10% of the nuclease activity of the non-mutated or wild type Cas9 enzyme or CRISPR enzyme). This is possible by introducing mutations into the RuvC and HNH nuclease domains of the SpCas9 and orthologs thereof. For example utilizing mutations in a residue selected from the group comprising, consisting essentially of, or consisting of D10, E762, H840, N854, N863, or D986 and more preferably introducing one or more of the mutations selected from the group comprising, consisting essentially of, or consisting of D10A, E762A, H840A, N854A, N863A or D986A. A preferable pair of mutations is D10A with H840A, more preferable is D10A with N863A of SpCas9 and orthologs thereof. The inactivated CRISPR enzyme may have associated (e.g., via fusion protein) one or more effector domains, e.g., at least one destabilizing domain; or, for instance like those as described herein for the modified sgRNA adaptor proteins, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 effector domains are provided to allow for an effector dimer and that sgRNAs are designed to provide proper spacing for effector use (Fok1) as specifically described in Tsai et al. Nature Biotechnology, Vol. 32, Number 6, June 2014). The adaptor protein may utilize known linkers to attach such effector domains. In some cases it is advantageous that additionally at least one NLS is provided. In some instances, it is advantageous to position the NLS at the N terminus. When more than one effector domain is included, the effector domains may be the same or different. In general, the positioning of the one or more effector domain on the inactivated AAV-CRISPR enzyme is one which allows for correct spatial orientation for the effector domain to affect the target with the attributed functional effect. For example, if the effector domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the AAV-CRISPR enzyme. Positioning the effector domain in the Rec1 domain, the Rec2 domain, the HNH domain, or the PI domain of the SpCas9 protein or any ortholog corresponding to these domains is advantageous; and again, it is mentioned that the effector domain can be a DD. Positioning of the effector domains to the Rec domain or the Rec2 domain, of the SpCas9 protein or any ortholog corresponding to these domains, in some instances may be preferred. Positioning of the effector domains to the Rec domain at position 553, Rec domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains, in some instances may be preferred. Fok1 effector domain may be attached at the N terminus. When more than one effector domain is included, the effector domains may be the same or different.

An adaptor protein may be any number of proteins that binds to an aptamer or recognition site introduced into the modified sgRNA and which allows proper positioning of one or more effector domains, once the sgRNA has been incorporated into the AAV-CRISPR complex, to affect the target with the attributed function. As explained in detail in this application such may be coat proteins, preferably bacteriophage coat proteins. The effector domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the effector domain is a transcription activator or transcription repressor it is advantageous that additionally at least an NLS is provided and preferably at the N terminus. When more than one effector domain is included, the effector domains may be the same or different. The adaptor protein may utilize known linkers to attach such effector domains. Such linkers may be used to associate the AAV (e.g., capsid or VP2) with the CRISPR enzyme or have the CRISPR enzyme comprise the AAV (or vice versa).

Thus, sgRNA, e.g., modified sgRNA, the inactivated AAV-CRISPR enzyme (with or without effector domains), and the binding protein with one or more effector domains, may each individually be comprised in a composition and administered to a host individually or collectively. Alternatively, these components may be provided in a single composition for administration to a host, e.g., the AAV-CRISPR enzyme can deliver the RNA or guide or sgRNA or modified sgRNA and/or other components of the CRISPR system. Administration to a host may be performed via viral vectors, advantageously using the AAV-CRISPR enzyme as the delivery vehicle, although other vehicles can be used to deliver components other than the enzyme of the CRISPR system, and such viral vectors can be, for example, lentiviral vector, adenoviral vector, AAV vector. Several variations are appropriate to elicit a genomic locus event, including DNA cleavage, gene activation, or gene deactivation. Using the provided compositions, the person skilled in the art can advantageously and specifically target single or multiple loci with the same or different effector domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

In an aspect, the invention provides a particle delivery system or the delivery system or the virus particle of any one of any one of the above embodiments or the cell of any one of the above embodiments for use in medicine or in therapy; or for use in a method of modifying an organism or a non-human organism by manipulation of a target sequence in a genomic locus associated with a disease or disorder; or for use in a method of treating or inhibiting a condition caused by one or more mutations in a genetic locus associated with a disease in a eukaryotic organism or a non-human organism; or for use in in vitro, ex vivo or in vivo gene or genome editing; or for use in in vitro, ex vivo or in vivo gene therapy.

In an aspect, the invention provides a pharmaceutical composition comprising the particle delivery system or the delivery system or the virus particle of any one of the above embodiment or the cell of any one of the above embodiment.

In an aspect, the invention provides a method of treating or inhibiting a condition or a disease caused by one or more mutations in a genomic locus in a eukaryotic organism or a non-human organism comprising manipulation of a target sequence within a coding, non-coding or regulatory element of said genomic locus in a target sequence in a subject or a non-human subject in need thereof comprising modifying the subject or a non-human subject by manipulation of the target sequence and wherein the condition or disease is susceptible to treatment or inhibition by manipulation of the target sequence comprising providing treatment comprising delivering a composition comprising the particle delivery system or the delivery system or the virus particle of any one of the above embodiment or the cell of any one of the above embodiment.

In an aspect, the invention provides use of the particle delivery system or the delivery system or the virus particle of any one of the above embodiment or the cell of any one of the above embodiment in ex vivo or in vivo gene or genome editing; or for use in in vitro, ex vivo or in vivo gene therapy.

In an aspect, the invention provides use of the particle delivery system or the delivery system or the virus particle of any one of the above embodiment or the cell of any one of the above embodiment in the manufacture of a medicament for in vitro, ex vivo or in vivo gene or genome editing or for use in in vitro, ex vivo or in vivo gene therapy or for use in a method of modifying an organism or a non-human organism by manipulation of a target sequence in a genomic locus associated with a disease or in a method of treating or inhibiting a condition or disease caused by one or more mutations in a genomic locus in a eukaryotic organism or a non-human organism.

In an aspect, the invention provides a method of individualized or personalized treatment of a genetic disease in a subject in need of such treatment comprising:
  (a) introducing one or more mutations ex vivo in a tissue, organ or a cell line, or in vivo in a transgenic non-human mammal, comprising delivering to cell(s) of the tissue, organ, cell or mammal a composition comprising the particle delivery system or the delivery system or the virus particle of any one of the above embodiment or the cell of any one of the above embodiment, wherein the specific mutations or precise sequence substitutions are or have been correlated to the genetic disease;
  (b) testing treatment(s) for the genetic disease on the cells to which the vector has been delivered that have the specific mutations or precise sequence substitutions correlated to the genetic disease; and
  (c) treating the subject based on results from the testing of treatment(s) of step (b).

In an aspect, the invention provides a method of modeling a disease associated with a genomic locus in a eukaryotic organism or a non-human organism comprising manipulation of a target sequence within a coding, non-coding or regulatory element of said genomic locus comprising delivering a non-naturally occurring or engineered composition comprising a viral vector system comprising one or more viral vectors operably encoding a composition for expression thereof, wherein the composition comprises particle delivery system or the delivery system or the virus particle of any one of the above embodiments or the cell of any one of the above embodiment.

In an aspect, the method provides a method of modifying an organism or a non-human organism by manipulation of a target sequence in a genomic locus of interest comprising administering a composition comprising the particle delivery system or the delivery system or the virus particle of any one of the above embodiment or the cell of any one of the above embodiment.

Delivery Generally

Vector delivery, e.g., plasmid, viral delivery: The nucleic acid modifying protein, for instance a protein comprising one or more domains of a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON-S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver Cas9 and gRNA (and, for instance, HR repair template) into cells using liposomes or particles. Thus delivery of the CRISPR enzyme, such as a Cas9 and/or delivery of the RNAs of the invention may be in RNA form and via microvesicles, liposomes or particles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via particles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purified and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA)

filled with phosphate-buffered saline (PBS) or free Tocsi-BACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 μmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKC7 for in vivo gene silencing in the spinal cord of rats. Zou et al. administered about 10 μl of a recombinant lentivirus having a titer of 1×109 transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of 1×109 transducing units (TU)/ml may be contemplated.

Anderson et al. (US 20170079916) provides a modified dendrimer nanoparticle for the delivery of therapeutic, prophylactic and/or diagnostic agents to a subject, comprising: one or more zero to seven generation alkylated dendrimers; one or more amphiphilic polymers; and one or more therapeutic, prophylactic and/or diagnostic agents encapsulated therein. One alkylated dendrimer may be selected from the group consisting of poly(ethyleneimine), poly(polypropylenimine), diaminobutane amine polypropylenimine tetramine and poly(amido amine). The therapeutic, prophylactic and diagnostic agent may be selected from the group consisting of proteins, peptides, carbohydrates, nucleic acids, lipids, small molecules and combinations thereof.

Anderson et al. (US 20160367686) provides a compound of Formula (I):

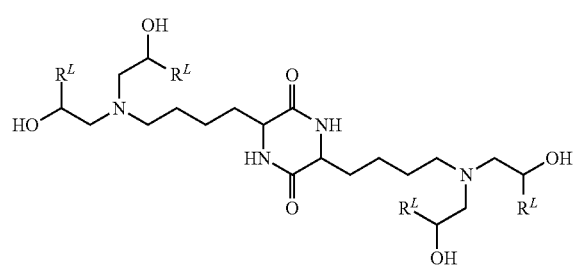

(I)

and salts thereof, wherein each instance of $R^L$ is independently optionally substituted $C_6$-$C_{40}$ alkenyl, and a composition for the delivery of an agent to a subject or cell comprising the compound, or a salt thereof, an agent; and optionally, an excipient. The agent may be an organic molecule, inorganic molecule, nucleic acid, protein, peptide, polynucleotide, targeting agent, an isotopically labeled chemical compound, vaccine, an immunological agent, or an agent useful in bioprocessing. The composition may further comprise cholesterol, a PEGylated lipid, a phospholipid, or an apolipoprotein.

Anderson et al. (US20150232883) provides a delivery particle formulations and/or systems, preferably nanoparticle delivery formulations and/or systems, comprising (a) a CRISPR-Cas system RNA polynucleotide sequence; or (b) Cas9; or (c) both a CRISPR-Cas system RNA polynucleotide sequence and Cas9; or (d) one or more vectors that contain nucleic acid molecule(s) encoding (a), (b) or (c), wherein the CRISPR-Cas system RNA polynucleotide sequence and the Cas9 do not naturally occur together. The delivery particle formulations may further comprise a surfactant, lipid or protein, wherein the surfactant may comprise a cationic lipid.

Anderson et al. (US20050123596) provides examples of microparticles that are designed to release their payload when exposed to acidic conditions, wherein the microparticles comprise at least one agent to be delivered, a pH triggering agent, and a polymer, wherein the polymer is selected from the group of polymethacrylates and polyacrylates.

Anderson et al. (US 20020150626) provides lipid-protein-sugar particles for delivery of nucleic acids, wherein the polynucleotide is encapsulated in a lipid-protein-sugar matrix by contacting the polynucleotide with a lipid, a protein, and a sugar; and spray drying mixture of the polynucleotide, the lipid, the protein, and the sugar to make microparticles.

In terms of local delivery to the brain, this can be achieved in various ways. For instance, material can be delivered intrastriatally e.g., by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package nucleic acid modifying protein coding nucleic acid molecules, e.g., DNA, into vectors, e.g., viral vectors, to mediate genome modification in vivo include:
To achieve NHEJ-mediated gene knockout:
Single virus vector:
Vector containing two or more expression cassettes:
Promoter-nucleic acid modifying protein coding nucleic acid molecule-terminator
Promoter-gRNA1-terminator
Promoter-gRNA2-terminator
Promoter-gRNA(N)-terminator (up to size limit of vector)
Double virus vector:
Vector 1 containing one expression cassette for driving the expression of nucleic acid modifying protein
Promoter-nucleic acid modifying protein coding nucleic acid molecule-terminator
Vector 2 containing one more expression cassettes for driving the expression of one or more guideRNAs
Promoter-gRNA1-terminator
Promoter-gRNA(N)-terminator (up to size limit of vector)
To mediate homology-directed repair.
In addition to the single and double virus vector approaches described above, an additional vector is used to deliver a homology-direct repair template.

The promoter used to drive nucleic acid modifying protein coding nucleic acid molecule expression can include:
- AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of nucleic acid modifying protein.
- For ubiquitous expression, can use promoters: CMV, CAG, CBh, PGK, SV40, Ferritin heavy or light chains, etc.
- For brain or other CNS expression, can use promoters: SynapsinI for all neurons, CaMKIIalpha for excitatory neurons, GAD67 or GAD65 or VGAT for GABAergic neurons, etc.
- For liver expression, can use Albumin promoter.
- For lung expression, can use SP-B.
- For endothelial cells, can use ICAM.
- For hematopoietic cells can use IFNbeta or CD45.
- For Osteoblasts can use OG-2.

The promoter used to drive guide RNA can include:
- Pol III promoters such as U6 or H1
- Use of Pol II promoter and intronic cassettes to express gRNA Adeno Associated Virus (AAV)

Nucleic acid modifying protein and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of nucleic acid modifying protein can be driven by a cell-type specific promoter. For example, liver-specific expression might use the Albumin promoter and neuron-specific expression (e.g., for targeting CNS disorders) might use the Synapsin I promoter.

In terms of in vivo delivery, AAV is advantageous over other viral vectors for a couple of reasons:
- Low toxicity (this may be due to the purification method not requiring ultra centrifugation of cell particles that can activate the immune response) and
- Low probability of causing insertional mutagenesis because it doesn't integrate into the host genome.

AAV has a packaging limit of 4.5 or 4.75 Kb. This means that nucleic acid modifying protein as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing nucleic acid modifying protein comprising one or more domains of homologs of Cas9. For example:

| Species | Cas9 Size (nt) |
| --- | --- |
| *Corynebacter diphtheriae* | 3252 |
| *Eubacterium ventriosum* | 3321 |
| *Streptococcus pasteurianus* | 3390 |
| *Lactobacillus farciminis* | 3378 |
| *Sphaerochaeta globus* | 3537 |
| *Azospirillum* B510 | 3504 |
| *Gluconacetobacter diazotrophicus* | 3150 |
| *Neisseria cinerea* | 3246 |
| *Roseburia intestinalis* | 3420 |
| *Parvibaculum lavamentivorans* | 3111 |
| *Staphylococcus aureus* | 3159 |
| *Nitratifractor salsuginis* DSM 16511 | 3396 |
| *Campylobacter lari* CF89-12 | 3009 |
| *Campylobacter jejuni* | 2952 |
| *Streptococcus thermophilus* LMD-9 | 3396 | rAAV vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

These species are therefore, in general, preferred Cas9 species.

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in an ultracentrifuge for 2 hours at 24,000 rpm. Viral pellets were resuspended in 50 ul of DMEM overnight at 4 C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (Cell-Genix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

Lentiviral vectors have been disclosed as in the treatment for Parkinson-s Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The nucleic acid modifying protein, for instance a DNa modifying protein comprising one or more domains of a Cas9, and/or any of the present RNAs, for instance a guide RNA, can also be delivered in the form of RNA. nucleic acid modifying protein mRNA can be generated using in vitro transcription. For example, nucleic acid modifying protein mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the nucleic acid modifying protein-coding sequence and/or the guide RNA can be modified to include one or more modified nucleoside e.g., using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particles

Liu et al. (US 20110212179) provides bimodal porous polymer microspheres comprising a base polymer, wherein the particle comprises macropores having a diameter ranging from about 20 to about 500 microns and micropores having a diameter ranging from about 1 to about 70 microns, and wherein the microspheres have a diameter ranging from about 50 to about 1100 microns.

Berg et al. (US20160174546) a nanolipid delivery system, in particular a nanoparticle concentrate, comprising: a composition comprising a lipid, oil or solvent, the composition having a viscosity of less than 100 cP at 25.degree. C. and a Kauri Butanol solvency of greater than 25 Kb; and at least one amphipathic compound selected from the group consisting of an alkoxylated lipid, an alkoxylated fatty acid, an alkoxylated alcohol, a heteroatomic hydrophilic lipid, a heteroatomic hydrophilic fatty acid, a heteroatomic hydrophilic alcohol, a diluent, and combinations thereof, wherein the compound is derived from a starting compound having a viscosity of less than 1000 cP at 50° C., wherein the concentrate is configured to provide a stable nano emulsion having a D50 and a mean average particle size distribution of less than 100 nm when diluted.

Liu et al. (US 20140301951) provides a protocell nanostructure comprising: a porous particle core comprising a plurality of pores; and at least one lipid bilayer surrounding the porous particle core to form a protocell, wherein the protocell is capable of loading one or more cargo components to the plurality of pores of the porous particle core and releasing the one or more cargo components from the porous particle core across the surrounding lipid bilayer.

Chromy et al. (US 20150105538) provides methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystalling transition temperature of the membrane forming lipid of the nanolipoprotein particle.

Bader et al. (US 20150250725), provides a method for producing a lipid particle comprising the following: i) providing a first solution comprising denatured apolipoprotein, ii) adding the first solution to a second solution comprising at least two lipids and a detergent but no apolipoprotein, and iii) removing the detergent from the solution obtained in ii) and thereby producing a lipid particle.

Mirkin et al., (US20100129793) provides a method of preparing a composite particle comprising the steps of (a) admixing a dielectric component and a magnetic component to form a first intermediate, (b) admixing the first intermediate and gold seeds to form a second intermediate, and (c) forming a gold shell on the second intermediate by admixing the second intermediate with a gold source and a reducing agent to form said composite particle.

CRISPR enzyme mRNA and guide RNA may be delivered simultaneously using nanoparticles or lipid envelopes. Similarly, synthetic nucleic acid modifying systems comprising DNA readers and one or more effector components can be delivered by nanoparticles.

Delivery of miniGEMs In Vivo.

In some embodiments, methods of delivery of miniGEMs in vivo can be accomplished by delivery of PNAs using Poly(lactic co-glycolic acids) (PLGA) nanoparticles. PLGA is a biodegradable polymer commonly used in drug delivery systems and medical devices. PLGA undergoes hydrolytic degradation into endogenous, non-toxic metabolites (lactic acid and glycolic acid) and has been approved by US Food and Drug Administration (USFDA). Given these attractive properties of PLGA, it is unsurprising that PLGA nanoparticles have been used for cellular delivery of PNAs in several studies. McNeer et al. and Scheifman et al. used PLGA nanoparticles to deliver triplex forming PNAs and donor DNAs for site specific genome editing of CD34+ HPSCs. In another study, McNeer et al. demonstrated the generalizability of this approach by introducing a 6 bp mutation into the CCR5 gene in human hematopoietic progenitor cells. Further, they have also demonstrated delivery in the human Œ ≤-globin gene in mice reconstituted with human hematopoietic cells as well as in an eGFP reporter mouse model providing evidence of direct, in vivo site specific gene editing by PNA-DNA NPs. Although PGLA nanoparticles are widely used in medicine due to its enhanced biocompatibility, it has limited DNA loading capacity. In order to increase, its oligonucleotide loading capacity, cationic polymers such as poly (beta-amino-esters) (PBAE) have been used in combination with PLGA. Bahal et al. have used single-stranded Œ ≥PNA along with DNA donor in PBAE-PLGA nanoparticles to correct a disease causing Œ ≥-thalassemia mutation both ex vivo and in a Œ ≤-globin/eGFP reporter mouse. Fields et al. used an intranasal delivery route to show increased cellular uptake and gene editing in the lungs of Œ ≤-globin/eGFP reporter mouse by PNA and donor DNA encapsulated in PBAE-PLGA NPs compared to PLGA NPs. Further, Mc.Neer and Anandalingam et al. demonstrated the correction of the most prevalent cystic fibrosis transmembrane conductance regulator (CFTR) mutation in human CBFE cells as well as in a mouse model. In the light of these numerous reports of delivery in primary cells and mouse models using PNAs encapsulated in nanoparticles, it is envisioned that the nanoparticle based delivery system to be ideal for intracellular delivery of our small-molecule PNA conjugates. To prepare nanoparticle formulations of small molecule-PNA conjugate and donor DNA the approach described by Bahal et al. will be employed. Briefly, small-molecule PNA conjugate and donor DNA will be encapsulated in PGLA nanoparticles using double emulsion solvent evaporation technique. The first emulsion is formed by dropwise addition of aqueous solution of small molecule-PNA conjugate and donor DNA to a solution containing 50:50 ester-terminated PGLA in dichloromethane, followed by ultrasonication. To form the second emulsion, the first emulsion is added slowly, dropwise to 5% aqueous polyvinyl alcohol and then ultrasonicated. This mixture was then poured into 0.3% aqueous polyvinyl alcohol and stirred at room temperature for 3 hrs to obtain nanoparticles. The nanoparticles are then thoroughly washed and collected by centrifugation, resuspended in water, frozen at −80-∞ C and then lyophilized. Nanoparticles will be resuspended in cell culture medium by vigorous vortexing and water sonication and directly added to the cells. In the event that the donor DNA template gets cleaved when co-encapsulated with the small-molecule strand breaker-PNA conjugate, they will be encapsulated in separate nanoparticles as these have also been shown to yield desired genomic modification albeit to a lower extent.

In some embodiments, delivery systems may include, for example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) which describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, nanoparticles that can deliver RNA to a cancer cell to stop tumor growth developed by Dan Anderson's lab at MIT may be used/and or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

The lipid particles developed by the Qiaobing Xu's lab at Tufts University may be used/adapted to the present delivery system for cancer therapy. See Wang et al., J. Control Release, 2017 Jan. 31. pii: 50168-3659(17)30038-X. doi: 10.1016/j.jconrel.2017.01.037. [Epub ahead of print]; Altmoglu et al., Biomater Sci., 4(12):1773-80, Nov. 15, 2016; Wang et al., PNAS, 113(11):2868-73 Mar. 15, 2016; Wang et al., PloS One, 10(11): e0141860. doi: 10.1371/journal.pone.0141860. eCollection 2015, Nov. 3, 2015; Takeda et al., Neural Regen Res. 10(5):689-90, May 2015; Wang et al., Adv. Healthc Mater., 3(9):1398-403, September 2014; and Wang et al., Agnew Chem Int Ed Engl., 53(11):2893-8, Mar. 10, 2014.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The minoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

Zhu et al. (US20140348900) provides for a process for preparing liposomes, lipid discs, and other lipid nanoparticles using a multi-port manifold, wherein the lipid solution stream, containing an organic solvent, is mixed with two or more streams of aqueous solution (e.g., buffer). In some aspects, at least some of the streams of the lipid and aqueous solutions are not directly opposite of each other. Thus, the process does not require dilution of the organic solvent as an additional step. In some embodiments, one of the solutions may also contain an active pharmaceutical ingredient (API). This invention provides a robust process of liposome manufacturing with different lipid formulations and different payloads. Particle size, morphology, and the manufacturing scale can be controlled by altering the port size and number of the manifold ports, and by selecting the flow rate or flow velocity of the lipid and aqueous solutions.

Cullis et al. (US 20140328759) provides limit size lipid nanoparticles with a diameter from 10-100 nm, in particular comprising a lipid bilayer surrounding an aqueous core. Methods and apparatus for preparing such limit size lipid nanoparticles are also disclosed.

Manoharan et al. (US 20140308304) provides cationic lipids of formula (I)

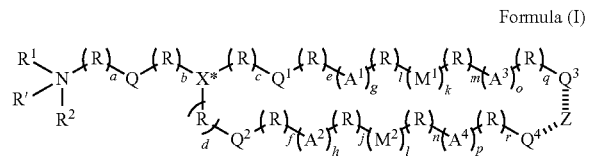

Formula (I)

or a salt thereof, wherein X is N or P; R' is absent, hydrogen, or alkyl; with respect to $R^1$ and $R^2$, (i) $R^1$ and $R^2$ are each, independently, optionally substituted alkyl, alkenyl, alkynyl, cycloalkyl, cycloalkylalkyl, heterocycle or $R^{10}$; (ii) $R^1$ and $R^2$, together with the nitrogen atom to which they are attached, form an optionally substituted heterocylic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl with (a) the adjacent nitrogen atom and (b) the $(R)_a$ group adjacent to the nitrogen atom; each occurrence of R is independently, —($CR^3R^4$)—; each occurrence of $R^3$ and $R^4$ are, independently H, halogen, OH, alkyl, alkoxy, —NH.sub.2, alkylamino, or dialkylamino; or $R^3$ and $R^4$, together with the carbon atom to which they are directly attached, form a cycloalkyl group, wherein no more than three R groups in each chain attached to the atom X* are cycloalkyl; each occurrence of R.sup.10 is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups; Q is absent or is —O—, —NH—, —S—, —C(O) O—, —OC(O)—, —C(O)N($R^4$)—, —N($R^5$)C(O)—, —S—S—, —OC(O)O—, —O—N.dbd.C($R^5$)—, —C($R^5$).dbd.N—O—, —OC(O)N($R^5$)—, —N($R^5$)C(O)N ($R^5$)—, —N($R^5$)C(O)O—, —C(O)S—, —C(S)O— or —C($R^5$).dbd.N—O—C(O)—; $Q^1$ and $Q^2$ are each, independently, absent, —O—, —S—, —OC(O)—, —C(O)O—, —SC(O)—, —C(O)S—, —OC(S)—, —C(S)O—, —S—S—, —C(O)(N$R^5$)—, —N($R^5$)C(O)—, —C(S)(N$R^5$)—, —N($R^5$)C(O)—, —N($R^5$)C(O)N($R^5$)—, or —OC(O)O—; $Q^3$ and $Q^4$ are each, independently, H, —($CR^3R^4$)—, aryl, or a cholesterol moiety; each occurrence of $A^1$, $A^2$, $A^3$ and $A^4$ is independently, —($CR^5R^5$—$CR^5$.dbd.$CR^5$)—; each occurrence of $R^5$ is independently, H or alkyl; $M^1$ and $M^2$ are each, independently, a biodegradable group (e.g., —OC(O)—, —C(O)O—, —SC(O)—, —C(O)S—, —OC(S)—, —C(S) O—, —S—S—, —C($R^5$).dbd.N—, —N.dbd.C($R^5$)—, —C($R^5$).dbd.N—O—, —O—N.dbd.C($R^5$)—, —C(O) (N$R^5$)—, —N($R^5$)C(O)—, —C(S)(N$R^5$)—, —N($R^5$)C (O)—, —N($R^5$)C(O)N($R^5$)—, —OC(O)O—, —OSi($R^5$).sub.2O—, —C(O)($CR^3R^4$)C(O)O—, or —OC (O)($CR^3R^4$)C(O)—); Z is absent, alkylene or —O—P(O) (OH)—O—; each - attached to Z is an optional bond, such that when Z is absent, $Q^3$ and $Q^4$ are not directly covalently bound together; a is 1, 2, 3, 4, 5 or 6; b is 0, 1, 2, or 3; c, d, e, f, i, j, m, n, q and r are each, independently, 0, 1, 2, 3, 4, 5, 6, 7, 8, 9, or 10; g and h are each, independently, 0, 1 or 2; k and l are each, independently, 0 or 1, where at least one of k and l is 1; and o and p are each, independently, 0, 1 or 2, wherein $Q^3$ and $Q^4$ are each, independently, separated from the tertiary atom marked with an asterisk (X*) by a chain of 8 or more atoms. The cationic lipid can be used with other lipid components such as cholesterol and PEG-lipids to form lipid nanoparticles with oligonucleotides, to facilitate the cellular uptake and endosomal escape, and to knockdown target mRNA both in vitro and in vivo.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethyl-ammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml of LNP or CRISPR-Cas RNA in or associated with the LNP may be contemplated, especially for a formulation containing DLinKC2-DMA.

Preparation of LNPs and CRISPR Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Liposomes

In one aspect, the invention provides a particle delivery system comprising a composite virus particle, wherein the composite virus particle comprises a lipid, a virus capsid protein, and a protein or peptide. The peptide or protein can be up to one megadalton in size.

In one embodiment, the particle delivery system comprises a virus particle adsorbed to a liposome. In one embodiment, the liposome comprises a cationic lipid.

In one embodiment, the liposome of the particle delivery system comprises the CRISPR-Cas system component.

In one aspect, the invention provides a delivery system comprising one or more hybrid virus capsid proteins in combination with a lipid particle, wherein the hybrid virus capsid protein comprises at least a portion of a virus capsid protein attached to at least a portion of a non-capsid protein.

In one embodiment, the virus capsid protein of the delivery system is attached to the surface of the lipid particle. In one embodiment, the virus capsid protein is attached to the surface of the lipid particle by an electrostatic interaction or by hydrophobic interaction.

In one embodiment, the lipid particle has a dof 50-1000 nm, preferably 100-1000 nm.

In one embodiment, the delivery system comprises a protein or peptide, wherein the protein or peptide has a molecular weight of up to a megadalton. In one embodiment, the protein or peptide has a molecular weight in the range of 110 to 160 kDa.

In one embodiment, the delivery system comprises a protein or peptide, wherein the protein or peptide comprises a nucleic acid modifying protein or peptide. In one embodiment, the protein or peptide comprises one or more domains of a Cas9, a Cpf1 or a $C_2c2$.

In one embodiment, the lipid, lipid particle or lipid layer of the delivery system comprises at least one cationic lipid.

In one embodiment, the lipid compound is preferably a bio-reducible material, e.g., a bio-reducible polymer and a bio-reducible lipid-like compound.

In one aspect, the lipid or lipid-like compound comprises a hydrophilic head, a hydrophobic tail, and a linker.

In one embodiment, the hydrophilic head contains one or more hydrophilic functional groups, e.g., hydroxyl, carboxyl, amino, sulfhydryl, phosphate, amide, ester, ether, carbamate, carbonate, carbamide and phosphodiester. These groups can form hydrogen bonds and are optionally positively or negatively charged.

In one embodiment, the hydrophobic tail is a saturated or unsaturated, linear or branched, acyclic or cyclic, aromatic or nonaromatic hydrocarbon moiety containing a disulfide bond and 8-24 carbon atoms. One or more of the carbon atoms can be replaced with a heteroatom, such as N, O, P, B, S, Si, Sb, Al, Sn, As, Se, and Ge. The lipid or lipid-like compounds containing disulfide bond can be bioreducible.

In one embodiment, the linker of the lipid or lipid-like compound links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate phosphate, phosphite, sulfate, sulfite, and thiosulfate.

The lipid or lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the nucleic acid modifying system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific nucleic acid modifying protein targeted in a SNALP are contemplated. The daily treatment may be over about three days and then weekly for about five weeks. In another embodiment, a specific nucleic acid modifying protein encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Niotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM Na2HPO4, 1 mM KH2PO4, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 m filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate nucleic acid modifying system or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11+0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume: 29, Pages: 154-157 (2011)) describes the use of lipid envelopes to deliver RNA. Use of lipid envelopes is also preferred in the present invention.

In another embodiment, lipids may be formulated with the nucleic acid modifying system of the present invention to form lipid nanoparticles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA (see, e.g., Novobrantseva, Molecular Therapy—Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The nucleic acid modifying system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to, PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P(O2)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterized by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116) (However, pilot experiments varying the dose of protein and RNA should be performed to optimize the procedure for specific cell lines):

(1) One day before treatment, plate $1\times10^5$ cells per well in a 48-well plate.

(2) On the day of treatment, dilute purified +36 GFP protein in serum free media to a final concentration 200 nM. Add RNA to a final concentration of 50 nM. Vortex to mix and incubate at room temperature for 10 min.

(3) During incubation, aspirate media from cells and wash once with PBS.

(4) Following incubation of +36 GFP and RNA, add the protein-RNA complexes to cells.

(5) Incubate cells with complexes at 37° C. for 4 h.

(6) Following incubation, aspirate the media and wash three times with 20 U/mL heparin PBS. Incubate cells with serum-containing media for a further 48 h or longer depending upon the assay for activity.

(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications:
(1) One day before treatment, plate $1\times10^5$ per well in a 48-well plate. (2) On the day of treatment, dilute purified þ 36 GFP protein in serum free media to a final concentration 2 mM. Add 1 mg of plasmid DNA. Vortex to mix and incubate at room temperature for 10 min.
(3) During incubation, aspirate media from cells and wash once with PBS.
(4) Following incubation of þ 36 GFP and plasmid DNA, gently add the protein-DNA complexes to cells.
(5) Incubate cells with complexes at 37 C for 4 h.
(6) Following incubation, aspirate the media and wash with PBS. Incubate cells in serum-containing media and incubate for a further 24-48 h.
(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in conjunction with herein teaching can be employed in the delivery of CRISPR Cas system(s) or component(s) thereof or nucleic acid molecule(s) coding therefor.

Cell Penetrating Peptides (CPPs)

In yet another embodiment, cell penetrating peptides (CPPs) are contemplated for the delivery of the CRISPR Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles, including nanoparticles, liposomes, chromophores, small molecules and radioactive materials. In aspects of the invention, the cargo may also comprise any component of the CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CRISPR-Cas system or components thereof. That CPPs can be employed to deliver the CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Schwarze et al. demonstrated that intraperitoneal injection of the 120-kilodalton (3-galactosidase protein, fused to the protein transduction domain from the human immunodeficiency virus TAT protein, results in delivery of the biologically active fusion protein to all tissues in mice, including the brain. Schwarze et al., 1999, In Vivo Protein Transduction: Delivery of a Biologically Active Protein into the Mouse, Science 285:1569.

Silvio et al. delivered a novel peptide inhibitor of CK2 phosphorylation to tumor cells by linkage to cell penetrating peptide Tat (48-68; GRKKRRQRRRPPQ (SEQ ID NO: 21)). Silvio et al., 2004, Antitumor Effect of a Novel Proapoptotic Peptide that Impairs the Phosphorylation by the Protein Kinase 2 (Casein Kinase 2), Cancer Res. 64:7127.

Jo et al. developed recombinant cell-penetrating (CP) forms of suppressor of cytokine signaling 3 (SOCS3) for intracellular delivery to counteract SEB-, LPS- and ConA-induced inflammation and found that CP-SOCS3 was distributed in multiple organs and persisted in leukocytes and lymphocytes. Jo et al., 2005, Intracellular protein therapy with SOCS3 inhibits inflammation and apoptosis, Nat. Medicine, 11:892.

Kamei et al. produced penetratin analogs indicating that chain length, hydrophobicity, and amphipathicity of the CPPs, as well as their basicity, contribute to their absorption-enhancing efficiency. It was further demonstrated that modified CPPs could be designed that had the capacity to complex with insulin and enhance insulin absorption to a greater extent that the original penetrating. Kamei et al., 2013, Determination of the Optimal Cell-Penetrating Peptide Sequence for Intestinal Insulin Delivery Based on Molecular Orbital Analysis with Self-Organizing Maps, J. Pharm. Sci. 102:469.

These and further examples are set forth in the table below.

together allows the first and second nucleic acid modifying protein fusion constructs to constitute a functional nucleic acid modifying protein (optionally wherein the nucleic acid modifying system comprises a guide RNA (gRNA) comprising a guide sequence capable of hybridizing to a target sequence in a genomic locus of interest in a cell, and wherein the functional nucleic acid modifying system binds to the target sequence and, optionally, edits the genomic locus to alter gene expression).

In an aspect of the invention in the inducible nucleic acid modifying system, the inducible dimer is or comprises or consists essentially of or consists of an inducible heterodimer. In an aspect, in inducible nucleic acid modifying system, the first half or a first portion or a first fragment of the inducible heterodimer is or comprises or consists of or consists essentially of an FKBP, optionally FKBP12. In an aspect of the invention, in the inducible nucleic acid modifying system, the second half or a second portion or a second fragment of the inducible heterodimer is or comprises or consists of or consists essentially of FRB. In an aspect of the invention, in the inducible nucleic acid modifying system, the arrangement of the first nucleic acid modifying protein fusion construct is or comprises or consists of or consists essentially of N' terminal nucleic acid modifying protein

| Peptides and proteins delivered by cell-penetrating peptides. | | | |
|---|---|---|---|
| CPP | Cargo | Formulation | Assay/result |
| Tat | β-galactosidase | Covalent conjugation | Tissue distribution of β-galactosidase in mice following IP administration. |
| Tat | P15 | Covalent conjugation | Apoptosis in various tumor cell lines and regression of tumor size upon intratumoral injections to mice. |
| FGF4-derived peptide | suppressor of cytokine signaling (SOCS3) | Covalent conjugation | Uptake into mouse macrophage cells and suppression of the production of inflammatory cytokines in mice following IP administration. |
| R9 | c-Myc, Sox2, Oct4. Klf4 | Covalent conjugation | Induction of fibroblasts from human newborn into pluripotent stem cells. |
| Pep-1 | Various peptides and proteins | Physical complexation | Uptake of cargo peptide or protein in cells of various cell culture models. |
| Penetratin | Insulin, GLP-1, exendin-4 | Physical complexation | Cargo plasma concentration following nasal or intestinal loop administration to rats. |
| PenetraMax | Insulin | Physical complexation | Insulin plasma concentration following intestinal loop administration to rats. |
| Tat | Bcl-x1 | Covalent conjugation | Brain distribution of Bcl-x1 and reduction of cerebral infarction. |
| Tat | NR2B9c | Covalent conjugation | Brain concentration of NR2B9c in rats and reduction of cerebral infarction in mice following IP administration. |
| Tat | GDNF | Covalent conjugation | Brain concentration of GDNF and reduction of cerebral infarction following intravenous administration to mice. |

Inducible Systems

In an aspect, the invention provides a (non-naturally occurring or engineered) inducible nucleic acid modifying protein according to the invention as described herein (nucleic acid modifying system), comprising: a first nucleic acid modifying protein fusion construct attached to a first half of an inducible dimer and a second nucleic acid modifying protein fusion construct attached to a second half of the inducible dimer, wherein the first nucleic acid modifying protein fusion construct is operably linked to one or more nuclear localization signals, wherein the second nucleic acid modifying protein protein fusion construct is operably linked to one or more nuclear export signals, wherein contact with an inducer energy source brings the first and second halves of the inducible dimer together, wherein bringing the first and second halves of the inducible dimer part-FRB-NES. In an aspect of the invention, in the inducible nucleic acid modifying system, the arrangement of the first nucleic acid modifying protein fusion construct is or comprises or consists of or consists essentially of NES-N' terminal nucleic acid modifying protein part-FRB-NES. In an aspect of the invention, in the inducible nucleic acid modifying system, the arrangement of the second nucleic acid modifying protein fusion construct is or comprises or consists essentially of or consists of C' terminal nucleic acid modifying protein part-FKBP-NLS. In an aspect the invention provides in the inducible nucleic acid modifying system, the arrangement of the second nucleic acid modifying protein fusion construct is or comprises or consists of or consists essentially of NLS-C' terminal nucleic acid modifying protein part-FKBP-NLS. In an aspect, in inducible nucleic acid modifying system there can be a linker that separates the nucleic acid modifying protein part from the half or portion or fragment of the inducible dimer. In an aspect, in the inducible nucleic acid modifying system, the inducer energy source is or comprises or consists essentially of or consists of rapamycin. In an aspect, in inducible nucleic acid modifying system, the inducible dimer is an inducible homodimer. In an aspect, in an inducible nucleic acid modifying system, the nucleic acid modifying protein comprises one or more domains of a AsCpf1, LbCpf1 or FnCpf1.

In an aspect, the invention provides a (non-naturally occurring or engineered) inducible nucleic acid modifying system, comprising: a first nucleic acid modifying protein fusion construct attached to a first half of an inducible heterodimer and a second nucleic acid modifying protein fusion construct attached to a second half of the inducible heterodimer, wherein the first nucleic acid modifying protein fusion construct is operably linked to one or more nuclear localization signals, wherein the second nucleic acid modifying protein fusion construct is operably linked to a nuclear export signal, wherein contact with an inducer energy source brings the first and second halves of the inducible heterodimer together, wherein bringing the first and second halves of the inducible heterodimer together allows the first and second nucleic acid modifying protein fusion constructs to constitute a functional nucleic acid modifying protein (optionally wherein the nucleic acid modifying system comprises a guide RNA (gRNA) comprising a guide sequence capable of hybridizing to a target sequence in a genomic locus of interest in a cell, and wherein the functional nucleic acid modifying system edits the genomic locus to alter gene expression).

Accordingly, the invention comprehends inter alia homodimers as well as heterodimers, dead-nucleic acid modifying protein or nucleic acid modifying protein having essentially no nuclease activity, e.g., through mutation, systems or complexes wherein there is one or more NLS and/or one or more NES; effector domain(s) linked to split nucleic acid modifying protein; methods, including methods of treatment, and uses.

An inducer energy source may be considered to be simply an inducer or a dimerizing agent. The term 'inducer energy source' is used herein throughout for consistency. The inducer energy source (or inducer) acts to reconstitute the enzyme. In some embodiments, the inducer energy source brings the two parts of the enzyme together through the action of the two halves of the inducible dimer. The two halves of the inducible dimer therefore are brought tougher in the presence of the inducer energy source. The two halves of the dimer will not form into the dimer (dimerize) without the inducer energy source.

Thus, the two halves of the inducible dimer cooperate with the inducer energy source to dimerize the dimer. This in turn reconstitutes the nucleic acid modifying protein by bringing the first and second parts of the nucleic acid modifying protein together.

The nucleic acid modifying protein fusion constructs each comprise one part of the split nucleic acid modifying protein. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer.

The nucleic acid modifying protein is split in the sense that the two parts of the nucleic acid modifying protein substantially comprise a functioning nucleic acid modifying protein. That nucleic acid modifying protein may function as a genome editing enzyme (when forming a complex with the target DNA and the guide), such as a nickase or a nuclease (cleaving both strands of the DNA), or it may be a dead-nucleic acid modifying protein which is essentially a DNA-binding protein with very little or no catalytic activity, due to typically mutation(s) in its catalytic domains.

The two parts of the split nucleic acid modifying protein can be thought of as the N' terminal part and the C' terminal part of the split nucleic acid modifying protein. The fusion is typically at the split point of the nucleic acid modifying protein. In other words, the C' terminal of the N' terminal part of the split nucleic acid modifying protein is fused to one of the dimer halves, whilst the N' terminal of the C' terminal part is fused to the other dimer half.

The nucleic acid modifying protein does not have to be split in the sense that the break is newly created. The split point is typically designed in silico and cloned into the constructs. Together, the two parts of the split nucleic acid modifying protein, the N' terminal and C' terminal parts, form a full nucleic acid modifying protein, comprising preferably at least 70% or more of the wildtype amino acids (or nucleotides encoding them), preferably at least 80% or more, preferably at least 90% or more, preferably at least 95% or more, and most preferably at least 99% or more of the wildtype amino acids (or nucleotides encoding them). Some trimming may be possible, and mutants are envisaged. Non-functional domains may be removed entirely. What is important is that the two parts may be brought together and that the desired nucleic acid modifying protein function is restored or reconstituted.

The dimer may be a homodimer or a heterodimer.

One or more, preferably two, NLSs may be used in operable linkage to the first nucleic acid modifying protein construct. One or more, preferably two, NESs may be used in operable linkage to the first nucleic acid modifying protein construct. The NLSs and/or the NESs preferably flank the split nucleic acid modifying protein-dimer (i.e., half dimer) fusion, i.e., one NLS may be positioned at the N' terminal of the first nucleic acid modifying protein construct and one NLS may be at the C' terminal of the first nucleic acid modifying protein construct. Similarly, one NES may be positioned at the N' terminal of the second nucleic acid modifying construct and one NES may be at the C' terminal of the second nucleic acid modifying protein construct. Where reference is made to N' or C' terminals, it will be appreciated that these correspond to 5' ad 3' ends in the corresponding nucleotide sequence.

A preferred arrangement is that the first nucleic acid modifying protein construct is arranged 5'-NLS-(N' terminal nucleic acid modifying protein part)-linker-(first half of the dimer)-NLS-3'. A preferred arrangement is that the second nucleic acid modifying protein construct is arranged 5'-NES-(second half of the dimer)-linker-(C' terminal nucleic acid modifying protein part)-NES-3'. A suitable promoter is preferably upstream of each of these constructs. The two constructs may be delivered separately or together.

In some embodiments, one or all of the NES(s) in operable linkage to the second nucleic acid modifying protein construct may be swapped out for an NLS. However, this may be typically not preferred and, in other embodiments, the localization signal in operable linkage to the second nucleic acid modifying protein construct is one or more NES(s).

It will also be appreciated that the NES may be operably linked to the N' terminal fragment of the split nucleic acid modifying protein and that the NLS may be operably linked to the C' terminal fragment of the split nucleic acid modifying protein. However, the arrangement where the NLS is operably linked to the N' terminal fragment of the split nucleic acid modifying protein and that the NES is operably linked to the C' terminal fragment of the split nucleic acid modifying protein may be preferred.

The NES functions to localize the second nucleic acid modifying protein fusion construct outside of the nucleus, at least until the inducer energy source is provided (e.g., at least until an energy source is provided to the inducer to perform its function). The presence of the inducer stimulates dimerization of the two nucleic acid modifying protein fusions within the cytoplasm and makes it thermodynamically worthwhile for the dimerized, first and second, nucleic acid modifying protein fusions to localize to the nucleus. Without being bound by theory, Applicants believe that the NES sequesters the second nucleic acid modifying protein fusion to the cytoplasm (i.e., outside of the nucleus). The NLS on the first nucleic acid modifying protein fusion localizes it to the nucleus. In both cases, Applicants use the NES or NLS to shift an equilibrium (the equilibrium of nuclear transport) to a desired direction. The dimerization typically occurs outside of the nucleus (a very small fraction might happen in the nucleus) and the NLSs on the dimerized complex shift the equilibrium of nuclear transport to nuclear localization, so the dimerized and hence reconstituted nucleic acid modifying protein enters the nucleus.

Beneficially, Applicants are able to reconstitute function in the split nucleic acid modifying protein. Transient transfection is used to prove the concept and dimerization occurs in the background in the presence of the inducer energy source. No activity is seen with separate fragments of the nucleic acid modifying protein. Stable expression through lentiviral delivery is then used to develop this and show that a split nucleic acid modifying protein approach can be used.

This present split nucleic acid modifying protein approach is beneficial as it allows the nucleic acid modifying protein activity to be inducible, thus allowing for temporal control. Furthermore, different localization sequences may be used (i.e., the NES and NLS as preferred) to reduce background activity from auto-assembled complexes. Tissue specific promoters, for example one for each of the first and second nucleic acid modifying protein fusion constructs, may also be used for tissue-specific targeting, thus providing spatial control. Two different tissue specific promoters may be used to exert a finer degree of control if required. The same approach may be used in respect of stage-specific promoters or there may a mixture of stage and tissue specific promoters, where one of the first and second nucleic acid modifying protein fusion constructs is under the control of (i.e. operably linked to or comprises) a tissue-specific promoter, whilst the other of the first and second nucleic acid modifying protein fusion constructs is under the control of (i.e. operably linked to or comprises) a stage-specific promoter.

The inducible nucleic acid modifying protein nucleic acid modifying system comprises one or more nuclear localization sequences (NLSs), as described herein, for example as operably linked to the first nucleic acid modifying protein fusion construct. These nuclear localization sequences are ideally of sufficient strength to drive accumulation of said first nucleic acid modifying protein fusion construct in a detectable amount in the nucleus of a eukaryotic cell. Without wishing to be bound by theory, it is believed that a nuclear localization sequence is not necessary for nucleic acid modifying complex activity in eukaryotes, but that including such sequences enhances activity of the system, especially as to targeting nucleic acid molecules in the nucleus, and assists with the operation of the present 2-part system.

Equally, the second nucleic acid modifying protein fusion construct is operably linked to a nuclear export sequence (NES). Indeed, it may be linked to one or more nuclear export sequences. In other words, the number of export sequences used with the second nucleic acid modifying protein fusion construct is preferably 1 or 2 or 3. Typically 2 is preferred, but 1 is enough and so is preferred in some embodiments. Suitable examples of NLS and NES are known in the art. For example, a preferred nuclear export signal (NES) is human protein tyrosin kinase 2. Preferred signals will be species specific.

Where the FRB and FKBP system are used, the FKBP is preferably flanked by nuclear localization sequences (NLSs). Where the FRB and FKBP system are used, the preferred arrangement is N' terminal nucleic acid modifying protein—FRB-NES. C' terminal nucleic acid modifying protein-FKBP-NLS. Thus, the first nucleic acid modifying protein fusion construct would comprise the C' terminal nucleic acid modifying protein part and the second DNA modifying protein fusion construct would comprise the N' terminal nucleic acid modifying protein part.

Another beneficial aspect to the present invention is that it may be turned on quickly, i.e. that is has a rapid response. It is believed, without being bound by theory, that nucleic acid modifying protein activity can be induced through dimerization of existing (already present) fusion constructs (through contact with the inducer energy source) more rapidly than through the expression (especially translation) of new fusion constructs. As such, the first and second nucleic acid modifying protein fusion constructs may be expressed in the target cell ahead of time, i.e. before nucleic acid modifying protein activity is required. nucleic acid modifying protein activity can then be temporally controlled and then quickly constituted through addition of the inducer energy source, which ideally acts more quickly (to dimerize the heterodimer and thereby provide nucleic acid modifying protein activity) than through expression (including induction of transcription) of nucleic acid modifying protein delivered by a vector, for example.

Applicants demonstrate that nucleic acid modifying protein can be split into two components, which reconstitute a functional nuclease when brought back together. Employing rapamycin sensitive dimerization domains, Applicants generate a chemically inducible nucleic acid modifying protein for temporal control of nucleic acid modifying protein-mediated genome editing and transcription modulation. Put another way, Applicants demonstrate that nucleic acid modifying protein can be rendered chemically inducible by being split into two fragments and that rapamycin-sensitive dimerization domains may be used for controlled reassembly of the nucleic acid modifying protein. Applicants show that the re-assembled nucleic acid modifying protein may be used to mediate genome editing (through nuclease/nickase activity) as well as transcription modulation (as a DNA-binding domain, the so-called "dead nucleic acid modifying protein").

As such, the use of rapamycin-sensitive dimerization domains is preferred. Reassembly of the nucleic acid modifying protein is preferred. Reassembly can be determined by restoration of binding activity. Where the nucleic acid modifying protein is a nickase or induces a double-strand break, suitable comparison percentages compared to a wildtype are described herein.

Rapamycin treatments can last 12 days. The dose can be 200 nM. This temporal and/or molar dosage is an example of an appropriate dose for Human embryonic kidney 293FT (HEK293FT) cell lines and this may also be used in other cell lines. This figure can be extrapolated out for therapeutic use in vivo into, for example, mg/kg. However, it is also envisaged that the standard dosage for administering rapamycin to a subject is used here as well. By the "standard dosage", it is meant the dosage under rapamycin's normal therapeutic use or primary indication (i.e. the dose used when rapamycin is administered for use to prevent organ rejection).

It is noteworthy that the preferred arrangement of nucleic acid modifying protein-FRB/FKBP pieces are separate and inactive until rapamycin-induced dimerization of FRB and FKBP results in reassembly of a functional full-length nucleic acid modifying protein nuclease. Thus, it is preferred that first nucleic acid modifying protein fusion construct attached to a first half of an inducible heterodimer is delivered separately and/or is localized separately from the second nucleic acid modifying protein fusion construct attached to a first half of an inducible heterodimer.

To sequester the nucleic acid modifying protein (N)-FRB fragment in the cytoplasm, where it is less likely to dimerize with the nuclear-localized nucleic acid modifying protein-(C)-FKBP fragment, it is preferable to use on nucleic acid modifying protein (N)-FRB a single nuclear export sequence (NES) from the human protein tyrosine kinase 2 (nucleic acid modifying protein (N)-FRB-NES). In the presence of rapamycin, nucleic acid modifying protein (N)-FRB-NES dimerizes with nucleic acid modifying protein (C)-FKBP-2xNLS to reconstitute a complete nucleic acid modifying protein, which shifts the balance of nuclear trafficking toward nuclear import and allows DNA targeting.

With respect to general information on nucleic acid modifying systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGR-NAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., "Crystal Structure of *Staphylococcus aureus* Cas9," Cell 162, 1113-1126 (Aug. 27, 2015)

Zetsche et al. (2015), "Cpf1 is a single RNA-guided endonuclease of a class 2 CRISPR-Cas system," Cell 163, 759-771 (Oct. 22, 2015) doi: 10.1016/j.cell.2015.09.038. Epub Sep. 25, 2015

Shmakov et al. (2015), "Discovery and Functional Characterization of Diverse Class 2 CRISPR-Cas Systems," Molecular Cell 60, 385-397 (Nov. 5, 2015) doi: 10.1016/j.molcel.2015.10.008. Epub Oct. 22, 2015

Dahlman et al., "Orthogonal gene control with a catalytically active Cas9 nuclease," Nature Biotechnology 33, 1159-1161 (November, 2015)

Gao et al, "Engineered Cpf1 Enzymes with Altered PAM Specificities," bioRxiv 091611; doi: http://dx.doi.org/10.1101/091611 Epub Dec. 4, 2016

Smargon et al. (2017), "Cas13b Is a Type VI-B CRISPR-Associated RNA-Guided RNase Differentially Regulated by Accessory Proteins Csx27 and Csx28," Molecular Cell 65, 618-630 (Feb. 16, 2017) doi: 10.1016/j.molcel.2016.12.023. Epub Jan. 5, 2017 each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry.

The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Gao et al. (2016) reported using a structure-guided saturation mutagenesis screen to increase the targeting range of Cpf1. AsCpf1 variants were engineered with the mutations S542R/K607R and S542R/K548V/N552R that can cleave target sites with TYCV/CCCC and TATV PAMs, respectively, with enhanced activities in vitro and in human cells.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, and of PCT application PCT/US14/70127, entitled "DELIVERY, USE AND THERAPEUTIC APPLICATIONS OF THE CRISPR-CAS SYSTEMS AND COMPOSITIONS FOR GENOME EDITING "(claiming priority from one or more or all of US provisional patent applications: 61/915,176; 61/915,192; 61/915,215; 61/915,107; 61/915,145; 61/915,148; and 61/915,153 each filed Dec. 12, 2013) ("the Eye PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30C, e.g., 20-25C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle, as well as particles from such admixing. Aspects of the instant invention can involve particles; for example, particles using a process analogous to that of the Particle Delivery PCT or that of the Eye PCT, e.g., by admixing a mixture comprising sgRNA and/or Cas9 as in the instant invention and components that form a particle, e.g., as in the Particle Delivery PCT or in the Eye PCT, to form a particle and particles from such admixing (or, of course, other particles involving sgRNA and/or Cas9 as in the instant invention).

The subject invention may be used as part of a research program wherein there is transmission of results or data. A computer system (or digital device) may be used to receive, transmit, display and/or store results, analyze the data and/or results, and/or produce a report of the results and/or data and/or analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers). In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users. A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution. Accordingly, the invention comprehends performing any method herein-discussed and storing and/or transmitting data and/or results therefrom and/or analysis thereof, as well as products from performing any method herein-discussed, including intermediates.

Target Sequences

Throughout this disclosure there has been mention of nucleic acid modifying protein or nucleic acid modifying complexes or systems. Nucleic acid modifying systems or complexes can target nucleic acid molecules, e.g., nucleic acid modifying complexes can target and cleave or nick or simply sit upon a target DNA molecule (depending if the nucleic acid modifying protein has mutations that render it a nickase or "dead"). Such systems or complexes are amenable for achieving tissue-specific and temporally controlled targeted deletion of candidate disease genes. Examples include but are not limited to genes involved in cholesterol and fatty acid metabolism, amyloid diseases, dominant negative diseases, latent viral infections, among other disorders. Accordingly, target sequences for such systems or complexes can be in candidate disease genes, e.g.:

| Disease | GENE | SPACER | PAM | Mechanism | References |
|---|---|---|---|---|---|
| Hypercholesterolemia | HMG-CR | GCCAAATT GGACGACC CTCG (SEQ ID NO: 6) | CGG | Knockout | Fluvastatin: a review of its pharmacology and use in the management of hypercholesterolaemia. (Plosker GL et al. Drugs 1996, 51(3): 433-459) |
| Hypercholesterolemia | SQLE | CGAGGAGA CCCCGTTT CGG (SEQ ID NO: 7) | TGG | Knockout | Potential role of nonstatin cholesterol lowering agents (Trapani et al. IUBMB Life, Volume 63, Issue 11, pages 964-971, November 2011) |
| Hyperlipidemia | DGAT1 | CCCGCCGCC GCCGTGGCT CG (SEQ ID NO: 8) | AGG | Knockout | DGAT1 inhibitors as anti-obesity and anti-diabetic agents. (Birch AM et al. Current Opinion in Drug Discovery & Development [2010, 13(4): 489-496) |
| Leukemia | BCR-ABL | TGAGCTCTA CGAGATCC ACA SEQ ID NO: 9) | AGG | Knockout | Killing of leukemic cells with a BCR/ABL fusion gene by RNA interference (RNAi). (Fuchs et al. Oncogene 2002, 21(37): 5716-5724) |

Thus, the present invention, with regard to nucleic acid modifying protein or nucleic acid modifying complexes contemplates correction of hematopoietic disorders. For example, Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-109). In the case of Adenosine Deaminase (ADA) deficiency, one of the SCID forms, patients can be treated by injection of recombinant Adenosine Deaminase enzyme. Since the ADA gene has been shown to be mutated in SCID patients (Giblett et al., Lancet, 1972, 2, 1067-1069), several other genes involved in SCID have been identified (Cavazzana-Calvo et al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., Annu. Rev. Med., 2005, 56, 585-602; Fischer et al., Immunol. Rev., 2005, 203, 98-109). In aspect of the invention, relating to CRISPR or CRISPR-Cas complexes contemplates system, the invention contemplates that it may be used to correct ocular defects that arise from several genetic mutations further described in Genetic Diseases of the Eye, Second Edition, edited by Elias I. Traboulsi, Oxford University Press, 2012. Non-limiting examples of ocular defects to be corrected include macular degeneration (MD), retinitis pigmentosa (RP). Non-limiting examples of genes and proteins associated with ocular defects include but are not limited to the following proteins: (ABCA4) ATP-binding cassette, sub-family A (ABC1), member 4 ACHM1 achromatopsia (rod monochromacy) 1 ApoE Apolipoprotein E (ApoE) C1QTNF5 (CTRP5) C1q and tumor necrosis factor related protein 5 (C1QTNF5) C2 Complement component 2 (C2) C3 Complement components (C3) CCL2 Chemokine (C-C motif) Ligand 2 (CCL2) CCR2 Chemokine (C-C motif) receptor 2 (CCR2) CD36 Cluster of Differentiation 36 CFB Complement factor B CFH Complement factor CFH H CFHR1 complement factor H-related 1 CFHR3 complement factor H-related 3 CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair cross-complementing rodent repair deficiency, complementation group 6 FBLN5 Fibulin-5 FBLN5 Fibulin 5 FBLN6 Fibulin 6 FSCN2 fascin (FSCN2) HMCN1 Hemicentrin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domain-containing family A member 1 (PLEKHA1) PROM1 Prominin 1 (PROM1 or CD133) PRPH2 Peripherin-2 RPGR retinitis pigmentosa GTPase regulator SERPINGI serpin peptidase inhibitor, clade G, member 1 (C1-inhibitor) TCOF1 Treacle TIMP3 Metalloproteinase inhibitor 3 (TIMP3) TLR3 Toll-like receptor 3 The present invention, with regard to CRISPR or CRISPR-Cas complexes contemplates also contemplates delivering to the heart. For the heart, a myocardium tropic adeno-associated virus (AAVM) is preferred, in particular AAVM41 which showed preferential gene transfer in the heart (see, e.g., Lin-Yanga et al., PNAS, Mar. 10, 2009, vol. 106, no. 10). For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. By way of example, the chromosomal sequence may comprise, but is not limited to, IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), CTSK (cathepsin K), PTGIR (prostaglandin 12 (prostacyclin) receptor (IP)), KCNJ11 (potassium inwardly-rectifying channel, subfamily J, member 11), INS (insulin), CRP (C-reactive protein, pentraxin-related), PDGFRB (platelet-derived growth factor receptor, beta polypeptide), CCNA2 (cyclin A2), PDGFB (platelet-derived growth factor beta polypeptide (simian sarcoma viral (v-sis) oncogene homolog)), KCNJ5 (potassium inwardly-rectifying channel, subfamily J, member 5), KCNN3 (potassium intermediate/small conductance calcium-activated channel, subfamily N, member 3), CAPN10 (calpain 10), PTGES (prostaglandin E synthase), ADRA2B (adrenergic, alpha-2B-, receptor), ABCG5 (ATP-binding cassette, sub-family G (WHITE), member 5), PRDX2 (peroxiredoxin 2), CAPN5 (calpain 5), PARP14 (poly (ADP-ribose) polymerase family, member 14), MEX3C (mex-3 homolog C (C. elegans)), ACE angiotensin I converting enzyme (peptidyl-dipeptidase A) 1), TNF (tumor necrosis factor (TNF superfamily, member 2)), IL6 (interleukin 6 (interferon, beta 2)), STN (statin), SERPINE1 (serpin peptidase inhibitor, clade E (nexin, plasminogen activator inhibitor type 1), member 1), ALB (albumin), ADIPOQ (adiponectin, C1Q and collagen domain containing), APOB (apolipoprotein B (including Ag(x) antigen)), APOE (apolipoprotein E), LEP (leptin), MTHFR (5,10-methylenetetrahydrofolate reductase (NADPH)), APOA1 (apolipoprotein A-I), EDN1 (endothelin 1), NPPB (natriuretic peptide precursor B), NOS3 (nitric oxide synthase 3 (endothelial cell)), PPARG (peroxisome proliferator-activated receptor gamma), PLAT (plasminogen activator, tissue), PTGS2 (prostaglandin-endoperoxide synthase 2 (prostaglandin G/H synthase and cyclooxygenase)), CETP (cholesteryl ester transfer protein, plasma), AGTR1 (angiotensin II receptor, type 1), HMGCR (3-hydroxy-3-methylglutaryl-Coenzyme A reductase), IGF1 (insulin-like growth factor 1 (somatomedin C)), SELE (selectin E), REN (renin), PPARA (peroxisome proliferator-activated receptor alpha), PON1 (paraoxonase 1), KNG1 (kininogen 1), CCL2 (chemokine (C-C motif) ligand 2), LPL (lipoprotein lipase), VWF (von Willebrand factor), F2 (coagulation factor II (thrombin)), ICAM1 (intercellular adhesion molecule 1), TGFB1 (transforming growth factor, beta 1), NPPA (natriuretic peptide precursor A), IL10 (interleukin 10), EPO (erythropoietin), SOD1 (superoxide dismutase 1, soluble), VCAM1 (vascular cell adhesion molecule 1), IFNG (interferon, gamma), LPA (lipoprotein, Lp(a)), MPO (myeloperoxidase), ESR1 (estrogen receptor 1), MAPK1 (mitogen-activated protein kinase 1), HP (haptoglobin), F3 (coagulation factor III (thromboplastin, tissue factor)), CST3 (cystatin C), COG2 (component of oligomeric golgi complex 2), MMP9 (matrix metallopeptidase 9 (gelatinase B, 92 kDa gelatinase, 92 kDa type IV collagenase)), SERPINC1 (serpin peptidase inhibitor, clade C (antithrombin), member 1), F8 (coagulation factor VIII, procoagulant component), HMOX1 (heme oxygenase (decycling) 1), APOC3 (apolipoprotein C-III), IL8 (interleukin 8), PROK1 (prokineticin 1), CBS (cystathionine-beta-synthase), NOS2 (nitric oxide synthase 2, inducible), TLR4 (toll-like receptor 4), SELP (selectin P (granule membrane protein 140 kDa, antigen CD62)), ABCA1 (ATP-binding cassette, sub-family A (ABC1), member 1), AGT (angiotensinogen (serpin peptidase inhibitor, clade A, member 8)), LDLR (low density lipoprotein receptor), GPT (glutamic-pyruvate transaminase (alanine aminotransferase)), VEGFA (vascular endothelial growth factor A), NR3C2 (nuclear receptor subfamily 3, group C, member 2), IL18 (interleukin 18 (interferon-gamma-inducing factor)), NOS1 (nitric oxide synthase 1 (neuronal)), NR3C1 (nuclear receptor subfamily 3, group C, member 1 (glucocorticoid receptor)), FGB (fibrinogen beta chain), HGF (hepatocyte growth factor (hepapoietin A; scatter factor)), IL1A (interleukin 1, alpha), RETN (resistin), AKT1 (v-akt murine thymoma viral oncogene homolog 1), LIPC (lipase, hepatic), HSPD1 (heat shock 60 kDa protein 1 (chaperonin)), MAPK14 (mitogen-activated protein kinase 14), SPP1 (secreted phosphoprotein 1), ITGB3 (integrin, beta 3 (platelet glycoprotein 111a, antigen CD61)), CAT (catalase), UTS2 (urotensin 2), THBD (thrombomodulin), F10 (coagulation factor X), CP (ceruloplasmin (ferroxidase)), TNFRSF11B (tumor necrosis factor receptor superfamily, member 11b), EDNRA (endothelin receptor type A), EGFR (epidermal growth factor receptor (erythroblastic leukemia viral (v-erb-b) oncogene homolog, avian)), MMP2 (matrix metallopeptidase 2 (gelatinase A, 72 kDa gelatinase, 72 kDa type IV collagenase)), PLG (plasminogen), NPY (neuropeptide Y), RHOD (ras homolog gene family, member D), MAPK8 (mitogen-activated protein kinase 8), MYC (v-myc myelocytomatosis viral oncogene homolog (avian)), FN1 (fibronectin 1), CMA1 (chymase 1, mast cell), PLAU (plasminogen activator, urokinase), GNB3 (guanine nucleotide binding protein (G protein), beta polypeptide 3), ADRB2 (adrenergic, beta-2-, receptor, surface), APOA5 (apolipoprotein A-V), SOD2 (superoxide dismutase 2, mitochondrial), F5 (coagulation factor V (proaccelerin, labile factor)), VDR (vitamin D (1,25-dihydroxyvitamin D3) receptor), ALOX5 (arachidonate 5-lipoxygenase), HLA-DRB1 (major histocompatibility complex, class II, DR beta 1), PARP1 (poly (ADP-ribose) polymerase 1), CD40LG (CD40 ligand), PON2 (paraoxonase 2), AGER (advanced glycosylation end product-specific receptor), IRS1 (insulin receptor substrate 1), PTGS1 (prostaglandin-endoperoxide synthase 1 (prostaglandin G/H synthase and cyclooxygenase)), ECE1 (endothelin converting enzyme 1), F7 (coagulation factor VII (serum prothrombin conversion accelerator)), URN (interleukin 1 receptor antagonist), EPHX2 (epoxide hydrolase 2, cytoplasmic), IGFBP1 (insulin-like growth factor binding protein 1), MAPK10 (mitogen-activated protein kinase 10), FAS (Fas (TNF receptor superfamily, member 6)), ABCB1 (ATP-binding cassette, sub-family B (MDR/TAP), member 1), JUN (jun oncogene), IGFBP3 (insulin-like growth factor binding protein 3), CD14 (CD14 molecule), PDE5A (phosphodiesterase 5A, cGMP-specific), AGTR2 (angiotensin II receptor, type 2), CD40 (CD40 molecule, TNF receptor superfamily member 5), LCAT (lecithin-cholesterol acyltransferase), CCR5 (chemokine (C-C motif) receptor 5), MMP1 (matrix metallopeptidase 1 (interstitial collagenase)), TIMP1 (TIMP metallopeptidase inhibitor 1), ADM (adrenomedullin), DYT10 (dystonia 10), STAT3 (signal transducer and activator of transcription 3 (acute-phase response factor)), MMP3 (matrix metallopeptidase 3 (stromelysin 1, progelatinase)), ELN (elastin), USF1 (upstream transcription factor 1), CFH (complement factor H), HSPA4 (heat shock 70 kDa protein 4), MMP12 (matrix metallopeptidase 12 (macrophage elastase)), MME (membrane metallo-endopeptidase), F2R (coagulation factor II (thrombin) receptor), SELL (selectin L), CTSB (cathepsin B), ANXA5 (annexin A5), ADRB1 (adrenergic, beta-1-, receptor), CYBA (cytochrome b-245, alpha polypeptide), FGA (fibrinogen alpha chain), GGT1 (gamma-glutamyltransferase 1), LIPG (lipase, endothelial), HIF1A (hypoxia inducible factor 1, alpha subunit (basic helix-loop-helix transcription factor)), CXCR4 (chemokine (C-X-C motif) receptor 4), PROC (protein C (inactivator of coagulation factors Va and VIIIa)), SCARB1 (scavenger receptor class B, member 1), CD79A (CD79a molecule, immunoglobulin-associated alpha), PLTP (phospholipid transfer protein), ADD1 (adducin 1 (alpha)), FGG (fibrinogen gamma chain), SAA1 (serum amyloid A1), KCNH2 (potassium voltage-gated channel, subfamily H (eag-related), member 2), DPP4 (dipeptidyl-peptidase 4), G6PD (glucose-6-phosphate dehydrogenase), NPR1 (natriuretic peptide receptor A/guanylate cyclase A (atrionatriuretic peptide receptor A)), VTN (vitronectin), KIAA0101 (KIAA0101), FOS (FBJ murine osteosarcoma viral oncogene homolog), TLR2 (toll-like receptor 2), PPIG (peptidylprolyl isomerase G (cyclophilin G)), IL1R1 (interleukin 1 receptor, type I), AR (androgen receptor), CYP1A1 (cytochrome P450, family 1, subfamily A, polypeptide 1), SERPINAl (serpin peptidase inhibitor, clade A (alpha-1 antiproteinase, antitrypsin), member 1), MTR (5-methyltetrahydrofolate-homocysteine methyltransferase), RBP4 (retinol binding protein 4, plasma), APOA4 (apolipoprotein A-IV), CDKN2A (cyclin-dependent kinase inhibitor 2A (melanoma, p16, inhibits CDK4)), FGF2 (fibroblast growth factor 2 (basic)), EDNRB (endothelin receptor type B), ITGA2 (integrin, alpha 2 (CD49B, alpha 2 subunit of VLA-2 receptor)), CABINI (calcineurin binding protein 1), SHBG (sex hormone-binding globulin), HMGB1 (high-mobility group box 1), HSP90B2P (heat shock protein 90 kDa beta (Grp94), member 2 (pseudogene)), CYP3A4 (cytochrome P450, family 3, subfamily A, polypeptide 4), GJA1 (gap junction protein, alpha 1, 43 kDa), CAV1 (caveolin 1, caveolae protein, 22 kDa), ESR2 (estrogen receptor 2 (ER beta)), LTA (lymphotoxin alpha (TNF superfamily, member 1)), GDF15 (growth differentiation factor 15), BDNF (brain-derived neurotrophic factor), CYP2D6 (cytochrome P450, family 2, subfamily D, polypeptide 6), NGF (nerve growth factor (beta polypeptide)), SP1 (Sp1 transcription factor), TGIF1 (TGFB-induced factor homeobox 1), SRC (v-src sarcoma (Schmidt-Ruppin A-2) viral oncogene homolog (avian)), EGF (epidermal growth factor (beta-urogastrone)), PIK3CG (phosphoinositide-3-kinase, catalytic, gamma polypeptide), HLA-A (major histocompatibility complex, class I, A), KCNQ1 (potassium voltage-gated channel, KQT-like subfamily, member 1), CNR1 (cannabinoid receptor 1 (brain)), FBN1 (fibrillin 1), CHKA (choline kinase alpha), BEST1 (bestrophin 1), APP (amyloid beta (A4) precursor protein), CTNNB1 (catenin (cadherin-associated protein), beta 1, 88 kDa), IL2 (interleukin 2), CD36 (CD36 molecule (thrombospondin receptor)), PRKAB1 (protein kinase, AMP-activated, beta 1 non-catalytic subunit), TPO (thyroid peroxidase), ALDH7A1 (aldehyde dehydrogenase 7 family, member A1), CX3CR1 (chemokine (C-X3-C motif) receptor 1), TH (tyrosine hydroxylase), F9 (coagulation factor IX), GH1 (growth hormone 1), TF (transferrin), HFE (hemochromatosis), IL17A (interleukin 17A), PTEN (phosphatase and tensin homolog), GSTM1 (glutathione S-transferase mu 1), DMD (dystrophin), GATA4 (GATA binding protein 4), F13A1 (coagulation factor XIII, A1 polypeptide), TTR (transthyretin), FABP4 (fatty acid binding protein 4, adipocyte), PON3 (paraoxonase 3), APOC1 (apolipoprotein C-I), INSR (insulin receptor), TNFRSF1B (tumor necrosis factor receptor superfamily, member 1), HTR2A (5-hydroxytryptamine (serotonin) receptor 2A), CSF3 (colony stimulating factor 3 (granulocyte)), CYP2C9 (cytochrome P450, family 2, subfamily C, polypeptide 9), TXN (thioredoxin), CYP11B2 (cytochrome P450, family 11, subfamily B, polypeptide 2), PTH (parathyroid hormone), CSF2 (colony stimulating factor 2 (granulocyte-macrophage)), KDR (kinase insert domain receptor (a type III receptor tyrosine kinase)), PLA2G2A (phospholipase A2, group IIA (platelets, synovial fluid)), B2M (beta-2-microglobulin), THBS1 (thrombospondin 1), GCG (glucagon), RHOA (ras homolog gene family, member A), ALDH2 (aldehyde dehydrogenase 2 family (mitochondrial)), TCF7L2 (transcription factor 7-like 2 (T-cell specific, HMG-box)), BDKRB2 (bradykinin receptor B2), NFE2L2 (nuclear factor (erythroid-derived 2)-like 2), NOTCHI (Notch homolog 1, translocation-associated (*Drosophila*)), UGT1A1 (UDP glucuronosyltransferase 1 family, polypeptide A1), IFNA1 (interferon, alpha 1), PPARD (peroxisome proliferator-activated receptor delta), SIRT1 (sirtuin (silent mating type information regulation 2 homolog) 1 (*S. cerevisiae*)), GNRH1 (gonadotropin-releasing hormone 1 (luteinizing-releasing hormone)), PAPPA (pregnancy-associated plasma protein A, pappalysin 1), ARR3 (arrestin 3, retinal (X-arrestin)), NPPC (natriuretic peptide precursor C), AHSP (alpha hemoglobin stabilizing protein), PTK2 (PTK2 protein tyrosine kinase 2), IL13 (interleukin 13), MTOR (mechanistic target of rapamycin (serine/threonine kinase)), ITGB2 (integrin, beta 2 (complement component 3 receptor 3 and 4 subunit)), GSTT1 (glutathione S-transferase theta 1), IL6ST (interleukin 6 signal transducer (gp130, oncostatin M receptor)), CPB2 (carboxypeptidase B2 (plasma)), CYP1A2 (cytochrome P450, family 1, subfamily A, polypeptide 2), HNF4A (hepatocyte nuclear factor 4, alpha), SLC6A4 (solute carrier family 6 (neurotransmitter transporter, serotonin), member 4), PLA2G6 (phospholipase A2, group VI (cytosolic, calcium-independent)), TNFSF11 (tumor necrosis factor (ligand) superfamily, member 11), SLC8A1 (solute carrier family 8 (sodium/calcium exchanger), member 1), F2RL1 (coagulation factor II (thrombin) receptor-like 1), AKR1A1 (aldo-keto reductase family 1, member A1 (aldehyde reductase)), ALDH9A1 (aldehyde dehydrogenase 9 family, member A1), BGLAP (bone gamma-carboxyglutamate (gla) protein), MTTP (microsomal triglyceride transfer protein), MTRR (5-methyltetrahydrofolate-homocysteine methyltransferase reductase), SULT1A3 (sulfotransferase family, cytosolic, 1A, phenol-preferring, member 3), RAGE (renal tumor antigen), C4B (complement component 4B (Chido blood group), P2RY12 (purinergic receptor P2Y, G-protein coupled, 12), RNLS (renalase, FAD-dependent amine oxidase), CREB1 (cAMP responsive element binding protein 1), POMC (proopiomelanocortin), RAC1 (ras-related C3 botulinum toxin substrate 1 (rho family, small GTP binding protein Rac1)), LMNA (lamin NC), CD59 (CD59 molecule, complement regulatory protein), SCN5A (sodium channel, voltage-gated, type V, alpha subunit), CYP1B1 (cytochrome P450, family 1, subfamily B, polypeptide 1), MIF (macrophage migration inhibitory factor (glycosylation-inhibiting factor)), MMP13 (matrix metallopeptidase 13 (collagenase 3)), TIMP2 (TIMP metallopeptidase inhibitor 2), CYP19A1 (cytochrome P450, family 19, subfamily A, polypeptide 1), CYP21A2 (cytochrome P450, family 21, subfamily A, polypeptide 2), PTPN22 (protein tyrosine phosphatase, non-receptor type 22 (lymphoid)), MYH14 (myosin, heavy chain 14, non-muscle), MBL2 (mannose-binding lectin (protein C) 2, soluble (opsonic defect)), SELPLG (selectin P ligand), AOC3 (amine oxidase, copper containing 3 (vascular adhesion protein 1)), CTSL1 (cathepsin L1), PCNA (proliferating cell nuclear antigen), IGF2 (insulin-like growth factor 2 (somatomedin A)), ITGB1 (integrin, beta 1 (fibronectin receptor, beta polypeptide, antigen CD29 includes MDF2, MSK12)), CAST (calpastatin), CXCL12 (chemokine (C-X-C motif) ligand 12 (stromal cell-derived factor 1)), IGHE (immunoglobulin heavy constant epsilon), KCNE1 (potassium voltage-gated channel, Isk-related family, member 1), TFRC (transferrin receptor (p90, CD71)), COL1A1 (collagen, type I, alpha 1), COL1A2 (collagen, type I, alpha 2), IL2RB (interleukin 2 receptor, beta), PLA2G10 (phospholipase A2, group X), ANGPT2 (angiopoietin 2), PROCR (protein C receptor, endothelial (EPCR)), NOX4 (NADPH oxidase 4), HAMP (hepcidin antimicrobial peptide), PTPN11 (protein tyrosine phosphatase, non-receptor type 11), SLC2A1 (solute carrier family 2 (facilitated glucose transporter), member 1), IL2RA (interleukin 2 receptor, alpha), CCL5 (chemokine (C-C motif) ligand 5), IRF1 (interferon regulatory factor 1), CFLAR (CASP8 and FADD-like apoptosis regulator), CALCA (calcitonin-related polypeptide alpha), EIF4E (eukaryotic translation initiation factor 4E), GSTP1 (glutathione S-transferase pi 1), JAK2 (Janus kinase 2), CYP3A5 (cytochrome P450, family 3, subfamily A, polypeptide 5), HSPG2 (heparan sulfate proteoglycan 2), CCL3 (chemokine (C-C motif) ligand 3), MYD88 (myeloid differentiation primary response gene (88)), VIP (vasoactive intestinal peptide), SOAT1 (sterol O-acyltransferase 1), ADRBK1 (adrenergic, beta, receptor kinase 1), NR4A2 (nuclear receptor subfamily 4, group A, member 2), MMP8 (matrix metallopeptidase 8 (neutrophil collagenase)), NPR2 (natriuretic peptide receptor B/guanylate cyclase B (atrionatriuretic peptide receptor B)), GCH1 (GTP cyclohydrolase 1), EPRS (glutamyl-prolyl-tRNA synthetase), PPARGC1A (peroxisome proliferator-activated receptor gamma, coactivator 1 alpha), F12 (coagulation factor XII (Hageman factor)), PECAM1 (platelet/endothelial cell adhesion molecule), CCL4 (chemokine (C-C motif) ligand 4), SERPINA3 (serpin peptidase inhibitor, clade A (alpha-1 antiproteinase, antitrypsin), member 3), CASR (calcium-sensing receptor), GJA5 (gap junction protein, alpha 5, 40 kDa), FABP2 (fatty acid binding protein 2, intestinal), TTF2 (transcription termination factor, RNA polymerase II), PROS1 (protein S (alpha)), CTF1 (cardiotrophin 1), SGCB (sarcoglycan, beta (43 kDa dystrophin-associated glycoprotein)), YMIE1L1 (YME1-like 1 (*S. cerevisiae*)), CAMP (cathelicidin antimicrobial peptide), ZC3H12A (zinc finger CCCH-type containing 12A), AKR1B1 (aldo-keto reductase family 1, member B1 (aldose reductase)), DES (desmin), MMP7 (matrix metallopeptidase 7 (matrilysin, uterine)), AHR (aryl hydrocarbon receptor), CSF1 (colony stimulating factor 1 (macrophage)), HDAC9 (histone deacetylase 9), CTGF (connective tissue growth factor), KCNMA1 (potassium large conductance calcium-activated channel, subfamily M, alpha member 1), UGT1A (UDP glucuronosyltransferase 1 family, polypeptide A complex locus), PRKCA (protein kinase C, alpha), COMT (catechol-.beta.-methyltransferase), S100B (S100 calcium binding protein B), EGR1 (early growth response 1), PRL (prolactin), IL15 (interleukin 15), DRD4 (dopamine receptor D4), CAMK2G (calcium/calmodulin-dependent protein kinase II gamma), SLC22A2 (solute carrier family 22 (organic cation transporter), member 2), CCL11 (chemokine (C-C motif) ligand 11), PGF (B321 placental growth factor), THPO (thrombopoietin), GP6 (glycoprotein VI (platelet)), TACR1 (tachykinin receptor 1), NTS (neurotensin), HNF1A (HNF1 homeobox A), SST (somatostatin), KCND1 (potassium voltage-gated channel, Shal-related subfamily, member 1), LOC646627 (phospholipase inhibitor), TBXAS1 (thromboxane A synthase 1 (platelet)), CYP2J2 (cytochrome P450, family 2, subfamily J, polypeptide 2), TBXA2R (thromboxane A2 receptor), ADH1C (alcohol dehydrogenase 1C (class I), gamma polypeptide), ALOX12 (arachidonate 12-lipoxygenase), AHSG (alpha-2-HS-glycoprotein), BHMT (betaine-homocysteine methyltransferase), GJA4 (gap junction protein, alpha 4, 37 kDa), SLC25A4 (solute carrier family 25 (mitochondrial carrier; adenine nucleotide translocator), member 4), ACLY (ATP citrate lyase), ALOX5AP (arachidonate 5-lipoxygenase-activating protein), NUMA1 (nuclear mitotic apparatus protein 1), CYP27B1 (cytochrome P450, family 27, subfamily B, polypeptide 1), CYSLTR2 (cysteinyl leukotriene receptor 2), SOD3 (superoxide dismutase 3, extracellular), LTC4S (leukotriene C4 synthase), UCN (urocortin), GHRL (ghrelin/obestatin prepropeptide), APOC2 (apolipoprotein C-II), CLEC4A (C-type lectin domain family 4, member A), KBTBD10 (kelch repeat and BTB (POZ) domain containing 10), TNC (tenascin C), TYMS (thymidylate synthetase), SHC1 (SHC (Src homology 2 domain containing) transforming protein 1), LRP1 (low density lipoprotein receptor-related protein 1), SOCS3 (suppressor of cytokine signaling 3), ADH1B (alcohol dehydrogenase 1B (class I), beta polypeptide), KLK3 (kallikrein-related peptidase 3), HSD11B1 (hydroxysteroid (11-beta) dehydrogenase 1), VKORC1 (vitamin K epoxide reductase complex, subunit 1), SERPINB2 (serpin peptidase inhibitor, clade B (ovalbumin), member 2), TNS1 (tensin 1), RNF19A (ring finger protein 19A), EPOR (erythropoietin receptor), ITGAM (integrin, alpha M (complement component 3 receptor 3 subunit)), PITX2 (paired-like homeodomain 2), MAPK7 (mitogen-activated protein kinase 7), FCGR3A (Fc fragment of IgG, low affinity 111a, receptor (CD16a)), LEPR (leptin receptor), ENG (endoglin), GPX1 (glutathione peroxidase 1), GOT2 (glutamic-oxaloacetic transaminase 2, mitochondrial (aspartate aminotransferase 2)), HIRH1 (histamine receptor H1), NR1I2 (nuclear receptor subfamily 1, group I, member 2), CRH (corticotropin releasing hormone), HTR1A (5-hydroxytryptamine (serotonin) receptor 1A), VDAC1 (voltage-dependent anion channel 1), HPSE (heparanase), SFTPD (surfactant protein D), TAP2 (transporter 2, ATP-binding cassette, sub-family B (MDR/TAP)), RNF123 (ring finger protein 123), PTK2B (PTK2B protein tyrosine kinase 2 beta), NTRK2 (neurotrophic tyrosine kinase, receptor, type 2), IL6R (interleukin 6 receptor), ACHE (acetylcholinesterase (Yt blood group)), GLP1R (glucagon-like peptide 1 receptor), GHR (growth hormone receptor), GSR (glutathione reductase), NQO1 (NAD(P)H dehydrogenase, quinone 1), NR5A1 (nuclear receptor subfamily 5, group A, member 1), GJB2 (gap junction protein, beta 2, 26 kDa), SLC9A1 (solute carrier family 9 (sodium/hydrogen exchanger), member 1), MAOA (monoamine oxidase A), PCSK9 (proprotein convertase subtilisin/kexin type 9), FCGR2A (Fc fragment of IgG, low affinity IIa, receptor (CD32)), SERPINF1 (serpin peptidase inhibitor, clade F (alpha-2 antiplasmin, pigment epithelium derived factor), member 1), EDN3 (endothelin 3), DIFR (dihydrofolate reductase), GAS6 (growth arrest-specific 6), SMPD1 (sphingomyelin phosphodiesterase 1, acid lysosomal), UCP2 (uncoupling protein 2 (mitochondrial, proton carrier)), TFAP2A (transcription factor AP-2 alpha (activating enhancer binding protein 2 alpha)), C4BPA (complement component 4 binding protein, alpha), SERPINF2 (serpin peptidase inhibitor, clade F (alpha-2 antiplasmin, pigment epithelium derived factor), member 2), TYMP (thymidine phosphorylase), ALPP (alkaline phosphatase, placental (Regan isozyme)), CXCR2 (chemokine (C-X-C motif) receptor 2), SLC39A3 (solute carrier family 39 (zinc transporter), member 3), ABCG2 (ATP-binding cassette, sub-family G (WHITE), member 2), ADA (adenosine deaminase), JAK3 (Janus kinase 3), HSPA1A (heat shock 70 kDa protein 1A), FASN (fatty acid synthase), FGF1 (fibroblast growth factor 1 (acidic)), F11 (coagulation factor XI), ATP7A (ATPase, Cu++ transporting, alpha polypeptide), CR1 (complement component (3b/4b) receptor 1 (Knops blood group)), GFAP (glial fibrillary acidic protein), ROCK1 (Rho-associated, coiled-coil containing protein kinase 1), MECP2 (methyl CpG binding protein 2 (Rett syndrome)), MYLK (myosin light chain kinase), BCHE (butyrylcholinesterase), LIPE (lipase, hormone-sensitive), PRDX5 (peroxiredoxin 5), ADORA1 (adenosine A1 receptor), WRN (Werner syndrome, RecQ helicase-like), CXCR3 (chemokine (C-X-C motif) receptor 3), CD81 (CD81 molecule), SMAD7 (SMAD family member 7), LAMC2 (laminin, gamma 2), MAP3K5 (mitogen-activated protein kinase kinase kinase 5), CHGA (chromogranin A (parathyroid secretory protein 1)), IAPP (islet amyloid polypeptide), RHO (rhodopsin), ENPP1 (ectonucleotide pyrophosphatase/phosphodiesterase 1), PTHLH (parathyroid hormone-like hormone), NRG1 (neuregulin 1), VEGFC (vascular endothelial growth factor C), ENPEP (glutamyl aminopeptidase (aminopeptidase A)), CEBPB (CCAAT/enhancer binding protein (C/EBP), beta), NAGLU (N-acetylglucosaminidase, alpha-), F2RL3 (coagulation factor II (thrombin) receptor-like 3), CX3CL1 (chemokine (C-X3-C motif) ligand 1), BDKRB1 (bradykinin receptor B1), ADAMTS13 (ADAM metallopeptidase with thrombospondin type 1 motif, 13), ELANE (elastase, neutrophil expressed), ENPP2 (ectonucleotide pyrophosphatase/phosphodiesterase 2), CISH (cytokine inducible SH2-containing protein), GAST (gastrin), MYOC (myocilin, trabecular meshwork inducible glucocorticoid response), ATP1A2 (ATPase, Na+/K+ transporting, alpha 2 polypeptide), NF1 (neurofibromin 1), GJB1 (gap junction protein, beta 1, 32 kDa), MEF2A (myocyte enhancer factor 2A), VCL (vinculin), BMPR2 (bone morphogenetic protein receptor, type II (serine/threonine kinase)), TUBB (tubulin, beta), CDC42 (cell division cycle 42 (GTP binding protein, 25 kDa)), KRT18 (keratin 18), HSF1 (heat shock transcription factor 1), MYB (v-myb myeloblastosis viral oncogene homolog (avian)), PRKAA2 (protein kinase, AMP-activated, alpha 2 catalytic subunit), ROCK2 (Rho-associated, coiled-coil containing protein kinase 2), TFPI (tissue factor pathway inhibitor (lipoprotein-associated coagulation inhibitor)), PRKG1 (protein kinase, cGMP-dependent, type I), BMP2 (bone morphogenetic protein 2), CTNND1 (catenin (cadherin-associated protein), delta 1), CTH (cystathionase (cystathionine gamma-lyase)), CTSS (cathepsin S), VAV2 (vav 2 guanine nucleotide exchange factor), NPY2R (neuropeptide Y receptor Y2), IGFBP2 (insulin-like growth factor binding protein 2, 36 kDa), CD28 (CD28 molecule), GSTA1 (glutathione S-transferase alpha 1), PPIA (peptidylprolyl isomerase A (cyclophilin A)), APOH (apolipoprotein H (beta-2-glycoprotein I)), S100A8 (S100 calcium binding protein A8), IL11 (interleukin 11), ALOX15 (arachidonate 15-lipoxygenase), FBLN1 (fibulin 1), NR1H3 (nuclear receptor subfamily 1, group H, member 3), SCD (stearoyl-CoA desaturase (delta-9-desaturase)), GIP (gastric inhibitory polypeptide), CHGB (chromogranin B (secretogranin 1)), PRKCB (protein kinase C, beta), SRD5A1 (steroid-5-alpha-reductase, alpha polypeptide 1 (3-oxo-5 alpha-steroid delta 4-dehydrogenase alpha 1)), HSD11B2 (hydroxysteroid (11-beta) dehydrogenase 2), CALCRL (calcitonin receptor-like), GALNT2 (UDP-N-acetyl-alpha-D-galactosamine.polypeptide N-acetylgalactosaminyltransferase 2 (GalNAc-T2)), ANGPTL4 (angiopoietin-like 4), KCNN4 (potassium intermediate/small conductance calcium-activated channel, subfamily N, member 4), PIK3C2A (phosphoinositide-3-kinase, class 2, alpha polypeptide), HBEGF (heparin-binding EGF-like growth factor), CYP7A1 (cytochrome P450, family 7, subfamily A, polypeptide 1), HLA-DRB5 (major histocompatibility complex, class II, DR beta 5), BNIP3 (BCL2/adenovirus E1B 19 kDa interacting protein 3), GCKR (glucokinase (hexokinase 4) regulator), S100A12 (S100 calcium binding protein A12), PADI4 (peptidyl arginine deiminase, type IV), HSPA14 (heat shock 70 kDa protein 14), CXCR1 (chemokine (C-X-C motif) receptor 1), H19 (H19, imprinted maternally expressed transcript (non-protein coding)), KRTAP19-3 (keratin associated protein 19-3), IDDM2 (insulin-dependent diabetes mellitus 2), RAC2 (ras-related C3 botulinum toxin substrate 2 (rho family, small GTP binding protein Rac2)), RYR1 (ryanodine receptor 1 (skeletal)), CLOCK (clock homolog (mouse)), NGFR (nerve growth factor receptor (TNFR superfamily, member 16)), DBH (dopamine beta-hydroxylase (dopamine beta-monooxygenase)), CHRNA4 (cholinergic receptor, nicotinic, alpha 4), CACNA1C (calcium channel, voltage-dependent, L type, alpha 1C subunit), PRKAG2 (protein kinase, AMP-activated, gamma 2 non-catalytic subunit), CHAT (choline acetyltransferase), PTGDS (prostaglandin D2 synthase 21 kDa (brain)), NR1H2 (nuclear receptor subfamily 1, group H, member 2), TEK (TEK tyrosine kinase, endothelial), VEGFB (vascular endothelial growth factor B), MEF2C (myocyte enhancer factor 2C), MAPKAPK2 (mitogen-activated protein kinase-activated protein kinase 2), TNFRSF11A (tumor necrosis factor receptor superfamily, member 11a, NFKB activator), HSPA9 (heat shock 70 kDa protein 9 (mortalin)), CYSLTR1 (cysteinyl leukotriene receptor 1), MAT1A (methionine adenosyltransferase I, alpha), OPRL1 (opiate receptor-like 1), IMPA1 (inositol (myo)-1(or 4)-monophosphatase 1), CLCN2 (chloride channel 2), DLD (dihydrolipoamide dehydrogenase), PSMA6 (proteasome (prosome, macropain) subunit, alpha type, 6), PSMB8 (proteasome (prosome, macropain) subunit, beta type, 8 (large multifunctional peptidase 7)), CHI3L1 (chitinase 3-like 1 (cartilage glycoprotein-39)), ALDH1B1 (aldehyde dehydrogenase 1 family, member B1), PARP2 (poly (ADP-ribose) polymerase 2), STAR (steroidogenic acute regulatory protein), LBP (lipopolysaccharide binding protein), ABCC6 (ATP-binding cassette, sub-family C(CFTR/MRP), member 6), RGS2 (regulator of G-protein signaling 2, 24 kDa), EFNB2 (ephrin-B2), GJB6 (gap junction protein, beta 6, 30 kDa), APOA2 (apolipoprotein A-II), AMPD1 (adenosine monophosphate deaminase 1), DYSF (dysferlin, limb girdle muscular dystrophy 2B (autosomal recessive)), FDFT1 (farnesyl-diphosphate farnesyltransferase 1), EDN2 (endothelin 2), CCR6 (chemokine (C-C motif) receptor 6), GJB3 (gap junction protein, beta 3, 31 kDa), IL1RL1 (interleukin 1 receptor-like 1), ENTPD1 (ectonucleoside triphosphate diphosphohydrolase 1), BBS4 (Bardet-Biedl syndrome 4), CELSR2 (cadherin, EGF LAG seven-pass G-type receptor 2 (flamingo homolog, *Drosophila*)), F11R (F11 receptor), RAPGEF3 (Rap guanine nucleotide exchange factor (GEF) 3), HYAL1 (hyaluronoglucosaminidase 1), ZNF259 (zinc finger protein 259), ATOX1 (ATX1 antioxidant protein 1 homolog (yeast)), ATF6 (activating transcription factor 6), KHK (ketohexokinase (fructokinase)), SAT1 (spermidine/spermine N1-acetyltransferase 1), GGH (gamma-glutamyl hydrolase (conjugase, folylpolygammaglutamyl hydrolase)), TIMP4 (TIMP metallopeptidase inhibitor 4), SLC4A4 (solute carrier family 4, sodium bicarbonate cotransporter, member 4), PDE2A (phosphodiesterase 2A, cGMP-stimulated), PDE3B (phosphodiesterase 3B, cGMP-inhibited), FADS1 (fatty acid desaturase 1), FADS2 (fatty acid desaturase 2), TMSB4X (thymosin beta 4, X-linked), TXNIP (thioredoxin interacting protein), LIMS1 (LIM and senescent cell antigen-like domains 1), RHOB (ras homolog gene family, member B), LY96 (lymphocyte antigen 96), FOXO1 (forkhead box O1), PNPLA2 (patatin-like phospholipase domain containing 2), TRH (thyrotropin-releasing hormone), GJC1 (gap junction protein, gamma 1, 45 kDa), SLC17A5 (solute carrier family 17 (anion/sugar transporter), member 5), FTO (fat mass and obesity associated), GJD2 (gap junction protein, delta 2, 36 kDa), PSRC1 (proline/serine-rich coiled-coil 1), CASP12 (caspase 12 (gene/pseudogene)), GPBAR1 (G protein-coupled bile acid receptor 1), PXK (PX domain containing serine/threonine kinase), IL33 (interleukin 33), TRIB1 (tribbles homolog 1 (*Drosophila*)), PBX4 (pre-B-cell leukemia homeobox 4), NUPR1 (nuclear protein, transcriptional regulator, 1), 15-Sep (15 kDa selenoprotein), CILP2 (cartilage intermediate layer protein 2), TERC (telomerase RNA component), GGT2 (gamma-glutamyltransferase 2), MT-CO1 (mitochondrially encoded cytochrome c oxidase I), and UOX (urate oxidase, pseudogene). In an additional embodiment, the chromosomal sequence may further be selected from Pon1 (paraoxonase 1), LDLR (LDL receptor), ApoE (Apolipoprotein E), Apo B-100 (Apolipoprotein B-100), ApoA (Apolipoprotein(a)), ApoA1 (Apolipoprotein A1), CBS (Cystathione B-synthase), Glycoprotein IIb/IIb, MTHRF (5,10-methylenetetrahydrofolate reductase (NADPH), and combinations thereof. In one iteration, the chromosomal sequences and proteins encoded by chromosomal sequences involved in cardiovascular disease may be chosen from Cacna1C, Sod1, Pten, Ppar(alpha), Apo E, Leptin, and combinations thereof. The text herein accordingly provides exemplary targets as to CRISPR or CRISPR-Cas systems or complexes.

The following are incorporated by reference.

Biosecurity Implications of Gene Drive Research (nas-sites.org/gene-drives/2015/10/07/implications-of-gene-drive-research-on-biosecurity-webinar/). You, E.

Biotechnology. A prudent path forward for genomic engineering and germline gene modification. Baltimore, D.; Berg, P.; Botchan, M.; Carroll, D.; Charo, R. A.; Church, G.; Corn, J. E.; Daley, G. Q.; Doudna, J. A.; Fenner, M.; Greely, H. T.; Jinek, M.; Martin, G. S.; Penhoet, E.; Puck, J.; Sternberg, S. H.; Weissman, J. S.; Yamamoto, K. R. Science 2015, 348, 36-8. PMC4394183

BIOSAFETY. Safeguarding gene drive experiments in the laboratory. Akbari, O. S.; Bellen, H. J.; Bier, E.; Bullock, S. L.; Burt, A.; Church, G. M.; Cook, K. R.; Duchek, P.; Edwards, O. R.; Esvelt, K. M.; Gantz, V. M.; Golic, K. G.; Gratz, S. J.; Harrison, M. M.; Hayes, K. R.; James, A. A.; Kaufman, T. C.; Knoblich, J.; Malik, H. S.; Matthews, K. A.; O'Connor-Giles, K. M.; Parks, A. L.; Perrimon, N.; Port, F.; Russell, S.; Ueda, R.; Wildonger, J. Science 2015, 349, 927-9. PMC4692367

Gene drive overdrive. Nat Biotech 2015, 33, 1019-1021

Opinion: Is CRISPR-based gene drive a biocontrol silver bullet or global conservation threat? Webber, B. L.; Raghu, S.; Edwards, O. R. Proceedings of the National Academy of Sciences 2015, 112, 10565-10567

Gene drives spread their wings. Saey, T. H. Science News 2015, 188, 16

Concerning RNA-guided gene drives for the alteration of wild populations. Esvelt, K. M.; Smidler, A. L.; Catteruccia, F.; Church, G. M. eLife 2014, 3, e03401

The dawn of active genetics. Gantz, V. M.; Bier, E. Bioessays 2016, 38, 50-63

Cheating evolution: engineering gene drives to manipulate the fate of wild populations. Champer, J.; Buchman, A.; Akbari, O. S. Nat Rev Genet 2016, 17, 146-159

Entomological terrorism: a tactic in assymmetrical warfare. Monthei, D.; Mueller, S.; Lockwood, J.; Debboun, M. US Army Med Dep J 2010, 11-21

CRISPR-mediated direct mutation of cancer genes in the mouse liver. Xue, W.; Chen, S.; Yin, H.; Tammela, T.; Papagiannakopoulos, T.; Joshi, N. S.; Cai, W.; Yang, G.; Bronson, R.; Crowley, D. G.; Zhang, F.; Anderson, D. G.; Sharp, P. A.; Jacks, T. Nature 2014, 514, 380-4. PMC4199937

Rapid modelling of cooperating genetic events in cancer through somatic genome editing. Sanchez-Rivera, F. J.; Papagiannakopoulos, T.; Romero, R.; Tammela, T.; Bauer, M. R.; Bhutkar, A.; Joshi, N. S.; Subbaraj, L.; Bronson, R. T.; Xue, W.; Jacks, T. Nature 2014, 516, 428-31. PMC4292871

CRISPR-Cas9 knockin mice for genome editing and cancer modeling. Platt, R. J.; Chen, S.; Zhou, Y.; Yim, M. J.; Swiech, L.; Kempton, H. R.; Dahlman, J. E.; Parnas, O.; Eisenhaure, T. M.; Jovanovic, M.; Graham, D. B.; Jhunjhunwala, S.; Heidenreich, M.; Xavier, R. J.; Langer, R.; Anderson, D. G.; Hacohen, N.; Regev, A.; Feng, G.; Sharp, P. A.; Zhang, F. Cell 2014, 159, 440-55. PMC4265475

Global microRNA depletion suppresses tumor angiogenesis. Chen, S.; Xue, Y.; Wu, X.; Le, C.; Bhutkar, A.; Bell, E. L.; Zhang, F.; Langer, R.; Sharp, P. A. Genes Dev 2014, 28, 1054-67. PMC4035535

Applications of the CRISPR-Cas9 system in cancer biology. Sanchez-Rivera, F. J.; Jacks, T. Nat Rev Cancer 2015, 15, 387-95

Genome-wide CRISPR screen in a mouse model of tumor growth and metastasis. Chen, S.; Sanjana, N. E.; Zheng, K.; Shalem, O.; Lee, K.; Shi, X.; Scott, D. A.; Song, J.; Pan, J. Q.; Weissleder, R.; Lee, H.; Zhang, F.; Sharp, P. A. Cell 2015, 160, 1246-60. PMC4380877

Increasing the efficiency of precise genome editing with CRISPR-Cas9 by inhibition of nonhomologous end joining. Maruyama, T.; Dougan, S. K.; Truttmann, M. C.; Bilate, A. M.; Ingram, J. R.; Ploegh, H. L. Nat Biotech 2015, 33, 538-542

Increasing the efficiency of homology-directed repair for CRISPR-Cas9-induced precise gene editing in mammalian cells. Chu, V. T.; Weber, T.; Wefers, B. Nat. Biotech 2015, 33, 543-8

Enhancing homology-directed genome editing by catalytically active and inactive CRISPR-Cas9 using asymmetric donor DNA. Richardson, C. D.; Ray, G. J.; DeWitt, M. A.; Curie, G. L.; Corn, J. E. Nat Biotech 2016, 34, 339-344

The cytotoxicity of (−)-lomaiviticin A arises from induction of double-strand breaks in DNA. Colis, L. C.; Woo, C. M.; Hegan, D. C.; Li, Z.; Glazer, P. M.; Herzon, S. B. Nature chemistry 2014, 6, 504-510

Structural basis for DNA cleavage by the potent antiproliferative agent (−)-lomaiviticin A. Woo, C. M.; Li, Z.; Paulson, E. K. 2016, 113, 2851-6

Rational design of human DNA ligase inhibitors that target cellular DNA replication and repair. Chen, X.; Zhong, S.; Zhu, X.; Dziegielewska, B.; Ellenberger, T.; Wilson, G.

M.; MacKerell, A. D., Jr.; Tomkinson, A. E. Cancer Res 2008, 68, 3169-77. PMC2734474

An inhibitor of nonhomologous end-joining abrogates double-strand break repair and impedes cancer progression. Srivastava, M.; Nambiar, M.; Sharma, S.; Karki, S. S.; Goldsmith, G.; Hegde, M.; Kumar, S.; Pandey, M.; Singh, R. K.; Ray, P.; Natarajan, R.; Kelkar, M.; De, A.; Choudhary, B.; Raghavan, S. C. Cell 2012, 151, 1474-87

Increasing the efficiency of precise genome editing with CRISPR-Cas9 by inhibition of nonhomologous end joining. Maruyama, T.; Dougan, S. K.; Truttmann, M. C.; Bilate, A. M.; Ingram, J. R.; Ploegh, H. L. Nat Biotechnol 2015, 33, 538-42. PMC4618510

Increasing the efficiency of homology-directed repair for CRISPR-Cas9-induced precise gene editing in mammalian cells. Chu, V. T.; Weber, T.; Wefers, B.; Wurst, W.; Sander, S.; Rajewsky, K.; Kuhn, R. Nat Biotechnol 2015, 33, 543-8

SCR7 is neither a selective nor a potent inhibitor of human DNA ligase IV. Greco, G. E.; Matsumoto, Y.; Brooks, R. C.; Lu, Z.; Lieber, M. R.; Tomkinson, A. E. DNA Repair (Amst) 2016, 43, 18-23. PMC5042453

A chemical compound that stimulates the human homologous recombination protein RAD51. Jayathilaka, K.; Sheridan, S. D.; Bold, T. D.; Bochenska, K.; Logan, H. L.; Weichselbaum, R. R.; Bishop, D. K.; Connell, P. P. Proc Natl Acad Sci USA 2008, 105, 15848-53. PMC2572930

Dual and Opposite Effects of hRAD51 Chemical Modulation on HIV-1 Integration. Thierry, S.; Benleulmi, M. S.; Sinzelle, L.; Thierry, E.; Calmels, C.; Chaignepain, S.; Waffo-Teguo, P.; Merillon, J. M.; Budke, B.; Pasquet, J. M.; Litvak, S.; Ciuffi, A.; Sung, P.; Connell, P.; Hauber, I.; Hauber, J.; Andreola, M. L.; Delelis, O.; Parissi, V. Chem Biol 2015, 22, 712-23. PMC4889029

Nuclear domain 'knock-in' screen for the evaluation and identification of small molecule enhancers of CRISPR-based genome editing. Pinder, J.; Salsman, J.; Dellaire, G. Nucleic Acids Res 2015, 43, 9379-92. PMC4627099

A guide to genome engineering with programmable nucleases. Kim, H.; Kim, J. S. Nat Rev Genet 2014, 15, 321-34

Synthetic mimetics of protein secondary structure domains. Ross, N. T.; Katt, W. P.; Hamilton, A. D. Philosophical transactions. Series A, Mathematical, physical, and engineering sciences 2010, 368, 989-1008

The crystal structure of TAL effector PthXol bound to its DNA target. Mak, A. N.-S.; Bradley, P.; Cernadas, R. A.; Bogdanove, A. J.; Stoddard, B. L. Science (New York, N.Y.) 2012, 335, 716-719

Calculating structures and free energies of complex molecules: combining molecular mechanics and continuum models. Kollman, P. A.; Massova, I.; Reyes, C.; Kuhn, B.; Huo, S.; Chong, L.; Lee, M.; Lee, T.; Duan, Y.; Wang, W. Accounts of chemical research 2000, 33, 889-897%@ 0001-4842

Antechamber: an accessory software package for molecular mechanical calculations. Wang, J.; Wang, W.; Kollman, P. A.; Case, D. A. J. Am. Chem. Soc 2001, 222, U403

Boronate-mediated biologic delivery. Ellis, G. A.; Palte, M. J.; Raines, R. T. J Am Chem Soc 2012, 134, 3631-4. Pmc3304437

Cell-penetrating peptides: 20 years later, where do we stand? Bechara, C.; Sagan, S. FEBS Lett 2013, 587, 1693-702

Click chemistry in complex mixtures: bioorthogonal bioconjugation. McKay, C. S.; Finn, M. G. Chem Biol 2014, 21, 1075-101. Pmc4331201

High-frequency off-target mutagenesis induced by CRISPR-Cas nucleases in human cells. Fu, Y.; Foden, J. A.; Khayter, C.; Maeder, M. L.; Reyon, D.; Joung, J. K.; Sander, J. D. Nat Biotechnol 2013, 31, 822-6. Pmc3773023

Multidimensional chemical control of CRISPR-Cas9. Maji, B.; Moore, C. L.; Zetsche, B.; Volz, S. E.; Zhang, F.; Shoulders, M. D.; Choudhary, A. Nat Chem Biol 2016, advance online publication Evolution and classification of the CRISPR-Cas systems. Makarova, K. S.; Haft, D. H.; Barrangou, R.; Brouns, S. J.; Charpentier, E.; Horvath, P.; Moineau, S.; Mojica, F. J.; Wolf, Y. I.; Yakunin, A. F.; van der Oost, J.; Koonin, E. V. Nat Rev Microbiol 2011, 9, 467-77. PMC3380444

An updated evolutionary classification of CRISPR-Cas systems. Makarova, K. S.; Wolf, Y. I.; Alkhnbashi, O. S.; Costa, F.; Shah, S. A.; Saunders, S. J.; Barrangou, R.; Brouns, S. J.; Charpentier, E.; Haft, D. H.; Horvath, P.; Moineau, S.; Mojica, F. J.; Terns, R. M.; Terns, M. P.; White, M. F.; Yakunin, A. F.; Garrett, R. A.; van der Oost, J.; Backofen, R.; Koonin, E. V. Nat Rev Microbiol 2015

Advances in CRISPR-Cas9 genome engineering: lessons learned from RNA interference. Barrangou, R.; Birmingham, A.; Wiemann, S.; Beijersbergen, R. L.; Hornung, V.; Smith, A. Nucleic Acids Res 2015, 43, 3407-19. PMC4402539

The mechanism of double-strand DNA break repair by the nonhomologous DNA end-joining pathway. Lieber, M. R. Annu Rev Biochem 2010, 79, 181-211. Pmc3079308

Reduced ciliary polycystin-2 in induced pluripotent stem cells from polycystic kidney disease patients with PKD1 mutations. Freedman, B. S.; Lam, A. Q.; Sundsbak, J. L.; Iatrino, R.; Su, X.; Koon, S. J.; Wu, M.; Daheron, L.; Harris, P. C.; Zhou, J.; Bonventre, J. V. J Am Soc Nephrol 2013, 24, 1571-86. Pmc3785271

Polycystic kidney disease. Wilson, P. D. N Engl J Med 2004, 350, 151-64

Fibrocystin/polyductin, found in the same protein complex with polycystin-2, regulates calcium responses in kidney epithelia. Wang, S.; Zhang, J.; Nauli, S. M.; Li, X.; Starremans, P. G.; Luo, Y.; Roberts, K. A.; Zhou, J. Mol Cell Biol 2007, 27, 3241-52. Pmc1899915

Site-specific C-terminal and internal loop labeling of proteins using sortase-mediated reactions. Guimaraes, C. P.; Witte, M. D.; Theile, C. S.; Bozkurt, G.; Kundrat, L.; Blom, A. E.; Ploegh, H. L. Nat Protoc 2013, 8, 1787-99. PMC3943461

Site-specific N-terminal labeling of proteins using sortase-mediated reactions. Theile, C. S.; Witte, M. D.; Blom, A. E.; Kundrat, L.; Ploegh, H. L.; Guimaraes, C. P. Nat Protoc 2013, 8, 1800-7. PMC3941705

Sortase-mediated ligations for the site-specific modification of proteins. Schmohl, L.; Schwarzer, D. Curr Opin Chem Biol 2014, 22, 122-8

A split-Cas9 architecture for inducible genome editing and transcription modulation. Zetsche, B.; Volz, S. E.; Zhang, F. Nat Biotechnol 2015, 33, 139-42. PMC4503468

Rational design of a split-Cas9 enzyme complex. Wright, A. V.; Sternberg, S. H.; Taylor, D. W.; Staahl, B. T.; Bardales, J. A.; Kornfeld, J. E.; Doudna, J. A. Proc Natl Acad Sci USA 2015, 112, 2984-9. PMC4364227

Rationally engineered Cas9 nucleases with improved specificity. Slaymaker, I. M.; Gao, L.; Zetsche, B.; Scott, D. A.; Yan, W. X.; Zhang, F. Science (New York, N.Y.) 2016, 351, 84-88

RNA-programmed genome editing in human cells. Jinek, M.; East, A.; Cheng, A.; Lin, S.; Ma, E.; Doudna, J. Elife 2013, 2, e00471. PMC3557905

Cationic lipid-mediated delivery of proteins enables efficient protein-based genome editing in vitro and in vivo. Zuris, J. A.; Thompson, D. B.; Shu, Y.; Guilinger, J. P.; Bessen, J. L.; Hu, J. H.; Maeder, M. L.; Joung, J. K.; Chen, Z. Y.; Liu, D. R. Nat Biotechnol 2015, 33, 73-80. PMC4289409

High-frequency off-target mutagenesis induced by CRISPR-Cas nucleases in human cells. Fu, Y.; Foden, J. A.; Khayter, C.; Maeder, M. L.; Reyon, D.; Joung, J. K.; Sander, J. D. Nat Biotechnol 2013, 31, 822-6. Pmc3773023

DNA repair targeted therapy: The past or future of cancer treatment? Gavande, N. S.; VanderVere-Carozza, P. S.; Hinshaw, H. D.; Jalal, S. I.; Sears, C. R.; Pawelczak, K. S.; Turchi, J. J. Pharmacol Ther 2016, 160, 65-83. PMC4811676

Although the present invention and its advantages have been described in detail, it should be understood that various changes, substitutions, and alterations can be made herein without departing from the spirit and scope of the invention as defined in the appended claims. The present invention will be further illustrated in the following Examples which are given for illustration purposes only and are not intended to limit the invention in any way.

WORKING EXAMPLES

Figure 5:
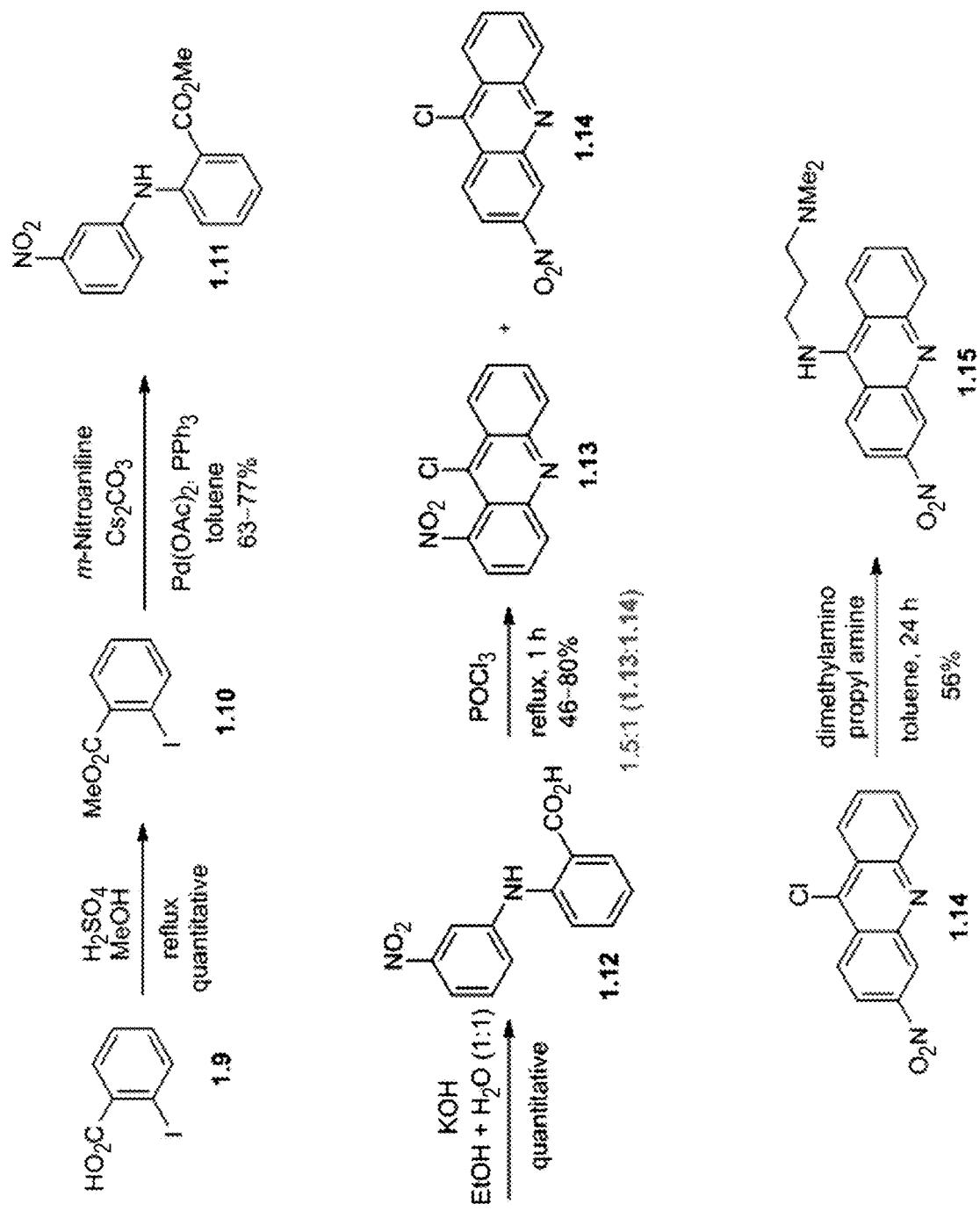
FIG. 5 is a flow chart depicting synthesis of nitracrine (compound 1.15).
Figure 6A:
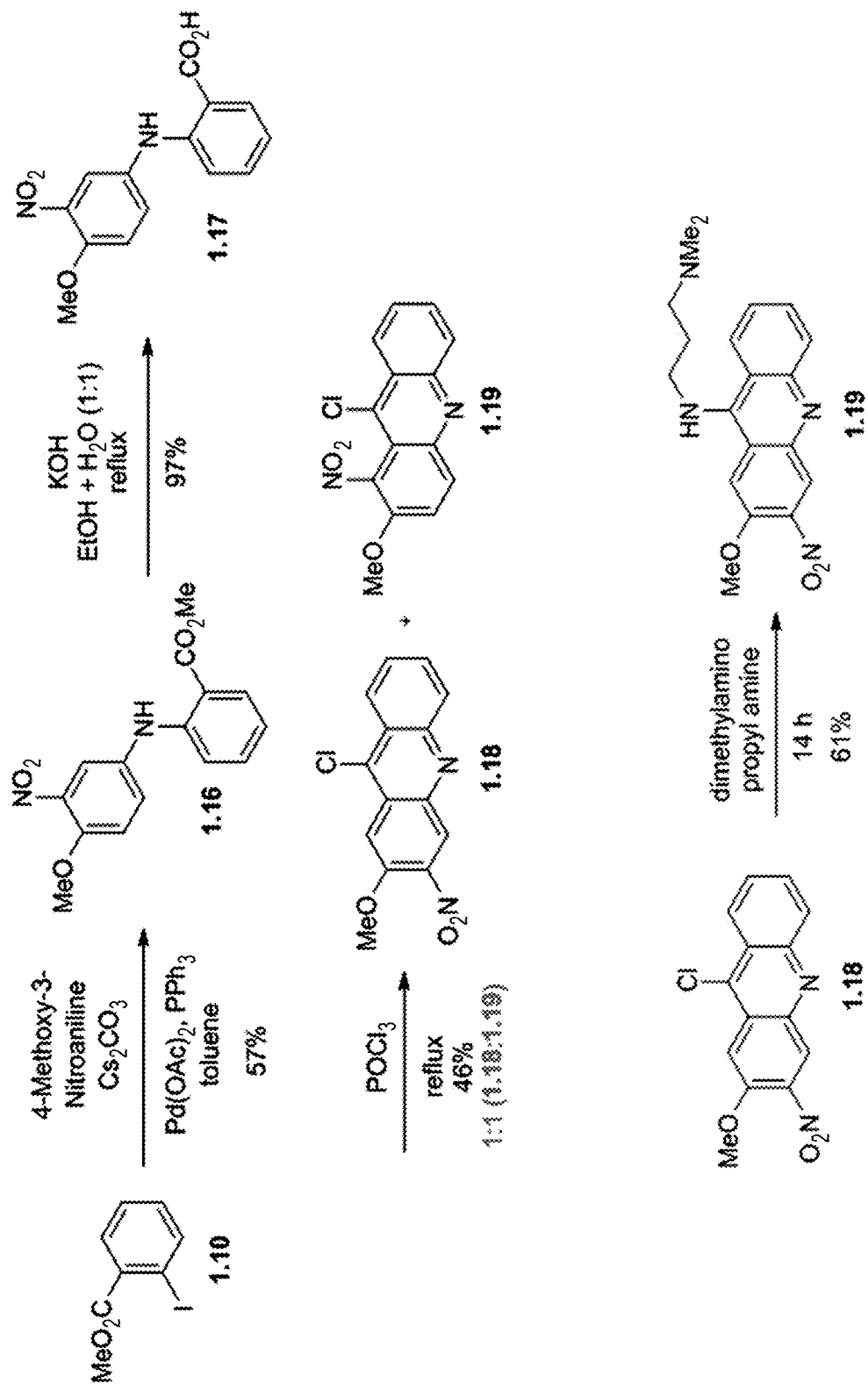
FIG. 6A is a flow chart depicting synthesis of alternative nitracrine analog A for attachment of PEG linker.
Figure 6B:
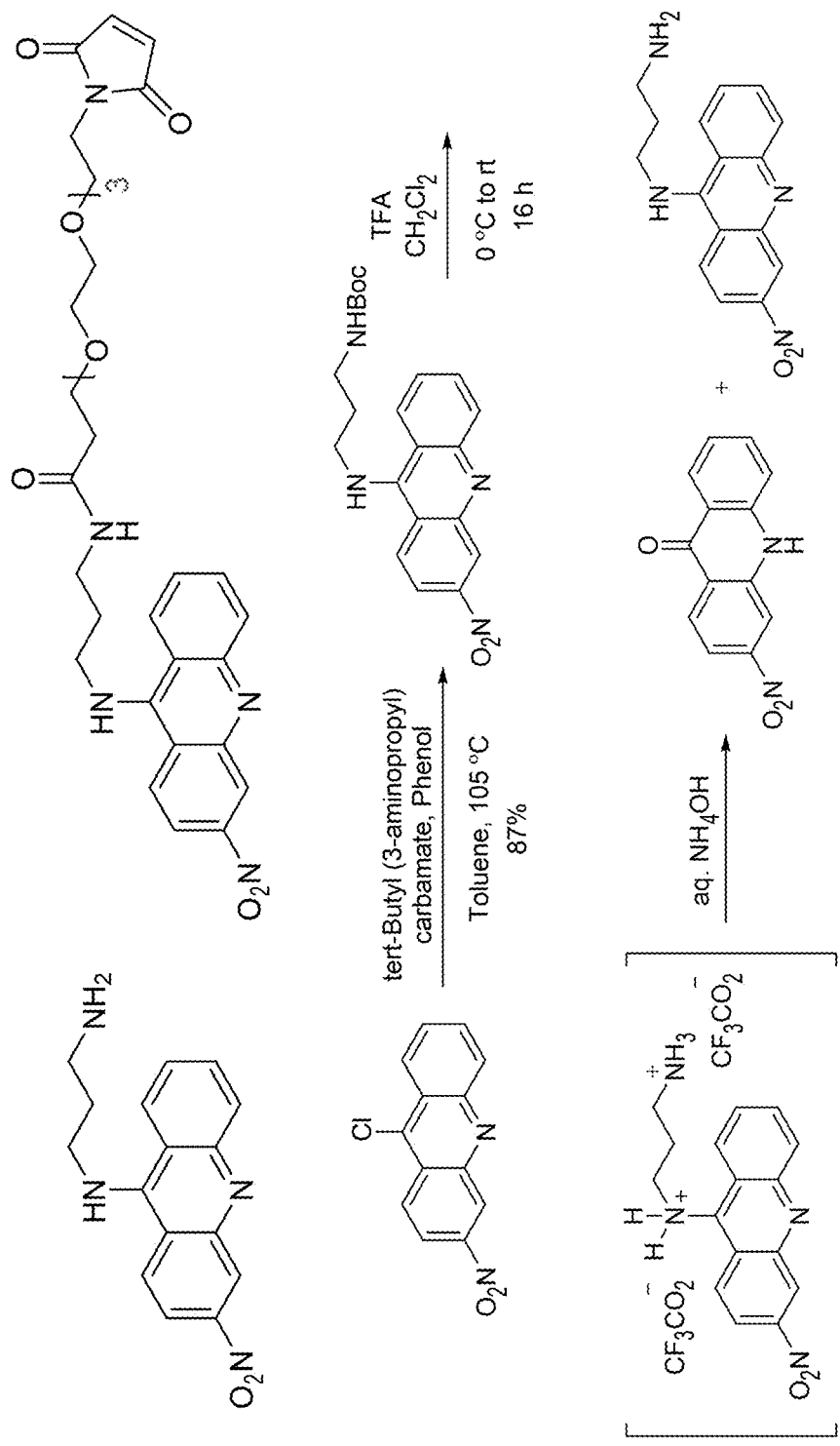
FIG. 6B is a flow chart depicting synthesis of alternative nitracrine analog B for attachment of PEG linker.
Figure 7A:
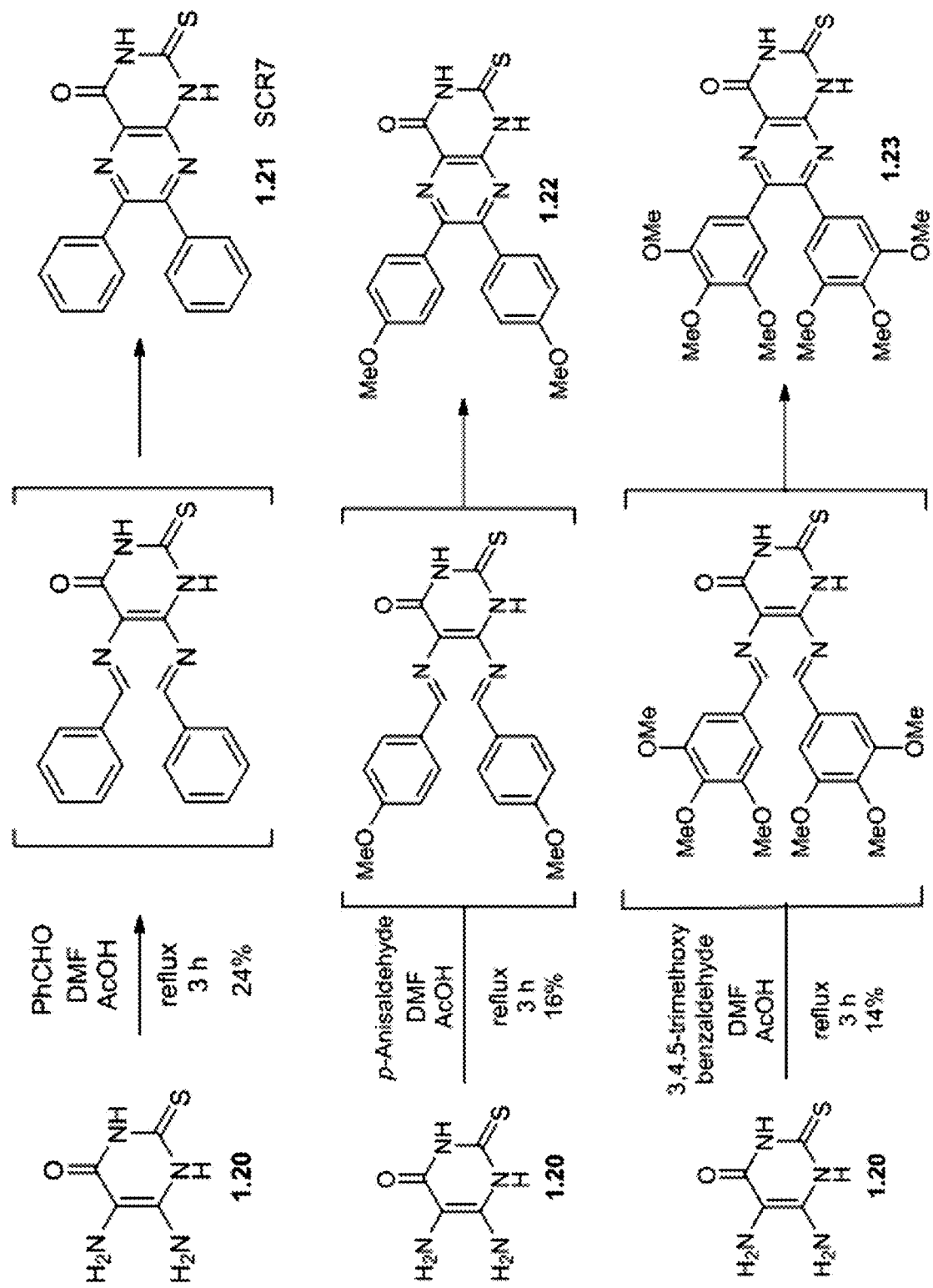
FIG. 7A is a flow chart depicting synthesis of alternative SCR7 analog A for addition of PEG linker.
Figure 7B:
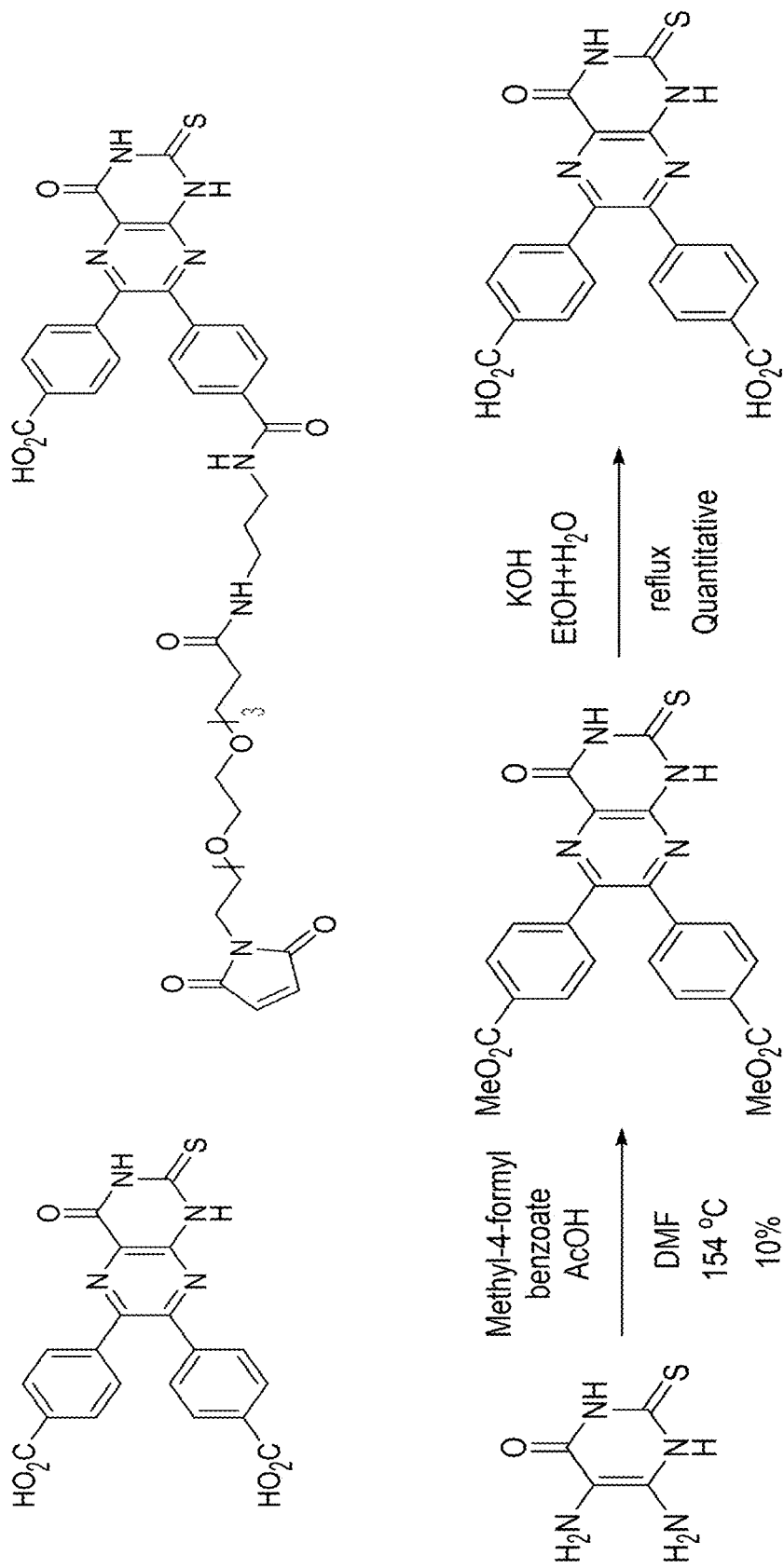
FIG. 7B is a flow chart depicting synthesis of alternative SCR7 analog B for addition of PEG linker.
Figure 8A:
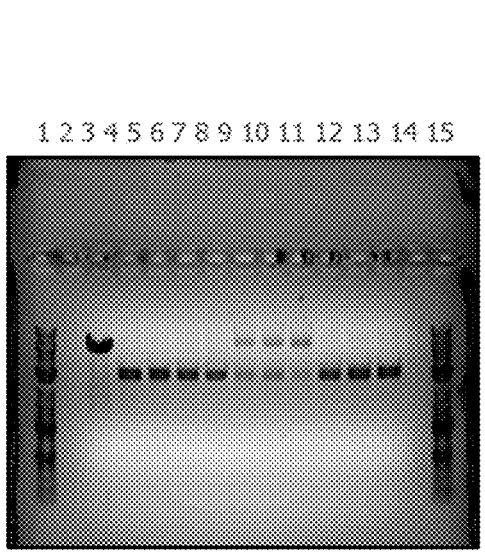
FIG. 8A is a gel electrophoresis image showing pcDNA cleavage by compound 1.15 (10, 12, and 14 µM) and incubation under UV (365 nm) in the presence and absence of reducing agent TCEP.
Figure 8B:
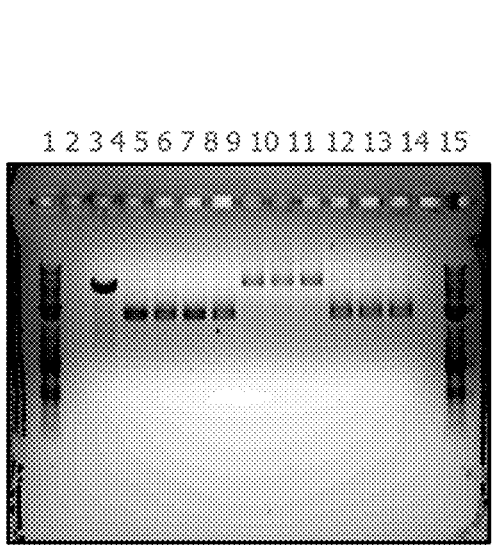
FIG. 8B is a gel electrophoresis image showing pcDNA cleavage by compound 1.15 (16, 18, and 20 µM) and incubation under UV (365 nm) in the presence and absence of reducing agent TCEP.

Example 1—DNA Cleavage by Nitracrine with Exposure to UV and Reducing Agent TCEP Nitracrine (compound 1.15) was synthesized according to the reaction scheme depicted in FIG. 5. Plasmid DNA was incubated with nitracrine alone (10, 12, 14 µM), nitracrine with exposure to UV (365 nm), or nitracrine with exposure to UV and reducing agent TCEP (FIG. 8A). The same experiment was repeated but using 16, 18, or 20 µM nitracrine (FIG. 8B). DNA cleavage was observed at all nitracrine concentrations with exposure to UV, but not in the presence of TCEP.

Figure 9A:
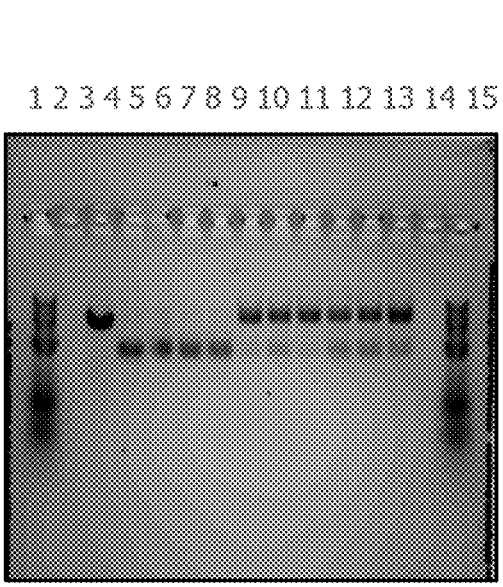
FIG. 9A is a gel electrophoresis image showing pcDNA cleavage by compound 1.15 (10, 12, and 14 µM) and incubation under UV (365 nm) in the presence and absence of reducing agent DTT.
Figure 9B:
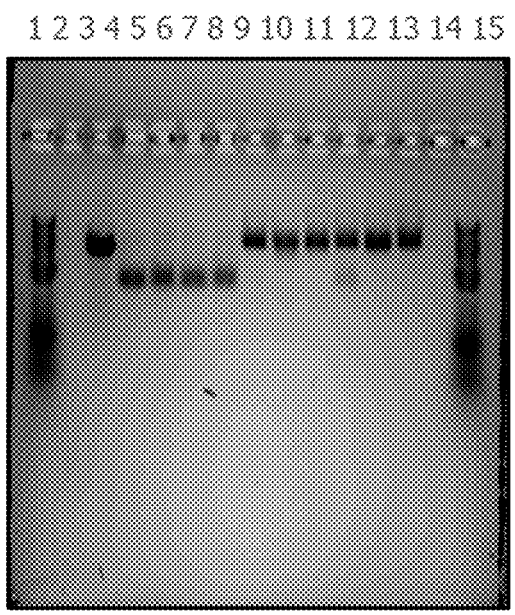
FIG. 9B is a gel electrophoresis image showing pcDNA cleavage by compound 1.15 (16, 18, and 20 µM) and incubation under UV (365 nm) in the presence and absence of reducing agent DTT.

Example 2—DNA Cleavage by Nitracrine with Exposure to UV and Reducing Agent DTT Plasmid DNA was incubated with nitracrine alone (10, 12, 14 µM), nitracrine with exposure to UV (365 nm), or nitracrine with exposure to UV and reducing agent DTT (FIG. 9A). The same experiment was repeated but using 16, 18, or 20 µM nitracrine (FIG. 9B). DNA cleavage was observed at all nitracrine concentrations with exposure to UV, including with DTT.

Example 3—DNA Cleavage by Nitracrine with Exposure to UV

Figure 10:
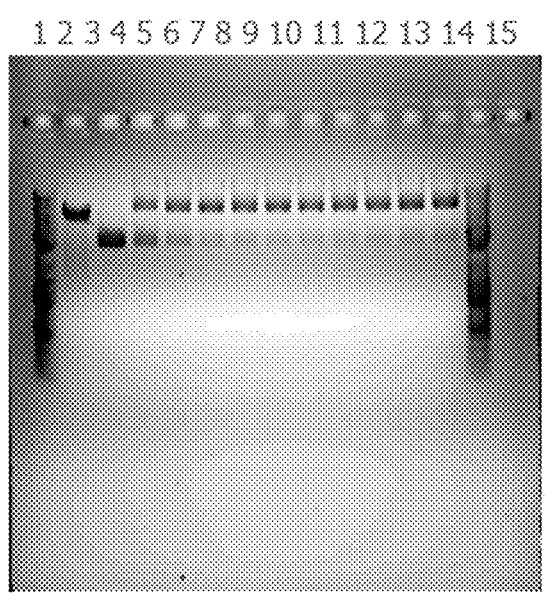
FIG. 10 is a gel electrophoresis image showing pcDNA cleavage by 16 µM compound 1.15 and incubation under UV (365 nm) from 30 to 60 min.
Figure 11:
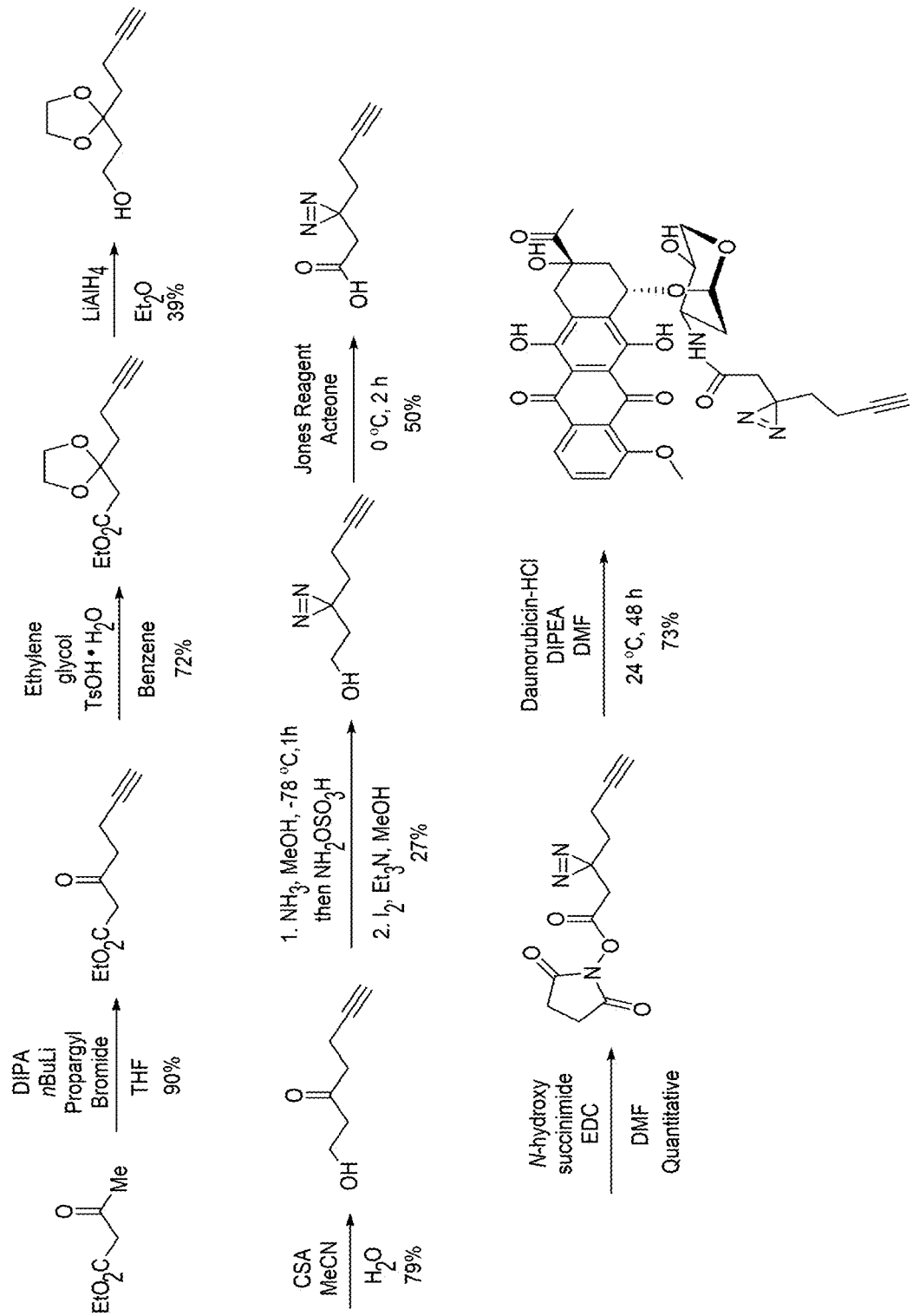
FIG. 11 is a flow chart depicting synthesis of a daunorubicin-attached diazirine.
Figure 12:
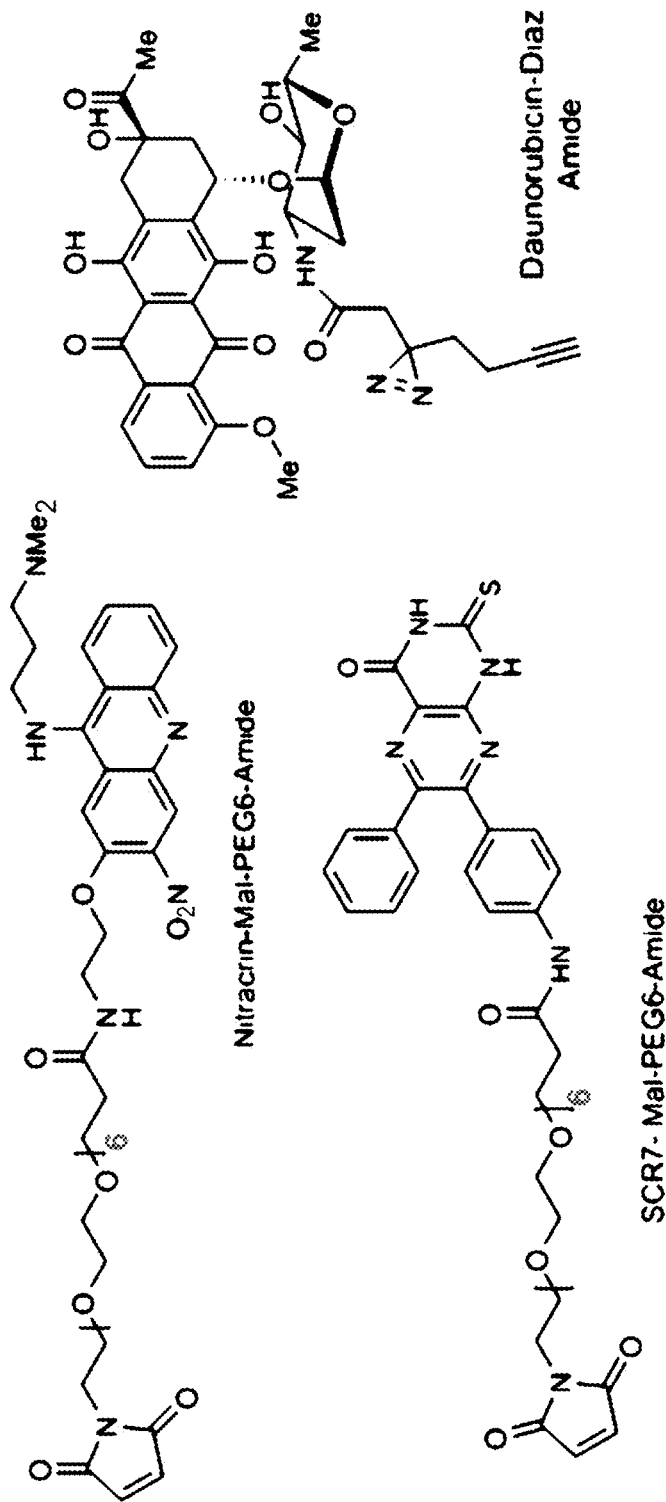
FIG. 12 is a graph showing linker-containing derivatives of nitracrine, SCR7, and daunorubicin for attachment to a nucleic acid reader.

Plasmid DNA was incubated with 16 µM nitracrine and exposed to UV (365 nm) over a range of 30-60 minutes (FIG. 10). Cleavage was observed under all conditions.

Example 4—Optimization of Site-Specific Cysteine Conjugation on Cas9

Cysteine/maleimide conjugation chemistry has been explored as a strategy to affix chemical cargo to Cas9. A cysteine-free Cas9 (ΔCys) was generated by mutating cysteines C80S and C574S to serine and it was found to retain nuclease activity. Guided by the Cas9 crystal structure (PDB: 5F9R), cysteines were introduced on solvent-exposed loops (FIG. 13A). Sites were chosen that sampled multiple Cas9 domains, and polar residues were mutated to minimize potential structure disruption. Seven mutants that were successfully expressed and purified from E. coli following reported procedures (FIG. 13B). Maleimide-biotin conjugation was used as a model system for Cas9 labeling, as conjugation efficiency can be quantified by separating labeled and unlabeled Cas9 through streptavidin pull-down (FIG. 13C). Multiple reaction conditions were tested, including reagent concentrations, reaction time, and temperature. The optimized conditions resulted in quantitative (S355C, E532C, E945C, E1068C, E1207C) or almost quantitative (S1116C, 94%) biotin conjugation of Cas9 (FIG. 13D). Only one of the mutants showed moderate conjugation efficiency (S1154C, 70%). Next, it was determined if the cysteine mutants and their biotin-labeled variants retain nuclease activity in an in vitro DNA cleavage assay. All cysteine mutants and biotin-labeled Cas9 were active (FIG. 13E), although some sites showed some modest reduction in activity. This suggests that the structure of cargos, especially the linker composition and length, should be optimized. Next, an eGFP disruption assay was used to determine the activity of the labelled mutants in cells. Briefly, ribonucleoprotein complex of Cas9 (or cysteine mutants) and guide RNA targeting the genomic eGFP locus in U2OS cells was delivered following the reported procedure (FIG. 13F). The loss of eGFP fluorescence was confirmed for several of biotin-labeled Cas9 mutants—E945C-biotin and E1068C-biotin were as active as unmodified wt Cas9, while S355C-biotin, E532C-biotin, E1207C-biotin also showed significant eGFP disruption. Only the S1116C-biotin Cas9 variant was weakly active in cells (FIG. 13G).

Example 5—Optimization of Sortase Ligation Chemistry on Cas9

Figure 3B:
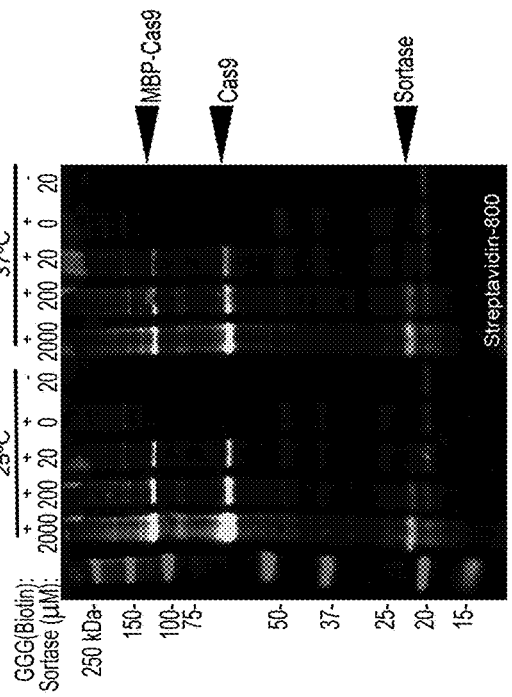
FIG. 3B is a spCas9 crystal structure showing solvent exposed loops where sortase recognition sequences (LPETG) are installed.
Figure 3C:
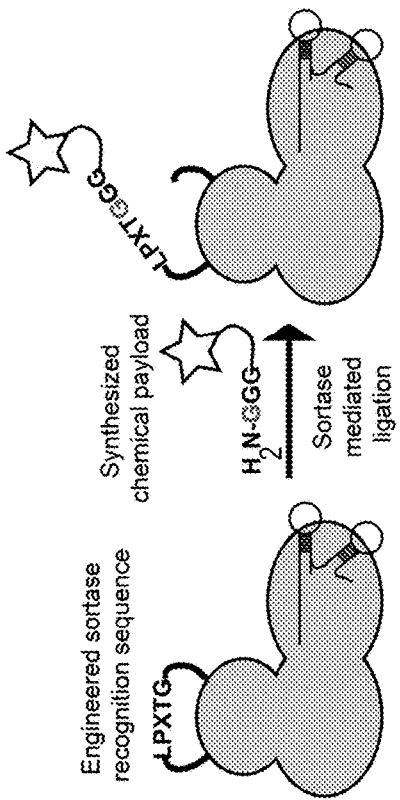
FIG. 3C is a graph showing expression of Cas9-SortLoops in mammalian cells illustrating retention of activity by next-generation sequencing.
Figure 3D:
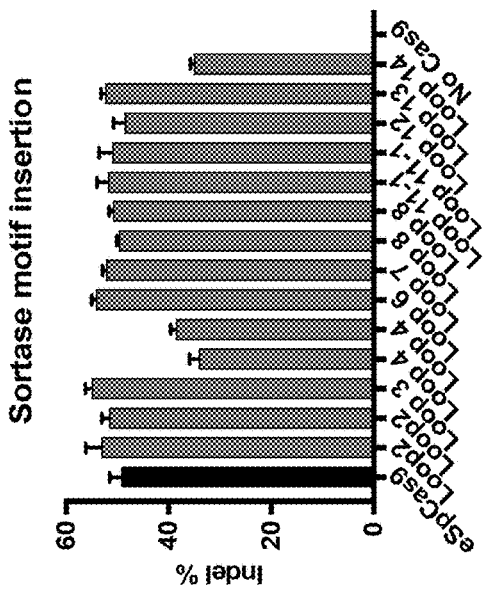
FIG. 3D is a gel electrophoresis image showing that recombinant expression and purification of MBP-Cas9 containing SortLoop #7 exhibits some labeling of a biotin-containing poly-glycine peptide (GGG-Bio).

Cas9 has also been engineered to accommodate a single sortase recognition sequence (Leu-Pro-Xxx-Thr-Gly (SEQ ID NO: 1)), where Xxx is any amino acid). Sortase is a transpeptidase that cleaves its recognition sequence between Thr-Gly, and ligates an acceptor peptide containing an N-terminal glycine to the newly formed Thr carboxylate (FIG. 3A). Thus, by engineering sortase recognition sequences onto Cas9, any chemical payload can be site-specifically conjugated to Cas9. Insertion sites were biased toward regions previously validated as cut sites for split Cas9, particularly those for which the N and C fragments have been shown to have a high affinity for each other. Several sites on Cas9 were identified where single sortase recognition sequence can be appended-some of these sites overlap with those used for cysteines in Example 4 (FIG. 3B). Expression of these sortase loop-containing Cas9 variants (Cas9-SortLoop) in mammalian cells verified that most retained activity compared to wtCas9, as validated by next-generation sequencing assays quantifying insertion/deletion (indel) mutations events against EMX1 (FIG. 3C). Sortase-mediated labelling of a model biotin-containing poly-Gly peptide for SortLoop #7 was confirmed (FIG. 3D). These studies confirm that incorporation of sortase loops on Cas9 does not perturb activity and that sortase chemistry can be used for labeling of Cas9.

Example 6—Demonstration of NHEJ Inhibition by Small-Molecules

Several known NHEJ inhibitors were synthesized or acquired, and preliminary structure-activity relationship studies were performed to determine potential sites for linker attachment. For example, for SCR7 it was envisioned that the aryl rings could be potential attachment sites for the linker and thus analogs bearing various groups at this site were synthesized. For simultaneous detection of HDR and NHEJ, a ddPCR reported by Miyaoka et al. was used. This assay uses three probes that target different regions of the same amplicon. The first, a reference probe (FAM-labeled) that binds away from the mutagenesis site, counts all genomic copies of the target. The second, an NHEJ probe (HEX-labeled) binds the nuclease cut site on the genomic DNA and has a wt sequence. If the nuclease-induced strand break is repaired by NHEJ, the NHEJ probe loses its binding site resulting in loss of HEX signal and leaving only the FAM signal of the reference probe. The third probe (also FAM-labeled) binds the desired HDR point mutation site, causing an additional gain in FAM signal when precise edits are made through HDR.

The efficacy of several reported NHEJ inhibitors and their analogs were tested in reducing repair through the NHEJ pathway using the ddPCR assay (FIG. 14A). ddPCR assay was used for point mutagenesis in RMB20, a gene important in hereditary cardiomyopathy following reported procedure. Briefly, HEK293FT cells were transfected with a plasmid expressing Cas9, a guide RNA, and a sense donor oligo with the desired point mutation. Cells were treated with various doses of the small-molecules immediately after transfection. Genomic DNA was extracted 72 hours after transfection, and ddPCR reactions were performed as described previously. Dose-dependent inhibition of NHEJ was seen as previously reported and also observed toxicity at doses above 4 µM in some cases. The data in FIG. 14B represents the most potent non-toxic inhibition attainable by these compounds. Interestingly, the SCR7 analog (PK 76) was found to be the most potent, inhibiting >50% of NHEJ at the target site. It is envisioned that local concentration of PK 76 at the target site will be much lower than 0.5 µM and that Cas9 display of this analog will lead to potent local inhibition of NHEJ.

Example 7—Identification of ~10-15 Single-Cysteine Mutants that are as Active as Wt Cas9

Six conjugation sites on Cas9 have already been validated and several sites have been identified where sortase loops can be appended without loss of activity. The ultimate goal is to generate ~10-15 single-cysteine mutants scanning all the domains of Cas9. Towards this end, additional 9 conjugation sites distributed throughout Cas9 have been identified following rational design and methods (FIG. 15A, 15B). Subcloning of a cysteine-free Cas9 can be performed to produce additional nine mutants containing a single cysteine. Efficient labelling using biotin-maleimide and whether these variants retain activity can be confirmed (no lower than 20% drop in activity compared to wt Cas9).

Example 8—Identification of Optimum Sites for Display of ssODN, NHEJ Inhibitors, and HDR Activators ~10 conjugates for each Cas9-ssODN, Cas9-NHEJ inhibitor, and Cas9-HDR activator will be generated. These conjugates will be tested in the ddPCR assay described above to identify the top two conjugates of each category that significantly enhance HDR. ssODN are typically >100 nucleotides and may have diverse secondary structures, which make chemical conjugation inefficient. Also, maleimide-containing ssODNs are expensive and difficult to obtain in high quantities. Therefore, short adaptor maleimide-oligonucleotides (~15 nucleotides) can be conjugated to Cas9 and hybridized with the long ssODN donor. For NHEJ inhibitors and HDR activators, NHEJ inhibitors tested above (e.g., SCR7 analogs, KU inhibitor KU-0060648) and HDR activators (e.g., RS1) will be synthesized to bear linkers (e.g., PEG) and a maleimide for chemical conjugation to Cas9 (FIG. 15C). Conjugation sites on SCR7 have already been identified where modifications do not affect potency. The linker-modified NHEJ inhibitors or HDR activators will be confirmed to retain activity in cells using ddPCR assay (<15% drop in activity). These studies will allow for the identification of top 2 conjugates for NHEJ inhibitors and HDR activators. The activity of the top six conjugates will also be confirmed in the "traffic light reporter" assay following the reported procedure.

Example 9—Multivalent Display of Top NHEJ Inhibitor or HDR Activator on Cas9

To further amplify the effect of NHEJ inhibitors/HDR activators on HDR efficiency, multiple moieties of NHEJ inhibitor or HDR activators will be displayed separately on Cas9. Multivalent display system shall consist of at the least 3 NHEJ inhibitors or HDR activators, and their activity shall be assessed in the ddPCR assay. For multivalent display, the scaffold recently described by Muir and co-workers will be used as they are easy to synthesize (FIG. 15D).

Next, a combination of NHEJ and HDR multivalent systems will be tested to confirm if simultaneous display enhances HDR efficiency over individual components (i.e., synergism). If synergism is observed, a multivalent display system consisting of NHEJ inhibitors and HDR activator conjugates will be synthesized and tested in the ddPCR assay and traffic light reporter assay.

Example 10—Simultaneous Display of ssODN, NHEJ Inhibitors, and HDR Activators

Following the identification of the most optimized systems for ssODN, NHEJ inhibition, and HDR activation, a synthetic Cas9 bearing all the three components will be generated. Simultaneous orthogonal conjugation of the three components can be challenging, and multiple orthogonal conjugation strategies can be used: cysteine-maleimide, sortase chemistry, and unnatural amino acids bearing groups with orthogonal reactivity to cysteine and sortase (FIG. 15B). For unnatural amino acid mutagenesis, genetic code expansion can be utilized by adding an engineered pyrrolysyl tRNA (PylT)/tRNA synthetase pair to the translational machinery of cells to enable the site-specific incorporation of p-Acetyl Phenylalanine (pAcF) into CRISPR/Cas9. This method relies on a unique codon-tRNA pair and corresponding aminoacyl tRNA synthetase (aaRS) for each unnatural amino acid that does not cross-react with any of the endogenous tRNAs, aaRSs, aminoacids or codons in the host organism. The ribosome translates mRNA into a polypeptide by complementing triplet-codons with matching aminoacylated tRNAs. Three of the 64 different triplet codons do not code for an amino acid, but cause recruitment of a release factor resulting in disengagement of the ribosome and termination of the synthesis of the growing polypeptide. These codons are called; ochre (TAA), opal (TGA), and amber (TAG). Of the three stop codons, the amber codon is the least used in E. coli (~7%) and rarely terminates essential genes. Amber suppression codons will be placed at the optimal sites identified above. While pAcF is proposed to be used as the unnatural amino acid that can react with aminooxy group, tetrazine chemistries which are also high yielding and orthogonal to the reactivity of pAcF, cysteines, and sortase will also be explored. It is noted that multiple reports for incorporation of unnatural amino acids in Cas9 exists in literature.

SynGEMs will be benchmarked for activity, specificity, and HDR enhancement against wt Cas9, as well the reported Cas9 conjugates bearing ssODN. For activity, an eGFP disruption assay (FIG. 13F) as well as next-generation sequencing experiments (target locus EMX1) as reported previously. Both wt Cas9 and SynGEMS will be delivered as ribonucleoprotein complex following reported procedures. Only those SynGEMs generated which do not reduce Cas9 activity by >20% will be chosen. Altering linker length in many cases will allow for prevention of the loss of activity. For specificity, off-target and on-target activity can be measured using BLESS and GUIDE-seq. An increase in off-target activity is not anticipated as our conjugation sites are positioned at locations not involved with sequence recognition. If necessary, SynGEMs using the reported high-fidelity Cas9 variants may be generated. The main focus is to demonstrate significant HDR enhancement. Based on the reported activities of NHEJ inhibitors, HDR activators, and ssODNs, It is anticipated that the SynGEMs will induce >80% incorporation of the donor DNA at double-strand break sites as measured by the ddPCR assay.

Activity, delivery, and specificity of SynGEMs will be optimized in disease models available via SCGE consortia. Proof-of-principle experiments can be performed to demonstrate precision genome editing of SynGEMs in cell-lines (e.g., HEK293T cells). It is possible that these optimized conditions for delivery, activity, specificity, and HDR enhancements may not transfer to primary cells, and work can be performed together with the SCGE consortia to optimize the activity of the SynGEMs and make them available to SCGE performers on demand. A large pool of SynGEMs that have been assembled, as well our large knowledge base of optimized parameters acquired from proof-of-principle studies will be leveraged.

Example 11—Arg Cysteine Conjugation

The conjugation via cysteine and unnatural amino acid mutagenesis will be high yielding, this may not be the case for conjugation via sortase. A new conjugation chemistry was developed by generating two types of cysteines that differ widely in their reactivity in the presence of a catalyst (FIG. 16A). Briefly, one cysteine type is surrounded by arginine (called "Arg cysteine"), and the other cysteine is surrounded by aspartic acid (called "Asp cysteine"). The cysteine surrounded by Arg has a lower pKa owing to stabilization of conjugate base and is more reactive than Asp cysteine. It was hypothesized that because the nucleophilic attack of a cysteine thiol on an electrophile is general base-catalyzed, increasing the effective molarity of the base catalyst around "Arg-cysteine" will dramatically increase their rate of nucleophilic attack over those of "Asp-cysteine." By using polycarboxylates (e.g., citric acid, mellitic acid) that interact with arginines through salt-bridges (FIG. 16B) and that can also act as a base catalyst, we demonstrated substantial selective enhancement of "Arg-cysteine" reactivity over that of "Asp-cysteine" was demonstrated (FIG. 16C). These cysteines with disparate reactivity were proposed to be deployed should sortase chemistry be low yielding.

Example 12—Develop Three Classes of miniGEMs

Different classes of genome editors can be developed in which a DNA sequence reader (i.e. PNA) is connected to a small-molecule synthetic nuclease that can induce strand-breaks or modify DNA (FIG. 17A, B, D). Many natural products and synthetic small-molecules display functional groups that induce single-strand DNA breaks with a wide variety of mechanisms. These small-molecule synthetic nuclease have several attractive features. First, they are typically <500 Da and the key reactive functional group is even smaller. Second, many of these small-molecule nucleases are modular. For example, while display of a single unit of the reactive functional group (diazofluorene) yields a single-strand breaker (e.g., Lomaiviticin C), display of two diazofluorene groups results in a double strand breaker (Lomaiviticin A) Third, some of these nucleases can be envisioned as split nucleases, as the key reactive group can be split into two fragments which must be brought together to reconstitute the strand-scission activity. Fourth, several of these small-molecules require a specific trigger (e.g., reducing agent, light) to initiate strand breaks (FIG. 17C, kinamycin C). Fifth, some of these strand-breakers operate by diffusible radicals (e.g., hydroxyl) which may interact with a backbone of both strands inducing double-strand breaks. On the other hand, others operate by carbon-centered radicals on the small-molecules, which are not as diffusible as small hydroxyl radicals. These carbon-centered radicals are often single-strand breakers. Interestingly, some natural products (e.g., enediynes) can generate two carbon-centered radicals allowing them to break double strands (FIG. 17C, Dynemicin).

Three different classes of miniature genome editors can be developed by exploiting the aforementioned advantages. In Class I (FIG. 17A), a PNA can be conjugated with a double strand breaking small-molecule. The class II (FIG. 17B) editor involves two PNA molecules, each bearing a fragment of the split-small molecule nucleases. For example, the zinc-complex (FIG. 17C) has two ligands and one can envision an editor where PNA strand bears the phenanthroline ligand while the other bears the remaining zinc complex. Similarly for the iron complex, the catechol moiety can be on PNA while the iron ion can be borne by the other PNA. In these two cases, it can be envisioned that the DNA acts as template for facilitating the coming together of two reactive components—a strategy that has been employed for DNA templated synthesis of molecules. Here, the high effective molarity drives a reaction that otherwise would not proceed efficiently in absence of the DNA template. A second type of Class II editors can also be developed in which one of the PNA strands will bear an inactive small-molecule while the other PNA will bear the trigger. For example, Kinamycin C and Dynemicin require a reducing agent (e.g., TCEP, GSH) to generate the carbon-radicals necessary for the strand cleavage.

Following double-strand breaks, the cell's repair machinery kicks in a highly heterogeneous repair response involving several protein complexes. Even in homogenous cell population, this may result in differing editing outcomes across different cells. Biasing the repair to a single outcome would necessitate perfect synchronization of the repair machinery across the entire cell population—a daunting task given the inherent stochasticity and large number of molecular players involved. Further, the synchronization method will not be general as different repair players are involved in different cell types. However, if the repair is merely dependent of on ligation, then biasing the outcome to a single event will be relatively easy. To accomplish this goal, Class III editors can also be developed (FIG. 17D). These editors will induce four precisely spaced nicks on the genomic DNA, excising ~20 base pairs fragment and leaving behind high-affinity "sticky ends." Simultaneously, this editor will facilitate delivery of a high-concentration of an exogenous DNA (~20 base pair) that will hybridize to the sticky ends and be inserted into the genome. Here the fact that the single-strand breaking small-molecules can be positioned at any site on the PNA will be leveraged, essentially allowing the introduction of any type of DNA break.

Synthesis of Various Classes of Small-Molecule Strand Breakers and DNA Modifiers Synthesis of several classes of small-molecules have been completed (FIG. 18A-18G). Described below are structural and mechanistic features of each class of synthetic nucleases:

Diazofluorenes. This class includes the natural products lomaiviticins C, A and kinamycins that contain the diazofluorene functional group. Some of these synthetic nucleases induce break upon stimulation by reducing agents. Nucleophilic addition to electrophilic diazofluorene triggers homolytic decomposition pathways that produce carbon-centered radicals from the diazo group. These radicals abstract hydrogen atoms from the deoxyribose of DNA, a process known to initiate strand cleavage.

Nitracrines. These compounds induce DNA strand breaks via intercalation. The polyaromatic chromopore of nitracrine confers a planar structure, allowing them to intercalate into DNA by stacking between base pairs. This process driven by stacking and charge-transfer interactions between the aromatic systems of the nitracrine compounds and the DNA bases, resulting in unwinding of the helix.

Metal complexes. Over last two decades, chemists have designed and synthesized 1000 metal complexes that cleave DNA by various mechanisms. Broadly, these complexes cleave DNA by either hydrolytic or oxidative mechanisms. The hydrolytic mechanisms are reminiscent of those encountered in nucleases where metal chelates the phosphate backbone making them prone to hydrolysis by a nearby base (usually a hydroxide ion). Oxidative cleavage mechanisms may involve reactive oxygen species (e.g., hydroxyl radical) or other diffusible oxidant. Singlet oxygen ($^1O_2$) is another radical species derived from oxygen, which is often involved in the oxidative cleavage of DNA with energy transfer. Oxidative cleavage has to be carefully controlled as the radicals can diffuse to non-target sites. Metal complexes that operate via hydrolytic mechanism are prioritized.

Enediynes. This class of natural products is characterized by either nine- and ten-membered rings containing two triple bonds separated by a double bond. Some examples include calicheamicin, esperamicin, dynemicin and neocarzinostatin. These natural products exhibit DNA cleavage activity through the generation of active biradical species via Bergman cyclization. In addition, the neocarzinostatin chromophore, which does not contain the classical conjugated enediyne system, demonstrates a very similar DNA cleavage mechanism via the generation biradical species through the Myers-Saito cyclization. Some enediynes are stable until they interact with DNA and subsequently become activated. After binding to minor groove, a nucleophile (eg: glutathione) attacks the central sulfur atom of the trisulfide group, resulting in the formation of a thiol which then performs an intramolecular Michael addition onto the proximally positioned Œ ±,Œ ≤-unsaturated ketone moiety to unlock the enediyne warhead. This reaction converts the trigonal bridgehead position to a tetragonal center leading to a significant change in structural geometry that induces strain on the 10 membered ring. Bergman cycloaromatization of the enediyne structural motif relieves the strain in the molecule while generating a highly reactive benzenoid diradical. This diradical then abstracts hydrogen from both strands of the duplex DNA leading to a double stranded break.

DNA modifiers. Cas9 is a single-turnover enzyme that essentially covalently binds to the substrate DN. Prying-off Cas9 from substrate DNA requires unusually harsh treatments of denaturing agents, protease, and RNAase. These lead us to speculate that small-molecules that form adducts with DNA or modify DNA could also be employed for genome edits. DNA modifier such as methoxsalen intercalates DNA and upon photoactivation forms [2+2] cycloadducts with adjacent bases. Daunorubicin is oxidized to semi-quinone, an unstable metabolite with the release of reactive oxygen species, which are also release by Juglones.

Figure 19A:
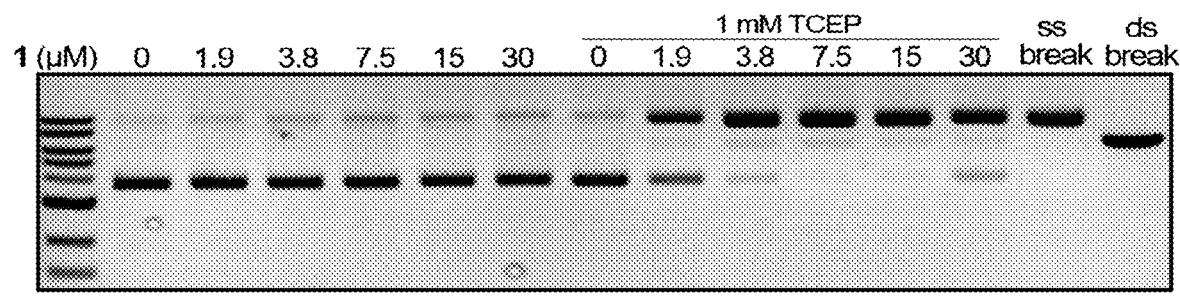
FIG. 19A is a gel electrophoresis image showing in vitro plasmid cleavage by Lomaiviticin C under non-reducing or TCEP-based reducing conditions at 37° C.
Figure 19B:
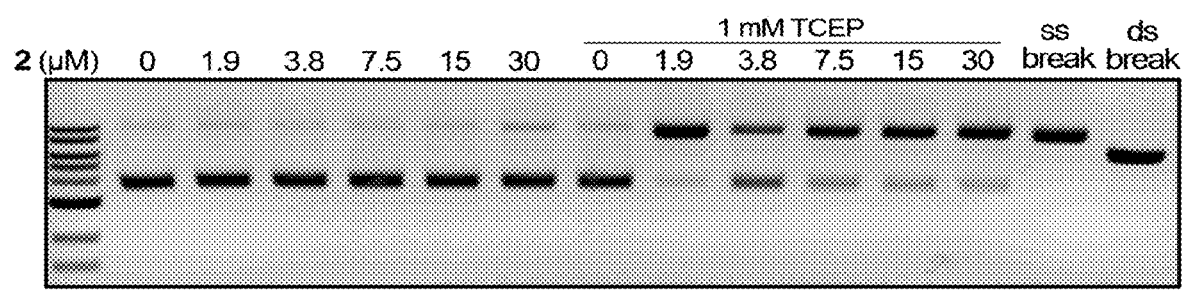
FIG. 19B is a gel electrophoresis image showing in vitro plasmid cleavage by FL-120B under non-reducing or TCEP-based reducing conditions at 37° C.
Figure 19C:
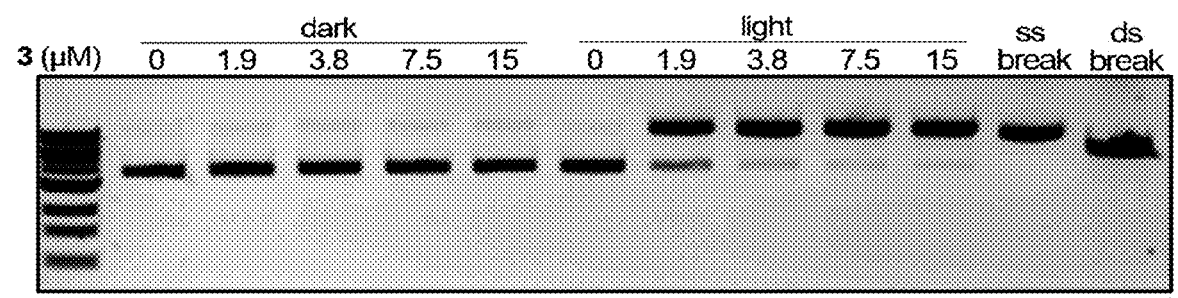
FIG. 19C is a gel electrophoresis image showing in vitro plasmid cleavage by nitracrine under dark or light conditions on ice.
Figure 19D:
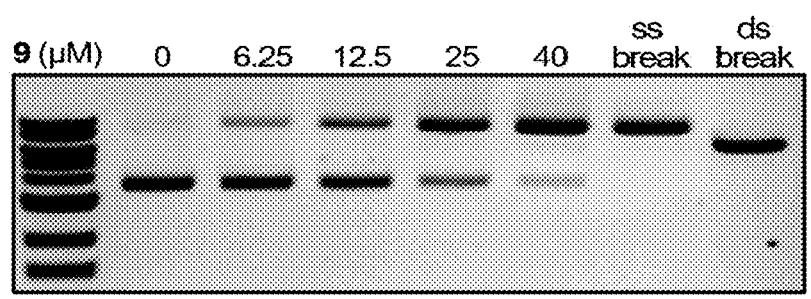
FIG. 19D is a gel electrophoresis image showing in vitro plasmid cleavage by iron complex 37° C.
Figure 21:
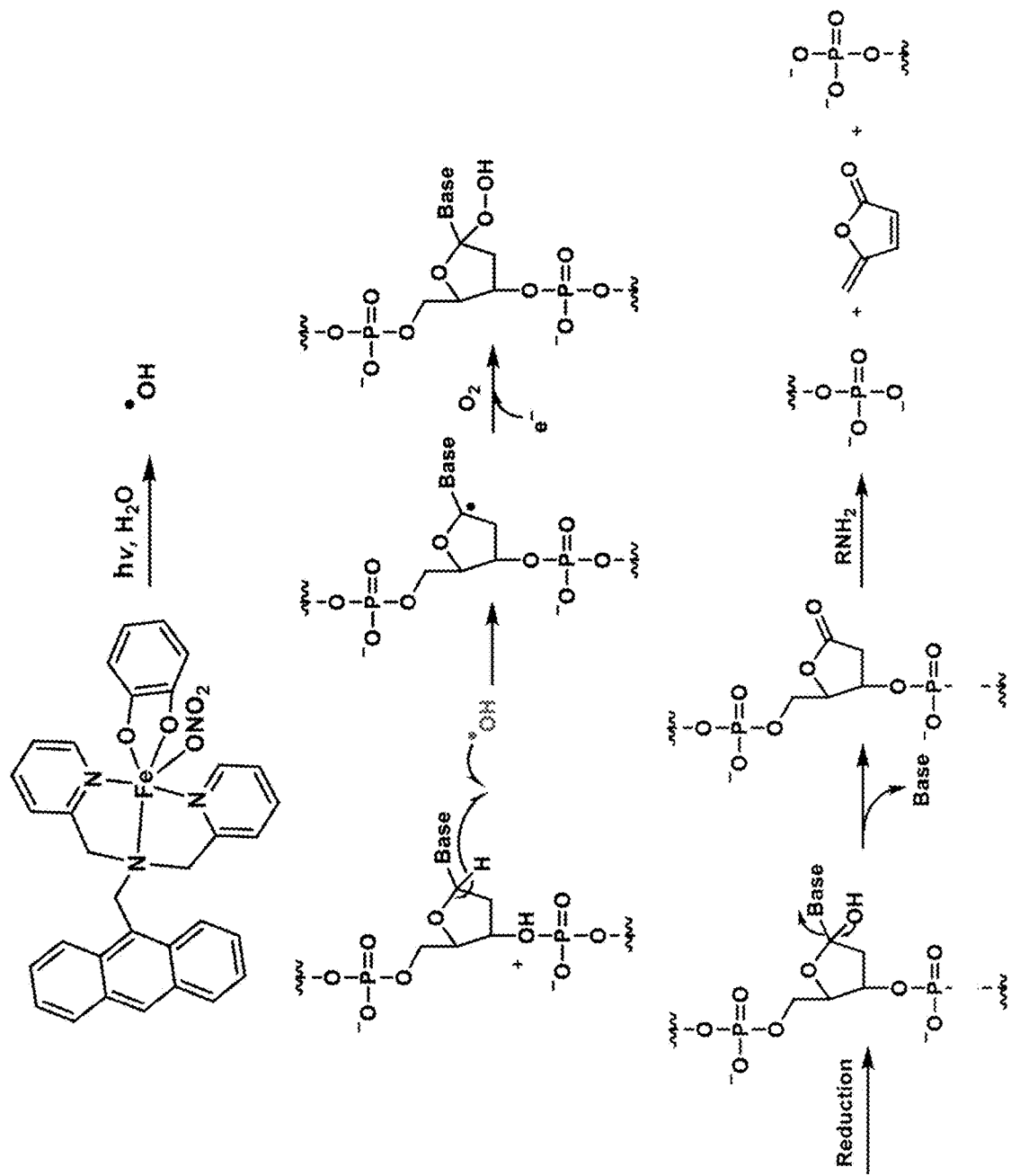
FIG. 21 is a diagram showing that some metal complexes induce strand breaks by locally generating hydroxyl radicals.
Figure 22:
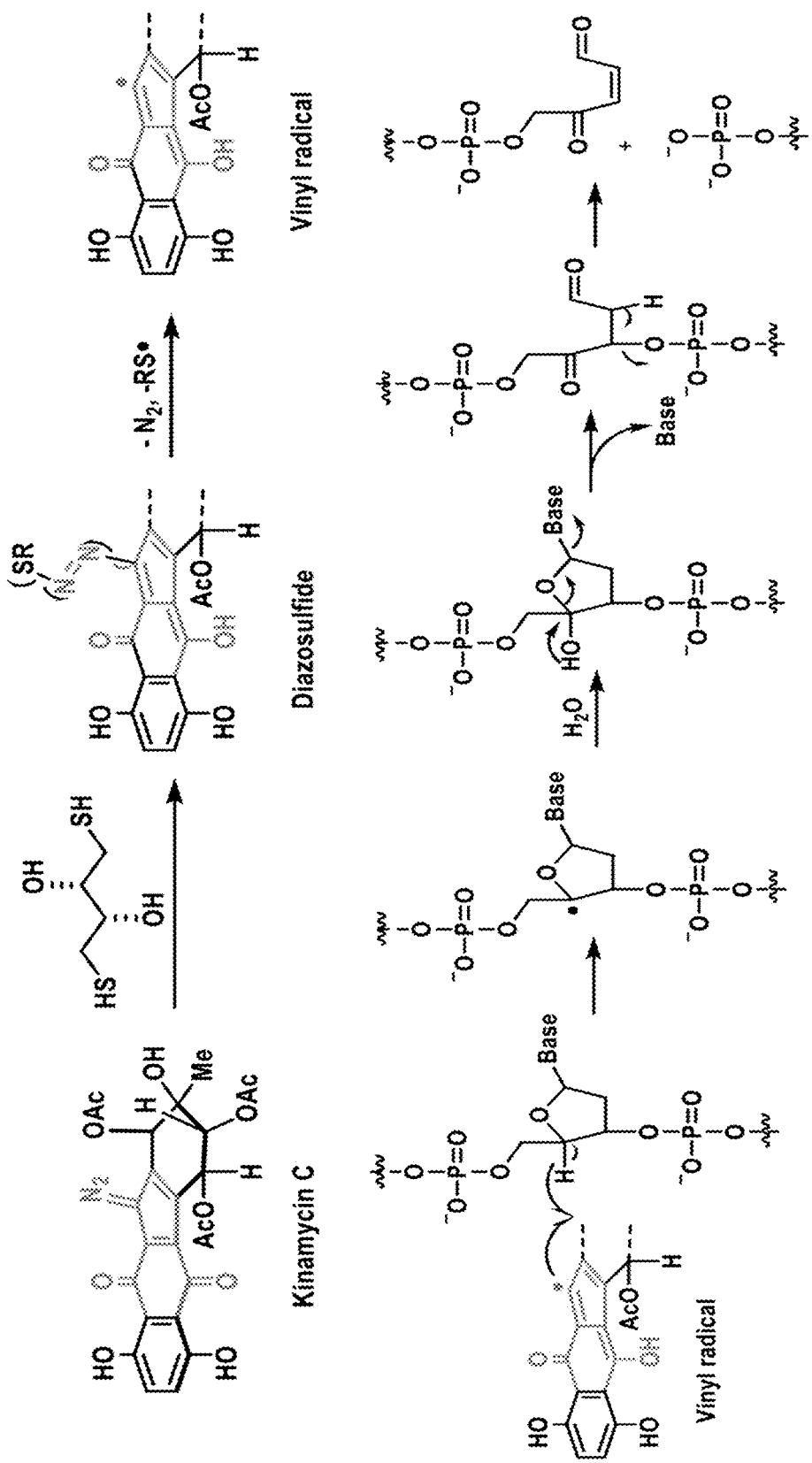
FIG. 22 is a diagram demonstrating that kinamycin C uses carbon-centered radical for strand breaks.
Figure 23:
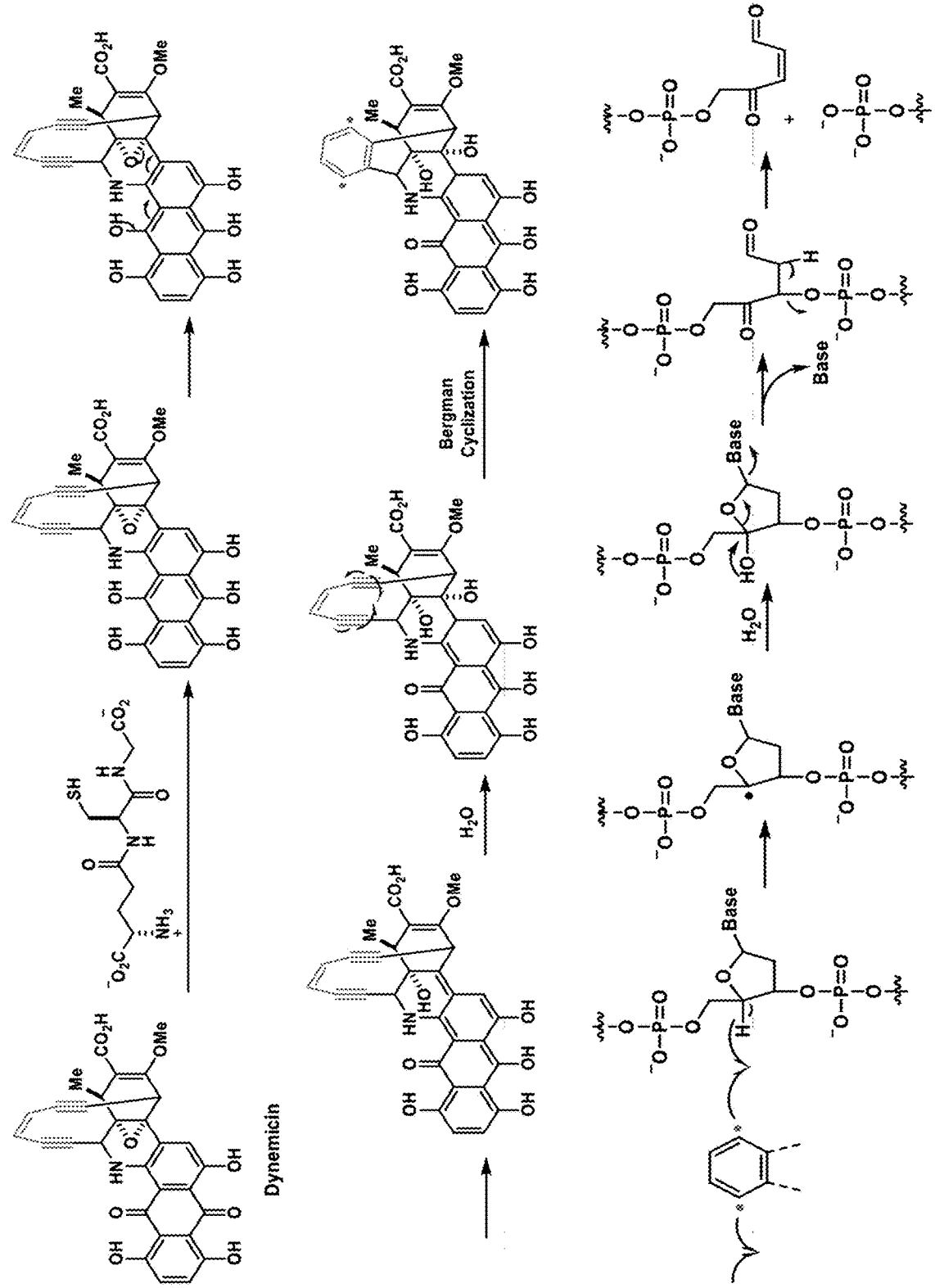
FIG. 23 is a diagram showing that dynemicin A requires reducing agent and generates biradicals.
Figure 24:
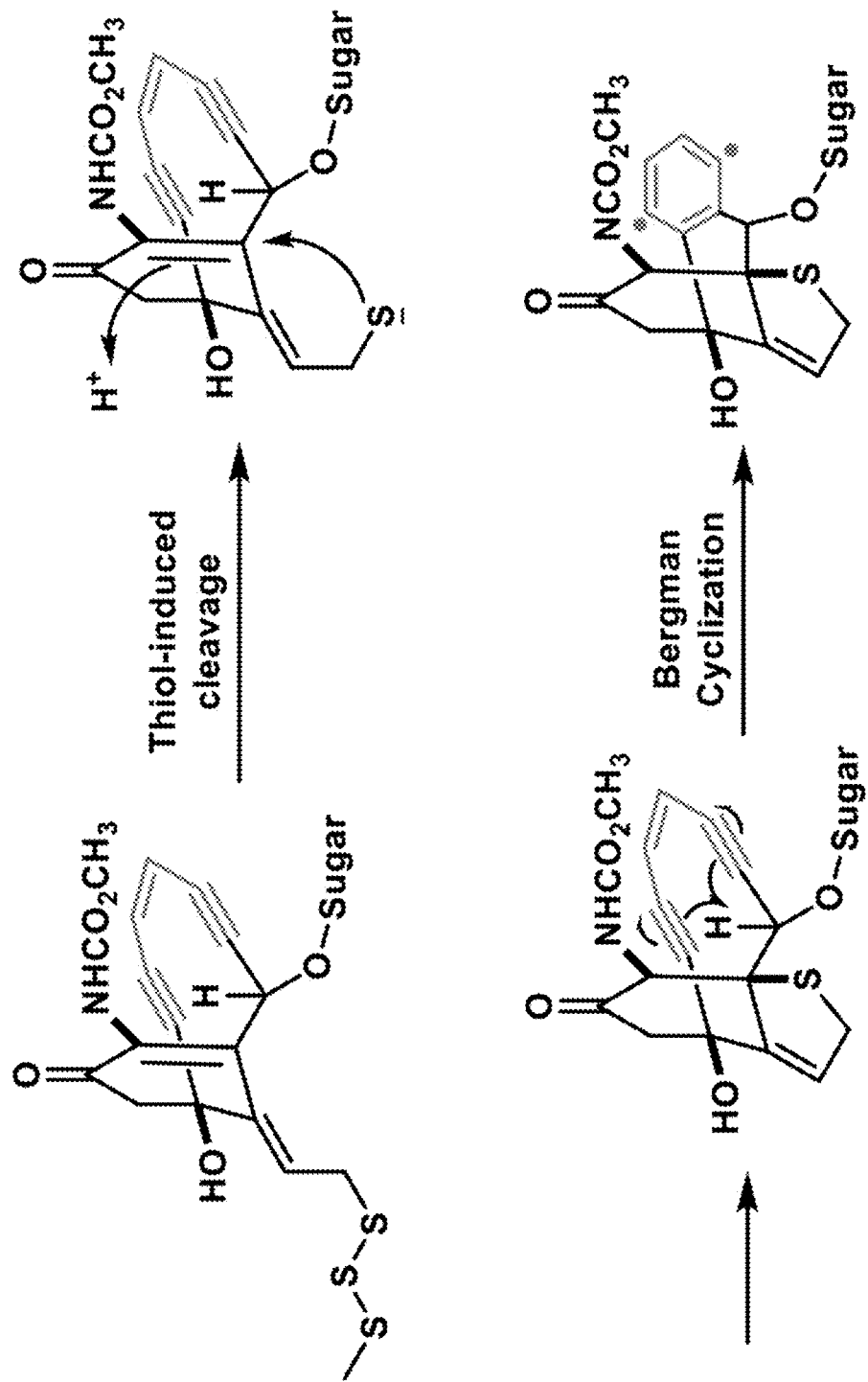
FIG. 24 is a diagram showing that calicheamicin requires a nucleophilic trigger to generate biradicals.
Figure 25A:
FIG. 25A is a schematic showing design strategy to covalently label adaptor, then ssODN binding by base pairing.
Figure 25B:
FIG. 25B is a diagram depicting selection of Cas9 residues based on its crystal structure. A short DNA adaptor (17 nucleotides) was covalently attached to Cas9 using thiol-maleimide chemistry. Cas9 was engineered to have a single cysteine at the desired site, then the mutant was reacted with the adaptor DNA having maleimide functionality. Therefore, we Cas9 was able to be site-specifically labeled with the adaptor DNA. Then long ssODN was bound to the adaptor simply by base pairing. This strategy is used because long ssODN (up to 200 nucleotides) is not commercially available (or very expensive) in maleimide-modified version. In addition, long ssODN tends to have diverse secondary structures, which might hamper the reaction with the protein. Labeling sites have been chosen based on the crystal structure of Cas9-gRNA-dsDNA complex (PDB ID: 5F9R). Because displaced DNA strand (green top right strand in FIG. 25B) is supposed to be the first binding site to ssODN, Cas9 was labeled around the displaced DNA strand.
Figure 28A:
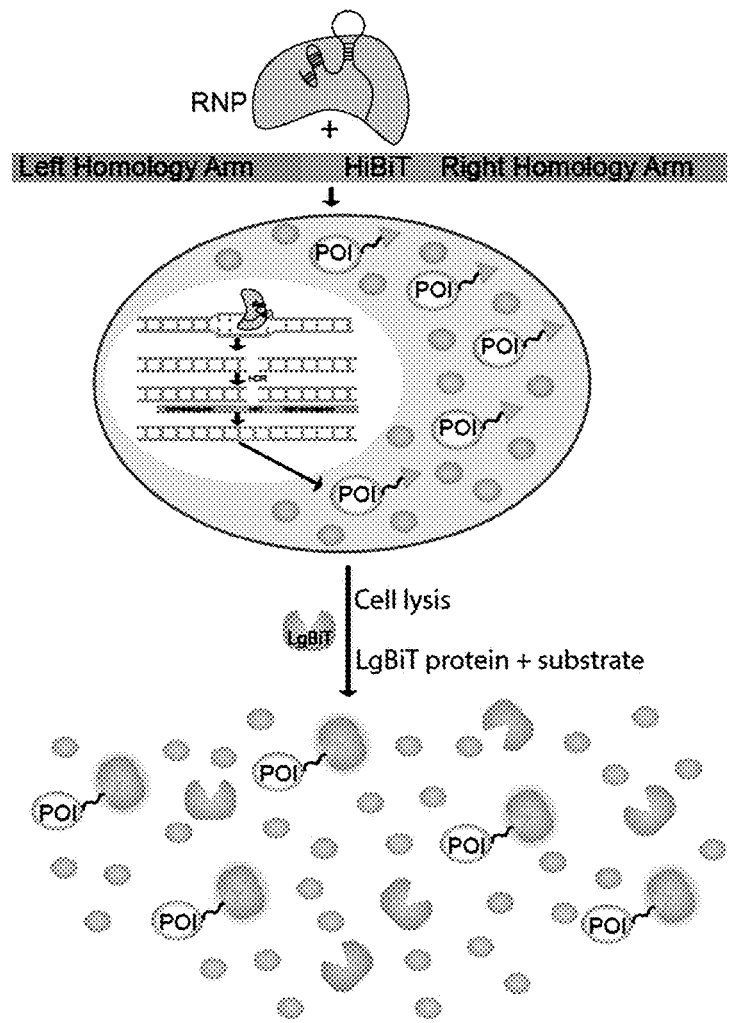
FIG. 28A is a cartoon showing the HiBiT assay scheme.
Figure 28B:
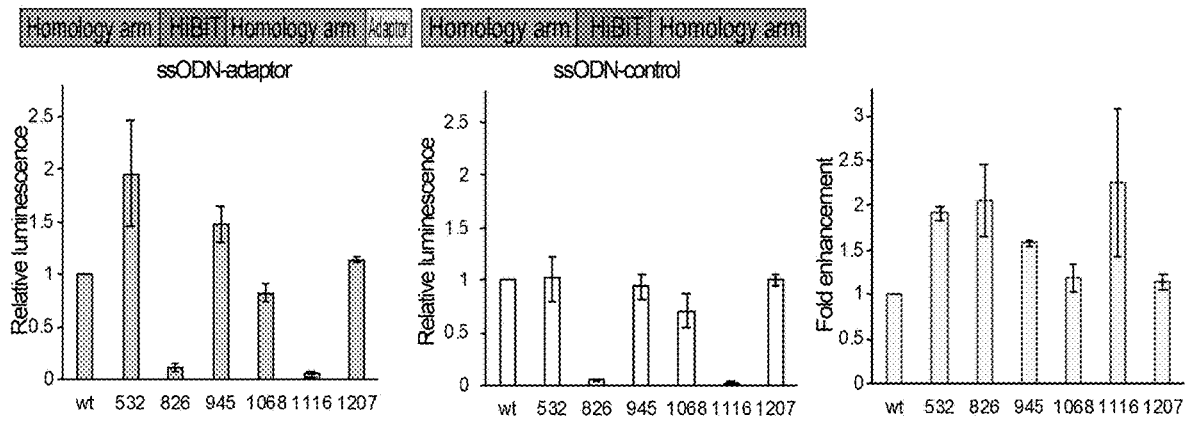
FIG. 28B are a set of graphs showing results in U2OS cells of various mutants. It was determined whether ssODN conjugation can increase HDR efficiency in U2OS cells. 'HiBiT assay' (from Promega) was used to check the HDR efficiency. It is a luciferase complementary assay. Cas9 ribonucleoprotein (RNP) complex was delivered into cells together with ssODN, which results in the HDR-mediated insertion of small HiBiT sequences (33 bases) at the end of the GAPDH gene. Therefore, cells can express GADH fused with HiBiT tag (11 amino acids, which is a fragment of the luciferase) at its C-terminus. Twenty-four hours after transfection, cells are lysed and the other luciferase fragment is added to the lysate, which results in the reconstitution of the functional full luciferase. Luminescence signal from this mixture is proportional to the HDR efficiency. This assay was conducted using various Cas9-ssODN conjugates and their activities were compared with that of wild type protein.
Figure 31:
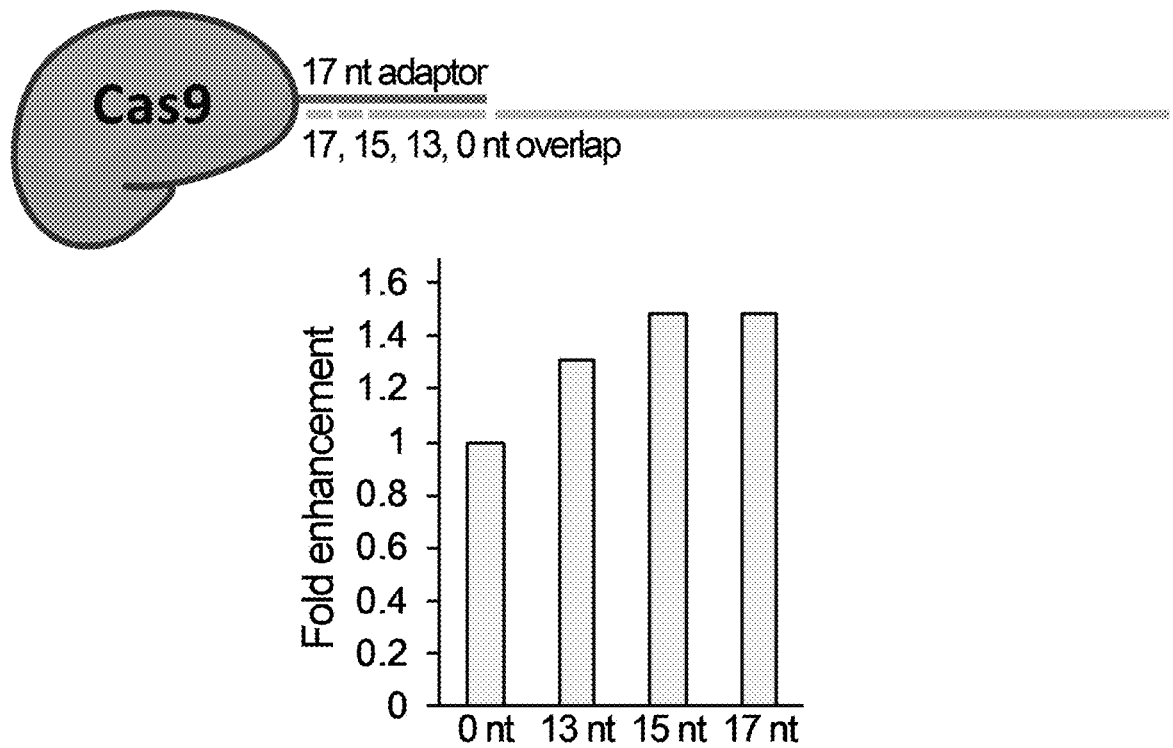
FIG. 31 is a graph showing effect of the adaptor length. The effect of the length of the base pairing between adaptor and ssODN was checked. Adaptor length was set at 17 nucleotides, but the corresponding ssODN had different length of overlap (0, 13, 15, 17 nt). As can be seen from the graph, shorter adaptor might not ensure base pairing between the protein and DNA, which resulted in less efficient HDR. 15 nt seems to be long enough.

DNA cleavage activity of synthetic strand breakers. A series of small molecule DNA strand breakers having diverse structures and cleavage mechanisms were tested (FIG. 19A-19D). A supercoiled plasmid was used as a model substrate DNA, as both single and double-strand breaks can easily be detected using gel electrophoresis. Lomaiviticin C and FL-120B cleave DNA at low micromolar concentrations and this is accelerated by a reducing agent (FIG. 19A, 19B). Nitracrine cleaves DNA when irradiated by light (FIG. 19C). DNA cleavage by an Iron complex was also observed (compound 9, FIG. 19D).

Synthesis and Biochemical Studies of DNA Cleavage Activity of Synthetic Strand Breakers Synthetic nucleases will continue to be synthesized and tested. The goal is to identify examples of synthetic nucleases with potencies ranging from low (>10 µM), medium (0.5-10 µM), and high (<1 nM) with single or double-strand cleavage activity. The focus will be on hydrolytic metal complexes and a large body of available literature will be leveraged. For example, Ce(IV)2-HXTA is among the most reactive bimetallic systems. Interestingly, this complex induced hydrolytic double strand break as well as single strand break with a high regioselectivity favoring the scission of the P-O3' bond. Fe(III)2-DTBP complex is another hydrolytic bimetallic system with cleavage efficiencies reaching those of restriction enzymes. Another example is dinuclear Zn-complexes of heptapeptides. They are active at low concentrations, and can induce both single and double strand breaks.

For split systems, a large body of structure-activity relationship data available for metal complexes will be leveraged. It is also noted that several other strategies exist for bringing two ligands together. For example, one can envision a set of ligands bearing reactive functional groups that do not react unless present at high-effective molarity akin to the DNA-template synthesis reactions. It is also noted that bimetallic complexes where each PNA bears the mononuclear complex can be used. In fact, both bimetallic zinc and iron-based complexes have been generated where proximity-induction is mediated by light and is key to the nuclease activity.

Conjugation of Strand-Breakers to PNA

In the PNA based genome editor that is envisioned, the PNA serves as the designer DNA reader that can be customized to target any desired genomic sequence while the DNA strand breaks will be induced by synthetic nucleases. This requires covalent conjugation of the small molecule DNA strand breakers to the PNA. Previous work on labeling PNA with small molecules have mainly focused on attachment of fluorophores or psoralen (DNA intercalator), chlorambucil (DNA alkylating agent) and camptothecin (Topoisomerase I inhibitor). Fluorescence labeling of PNAs has been achieved at both the N and C terminus by several groups employing diverse strategies. Mayfield and Corey have described labeling of the PNA N terminus with an activated carboxylic acid derivative of the fluorophore as the last step in solid phase synthesis. An alternative is to use custom monomers, such as lysine conjugated with fluorescein at the Œ µ-amino group as demonstrated by Lohse et al. and Muse et al. Custom made monomers can also be used in labeling of the C-terminus. For instance Liu et al. achieved C-terminal labeling of PNA by loading the solid support with S-t-butylmercapto-L-cysteine allowing conjugation of the thiol group with maleimido functionalized rhodamine dye directly on solid support. Alternatively, an Œ µ-amino-lysine-dye conjugate can be attached to solid support as the first step of PNA synthesis yielding the C-terminus labeled product as demonstrated by Robertson et al. Seitz et al. and Robertson et al. have also described labeling of PNA after its solid phase synthesis. While this is a viable alternative, it involves changes in the PNA structure and is time consuming. Additionally, Kim et al. and Birkedal et al. have described the conjugation of psoralen, chlorambucil and camptothecin to the N-terminus of PNA linked by an ethylene glycol linker. Inspired by these approaches, we will design our small molecules strand breakers to include maleimide, azide or alkyne functional groups while installing a PEG linker with thiol, alkyne or azide functional handles on the PNA respectively to allow for efficient conjugation. Further, by varying the length of the PEG linker, it is possible to effect the DNA cut close to or away from the PNA binding site, which provides additional flexibility in designing the DNA cut sites. To create staggered double stranded breaks on the DNA, two PNA molecules will be conjugated to single strand breakers at both N and C termini designed to bind the target DNA in a staggered fashion. This will effect four staggered cuts in the DNA such that the donor DNA with complementary staggered ends can anneal to bring about precise genomic modification without involving DNA repair pathway.

Biochemical and Cell Based Validation of PNA-Strand Breaker Conjugates

The activity of the small molecule-PNA conjugates in effecting single and double stranded DNA breaks will be assessed by using a modified version of the previously reported in vitro DNA repair assay with the supFG1 reporter gene. The small molecule strand breaker-PNA conjugates will be designed to bind the supFG1 reporter gene based on the design of the triplex forming PNA described previously. For small molecules that introduce single strand breaks, two PNAs will be used such that the single strand breaks are staggered. Small molecule-PNA conjugates and supFG1 reporter plasmid will be incubated in 10 mM Tris (pH 7.5) at 37° C. Site specific DNA strand cleavage will be identified at different time points by gel electrophoresis of the supFG1 reporter plasmid compared to a negative control plasmid that lacks the PNA binding sites.

Upon validation of the small molecule strand breaker-PNA conjugates in the biochemical assay, activity of these conjugates will be tested in a cell-based system. For this purpose, an EGFP to BFP conversion assay will be employed described by Glaser et al. In this assay, the chromophore of EGFP is targeted by the Cas9-gRNA system and the donor repair template is provided in the form of a single stranded repair template resulting in three nucleotide changes (194C>G, 196T>C and 201C>G). The small molecule strand breaker-PNA conjugates will be designed to target the same region of EGFP chromophore as that of the guide RNA and use the donor sequence as described by Glaser et al. Loss of EGFP fluorescence in absence of the donor template will indicate efficient and site specific DNA cleavage by the PNA conjugate. Similarly, gain of BFP fluorescence will indicate site-specific genome editing mediated by the small molecule-PNA conjugate. Further, this assay can be employed to detect increase in HDR frequency as indicated by an increase in BFP fluorescence upon conjugation of NHEJ inhibitors/HDR activators to PNAs.

HDR Enhancement Using miniGEMs.

Upon identification of the best-performing PNA-strand breaker conjugates, NHEJ inhibitors and HDR activators will be displayed to enhance HDR as discussed. Simultaneous display of NHEJ inhibitors/HDR activators and DNA strand breakers requires multiple attachment sites on the PNA. The peptide backbone of the PNA provides such additional sites of attachment. Work by Sahu et al. describes functionalization of PNA at the Œ ≥position by attachment of (R)-diethylene glycol miniPEG (MP) which transforms a randomly folded PNA into a right handed helix. The right handed helical, R-MPŒ ≥PNA oligomers hybridize to DNA and RNA with greater affinity and sequence selectivity than the parental PNA oligomers. Further, the miniPEG PNA has also been successfully used in ex vivo and in vivo studies for gene editing applications. Therefore, the Œ ≥miniPEG provides us with an additional site of functionalization on the PNA which will be explored for display of NHEJ inhibitors on the PNA. Conveniently, several functionalized PEG linkers (alkyne, azide, cyclooctyne etc.) are commercially available which will be employed for conjugation of NHEJ inhibitors at the Œ ≥position.

Benchmarking miniGEMs Generated Above Against Cas9.

miniGEMs will be benchmarked for activity, and specificity against wt Cas9. For activity, eGFP disruption assay will be used as described above as well as next-generation sequencing experiments (target locus EMX1) as has been reported previously. Both wt Cas9 and miniGEMS will be delivered as complex following reported procedures. Only those miniGEMs generated with comparable activity to that of Cas9 (within ~10%) will be chosen. For specificity, it is proposed to measure off-target and on-target activity using BLESS and GUIDE-seq.

Delivery of miniGEMs In Vivo.

Cellular delivery of PNAs have used Poly(lactic co-glycolic acids) (PLGA) nanoparticles. PLGA is a biodegradable polymer commonly used in drug delivery systems and medical devices. PLGA undergoes hydrolytic degradation into endogenous, non-toxic metabolites (lactic acid and glycolic acid) and has been approved by US Food and Drug Administration (USFDA). Given these attractive properties of PLGA, it is unsurprising that PLGA nanoparticles have been used for cellular delivery of PNAs in several studies. McNeer et al. and Scheifman et al. used PLGA nanoparticles to deliver triplex forming PNAs and donor DNAs for site specific genome editing of CD34+ HPSCs. In another study, McNeer et al. demonstrated the generalizability of this approach by introducing a 6 bp mutation into the CCR5 gene in human hematopoietic progenitor cells. Further, they have also demonstrated delivery in the human Œ ≤-globin gene in mice reconstituted with human hematopoietic cells as well as in an eGFP reporter mouse model providing evidence of direct, in vivo site specific gene editing by PNA-DNA NPs. Although PGLA nanoparticles are widely used in medicine due to its enhanced biocompatibility, it has limited DNA loading capacity. In order to increase, its oligonucleotide loading capacity, cationic polymers such as poly (beta-amino-esters) (PBAE) have been used in combination with PLGA. Bahal et al. have used single-stranded Œ ≥PNA along with DNA donor in PBAE-PLGA nanoparticles to correct a disease causing Œ ≤-thalassemia mutation both ex vivo and in a Œ ≤-globin/eGFP reporter mouse. Fields et al. used an intranasal delivery route to show increased cellular uptake and gene editing in the lungs of Œ ≤-globin/eGFP reporter mouse by PNA and donor DNA encapsulated in PBAE-PLGA NPs compared to PLGA NPs. Further, Mc.Neer and Anandalingam et al. demonstrated the correction of the most prevalent cystic fibrosis transmembrane conductance regulator (CFTR) mutation in human CBFE cells as well as in a mouse model. In the light of these numerous reports of delivery in primary cells and mouse models using PNAs encapsulated in nanoparticles, it is envisioned that the nanoparticle based delivery system to be ideal for intracellular delivery of our small-molecule PNA conjugates. To prepare nanoparticle formulations of small molecule-PNA conjugate and donor DNA the approach described by Bahal et al. will be employed. Briefly, small-molecule PNA conjugate and donor DNA will be encapsulated in PGLA nanoparticles using double emulsion solvent evaporation technique. The first emulsion is formed by dropwise addition of aqueous solution of small molecule-PNA conjugate and donor DNA to a solution containing 50:50 ester-terminated PGLA in dichloromethane, followed by ultrasonication. To form the second emulsion, the first emulsion is added slowly, dropwise to 5% aqueous polyvinyl alcohol and then ultrasonicated. This mixture was then poured into 0.3% aqueous polyvinyl alcohol and stirred at room temperature for 3 hrs to obtain nanoparticles. The nanoparticles are then thoroughly washed and collected by centrifugation, resuspended in water, frozen at −80-∞ C and then lyophilized. Nanoparticles will be resuspended in cell culture medium by vigorous vortexing and water sonication and directly added to the cells. In the event that the donor DNA template gets cleaved when co-encapsulated with the small-molecule strand breaker-PNA conjugate, they will be encapsulated in separate nanoparticles as these have also been shown to yield desired genomic modification albeit to a lower extent.

Optimizing Activity, Delivery, and Specificity of miniGEMs in Disease Models Available Via SCGE Consortia.

As with SynGEMs, it is anticipated that optimized conditions for delivery, activity, specificity, and HDR enhancements may not transfer to primary cells, and it is proposed to work together the SCGE members to optimize the activity of the miniGEMs and make them available to SCGE performers on demand.

The following references apply to Examples 4-12:
(1) Therapeutic genome editing: prospects and challenges. Cox, D. B.; Platt, R. J.; Zhang, F. Nat Med 2015, 21, 121-31.PMC4492683
(2) Cornerstones of CRISPR-Cas in drug discovery and therapy. Fellmann, C.; Gowen, B. G.; Lin, P. C.; Doudna, J. A.; Corn, J. E. Nat Rev Drug Discov 2017, 16, 89-100
(3) Identification of Pre-Existing Adaptive Immunity to Cas9 Proteins in Humans. Carsten Trevor Charlesworth, P. S. D., Daniel P Dever, Beruh Dejene, Natalia Gomez-Ospina, Sruthi Mantri, Mara Pavel-Dinu, Joab Camarena, Kenneth I Weinberg, Matthew H Porteus BioRxiv, 2018; Vol. January 5, p 1-15
(4) CRISPR/Cas9-based generation of knockdown mice by intronic insertion of artificial microRNA using longer single-stranded DNA. Miura, H.; Gurumurthy, C. B.; Sato, T.; Sato, M.; Ohtsuka, M. Sci Rep 2015, 5, 12799.PMC4525291
(5) Rational design of human DNA ligase inhibitors that target cellular DNA replication and repair. Chen, X.; Zhong, S.; Zhu, X.; Dziegielewska, B.; Ellenberger, T.; Wilson, G. M.; MacKerell, A. D., Jr.; Tomkinson, A. E. Cancer Res 2008, 68, 3169-77.PMC2734474
(6) An inhibitor of nonhomologous end-joining abrogates double-strand break repair and impedes cancer progression. Srivastava, M.; Nambiar, M.; Sharma, S.; Karki, S. S.; Goldsmith, G.; Hegde, M.; Kumar, S.; Pandey, M.; Singh, R. K.; Ray, P.; Natarajan, R.; Kelkar, M.; De, A.; Choudhary, B.; Raghavan, S. C. Cell 2012, 151, 1474-87
(7) Increasing the efficiency of precise genome editing with CRISPR-Cas9 by inhibition of nonhomologous end joining. Maruyama, T.; Dougan, S. K.; Truttmann, M. C.; Bilate, A. M.; Ingram, J. R.; Ploegh, H. L. Nat Biotechnol 2015, 33, 538-42.PMC4618510
(8) Increasing the efficiency of homology-directed repair for CRISPR-Cas9-induced precise gene editing in mammalian cells. Chu, V. T.; Weber, T.; Wefers, B.; Wurst, W.; Sander, S.; Rajewsky, K.; Kuhn, R. Nat Biotechnol 2015, 33, 543-8
(9) SCR7 is neither a selective nor a potent inhibitor of human DNA ligase IV. Greco, G. E.; Matsumoto, Y.; Brooks, R. C.; Lu, Z.; Lieber, M. R.; Tomkinson, A. E. DNA Repair (Amst) 2016, 43, 18-23.PMC5042453
(10) Modulating DNA Repair Pathways to Improve Precision Genome Engineering. Pawelczak, K. S.; Gavande, N. S.; VanderVere-Carozza, P. S.; Turchi, J. J. ACS Chem Biol 2018, 13, 389-396
(11) A chemical compound that stimulates the human homologous recombination protein RAD51. Jayathilaka, K.; Sheridan, S. D.; Bold, T. D.; Bochenska, K.; Logan, H. L.; Weichselbaum, R. R.; Bishop, D. K.; Connell, P. P. Proc Natl Acad Sci USA 2008, 105, 15848-53.PMC2572930
(12) Dual and Opposite Effects of hRAD51 Chemical Modulation on HIV-1 Integration. Thierry, S.; Benleulmi, M. S.; Sinzelle, L.; Thierry, E.; Calmels, C.; Chaignepain, S.; Waffo-Teguo, P.; Merillon, J. M.; Budke, B.; Pasquet, J. M.; Litvak, S.; Ciuffi, A.; Sung, P.; Connell, P.; Hauber, I.; Hauber, J.; Andreola, M. L.; Delelis, O.; Parissi, V. Chem Biol 2015, 22, 712-23.PMC4889029
(13) Nuclear domain 'knock-in' screen for the evaluation and identification of small molecule enhancers of CRISPR-based genome editing. Pinder, J.; Salsman, J.; Dellaire, G. Nucleic Acids Res 2015, 43, 9379-92.PMC4627099
(14) The Mechanism of Action of (−)-Lomaiviticin A. Herzon, S. B. Acc Chem Res 2017, 50, 2577-2588.PMC5874803
(15) Hydrolytic DNA Cleavage by Non-Lanthanide Metal Complexes. Thomas, A. S.; Debra, L. M. Curr Org Chem 2007, 11, 1525-1542
(16) Design of artificial metallonucleases with oxidative mechanism. Jiang, Q.; Xiao, N.; Shi, P.; Zhu, Y.; Guo, Z. Coordin Chem Rev 2007, 251, 1951-1972

(17) Design of artificial nucleases and studies of their interaction with DNA. Zhang, J.; Shao, Y.; Wei, L.; Li, Y.; Sheng, X.; Liu, F.; Lu, G. Sci China Chem 2009, 52, 402-414

(18) Copper(II), zinc(II) and nickel(II) complexes as nuclease mimetics. Desbouis, D.; Troitsky, I. P.; Belousoff, M. J.; Spiccia, L.; Graham, B. Coordin Chem Rev 2012, 256, 897-937

(19) Sequence-selective recognition of DNA by strand displacement with a thymine-substituted polyamide. Nielsen, P. E.; Egholm, M.; Berg, R. H.; Buchardt, O. Science 1991, 254, 1497-500

(20) Peptide Nucleic Acids as a Tool for Site-Specific Gene Editing. Ricciardi, A. S.; Quijano, E.; Putman, R.; Saltzman, W. M.; Glazer, P. M. Molecules 2018, 23

(21) Stability of peptide nucleic acids in human serum and cellular extracts. Demidov, V. V.; Potaman, V. N.; Frank-Kamenetskii, M. D.; Egholm, M.; Buchard, O.; Sonnichsen, S. H.; Nielsen, P. E. Biochem Pharmacol 1994, 48, 1310-3

(22) Refining strategies to translate genome editing to the clinic. Cornu, T. I.; Mussolino, C.; Cathomen, T. Nat Med 2017, 23, 415-423

(23) Site-specific PEGylation of proteins: recent developments. Nischan, N.; Hackenberger, C. P. J Org Chem 2014, 79, 10727-33

(24) Antibody-drug conjugates: an emerging concept in cancer therapy. Chari, R. V.; Miller, M. L.; Widdison, W. C. Angew Chem Int Ed Engl 2014, 53, 3796-827

(25) Editing the Genome Without Double-Stranded DNA Breaks. Komor, A. C.; Badran, A. H.; Liu, D. R. ACS Chem Biol 2018, 13, 383-388

(26) Increasing Cas9-mediated homology-directed repair efficiency through covalent tethering of DNA repair template. Aird, E. J.; Lovendahl, K. N.; St. Martin, A.; Harris, R. S.; Gordon, W. R. bioRxiv 2017

(27) Covalent linkage of the DNA repair template to the CRISPR/Cas9 complex enhances homology-directed repair. Savic, N.; Ringnalda, F.; Bargsten, K.; Li, Y.; Berk, C.; Hall, J.; Neri, D.; Jinek, M.; Schwank, G. bioRxiv 2017

(28) Efficient Homology Directed Repair by Cas9:DNA Localization and Cationic Polymeric Transfection in Mammalian Cells. Roche, P. J. R.; Gytz, H.; Hussain, F.; Cameron, C. J. F.; Paquette, D.; Blanchette, M.; Dostie, J.; Nagar, B.; Akavia, U. D. bioRxiv 2018

(29) Synthesis of the fully glycosylated cyclohexenone core of lomaiviticin A. Gholap, S. L.; Woo, C. M.; Ravikumar, P. C.; Herzon, S. B. Org Lett 2009, 11, 4322-5

(30) Development of a convergent entry to the diazofluorene antitumor antibiotics: enantioselective synthesis of kinamycin F. Woo, C. M.; Lu, L.; Gholap, S. L.; Smith, D. R.; Herzon, S. B. J Am Chem Soc 2010, 132, 2540-1

(31) 11-Step enantioselective synthesis of (−)-lomaiviticin aglycon. Herzon, S. B.; Lu, L.; Woo, C. M.; Gholap, S. L. J Am Chem Soc 2011, 133, 7260-3.PMC5357143

(32) The diazofluorene antitumor antibiotics: structural elucidation, biosynthetic, synthetic, and chemical biological studies. Herzon, S. B.; Woo, C. M. Nat Prod Rep 2012, 29, 87-118

(33) Isolation of lomaiviticins C-E, transformation of lomaiviticin C to lomaiviticin A, complete structure elucidation of lomaiviticin A, and structure-activity analyses. Woo, C. M.; Beizer, N. E.; Janso, J. E.; Herzon, S. B. J Am Chem Soc 2012, 134, 15285-8

(34) Development of enantioselective synthetic routes to (−)-kinamycin F and (−)-lomaiviticin aglycon. Woo, C. M.; Gholap, S. L.; Lu, L.; Kaneko, M.; Li, Z.; Ravikumar, P. C.; Herzon, S. B. J Am Chem Soc 2012, 134, 17262-73.PMC3505684

(35) Insights into lomaiviticin biosynthesis. Isolation and structure elucidation of (−)-homoseongomycin. Woo, C. M.; Gholap, S. L.; Herzon, S. B. J Nat Prod 2013, 76, 1238-41

(36) The cytotoxicity of (−)-lomaiviticin A arises from induction of double-strand breaks in DNA. Colis, L. C.; Woo, C. M.; Hegan, D. C.; Li, Z.; Glazer, P. M.; Herzon, S. B. Nat Chem 2014, 6, 504-10.PMC4090708

(37) Analysis of diazofluorene DNA binding and damaging activity: DNA cleavage by a synthetic monomeric diazofluorene. Woo, C. M.; Ranjan, N.; Arya, D. P.; Herzon, S. B. Angew Chem Int Ed Engl 2014, 53, 9325-8.PMC4206835

(38) Structural basis for DNA cleavage by the potent antiproliferative agent (−)-lomaiviticin A. Woo, C. M.; Li, Z.; Paulson, E. K.; Herzon, S. B. Proc Natl Acad Sci USA 2016, 113, 2851-6.PMC4801295

(39) Prodrugs: design and clinical applications. Rautio, J.; Kumpulainen, H.; Heimbach, T.; Oliyai, R.; Oh, D.; Jarvinen, T.; Savolainen, J. Nat Rev Drug Discov 2008, 7, 255

(40) Sequence-unrestricted, Watson-Crick recognition of double helical B-DNA by (R)-miniPEG-gammaPNAs. Bahal, R.; Sahu, B.; Rapireddy, S.; Lee, C. M.; Ly, D. H. Chembiochem 2012, 13, 56-60

(41) PNA hybridizes to complementary oligonucleotides obeying the Watson-Crick hydrogen-bonding rules. Egholm, M.; Buchardt, O.; Christensen, L.; Behrens, C.; Freier, S. M.; Driver, D. A.; Berg, R. H.; Kim, S. K.; Norden, B.; Nielsen, P. E. Nature 1993, 365, 566-8

(42) Kinetics for hybridization of peptide nucleic acids (PNA) with DNA and RNA studied with the BIAcore technique. Jensen, K. K.; Orum, H.; Nielsen, P. E.; Norden, B. Biochemistry 1997, 36, 5072-7

(43) Variability in the stability of DNA-peptide nucleic acid (PNA) single-base mismatched duplexes: real-time hybridization during affinity electrophoresis in PNA-containing gels. Igloi, G. L. Proc Natl Acad Sci USA 1998, 95, 8562-7.PMC21115

(44) An introduction to peptide nucleic acid. Nielsen, P. E.; Egholm, M. Curr Issues Mol Biol 1999, 1, 89-104

(45) Thermodynamic comparison of PNA/DNA and DNA/DNA hybridization reactions at ambient temperature. Schwarz, F. P.; Robinson, S.; Butler, J. M. Nucleic Acids Res 1999, 27, 4792-800.PMC148780

(46) The first crystal structures of RNA-PNA duplexes and a PNA-PNA duplex containing mismatches—toward antisense therapy against TREDs. Kiliszek, A.; Banaszak, K.; Dauter, Z.; Rypniewski, W. Nucleic Acids Res 2016, 44, 1937-43.PMC4770230

(47) Nanoparticles deliver triplex-forming PNAs for site-specific genomic recombination in CD34+ human hematopoietic progenitors. McNeer, N. A.; Chin, J. Y.; Schleifman, E. B.; Fields, R. J.; Glazer, P. M.; Saltzman, W. M. Mol Ther 2011, 19, 172-80.PMC3017438

(48) Systemic delivery of triplex-forming PNA and donor DNA by nanoparticles mediates site-specific genome editing of human hematopoietic cells in vivo. McNeer, N. A.; Schleifman, E. B.; Cuthbert, A.; Brehm, M.; Jackson, A.; Cheng, C.; Anandalingam, K.; Kumar, P.; Shultz, L. D.; Greiner, D. L.; Saltzman, W. M.; Glazer, P. M. Gene Ther 2013, 20, 658-69.3713493

(49) Site-specific Genome Editing in PBMCs With PLGA Nanoparticle-delivered PNAs Confers HIV-1 Resistance

(50) Single-stranded gammaPNAs for in vivo site-specific genome editing via Watson-Crick recognition. Bahal, R.; Quijano, E.; McNeer, N. A.; Liu, Y.; Bhunia, D. C.; Lopez-Giraldez, F.; Fields, R. J.; Saltzman, W. M.; Ly, D. H.; Glazer, P. M. Curr Gene Ther 2014, 14, 331-42.PMC4333085

(51) Modified poly(lactic-co-glycolic acid) nanoparticles for enhanced cellular uptake and gene editing in the lung. Fields, R. J.; Quijano, E.; McNeer, N. A.; Caputo, C.; Bahal, R.; Anandalingam, K.; Egan, M. E.; Glazer, P. M.; Saltzman, W. M. Adv Healthc Mater 2015, 4, 361-6.PMC4339402

(52) Nanoparticles that deliver triplex-forming peptide nucleic acid molecules correct F508del CFTR in airway epithelium. McNeer, N. A.; Anandalingam, K.; Fields, R. J.; Caputo, C.; Kopic, S.; Gupta, A.; Quijano, E.; Polikoff, L.; Kong, Y.; Bahal, R.; Geibel, J. P.; Glazer, P. M.; Saltzman, W. M.; Egan, M. E. Nat Commun 2015, 6, 6952.PMC4480796

(53) In vivo correction of anaemia in beta-thalassemic mice by gammaPNA-mediated gene editing with nanoparticle delivery. Bahal, R.; Ali McNeer, N.; Quijano, E.; Liu, Y.; Sulkowski, P.; Turchick, A.; Lu, Y. C.; Bhunia, D. C.; Manna, A.; Greiner, D. L.; Brehm, M. A.; Cheng, C. J.; Lopez-Giraldez, F.; Ricciardi, A.; Beloor, J.; Krause, D. S.; Kumar, P.; Gallagher, P. G.; Braddock, D. T.; Mark Saltzman, W.; Ly, D. H.; Glazer, P. M. Nat Commun 2016, 7, 13304.PMC5095181 application. The remaining authors declare no competing financial interests.

(54) Multidimensional chemical control of CRISPR-Cas9. Maji, B.; Moore, C. L.; Zetsche, B.; Volz, S. E.; Zhang, F.; Shoulders, M. D.; Choudhary, A. Nat Chem Biol 2017, 13, 9-11

(55) Site-specific C-terminal and internal loop labeling of proteins using sortase-mediated reactions. Guimaraes, C. P.; Witte, M. D.; Theile, C. S.; Bozkurt, G.; Kundrat, L.; Blom, A. E.; Ploegh, H. L. Nat Protoc 2013, 8, 1787-99.PMC3943461

(56) Site-specific N-terminal labeling of proteins using sortase-mediated reactions. Theile, C. S.; Witte, M. D.; Blom, A. E.; Kundrat, L.; Ploegh, H. L.; Guimaraes, C. P. Nat Protoc 2013, 8, 1800-7.PMC3941705

(57) Sortase-mediated ligations for the site-specific modification of proteins. Schmohl, L.; Schwarzer, D. Curr Opin Chem Biol 2014, 22, 122-8

(58) A split-Cas9 architecture for inducible genome editing and transcription modulation. Zetsche, B.; Volz, S. E.; Zhang, F. Nat Biotechnol 2015, 33, 139-42.Pmc4503468

(59) Rational design of a split-Cas9 enzyme complex. Wright, A. V.; Sternberg, S. H.; Taylor, D. W.; Staahl, B. T.; Bardales, J. A.; Kornfeld, J. E.; Doudna, J. A. Proc Natl Acad Sci USA 2015, 112, 2984-9.PMC4364227

(60) Rationally engineered Cas9 nucleases with improved specificity. Slaymaker, I M.; Gao, L.; Zetsche, B.; Scott, D. A.; Yan, W. X.; Zhang, F. Science 2016, 351, 84-88

(61) Systematic quantification of HDR and NHEJ reveals effects of locus, nuclease, and cell type on genome-editing. Miyaoka, Y.; Berman, J. R.; Cooper, S. B.; Mayerl, S. J.; Chan, A. H.; Zhang, B.; Karlin-Neumann, G. A.; Conklin, B. R. In Sci Rep 2016; Vol. 6. PMCID.

(62) Mutations in RNA Binding Protein Gene Cause Familial Dilated Cardiomyopathy. Brauch, K. M.; Karst, M. L.; Herron, K. J.; de Andrade, M.; Pellikka, P. A.; Rodeheffer, R. J.; Michels, V. V.; Olson, T. M. J Am Coll Cardiol 2009, 54, 930-41.2782634

(63) Genomic targeting of epigenetic probes using a chemically tailored Cas9 system. Liszczak, G. P.; Brown, Z. Z.; Kim, S. H.; Oslund, R. C.; David, Y.; Muir, T. W. Proc Natl Acad Sci USA 2017, 114, 681-686.PMC5278450

(64) Adding new chemistries to the genetic code. Liu, C. C.; Schultz, P. G. Annu Rev Biochem 2010, 79, 413-44

(65) An enhanced system for unnatural amino acid mutagenesis in E. coli. Young, T. S.; Ahmad, I.; Yin, J. A.; Schultz, P. G. J Mol Biol 2010, 395, 361-74

(66) Optical Control of CRISPR/Cas9 Gene Editing. Hemphill, J.; Borchardt, E. K.; Brown, K.; Asokan, A.; Deiters, A. J Am Chem Soc 2015, 137, 5642-5.PMC4919123

(67) Discovery of a Small-Molecule Inhibitor of Protein-MicroRNA Interaction Using Binding Assay with a Site-Specifically Labeled Lin28. Lim, D.; Byun, W. G.; Koo, J. Y.; Park, H.; Park, S. B. J Am Chem Soc 2016

(68) In Vivo Evaluation of Site-Specifically PEGylated Chemically Self-Assembled Protein Nanostructures. Shah, R.; Petersburg, J.; Gangar, A. C.; Fegan, A.; Wagner, C. R.; Kumarapperuma, S. C. Mol Pharm 2016, 13, 2193-203

(69) The cytotoxicity of (−)-lomaiviticin A arises from induction of double-strand breaks in DNA. Colis, L. C.; Woo, C. M.; Hegan, D. C.; Li, Z.; Glazer, P. M.; Herzon, S. B. Nature Chemistry 2014, 6, 504

(70) Mechanisms of in situ activation for DNA-targeting antitumor agents. Wolkenberg, S. E.; Boger, D. L. Chemical Reviews 2002, 102, 2477-2495

(71) DNA-Binding and Cleavage Studies of Zinc(II) Mixed-polypyridyl Complex. Yang, C. X. Y. Y. B. W. P. Chinese Journal of Chemistry 2006, 24, 1006-1012

(72) The Evolution of DNA-Templated Synthesis as a Tool for Materials Discovery. O'Reilly, R. K.; Turberfield, A. J.; Wilks, T. R. Acc Chem Res 2017, 50, 2496-2509.PMC5746846

(73) The Mechanism of Action of (−)-Lomaiviticin A. Herzon, S. B. Accounts of Chemical Research 2017, 50, 2577-2588

(74) Products of metabolic activation of the antitumor drug ledakrin (Nitracrine) in vitro. Gorlewska, K.; Mazerska, Z.; Sowinski, P.; Konopa, J. Chemical Research in Toxicology 2001, 14, 1-10

(75) Beyond DNA binding—a review of the potential mechanisms mediating quinacrine's therapeutic activities in parasitic infections, inflammation, and cancers. Ehsanian, R.; Van Waes, C.; Feller, S. M. Cell Communication and Signaling 2011, 9, 13

(76) Photodynamic effect in near-IR light by a photocytotoxic iron(III) cellular imaging agent. Basu, U.; Khan, I.; Hussain, A.; Kondaiah, P.; Chakravarty, A. R. Angew Chem IntEdEngl2012, 51, 2658-61

(77) Photocytotoxic oxovanadium(IV) complexes of ferrocenyl-terpyridine and acetylacetonate derivatives. Balaji, B.; Balakrishnan, B.; Perumalla, S.; Karande, A. A.; Chakravarty, A. R. Eur J Med Chem 2015, 92, 332-341

(78) Neocarzinostatin, an antitumor antibiotic of high molecular weight. Isolation, physiochemical properties, and biological activities. Ishida, N.; Miyazaki, K.; Kumagai, K.; Rikimaru, M. J Antibiot (Tokyo) 1965, 18, 68-76

(79) Esperamicins, a class of potent antitumor antibiotics: mechanism of action. Long, B. H.; Golik, J.; Forenza, S.; Ward, B.; Rehfuss, R.; Dabrowiak, J. C.; Catino, J. J.; Musial, S. T.; Brookshire, K. W.; Doyle, T. W. Proc Natl Acad Sci USA 1989, 86, 2-6.286391

(80) Calicheamicins, a novel family of antitumor antibiotics. 3. Isolation, purification and characterization of calicheamicins beta 1Br, gamma 1Br, alpha 21, alpha 31, beta 11, gamma 11 and delta 11. Lee, M. D.; Manning, J. K.; Williams, D. R.; Kuck, N. A.; Testa, R. T.; Borders, D. B. J Antibiot (Tokyo) 1989, 42, 1070-87

(81) Crystal and molecular structure of dynemicin A: a novel 1,5-diyn-3-ene antitumor antibiotic. Konishi, M.; Ohkuma, H.; Tsuno, T.; Oki, T.; VanDuyne, G. D.; Clardy, J. 2002

(82) Mechanisms of in situ activation for DNA-targeting antitumor agents. Wolkenberg, S. E.; Boger, D. L. Chem Rev 2002, 102, 2477-2495

(83) Photochemical Activation of Enediyne Warheads: A Potential Tool for Targeted Antitumor Therapy. Bhattacharya, P.; Basak, A.; Campbell, A.; Alabugin, I. V. Mol Pharm 2018, 15, 768-797

(84) Chemistry and biology of natural and designed enediynes. Nicolaou, K. C.; Smith, A. L.; Yue, E. W. Proc Natl Acad Sci USA 1993, 90, 5881-8.PMC46830

(85) Structure of a psoralen-thymine monoadduct formed in photoreaction with DNA. Peckler, S.; Graves, B.; Kanne, D.; Rapoport, H.; Hearst, J. E.; Kim, S. H. J Mol Biol 1982, 162, 157-72

(86) Molecular structure of an anticancer drug-DNA complex: daunomycin plus d(CpGpTpApCpG). Quigley, G. J.; Wang, A. H.; Ughetto, G.; van der Marel, G.; van Boom, J. H.; Rich, A. Proc Natl Acad Sci USA 1980, 77, 7204-8.PMC350470

(87) Plumbagin and juglone induce caspase-3-dependent apoptosis involving the mitochondria through ROS generation in human peripheral blood lymphocytes. Seshadri, P.; Rajaram, A.; Rajaram, R. Free Radic Biol Med 2011, 51, 2090-107

(88) Studies toward the synthesis of the epoxykinamycin FL-120B': discovery of a decarbonylative photocyclization. Scully, S. S.; Porco, J. A., Jr. Org Lett 2012, 14, 2646-9.PMC3433630

(89) Double-strand hydrolysis of plasmid DNA by dicerium complexes at 37 degrees C. Branum, M. E.; Tipton, A. K.; Zhu, S. R.; Que, L. J Am Chem Soc 2001, 123, 1898-1904

(90) DNA hydrolytic cleavage by the diiron(III) complex Fe-2(DTPB)(mu-O(mu-Ac)Cl(BF4)(2): Comparison with other binuclear transition metal complexes. Liu, C. L.; Yu, S. W.; Li, D. F.; Liao, Z. R.; Sun, X. H.; Xu, H. B. Inorg Chem 2002, 41, 913-922

(91) Dinuclear Zn2+ complexes of synthetic heptapeptides as artificial nucleases. Sissi, C.; Rossi, P.; Felluga, F.; Formaggio, F.; Palumbo, M.; Tecilla, P.; Toniolo, C.; Scrimin, P. J Am Chem Soc 2001, 123, 3169-3170

(92) Photocontrol of spatial orientation and DNA cleavage activity of copper(II)-bound dipeptides linked by an azobenzene derivative. Prakash, H.; Shodai, A.; Yasui, H.; Sakurai, H.; Hirota, S. Inorg Chem 2008, 47, 5045-5047

(93) DNA Cleavage by the Photocontrolled Cooperation of Zn-II Centers in an Azobenzene-Linked Dizinc Complex. Panja, A.; Matsuo, T.; Nagao, S.; Hirota, S. Inorg Chem 2011, 50, 11437-11445

(94) Site-specific gene modification by PNAs conjugated to psoralen. Kim, K. H.; Nielsen, P. E.; Glazer, P. M. Biochemistry 2006, 45, 314-23

(95) Targeted gene correction using psoralen, chlorambucil and camptothecin conjugates of triplex forming peptide nucleic acid (PNA). Birkedal, H.; Nielsen, P. E. Artif DNA PNA XNA 2011, 2, 23-32.PMC3116579

(96) Enhancing solid phase synthesis by a noncovalent protection strategy-efficient coupling of rhodamine to resin-bound peptide nucleic acids. Mayfield, L. D.; Corey, D. R. Bioorg Med Chem Lett 1999, 9, 1419-22

(97) Fluorescein-conjugated lysine monomers for solid phase synthesis of fluorescent peptides and PNA oligomers. Lohse, J.; Nielsen, P. E.; Harrit, N.; Dahl, O. Bioconjug Chem 1997, 8, 503-9

(98) Sequence selective recognition of double-stranded RNA at physiologically relevant conditions using PNA-peptide conjugates. Muse, O.; Zengeya, T.; Mwaura, J.; Hnedzko, D.; McGee, D. W.; Grewer, C. T.; Rozners, E. ACS Chem Biol 2013, 8, 1683-6.PMC3745792

(99) Strategies for the synthesis of fluorescently labelled PNA. Liu, X.; Balasubramanian, S. Tetrahedron Lett 2000, 41, 6153-6156

(100) Fluorescent PNA probes as hybridization labels for biological RNA. Robertson, K. L.; Yu, L.; Armitage, B. A.; Lopez, A. J.; Peteanu, L. A. Biochemistry 2006, 45, 6066-74

(101) Convergent strategies for the attachment of fluorescing reporter groups to peptide nucleic acids in solution and on solid phase. Seitz, O.; Kohler, O. Chemistry 2001, 7, 3911-25

(102) Site-directed recombination via bifunctional PNA-DNA conjugates. Rogers, F. A.; Vasquez, K. M.; Egholm, M.; Glazer, P. M. Proc Natl Acad Sci USA 2002, 99, 16695-700.PMC139206

(103) Targeted gene modification of hematopoietic progenitor cells in mice following systemic administration of a PNA-peptide conjugate. Rogers, F. A.; Lin, S. S.; Hegan, D. C.; Krause, D. S.; Glazer, P. M. Mol Ther 2012, 20, 109-18.PMC3255600

(104) Peptide nucleic acid-targeted mutagenesis of a chromosomal gene in mouse cells. Faruqi, A. F.; Egholm, M.; Glazer, P. M. In Proc Natl Acad Sci USA 1998; Vol. 95, p 1398-403. PMCID.

(105) GFP to BFP Conversion: A Versatile Assay for the Quantification of CRISPR/Cas9-mediated Genome Editing. Glaser, A.; McColl, B.; Vadolas, J. In Mol Ther Nucleic Acids 2016; Vol. 5, p e334-. PMCID.

(106) Pharmacological inhibition of DNA-PK stimulates Cas9-mediated genome editing. Robert, F.; Barbeau, M.; Ethier, S.; Dostie, J.; Pelletier, J. Genome Med 2015, 7, 93.PMC4550049

(107) Synthesis and Characterization of Conformationally-Preorganized, MiniPEG-Containing 7PNAs with Superior Hybridization Properties and Water Solubility. Sahu, B.; Sacui, I.; Rapireddy, S.; Zanotti, K. J.; Bahal, R.; Armitage, B. A.; Ly, D. H. J Org Chem 2011, 76, 5614-27.3175361

(108) Anti-tumor Activity of miniPEG-γ-Modified PNAs to Inhibit MicroRNA-210 for Cancer Therapy. Gupta, A.; Quijano, E.; Liu, Y.; Bahal, R.; Scanlon, S. E.; Song, E.; Hsieh, W. C.; Braddock, D. E.; Ly, D. H.; Saltzman, W. M.; Glazer, P. M. In Mol Ther Nucleic Acids 2017; Vol. 9, p 111-9. PMCID.

(109) Pre-B cell proliferation and lymphoblastic leukemia/high-grade lymphoma in E(mu)-miR155 transgenic mice. Costinean, S.; Zanesi, N.; Pekarsky, Y.; Tili, E.; Volinia, S.; Heerema, N.; Croce, C. M. Proc Natl Acad Sci USA 2006, 103, 7024-9.PMC1459012

(110) Biodegradable polymeric nanoparticles based drug delivery systems. Kumari, A.; Yadav, S. K.; Yadav, S. C. Colloids Surf B Biointerfaces 2010, 75, 1-18

(111) PLGA-based nanoparticles: an overview of biomedical applications. Danhier, F.; Ansorena, E.; Silva, J. M.; Coco, R.; Le Breton, A.; Preat, V. J Control Release 2012, 161, 505-22

(112) High loading efficiency and tunable release of plasmid DNA encapsulated in submicron particles fabricated from PLGA conjugated with poly-L-lysine. Blum, J. S.; Saltzman, W. M. J Control Release 2008, 129, 66-72.PMC2494593
(113) Degradable Poly(O-amino esters): Synthesis, Characterization, and Self-Assembly with Plasmid DNA. and, D. M. L.; Langer*, R. 2000
(114) Biodistribution and pharmacokinetic analysis of Paclitaxel and ceramide administered in multifunctional polymer-blend nanoparticles in drug resistant breast cancer model. van Vlerken, L. E.; Duan, Z.; Little, S. R.; Seiden, M. V.; Amiji, M. M. Mol Pharm 2008, 5, 516-26.PMC2646668

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features hereinbefore set forth.

What is claimed is:

1. A composition comprising:

a truncated CRISPR-Cas protein comprising a nucleic acid binding domain, wherein the nucleic acid binding domain comprises amino acids of (i) a RuvC domain, a bridge helix (BH) domain, a REC1 domain, and a PAM-interacting (PI) domain of *Streptococcus pyogenes* Cas9 (SpCas9), (ii) the RuvC, BH, REC, Wedge (WED), phosphate lock loop (PLL), and PI domains of *Staphylococcus aureus* Cas9 (SaCas9), or (iii) a WED domain, a REC1 domain, a REC2 domain, a PI domain, a BH domain, and a RuvC domain of *Acidaminococcus* sp. BV3L6 Cpf1 (AsCpf1);

a guide RNA capable of complexing with the truncated CRISPR-Cas protein;

a single-stranded oligo donor (ssODN) wherein the ssODN is connected to the truncated CRISPR-Cas protein by an adaptor oligonucleotide that is at least 10 nucleotides in length and capable of hybridizing to a portion of the ssODN;

one or more small molecule NHEJ inhibitors connected to the truncated CRISPR-Cas protein and selected from the group consisting of SCR7-G, SCR7, L189, PK 76, KU-0060648, KU inhibitor, and analogs thereof, an inhibitor of DNA ligase IV, KU70, or KU80;
one or more small molecule HDR activators connect to the truncated CRISPR-Cas protein and selected from the group consisting of RS1 or analogs thereof or stimulator of RAD51 activity, or a combination thereof.

2. The composition of claim 1, wherein the guide RNA is a single guide RNA (sgRNA).

3. The composition of claim 1, wherein the guide RNA is in a duplex with a target nucleic acid.

4. The composition of claim 3, wherein the target nucleic acid comprises chromosomal DNA, mitochondrial DNA, viral, bacterial or fungal DNA or RNA.

5. The composition of claim 1, wherein the nucleic acid binding domain comprises amino acids of the RuvC, BH, REC1, and PI domains of SpCas9 that interact with SpCas9 guide RNAs wherein the nucleic acid binding domain is truncated as to one or more of the RuvC, BH, REC1, and PI domains of SpCas9.

6. The composition of claim 1, wherein the nucleic acid binding domain comprises one or more binding residues at one or more of amino acid positions Lys30, Lys33, Arg40, Lys44, Asn46, Glu57, Thr62, Arg69, Asn77, Leu101, Ser104, Phe105, Arg115, His116, Ile135, His160, Lys163, Arg165, Gly166, Tyr325, His328, Arg340, Phe351, Asp364, Gln402, Arg403, Thr404, Asn407, Arg447, Ile448, Leu455, Ser460, Arg467, Thr472, Ile473, Lys510, Tyr515, Trp659, Arg661, Met694, Gln695, His698, His721, Ala728, Lys742, Gln926, Val1009, Lys1097, Val1100, Gly1103, Thr1102, Phe1105, Ile1110, Tyr1113, Arg1122, Lys1123, Lys1124, Tyr1131, Glu1225, Ala1227, Gln1272, His1349, Ser1351, and Tyr1356, with reference to an amino acid sequence of wildtype SpCas9; wherein the nucleic acid binding domain further comprises one or more binding residues at one or more of the amino acid positions Ala59, Arg63, Arg66, Arg70, Arg74, Arg78, Lys50, Tyr515, Arg661, Gln926, and Val1009 with reference to the amino acid sequence of wildtype SpCas9, or further comprises one or more binding residues at one or more of the amino acid positions Leu169, Tyr450, Met495, Asn497, Trp659, Arg661, Met694, Gln695, His698, Ala728, Gln926, and Glu1108 with reference to the amino acid sequence of wildtype SpCas9.

7. The composition of claim 1, wherein the nucleic acid binding domain comprises amino acids of the RuvC, BH, REC, WED, PLL, and PI domains of SaCas9 that interact with SaCas9 guide RNAs wherein the nucleic acid binding domain is truncated as to one or more of the RuvC, BH, REC, WED, and PI domains of SaCas9.

8. The composition of claim 1, wherein the nucleic acid binding domain comprises one or more binding residues at one or more of amino acid positions Asn47, Lys50, Arg54, Lys57, Arg58, Arg61, His62, His111, Lys114, Gly162, Val164, Arg165, Arg209, Glu213, Gly216, Ser219, Asn780, Arg781, Leu783, Leu788, Ser790, Arg792, Asn804, Lys867, Tyr868, Lys870, Lys878, Lys879, Lys881, Leu891, Tyr897, Arg901, and Lys906, with reference to an amino acid sequence of wildtype SaCas9 wherein the nucleic acid binding domain further comprises one or more binding residues at one or more of the amino acid positions Asn44, Arg48, Arg51, Arg55, Arg59, Arg60, Arg116, Gly117, Arg165, Gly166, Arg208, Arg209, Tyr211, Thr238, Tyr239, Lys248, Tyr256, Arg314, and Asn394, with reference to the amino acid sequence of wildtype SaCas9 or further comprises one or more binding residues at one or more of the amino acid positions Tyr211, Trp229, Tyr230, Gly235, Arg245, Gly391, Thr392, Asn419, Leu446, Tyr651, and Arg654 with reference to the amino acid sequence of wildtype SaCas9.

9. The composition of claim 1, wherein the nucleic acid binding domain comprises amino acids of WED, REC1, REC2, PI, BH, and RuvC domains of AsCpf1 that interact with AsCpf1 guide RNAs wherein the nucleic acid binding domain is truncated as to one or more of the WED, REC1, REC2, PI, BH, and RuvC domains of AsCpf1.

10. The composition of claim 1, wherein the nucleic acid binding domain comprises one or more binding residues at one or more of amino acid positions Lys15, Arg18, Lys748, Gly753, His755, Gly756, Lys757, Asn759, His761, Arg790, Met806, Leu807, Asn808, Lys809, Lys810, Lys852, His856, Ile858, Arg863, Tyr940, Lys943, Asp966, His977, Lys1022 and Lys1029, with reference to an amino acid sequence of wildtype AsCpf1 wherein the nucleic acid binding domain further comprises one or more binding residues at one or more of the amino acid positions Tyr47, Lys51, Arg176, Arg192, Gly270, Gln286, Lys273, Lys307, Leu310, Lys369, Lys414, His 479, Asn515, Arg518, Lys530, Glu786, His872, Arg955, and Gln956 with reference to the amino acid sequence of wildtype AsCpf1 or further comprises one or more binding residues at one or more of the amino acid positions Asn178, Ser186, Asn278, Arg301, Thr315, Ser376, Lys524, Lys603, Lys780, Gly783, Gln784, Arg951, Ile964, Lys965, Gnl1014, Phe1052, and Ala1053 with reference to the amino acid sequence of wildtype AsCpf1.

11. The composition of claim 1, wherein the nucleic acid binding domain lacks one or more amino acid positions K169, Y450, N497, R661, Q695, Q926, K810, K848, K1003, R1060, or D1135, with reference to an amino acid sequence of wildtype SpCas9, or wherein the nucleic acid binding domain lacks one or more of RuvCI, RuvCII, RuvCIII, NUC, PI, or BH.

12. The composition of claim 1, wherein the guide comprises RNA or wherein the guide comprises a nucleotide analog.

13. The composition of claim 1, comprising one or more effector domains, wherein the nucleic acid binding domain and the one or more effector domains are covalently linked by a linker.

14. The composition of claim 13, wherein the linker comprises a chemical linker, an amino acid linker, a Gly-Gly-Gly-Gly-Ser (GGGGS) (SEQ ID NO: 10) linker, a polyethylene glycol (PEG) linker and is cleavable in vivo.

15. The composition of claim 1, comprising one or more effector domains, wherein the one or more effector domain comprises one or more of a single stranded nuclease, a double strand nuclease, α helicase, a methylase, a demethylase, an acetylase, a deacetylase, a deaminase, an integrase, a recombinase, of a cellular uptake activity associated domain or wherein the one or more effector domain comprises a small molecule that induces single- or double-strand breaks in the nucleic acid target.

16. The composition of claim 1, wherein the composition comprises one or more nuclear localization signals (NLSs) and one or more effector domains, wherein the one or more NLSs is linked to the nucleic acid binding domain or one or more effector domains.

17. A method of repairing DNA damage in an isolated cell, which comprises contacting the damaged DNA of the isolated cell with the composition of claim 1.

18. A DNA repair kit comprising the composition of claim 1.

19. A vector system for delivering to a mammalian isolated cell the composition of claim 1.

20. The composition of claim 1, wherein the CRISPR-Cas protein comprises one or more engineered cysteine amino acids, wherein the CRISPR-Cas protein is an SpCas9 protein comprising C80S and C574S mutations and one or more mutations selected from the group consisting of M1C, D435C, E532C, Q826C, S867C, S1025C, E1026C, N1054C, E1068C, S1116C, K1153C, and E1207C, wherein the CRISPR-Cas protein comprises a sortase recognition sequence Leu-Pro-Xxx-Thr-Gly (SEQ ID NO: 1) or wherein the CRISPR-Cas protein comprises one or more unnatural amino acid p-Acetyl Phenylalanine (pAcF), or one or more unnatural amino acid comprising tetrazine.

21. The composition of claim 1, comprising one or more effector components, wherein the one or more effector components are covalently linked to the CRISPR-Cas protein or are linked to the CRISPR-Cas protein via cysteines, sortase chemistry, or unnatural amino acids, wherein the one or more effector components are linker modified, wherein the linker comprises a maleimide group, PEG, or a poly-Gly peptide.

22. The composition of claim 1, wherein the CRISPR-Cas protein is an SpCas9 protein comprising C80S and C574S mutations and one or more mutations selected from the group consisting of M1C, D435C, E532C, Q826C, S867C, S1025C, E1026C, N1054C, E1068C, S1116C, K1153C, E1207C, wherein the one or more adaptor oligonucleotides are linked to the CRISPR-Cas protein via thiol-maleimide chemistry.

23. A method for enhancing HDR at one or more target loci in a target isolated cell, comprising delivering the composition of claim 1 to the target isolated cell.

24. A method of precise genome editing in an isolated cell, comprising delivering the composition of claim 1 to the isolated cell.

25. The method of claim 23, wherein the composition is delivered to the target isolated cell via electroporation or via lipid-mediated delivery.

26. The method of claim 24, wherein the composition is delivered using Poly(lactic co-glycolic acids) (PLGA) nanoparticles.

* * * * *

UNITED STATES PATENT AND TRADEMARK OFFICE
CERTIFICATE OF CORRECTION

| | | |
|---|---|---|
| PATENT NO. | : 12,227,742 B2 | Page 1 of 1 |
| APPLICATION NO. | : 16/758840 | |
| DATED | : February 18, 2025 | |
| INVENTOR(S) | : Choudhary et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 669 days.

Signed and Sealed this
Fifth Day of August, 2025

Coke Morgan Stewart
*Acting Director of the United States Patent and Trademark Office*

SEQUENCE LISTING

```
<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Leu Pro Xaa Thr Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Lysine at Postiion 4 if Biotinylated

<400> SEQUENCE: 2

Gly Gly Gly Lys
1

<210> SEQ ID NO 3
<211> LENGTH: 12
<212> TYPE: DNA
<213> ORGANISM: Artificial Sequence
<220> FEATURE:
<223> OTHER INFORMATION: Synthetic

<400> SEQUENCE: 3
acttgtttaa gt                                                        12

<210> SEQ ID NO 4
<211> LENGTH: 16
<212> TYPE: DNA
<213> ORGANISM: Artificial Sequence
<220> FEATURE:
<223> OTHER INFORMATION: Synthetic

<400> SEQUENCE: 4
```
ggcaccgagt cggtgc                                                       16

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Gly Gly Gly Gly Ser Gly Gly Gly Gly Ser Gly Gly Gly Gly Ser
1               5                  10                  15

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gccaaattgg acgaccctcg                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cgaggagacc cccgtttcgg                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cccgccgccg ccgtggctcg                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tgagctctac gagatccaca                                                   20

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Gly Gly Gly Gly Ser
1               5

<210> SEQ ID NO 11
<211> LENGTH: 7

```
<212> TYPE: PRT
<213> ORGANISM: Artificial Sequence
<220> FEATURE:
<223> OTHER INFORMATION: Synthetic Peptide

<400> SEQUENCE: 11

Glu Asn Leu Tyr Phe Gln Gly
1               5

<210> SEQ ID NO 12
<211> LENGTH: 14
<212> TYPE: DNA
<213> ORGANISM: Artificial Sequence
<220> FEATURE:
<223> OTHER INFORMATION: Synthetic

<400> SEQUENCE: 12
gaatcgatct gcgt                                                        14

<210> SEQ ID NO 13
<211> LENGTH: 14
<212> TYPE: DNA
<213> ORGANISM: Artificial Sequence
<220> FEATURE:
<223> OTHER INFORMATION: Synthetic

<400> SEQUENCE: 13
acgcagatcg attc                                                        14

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Ala Pro Arg Pro Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: PEG-modified

<400> SEQUENCE: 15

Ala Pro Arg Pro Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Gly Pro Leu Gly Ile Ala Gly Gln
1               5

<210> SEQ ID NO 17
```

```
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Arg Gly Asp Tyr Cys
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide

<400> SEQUENCE: 18

Ala Ser Ser His Asn
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Lys Cys Cys Tyr Ser Leu
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Tyr Glu Val Gly His Arg Cys
1               5

<210> SEQ ID NO 21
<211> LENGTH: 13
<212> TYPE: PRT
<213> ORGANISM: Artificial Sequence
<220> FEATURE:
<223> OTHER INFORMATION: Synthetic peptide

<400> SEQUENCE: 21

Gly Arg Lys Lys Arg Arg Gln Arg Arg Pro Pro Gln
1               5                   10
```